United States Patent
Hibi et al.

(10) Patent No.: US 7,625,925 B2
(45) Date of Patent: *Dec. 1, 2009

(54) PYRAZOLO[1,5-A]PYRIDINES AND MEDICINES CONTAINING THE SAME

(75) Inventors: Shigeki Hibi, Tsukuba (JP); Koichi Kikuchi, Tsuchiura (JP); Yorihisa Hoshino, Tsukuba (JP); Motohiro Soejima, Tsukuba (JP); Tatsuya Yoshiuchi, Moriya (JP); Kogyoku Shin, Tsukuba (JP); Mutsuko Ono, Ushiku (JP); Yoshinori Takahashi, Tsukuba (JP); Hisashi Shibata, Ushiju (JP); Mitsuhiro Ino, Ushiku (JP); Tetsuya Hirakawa, Tsukuba (JP)

(73) Assignee: Eisai R&D Management Co., Ltd, Tokyo (JP)

(*) Notice: Subject to any disclaimer, the term of this patent is extended or adjusted under 35 U.S.C. 154(b) by 97 days.

This patent is subject to a terminal disclaimer.

(21) Appl. No.: 11/757,595

(22) Filed: Jun. 4, 2007

(65) Prior Publication Data

US 2007/0249663 A1  Oct. 25, 2007

Related U.S. Application Data

(62) Division of application No. 11/446,416, filed on Jun. 5, 2006, now Pat. No. 7,285,666, which is a division of application No. 10/250,693, filed as application No. PCT/JP02/04173 on Apr. 25, 2002, now Pat. No. 7,091,215.

(30) Foreign Application Priority Data

Apr. 27, 2001   (JP)   ............................ P2001-133207

(51) Int. Cl.
A61K 31/437 (2006.01)
(52) U.S. Cl. .................................................... 514/303
(58) Field of Classification Search ................. 514/300, 514/303
See application file for complete search history.

(56) References Cited

U.S. PATENT DOCUMENTS

| | | | |
|---|---|---|---|
| 4,925,849 A | 5/1990 | Shiokawa et al. | |
| 4,957,925 A | 9/1990 | Gubin et al. | |
| 4,990,516 A | 2/1991 | Ohashi et al. | |
| 5,190,862 A | 3/1993 | Wielinger et al. | |
| 5,234,818 A | 8/1993 | Zimmermann et al. | |
| 5,338,743 A | 8/1994 | Shiokawa et al. | |
| 5,445,943 A | 8/1995 | Hoenes | |
| 5,457,200 A | 10/1995 | Zimmermann et al. | |
| 5,525,480 A | 6/1996 | Zimmermann et al. | |
| 5,565,468 A | 10/1996 | Larsen et al. | |
| 5,691,347 A | 11/1997 | Corbier et al. | |
| 7,176,216 B2 * | 2/2007 | Hibi et al. ................. | 514/300 |

FOREIGN PATENT DOCUMENTS

| | | |
|---|---|---|
| EP | 0368343 A2 | 5/1990 |
| EP | 0 433 853 A1 | 6/1991 |
| EP | 0 433 854 A2 | 6/1991 |
| EP | 0497258 A2 | 8/1992 |
| EP | 0 611 766 A1 | 8/1994 |
| EP | 0 659 747 A1 | 6/1995 |
| EP | 97/29110 A1 | 8/1997 |
| EP | 0812831 A1 | 12/1997 |
| JP | 50011399 | 4/1975 |
| JP | 2-131424 A | 5/1990 |
| JP | 05001063 | 1/1993 |
| JP | 5-68913 A | 3/1993 |
| JP | 06016667 | 1/1994 |
| JP | 6-220345 A | 8/1994 |
| JP | 2000-503661 A | 3/2000 |
| JP | 2400-502723 A | 3/2000 |
| JP | 2001-089368 A | 4/2001 |
| WO | WO-94/13643 A1 | 6/1994 |
| WO | WO-94/13644 A1 | 6/1994 |
| WO | WO-94/13661 A1 | 6/1994 |
| WO | WO-94/13676 A1 | 6/1994 |
| WO | WO-94/13677 A1 | 6/1994 |
| WO | WO-95/10506 A1 | 4/1995 |
| WO | WO-96/34563 A1 | 12/1995 |
| WO | WO-97/29109 A1 | 8/1997 |
| WO | WO-98/08847 A1 | 3/1998 |
| WO | WO-98/35967 A2 | 8/1998 |

(Continued)

OTHER PUBLICATIONS

Agid et al., Molecular psychiatry, (Mar. 1999) vol. 4, No. 2, pp. 163-172.*

(Continued)

*Primary Examiner*—D. Margaret Seaman
*Assistant Examiner*—Niloofar Rahmani
(74) *Attorney, Agent, or Firm*—Birch, Stewart, Kolasch & Birch, LLP

(57) ABSTRACT

Compounds represented by the general formula:

(I)

[wherein $R^1$ represents methoxy, ethyl, methylthio, etc., $R^2$, $R^3$ and $R^4$ each represent hydrogen, a halogen, etc., $R^5$ and $R^6$ each represent —$X^5$—$X^6$—$X^7$ (wherein $X^5$ represents a single bond or —CO—, $X^6$ represents a single bond, —$NR^{3a}$, etc. and $X^7$ and $R^{3a}$ each represent hydrogen, $C_{1-10}$ alkyl, etc.), and Ar represents phenyl, pyridyl, etc.], salts thereof and hydrates of the foregoing.

8 Claims, No Drawings

FOREIGN PATENT DOCUMENTS

| | | |
|---|---|---|
| WO | WO-99/01454 A1 | 1/1999 |
| WO | WO-99/10350 A1 | 3/1999 |
| WO | WO-00/01697 A1 | 1/2000 |
| WO | WO-00/39127 A1 | 7/2000 |
| WO | WO-00/59907 A2 | 10/2000 |
| WO | WO-00/59908 A2 | 10/2000 |
| WO | WO-01/35917 A1 | 5/2001 |
| WO | WO-01/44248 A1 | 6/2001 |
| WO | WO-02/06286 A2 | 1/2002 |
| WO | WO-02/18320 A2 | 3/2002 |
| WO | WO-02/076419 | 3/2002 |
| WO | WO-02/058704 A1 | 8/2002 |
| WO | WO-02/088121 A1 | 11/2002 |
| WO | WO-03/072536 A1 | 9/2003 |
| WO | WO-03/078435 A1 | 9/2003 |

OTHER PUBLICATIONS

Sagami et al., Gut, 2004, pp. 958-964.*
Characterization of a 41-Residue Ovine Hypothalamic . . . , Science, vol. 213, pp. 1394-1397, (1981).
Dieterich et al., Exp. Clin. Endocrinol Diabetes, vol. 105, pp. 65-82, (1997).
Vale et al., Recent Progress in Hormone Research, vol. 39, pp. 245-270, (1983).
Arborelius et al., J. of Endocrinology, vol. 160, pp. 1-12, (1999).
Chalmers et al., TIPS, vol. 17, pp. 166-172, (1996).
Tache et al., Annals of the New York Academy of Sciences, vol. 697, pp. 233-243, (1993).
Stenzel-Poore, J. of Neuroscience, vol. 14, No. 5, pp. 2579-2584, (1994).
Vale et al., Science, vol. 213, pp. 1394-1397, (1981).
Rivier et al., Proc. Natl. Acad. Sci, vol. 80, p. 4851-4855, (1983).
Shibahara et al., EMBO Journal, vol. 2, No. 5, pp. 775-779, (1983).
Sasaki et al., J. of Clin. End. And Metab., vol. 65, No. 1, pp. 176-182, (1987).
Sasaki et al., J. of Clin. End, and Metab., vol. 37, No. 4, pp. 768-773, (1988).
Garrick et al., Reg. Peptides, vol. 21, pp. 173-181, (1988).
Petrusz et al., Peptides, vol. 5, Sup. 1, pp. 71-78, (1984).
Chalmers et al., J. of Neuro., vol. 15, No. 10, pp. 6340-6350, (1995).
Liaw et al., Endocrinology, vol. 137, No. 1, pp. 72-77, (1996).
Valdenaire et al., BBA, vol. 1352, pp. 129-132, (1997).
Greep, R., Recent Prog. Horm. Res., vol. 39, pp. 245-270, (1983).
Dunn et al., Brain Research Reviews, vol. 15, pp. 71-100, (1990).
Owens et al., Pharmacol. Rev., vol. 43, No. 4, pp. 425-473, (1991).
Banki et al., Am. J. Psychiatry, vol. 144, No. 7, pp. 873-877, (1987).
Raadsheer et al., Am. J. Psychiatry, vol. 152, No. 9, pp. 1372-1376, (1995).
Nemeroff et al., Arch. Gen. Psychiatry, vol. 45, pp. 577-579, (1988).
Gold et al., N. Engl. J. Med., vol. 314, No. 21, pp. 1329-1335, (1986).
Altemus et al., Arch. Gen. Psychiatry, vol. 51, pp. 794-803, (1994).
Bremner et al., Am. J. Psychiatry, vol. 154, No. 5, pp. 624-629, (1997).
Chappell et al., Biol. Psychiatry, vol. 39, pp. 776-783, (1996).
Roy-Byrne et al., Am. J. Psychiatry, vol. 143, No. 7, pp. 896-899, (1986).
Mönnikes et al., Brain Research, vol. 574, pp. 70-76, (1992).
Butler et al., J. of Neuroscience, vol. 10, No. 1, pp. 176-183, (1990).
Owens et al., J. of Pharm. And Exp. Ther., vol. 258, No. 1, pp. 349-356, (1991).
Kalin et al., Brain Research, vol. 509, pp. 80-84, (1990).
Tazi et al., Reg. Peptides, vol. 18, pp. 37-42, (1987).
Baldwin et al., Psychopharmacology, vol. 103, pp. 227-232, (1991).
Sirinathsinghji et al., Nature, vol. 305, pp. 232-235, (1983).
Sherman et al., Pharm. Bio. & Behavior, vol. 26, pp. 699-703, (1987).
Lyons et al., Brain Research, vol. 545, pp. 339-342, (1991).
Strijbos et al., Brain Research, vol. 656, pp. 405-408, (1994).
Ehlers et al., Brain Research, vol. 278, pp. 332-336, (1983).
Whitehouse et al., Neurology, vol. 37, pp. 905-909, (1987).
De Souza et al., Brain Research, vol. 437, pp. 355-359, (1987).
Behan et al., Nature, vol. 378, pp. 284-287, (1995).
Diamant et al., Neuroendocrinology, vol. 57, pp. 1071-1081, (1993).
Stenzel-Poore et al., Endocrinology, vol. 130, No. 6, pp. 3378-3386, (1992).
Hotta et al., J. Clin. Endocrinology, vol. 62, No. 2, pp. 319-324, (1986).
Levine et al., Neuropharmacology, vol. 22, No. 3A, pp. 337-339, (1983).
Krahn et al., Brain Research Bulletin, vol. 17, pp. 285-289, (1986).
Arase et al., Physiology & Behavior, vol. 4 , pp. 565-570, (1989).
Plotsky et al., Endocrinology, vol. 130, No. 4, pp. 1931-1941, (1992).
Nicholson et al., Regulatory Peptides, vol. 18, pp. 173-188, (1987).
Tache et al., Am. J. Physiol., vol. 253, pp. G241-G245, (1987).
Barquist et al., Am. J. Physiol., vol. 262, pp. G616-G620, (1992).
Gunion et al., Am. J. Physiol., vol. 258, pp. G152-G157, (1990).
Bakke et al., Life Sciences, vol. 45, pp. 907-916, (1989).
Lenz et al., Gastroenterology, vol. 95, pp. 1510-1517, (1988).
Ford et al., Gastroenterology, vol. 109, pp. 1772-1780, (1995).
Lembo et al., Neurogastroenterol. Mot., vol. 8, pp. 9-18, (1996).
Fukudo et al., Gut, vol. 42, pp. 845-849, (1998).
Morimoto et al., J. of Physiology, vol. 460, pp. 221-229, (1993).
Karalis et al., Science, vol. 254, pp. 421-423, (1991).
Crofford et al., J. Clin. Invest., vol. 90, pp. 2555-2564, (1992).
Crofford et al., J. of Immun., vol. 151, No. 3, pp. 1587-1596, (1993).
Theoharides et al., Endocrinology, vol. 139, No. 1, pp. 403-413, (1998).
Singh et al., J. Pharmacol. Exp. Ther., vol. 288, No. 3, pp. 1349-1356, (1999).
Scopa et al., Am. J. of Pathology, vol. 145 No. 5, pp. 1159-1167, (1994).
Poliak et al., J. Immunol., vol. 158, pp. 5751-5756, (1997).
Murakami et al., Endocrine Journal, vol. 44, No. 4, pp. 627-629, (1997).
Singh et al., J. of Neuroimmunology, vol. 23, pp. 257-262, (1989).
Singh et al., Neuroscience Letters, vol. 120, pp. 151-154, (1990).
Jain et al., Endocrinology, vol. 128, No. 3, pp. 1329-1336, (1991).
Böhmer et al., E. J. of Pharmacology, vol. 182, pp. 405-411, (1990).
Nink et al., Acta Endocrinologica, vol. 127, pp. 200-204, (1992).
Rivier et al., Science, vol. 224, pp. 889-891, (1984).
Menzachi et al., J. of Pharm. & Exp. Ther., vol. 269, No. 2, pp. 564-572, (1994).
Chen et al., J. Med. Chem., vol. 39, pp. 4358-4360, (1996).
Whitten et al., J. Med. Chem., vol. 39, pp. 4354-4357, (1996).
Leonard et al., Int. J. Devl. Neuroscience, vol. 19, pp. 305-312 (2001).
Gubin et al., Journal of Medicinal Chemisty, vol. 36, pp. 1425-1433 (1993).
Fujito et al., Heterocycles, vol. 6, pp. 379-382 (1977).
Tominaga et al., Yakugaku Zasshi, vol. 104, pp. 440-448 (1984).
Ochi et al., Bulletin of Chemical Society of Japan, vol. 49, pp. 1980-1984 (1976).

* cited by examiner

PYRAZOLO[1,5-A]PYRIDINES AND MEDICINES CONTAINING THE SAME

CROSS-REFERENCE TO RELATED APPLICATIONS

This is a 37 C.F.R. § 1.53(b) divisional of U.S. application Ser. No. 11/446,416 filed Jun. 5, 2006 now U.S. Pat. No. 7,285,666, which is a 37 C.F.R. § 1.53(b) divisional of application Ser. No. 10/250,693 filed Oct. 27, 2003 now U.S. Pat. No. 7,091,215, which is the National Phase of PCT International Application No. PCT/JP02/04173 filed Apr. 25, 2002, which claims priority on Japanese Patent Application No. 2001-133207 filed Apr. 27, 2001. Each of these applications is hereby incorporated by reference.

TECHNICAL FIELD

The present invention relates to novel compounds having Corticotropin-Releasing Factor receptor antagonistic activity, salts thereof and hydrates of the foregoing, to process for producing the same and to the use of the same as medicine.

BACKGROUND ART

Corticotropin-Releasing Factor (hereinafter abbreviated as "CRF") is a neuropeptide consisting of 41 amino acids which was first isolated from ovine hypothalamus [Science, 213, 1394 (1981)], after which its presence was also confirmed in rats [Proc. Natl. Acad. Sci. USA, 80, 4851 (1983)] and in humans [EMBO J. 5, 775 (1983)]. CRF is most abundant in the pituitary gland and hypothalamus, and is also widely distributed throughout the cerebral cortex, cerebellum and other area of the brain. Its presence has also been confirmed in peripheral tissue such as the placenta, adrenal gland, lung, liver, pancreas and digestive tract [J. Clin. Endocrinol. Metab., 67, 768 (1988), Regul. Pept. 18, 173 (1988), Peptides, 5 (Suppl. 1), 71 (1984)]. Two subtype CRF receptor has been described, CRF1 and CRF2, and the CRF1 receptor is reported to be widely distributed in the cerebral cortex, cerebellum, olfactory bulb, pituitary gland, amygdaloid nucleus and elsewhere. Recently, 2 subtypes of the CRF2 receptor have been confirmed, CRF2α and CRF2β, of which it has been discovered that CRF2α receptors are abundantly distributed in the hypothalamus, septal nucleus and choroids plexus, while CRF2β receptors are primarily distributed in peripheral tissue such as the skeletal muscle, or in the cerebral blood vessels of the central nervous system [J. Neuroscience, 15(10)6340 (1995); Endocrinology, 137, 72, (1996); BBA, 1352, 129 (1997)]. The fact that each of these receptors has a different distribution profile suggests that their roles are also different. CRF is produced and secreted in the hypothalamus and promotes stress-induced release of adrenocorticotropic hormone (ACTH) [Recent Prog. Horm. Res., 39, 245 (1983)]. In addition to its endocrine role, CRF also functions as a neurotransmitter or neuromodulator in the brain, integrating electrophysiological, autonomic and behavioral changes in response to stress [Brain Res. Rev., 15, 71 (1990); Pharmacol. Rev., 43, 425 (1991)].

CRF has been implicated in a variety of disease to date, as indicated by the following publications.

It was reported that elevated concentrations of CRF in the cerebrospinal fluid of patients with major depression compared with healthy controls [Am. J. Psychiatry, 144(7), 873 (1987)]; CRF-mRNA levels in the hypothalamus of depressive patients are higher than that of healthy individuals [Am. J. Psychiatry, 152, 1372 (1995)]; CRF receptors in cerebral cortex are reduced in suicide victims [Arch. Gen. Psychiatry, 45, 577 (1988)]; plasma ACTH increase is diminished with administration of CRF to depressive patients [N. Engl. J. Med., 314, 1329 (1986)]; CRF levels in the cerebrospinal fluid of some anxiety patients with obsessive-compulsive disorder, posttraumatic stress disorder or Tourette's syndrome are higher than in that of healthy individuals [Arch. Gen. Psychiatry, 51, 794 (1994); Am. J. Psychiatry, 154, 624 (1997); Biol. Psychiatry, 39, 776 (1996)]; plasma ACTH increase is diminished with administration of CRF to panic disorder patients [Am. J. Psychiatry, 143, 896 (1986)]; anxiety behavior has been observed in experimental animals by central administration of CRF [Brain Res., 574, 70 (1992); J. Neurosci., 10(1), 176 (1992)]. In addition, anxiety behavior is observed more frequently in CRF overexpressing mice than in normal mice [J. Neurosci., 14(5), 2579 (1994)], and CRF levels in the locus coeruleus are reduced by administration of anxiolytics [J. Pharmaco. Exp. Ther., 258, 349 (1991)]. Also, the peptide CRF antagonist α-helical CRF (9-41) exhibits an anxiolytic effect in animal models [Brain Res., 509, 80 (1990); Regulatory Peptides, 18, 37 (1987); J. Neurosci., 14(5), 2579 (1994)]; abnormal behavior withdrawal from alcohol or addictive drugs such as cocaine are inhibited by the peptide CRF antagonist α-helical CRF (9-41) [Psychopharmacology, 103, 227 (1991)]; CRF inhibits sexual behavior in rats [Nature, 305, 232 (1983)]; CRF reduces sleep in rats and is thus implicated the involvement in sleep disorder [Pharmacol. Biochem. Behav., 26, 699 (1987)]; the peptide CRF antagonist α-helical CRF (9-41) suppresses brain damage or electroencephalogram disturbances due to brain ischemia or NMDA receptor activation [Brain Res., 545, 339 (1991), Brain Res., 656, 405 (1994)]; CRF elicits electroencephalogram and induces convulsions [Brain Res., 278, 332 (1983)]; cerebrospinal CRF levels are elevated in schizophrenic patients compared with healthy individuals [Am. J. Psychiatry, 144(7), 873 (1987)]; CRF contents in cerebral cortex is reduced in Alzheimer's patients, Parkinson's patients and progressive supranuclear palsy patients [Neurology, 37, 905 (1987)]; and CRF is reduced in the ganglia in Huntington's disease [Brain Res., 437, 355 (1987), Neurology, 37, 905 (1987)]. In addition, CRF administration has been found to enhance learning and memory in rats [Nature, 378, 284 (1995); Neuroendocrinology, 57, 1071 (1993)], and CRF levels of cerebrospinal fluid are reduced in amyotrophic lateral sclerosis patients. Oversecretion of ACTH and adrenocorticosteroids are exhibited in CRF overexpressing mice, these mice display abnormalities similar to Cushing's syndrome, including muscular atrophy, alopecia and infertility [Endocrinology, 130(6), 3378 (1992)]; cerebrospinal CRF levels are elevated in anorexia nervosa patients compared with healthy individuals, and plasma ACTH increase is low with administration of CRF to anorexia nervosa patients [J. Clin. Endocrinol. Metab., 62, 319 (1986)]; and CRF suppress food consumption in experimental animals [Neuropharmacology, 22 (3A), 337 (1983)]. Moreover, the peptide CRF antagonist α-helical CRF (9-41) reverses stress-induced reduction in food intake in animal models [Brain Res. Bull., 17(3), 285 (1986)]; CRF has suppressed body weight gain in genetically obese animals [Physiol. Behav., 45, 565 (1989)]; a link has been suggested between low CRF levels and obesity syndrome [Endocrinology, 130, 1931 (1992)]; the anorexic action and body weight-reducing effects of serotonin reuptake inhibitors has been possibly linked to CRF release [Pharmacol. Rev., 43, 425 (1991)]; and CRF acts centrally or peripherally to inhibit gastric contraction and reduce gastric emptying [Regulatory Peptides, 21, 173 (1988); Am. J. Physiol., 253, G241 (1987)]. Furthermore, abdominal surgery-induced reduced gastric function is reversed by the peptide CRF antagonist α-helical CRF (9-41) [Am. J. Physiol., 262, G616 (1992)]; and CRF promotes secretion of bicarbonate ion in the stomach, thereby lowering gastric acid secretion and suppressing cold restraint stress ulcers [Am. J. Physiol., 258, G152 (1990)]. Also, administration of CRF increases ulcers in non-restraint stress animals [Life Sci., 45, 907 (1989)], and CRF suppresses small intestinal transit and promotes large intestinal transit, and defecation is induced. In addition, the peptide CRF antagonist α-helical CRF (9-41) has a inhibiting effect against restraint stress-induced gastric acid secretion reduced gastric emptying, and small intestinal transit and accelerated large intestinal transit [Gastroenterology, 95, 1510 (1988)]; psychological stress in healthy individuals increases anxiety or sensations of gas and abdominal pain during colonic distension and CRF lowers the discomfort threshold [Gastroenterol., 109, 1772 (1995); Neurogastroenterol. Mot., 8, 9 (1996)]; irritable bowel syndrome patients experience excessive acceleration of colonic motility with CRF administration compared to healthy individuals [Gut, 42, 845 (1998)]; administration of CRF increases blood pressure, heart rate and body temperature, while the peptide CRF antagonist α-helical CRF (9-41) suppresses stress-induced increases in blood pressure, heart rate and body temperature [J. Physiol., 460, 221 (1993)]; CRF production is increased locally in inflammation sites in experimental animals and in the synovial fluid of rheumatic arthritis patients [Science, 254, 421 (1991); J. Clin. Invest., 90, 2555 (1992); J. Immunol., 151, 1587 (1993)]; CRF provokes degranulation of mast cells and promotes vascular permeability [Endocrinology, 139(1), 403 (1998); J. Pharmacol. Exp. Ther., 288(3), 1349 (1999)]; CRF is detected in autoimmune thyroiditis patients [Am. J. Pathol., 145, 1159 (1994)]; administration of CRF to experimental autoimmune encephalomyelitis rats has notably suppressed progression of symptoms such as paralysis [J. Immumol., 158, 5751 (1997)]; and urocortin (a CRF analogue) has increased growth hormone secretion in a pituitary adenoma culture system from an acromegalia patient [Endocri. J, 44, 627 (1997)]. Furthermore, CRF simulates secretion of cytokines such as interleukin-1 and interleukin-2 by leukocytes [J. Neuroimmunol., 23, 256 (1989); Neurosci. Lett., 120, 151 (1990)]; and CRF administration and stress both suppress T lymphocyte proliferation and natural killer cell activity. The peptide CRF antagonist α-helical CRF (9-41) improves the reduced function of these immune cells caused by CRF administration or stress [Endocrinology, 128 (3), 1329 (1991)], and ventilation is notably increased by administration of CRF [Eur. J. Pharmacol., 182, 405 (1990)]. Finally, aggravated breathing and insomnia have been observed as a result of CRF administration to elderly patients under chronic artificial respiration [Acta Endocrinol. Copenh., 127, 200 (1992)].

The research cited above suggests that CRF antagonists may be expected to exhibit excellent effects for treatment or prevention of depression and depressive symptoms such as major depression, single-episode depression, recurrent depression, depression-induced child abuse and postpartum depression, mania, anxiety, generalized anxiety disorder, panic disorder, phobias, obsessive-compulsive disorder, post-traumatic stress disorder, Tourette's syndrome, autism, affective disorder, dysthymia, bipolar disorder, cyclothymic personality, schizophrenia, Alzheimer's disease, senile dementia of Alzheimer's type, neurodegenerative disease such as Parkinson's disease and Huntington's disease, multi-infarct dementia, senile dementia, anorexia nervosa, increased appetite and other eating disorders, obesity, diabetes, alcohol dependence, pharmacophilia for drugs such as cocaine, heroin or benzodiazepines, drug or alcohol withdrawal symptoms, sleep disorder, insomnia, migraine, stress-induced headache, muscle contraction induced headache, ischemic neuronal damage, excitotoxic neuronal damage, stroke, progressive supranuclear palsy, amyotrophic lateral sclerosis, multiple sclerosis, muscular spasm, chronic fatigue syndrome, psychosocial dwarfism, epilepsy, head trauma, spinal cord injury, cheirospasm, spasmodic torticollis, cervicobrachial syndrome, primary glaucoma, Meniere's syndrome, autonomic imbalance, alopecia, neuroses such as cardiac neurosis, gastric neurosis and bladder neurosis, peptic ulcer, irritable bowel syndrome, ulcerative colitis, Crohn's disease, diarrhea, constipation, postoperative ileus, stress-associated gastrointestinal disorders and nervous vomiting, hypertension, cardiovascular disorders such as angina pectoris nervosa, tachycardia, congestive heart failure, hyperventilation syndrome, bronchial asthma, apneusis, sudden infant death syndrome, inflammatory disorders (for example, rheumatic arthritis, osteoarthritis, lumbago, etc.), pain, allergosis (for example, atopic dermatitis, eczema, hives, psoriasis, etc.), impotence, menopausal disorder, fertilization disorder, infertility, cancer, HIV infection-related immune dysfunction, stress-induced immune dysfunction, hemorrhagic stress, Cushing's syndrome, thyroid function disorder, encephalomyelitis, acromegaly, incontinence, osteoporosis, and the like. As examples of CRF antagonists there have been reported peptide CRF receptor antagonists with modifications or deletions of portions of the amino acid sequence of human or other mammalian CRF, and such antagonists have shown ACTH release-inhibiting effects or anxiolytic effects [Science, 224, 889 (1984), J. Pharmacol. Exp. Ther., 269, 564 (1994), Brain Research Reviews, 15, 71 (1990)]. However, peptide derivatives have low utility value as drugs from the standpoint of pharmacokinetics including their chemical stability in the body, oral absorption, bioavailability and migration into the brain.

On the other hand, the following non-peptide CRF antagonists have also been reported.

[1] Compounds represented by the formula:

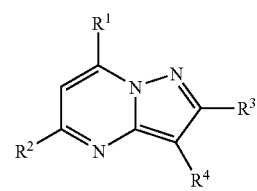

[wherein $R^1$ represents $NR^4R^5$, etc.; $R^2$ represents $C_{1-6}$ alkyl, etc.; $R^3$ represents $C_{1-6}$ alkyl, etc.; $R^4$ represents $C_{1-6}$ alkyl, etc.; $R^5$ represents $C_{1-8}$ alkyl, etc.; and Ar represents phenyl, etc.], stereoisomers thereof or pharmacologically acceptable acid addition salts of the foregoing (WO97/29109);

[2] Compounds represented by the formula:

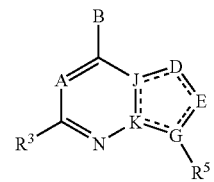

[wherein the dotted lines represent single bonds or double bonds; A represents $CR^7$, etc.; B represents $NR^1R^2$, etc.; J and K are the same or different and represent nitrogen, etc.; D and E are the same or different and represent nitrogen, etc.; G represents nitrogen, etc.; $R^1$ represents $C_1$-$C_6$ alkyl, etc.; $R^2$ represents $C_1$-$C_{12}$ alkyl, etc.; and $R^7$ represents hydrogen, etc.] or pharmacologically acceptable salts thereof (WO98/08847);

[3] The anilinopyrimidine compounds described in WO95/10506, the pyrazolopyridine compounds described in WO95/34563, the pyrazole compounds described in WO94/13661, the pyrazole compounds and pyrazolopyrimidine compounds described in WO94/13643, the aminopyrazole compounds described in WO94/13644, the pyrazolopyrimidine compounds described in WO94/13677, the pyrrolopyrimidine compounds described in WO94/13676, the thiazole compounds described in EP-659747 and EP-611766, the anilinopyrimidine compounds described in J. Med. Chem., 39, 4358 (1996), the anilinotriazine compounds described in ibid. 39, 4354 (1996) and the thienopyrimidine compounds described in WO97/29110; and

[4] As pyrazolo[1,5-a]pyridine compounds, the compounds described, for example, in EP433854, EP433853 or U.S. Pat. No. 5,445,943.

DISCLOSURE OF THE INVENTION

As mentioned above, it is ardently desired to provide CRF receptor antagonists which are useful as drugs, but clinically effective agents that exhibit excellent CRF receptor antagonism and satisfy the requirements of pharmacological activity, dosage and safety as medicines have not yet been discovered. It is therefore an object of the present invention to investigate and discover such excellent CRF receptor antagonists.

As a result of much diligent examination and research in light of the circumstances described above, the present inventors have discovered novel pyrazolo[1,5-a]pyridine compounds exhibiting excellent CRF receptor antagonism.

The invention provides:

<1> a compound represented by the general formula:

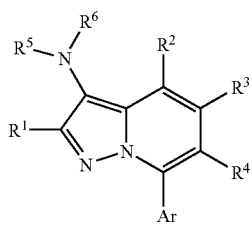

(I)

[wherein $R^1$ represents hydrogen, halogen, nitro, cyano or the formula —$G^1$—$R^{1a}$ (wherein $G^1$ represents a single bond, methylene, oxygen, sulfur, sulfinyl, sulfonyl, —C(O)—, —C(O)O—, —OC(O)—, —$NR^{1b}$—, —C(O)—$NR^{1b}$—, —$S(O)_2$—$NR^{1b}$—, —$NR^{1b}$—C(O)— or —$NR^{1b}$—$S(O)_2$—; and $R^{1a}$ and $R^{1b}$ each independently represent hydrogen, $C_{1-10}$ alkyl, $C_{2-10}$ alkenyl, $C_{2-10}$ alkynyl, $C_{3-8}$ cycloalkyl or $C_{5-8}$ cycloalkenyl);

$R^2$, $R^3$ and $R^4$ each independently represent hydrogen, halogen, cyano, nitro, hydroxyl, $C_{6-14}$ aryl, a 5- to 14-membered heteroaryl group or the formula —$G^2$—$R^{2a}$ (wherein $G^2$ represents a single bond, $C_{1-6}$ alkylene, oxygen, sulfur, sulfinyl, sulfonyl, —C(O)—, —C(O)O—, —OC(O)—, —$NR^{2b}$—, —C(O)—$NR^{2b}$—, —$S(O)_2$—$NR^{2b}$—, —$NR^{2b}$—C(O)— or —$NR^{2b}$—$S(O)_2$—;

$R^{2a}$ and $R^{2b}$ each independently represent hydrogen, $C_{1-6}$ alkyl optionally substituted with 1-3 halogen, $C_{2-10}$ alkenyl, $C_{2-10}$ alkynyl, $C_{3-8}$ cycloalkyl or $C_{5-8}$ cycloalkenyl);

$R^2$ and $R^3$ or $R^3$ and $R^4$ may bond together to form a 5- to 7-membered ring optionally containing 1 to 4 hetero atoms in the ring and optionally containing carbonyl in the ring;

$R^5$ and $R^6$ each independently represent the formula —$X^5$—$X^6$—$X^7$ (wherein $X^5$ represents a single bond or —CO—; $X^6$ represents a single bond, —$NR^{3a}$—, oxygen, sulfur, sulfinyl, sulfonyl, $C_{1-10}$ alkylene, $C_{2-10}$ alkenylene or $C_{2-10}$ alkynylene; and $X^7$ and $R^{3a}$ each independently represent hydrogen, $C_{1-10}$ alkyl, $C_{2-10}$ alkenyl, $C_{2-10}$ alkynyl, $C_{3-8}$ cycloalkyl, $C_{5-8}$ cycloalkenyl, $C_{6-14}$ aryl, a 5- to 14-membered heteroaryl group, a 4- to 14-membered heterocyclic group, a 9- to 11-membered benzene fused ring group, an 8- to 11-membered heteroaryl fused ring group or a bicyclic 7- to 12-membered hydrocarbon ring group);

$R^5$ and $R^6$ may bond together to form a 5- to 10-membered ring optionally containing 1 to 4 hetero atoms in the ring and optionally containing carbonyl in the ring;

$R^6$ and $R^2$ may bond together to form a 6- to 7-membered ring optionally containing 1 or 2 hetero atoms in the ring and optionally containing carbonyl in the ring; and Ar represents $C_{6-14}$ aryl, a 5- to 14-membered heteroaryl group, a 9- to 11-membered benzene fused ring group or an 8- to 11-membered heteroaryl fused ring group; with the proviso that $R^{1a}$, $R^{1b}$, $R^{3a}$, $X^6$, $X^7$ and Ar may each independently have 1 to 4 groups selected from Substituent Group A below;

<Substituent Group A>

The group consisting of methylenedioxy, ethylenedioxy and the formula —$V^1$—$V^2$—$V^3$ (wherein $V^1$ represents a single bond, $C_{1-6}$ alkylene, $C_{2-6}$ alkenylene, $C_{2-6}$ alkynylene, oxygen, sulfur, carbonyl, —CO—O—, —O—CO— or —$NR^{3b}$—; $V^2$ represents a single bond or $C_{1-6}$ alkylene; and $V^3$ and $R^{3b}$ each independently represent $C_{1-6}$ alkyl, $C_{2-6}$ alkenyl, $C_{2-6}$ alkynyl, $C_{3-8}$ cycloalkyl, $C_{5-8}$ cycloalkenyl, $C_{6-14}$ aryl, a 5- to 14-membered heteroaryl group, a 4- to 14-membered heterocyclic group, hydrogen, halogen, hydroxyl, cyano, $C_{1-6}$ alkoxy or the formula —$N(R^{3c})R^{3d}$ (wherein $R^{3c}$ and $R^{3d}$ each independently represent hydrogen or $C_{1-6}$ alkyl))], a salt thereof or a hydrate of the foregoing.

<2> a compound according to <1>, a salt of the compound or a hydrate of the foregoing, wherein $R^1$ is the formula —$G^{10}$—$R^{10}$ (wherein $G^{10}$ represents a single bond, methylene, oxygen, sulfur, sulfinyl or sulfonyl and $R^{10}$ represents $C_{1-6}$ alkyl optionally substituted with 1 to 3 halogen, $C_{2-6}$ alkenyl, $C_{2-6}$ alkynyl or $C_{3-8}$ cycloalkyl);

<3> a compound according to <2>, a salt of the compound or a hydrate of the foregoing, wherein $R^{10}$ is methyl, ethyl, n-propyl, iso-propyl, trifluoromethyl, difluoromethyl, monofluoromethyl, cyclopropyl or cyclobutyl;

<4> a compound according to <1>, a salt of the compound or a hydrate of the foregoing, wherein $R^1$ is methoxy;

<5> a compound according to <1>, a salt of the compound or a hydrate of the foregoing, wherein $R^1$ is ethyl;

<6> a compound according to <1>, a salt of the compound or a hydrate of the foregoing, wherein $R^1$ is methylthio;

<7> a compound according to any one of <1> to <6>, a salt of the compound or a hydrate of the foregoing, wherein $R^2$, $R^3$ and $R^4$ each independently represent hydrogen, halogen, cyano, nitro, hydroxyl, or the formula —$G^{20}$—$R^{20}$ (wherein $G^{20}$ represents a single bond, oxygen, sulfur, sulfinyl or sulfonyl, and $R^{20}$ represents $C_{1-6}$ alkyl optionally substituted with 1 to 3 halogen, $C_{2-10}$ alkenyl, $C_{2-10}$ alkynyl or $C_{3-8}$ cycloalkyl);

<8> a compound according to any one of <1> to <6>, a salt of the compound or a hydrate of the foregoing, wherein $R^2$, $R^3$ and $R^4$ are hydrogen;

<9> a compound according to any one of <1> to <8>, a salt of the compound or a hydrate of the foregoing, wherein Ar is phenyl, 1,3-benzodioxolyl, naphthyl, pyridyl, pyrazyl, pyrimidyl, pyridazyl, thienyl, furanyl, imidazolyl, thiazolyl, quinolinyl, isoquinolinyl, indolinyl, benzofuranyl, benzothienyl, oxazolyl or isoxazolyl, and Ar may have 1 to 4 groups selected from Substituent Group B below;

<Substituent Group B>

The group consisting of halogen, cyano, hydroxyl, nitro, methylenedioxy, ethylenedioxy, the formula —$V^4$—$V^5$ (wherein $V^4$ represents a single bond, oxygen, sulfur, sulfinyl or sulfonyl and $V^5$ represents $C_{1-6}$ alkyl optionally substituted with 1 to 3 halogen or $C_{3-8}$ cycloalkyl) and the formula —$N(R^{5a})R^{5b}$ (wherein $R^{5a}$ and $R^{5b}$ each independently represent hydrogen or $C_{1-6}$ alkyl);

<10> A compound according to any one of <1> to <9>, a salt of the compound or a hydrate of the foregoing, wherein Ar is phenyl or pyridyl, and Ar may optionally have 1 to 3 groups selected from Substituent Group B in <9>;

11> a compound according to <9> or <10>, a salt of the compound or a hydrate of the foregoing, wherein Substituent Group B is the group consisting of halogen, cyano, $C_{1-6}$ alkyl optionally substituted with 1 to 3 halogen, $C_{3-8}$ cycloalkyl, dimethylamino and $C_{1-6}$ alkoxy optionally substituted with 1 to 3 halogen;

<12> a compound according to any one of <1> to <8>, a salt of the compound or a hydrate of the foregoing, wherein Ar is the formula:

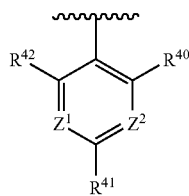

(wherein $R^{40}$ and $R^{41}$ each independently represent methoxy, ethoxy, ethyl, methyl, dimethylamino or halogen, $R^{42}$ represents hydrogen, methoxy, methyl, dimethylamino or halogen, and $Z^1$ and $Z^2$ each independently represent methine or nitrogen);

<13> a compound according to <12>, a salt of the compound or a hydrate of the foregoing, wherein $Z^1$ and $Z^2$ are methine;

<14> a compound according to any one of <1> to <13>, a salt of the compound or a hydrate of the foregoing, wherein $X^5$ is a single bond, and $X^6$ is a single bond, $C_{1-6}$ alkylene optionally having 1 to 3 groups selected from Substituent Group A, $C_{2-6}$ alkenylene optionally having 1 to 3 groups selected from Substituent Group A or $C_{2-6}$ alkynylene optionally having 1 to 3 groups selected from Substituent Group A.

<15> a compound according to any one of <1> to <13>, a salt of the compound or a hydrate of the foregoing, wherein $X^5$ is a single bond, and $X^6$ is a single bond or $C_{1-6}$ alkylene optionally having 1 to 3 groups selected from Substituent Group C below;

<Substituent Group C>

The group consisting of halogen, hydroxyl, $C_{1-6}$ alkoxy, nitrile, $C_{3-8}$ cycloalkyl, and $C_{1-6}$ alkyl;

<16> a compound according to any one of <1> to <13>, a salt of the compound or a hydrate of the foregoing, wherein $X^5$ is a single bond, and $X^6$ is a single bond, 1,2-ethylene or methylene;

<17> a compound according to any one of <1> to <16>, a salt of the compound or a hydrate of the foregoing, wherein $X^7$ is $C_{1-10}$ alkyl optionally having 1 to 3 groups selected from Substituent Group A, $C_{2-10}$ alkenyl optionally having 1 to 3 groups selected from Substituent Group A, $C_{2-10}$ alkynyl optionally having 1 to 3 groups selected from Substituent Group A, $C_{3-8}$ cycloalkyl optionally having 1 to 3 groups selected from Substituent Group A, $C_{5-8}$ cycloalkenyl optionally having 1 to 3 groups selected from Substituent Group A, $C_{6-14}$ aryl optionally having 1 to 3 groups selected from Substituent Group A, a 5- to 14-membered heteroaryl group optionally having 1 to 3 groups selected from Substituent Group A, a 4- to 14-membered heterocyclic group optionally having 1 to 3 groups selected from Substituent Group A or a bicyclic 7- to 12-membered hydrocarbon ring group optionally having 1 to 3 groups selected from Substituent Group A;

<18> a compound according to any one of <1> to <16>, a salt of the compound or a hydrate of the foregoing, wherein $X^7$ is $C_{1-10}$ alkyl optionally having 1 to 3 groups selected from Substituent Group A, $C_{3-8}$ cycloalkyl optionally having 1 to 3 groups selected from Substituent Group A, a 5- to 6-membered heteroaryl group optionally having 1 to 3 groups selected from Substituent Group A or a 4- to 7-membered heterocyclic group optionally having 1 to 3 groups selected from Substituent Group A;

<19> a compound according to any one of <1> to <16>, a salt of the compound or a hydrate of the foregoing, wherein $X^7$ is $C_{1-10}$ alkyl optionally having 1 to 3 groups selected from Substituent Group D below, $C_{3-8}$ cycloalkyl optionally having 1 to 3 groups selected from Substituent Group D below, a 5- to 6-membered heteroaryl group optionally having 1 to 3 groups selected from Substituent Group D below or a 4- to 7-membered heterocyclic group optionally having 1 to 3 groups selected from Substituent Group D below;

<Substituent Group D>

The group consisting of halogen, hydroxyl, $C_{1-6}$ alkoxy, nitrile, $C_{3-8}$ cycloalkyl, dimethylamino and $C_{1-6}$ alkyl;

<20> a compound according to any one of <1> to <16>, a salt of the compound or a hydrate of the foregoing, wherein $X^7$ is hydrogen, $C_{1-10}$ alkyl optionally having 1 or 2 groups selected from Substituent Group E below, $C_{3-8}$ cycloalkyl optionally having 1 or 2 groups selected from Substituent Group E below, tetrahydrofuranyl optionally having 1 or 2 groups selected from Substituent Group E below, tetrahydrothiophenyl optionally having 1 or 2 groups selected from Substituent Group E below, dihydropyranyl optionally having 1 or 2 groups selected from Substituent Group E below, tetrahydropyranyl optionally having 1 or 2 groups selected from Substituent Group E below, dioxolanyl optionally having 1 or 2 groups selected from Substituent Group E below, pyrrolidin-2-onyl optionally having 1 or 2 groups selected from Substituent Group E below, dihydrofuran-2-onyl optionally having 1 or 2 groups selected from Substituent Group E below, furanyl optionally having 1 or 2 groups selected from Substituent Group E below, thienyl optionally having 1 or 2 groups selected from Substituent Group E below, pyrrolidinyl optionally having 1 or 2 groups selected from Substituent Group E below, piperidyl optionally having 1 or 2 groups selected from Substituent Group E below, oxazolyl optionally having 1 or 2 groups selected from Substituent Group E below, isoxazolyl optionally having 1 or 2 groups selected from Substituent Group E below, thiazolyl optionally having 1 or 2 groups selected from Substituent Group E below, pyrrolyl optionally having 1 or 2 groups selected from Substituent Group E below, pyrazolyl optionally having 1 or 2 groups selected from Substituent Group E below, morpholinyl optionally having 1 or 2 groups selected from Substituent Group E below, dioxanyl optionally having 1 or 2 groups selected from Substituent Group E below or pyridyl optionally having 1 or 2 groups selected from Substituent Group E below;

<Substituent Group E>

The group consisting of hydroxyl, methyl, ethyl, methoxy, dimethylamino, cyano, chlorine and fluorine;

<21> a compound according to <20>, a salt of the compound or a hydrate of the foregoing, wherein Substituent Group E is the group consisting of methyl, methoxy, dimethylamino, chlorine and fluorine;

<22> a compound according to any one of <1> to <16>, a salt of the compound or a hydrate of the foregoing, wherein $X^7$ is hydrogen, $C_{1-10}$ alkyl, $C_{3-8}$ cycloalkyl, tetrahydrofuranyl, tetrahydrothiophenyl, dihydropyranyl, tetrahydropyranyl, dioxolanyl, pyrrolidin-2-onyl, dihydrofuran-2-onyl, furanyl, thienyl, pyrrolidinyl, piperidyl, oxazolyl, isoxazolyl, thiazolyl, pyrrolyl, pyrazolyl, morpholinyl, dioxanyl or pyridyl;

<23> a compound according to any one of <1> to <16>, a salt of the compound or a hydrate of the foregoing, wherein $X^7$ is hydrogen, $C_{1-10}$ alkyl, $C_{3-8}$ cycloalkyl, tetrahydrofuranyl, tetrahydrothiophenyl, tetrahydropyranyl, dioxolanyl, furanyl, thienyl, oxazolyl, dioxanyl, pyridyl, piperidyl or thiazolyl;

<24> a compound represented by the general formula:

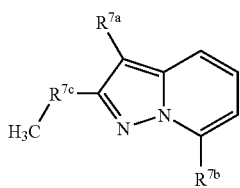

(IIa)

[wherein $R^{7a}$ represents hydrogen, nitro, —NO or —NHR$^{7d}$ (wherein $R^{7d}$ represents hydrogen, t-butoxycarbonyl or benzyloxycarbonyl);

$R^{7c}$ represents methylene, oxygen or sulfur; and $R^{7b}$ represents hydrogen, halogen, the formula:

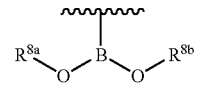

(wherein $R^{8a}$ and $R^{8b}$ each independently represent hydrogen or $C_{1-6}$ alkyl, or $R^{8a}$ and $R^{8b}$ may bond together to form 1,2-ethylene, 1,3-propylene or 2,3-dimethylbutan-2,3-diyl), the formula:

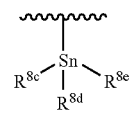

(wherein $R^{8c}$, $R^{8d}$ and $R^{8e}$ each independently represent $C_{1-6}$ alkyl) or the formula:

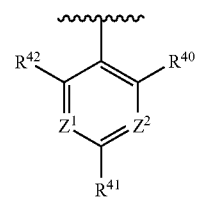

(wherein $R^{40}$ and $R^{41}$ each independently represent methoxy, ethoxy, ethyl, dimethylamino, methyl or halogen, $R^{42}$ represents hydrogen, methoxy, methyl or halogen, and $Z^1$ and $Z^2$ each independently represent methine or nitrogen), with the proviso that compounds satisfying the following conditions (1), (2) or (3) are not included in the above definitions:

(1) $R^{7c}$ is oxygen, $R^{7b}$ is hydrogen and $R^{7a}$ is hydrogen, nitro, —NO or —NH$_2$, (2) $R^{7c}$ is sulfur, $R^{7b}$ is hydrogen and $R^{7a}$ is nitro or —NH$_2$, or (3) $R^{7c}$ is methylene, $R^{7b}$ is hydrogen and $R^{7a}$ is —NO], a salt thereof or a hydrate of the foregoing;

<25> a compound according to <24>, a salt of the compound or a hydrate of the foregoing, wherein $R^{7a}$ and $R^{7b}$ are hydrogen;

<26> a compound according to <24>, a salt of the compound or a hydrate of the foregoing, wherein $R^{7b}$ is not hydrogen;

<27> a compound represented by the general formula:

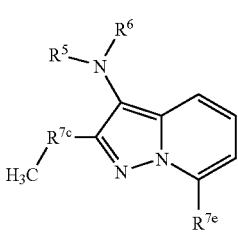

(IIb)

[wherein $R^5$ and $R^6$ have the same definitions as $R^5$ and $R^6$ in <1>, respectively;

$R^{7c}$ represents methylene, oxygen or sulfur; and $R^{7e}$ represents halogen, the formula:

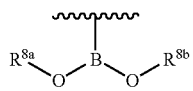

(wherein $R^{8a}$ and $R^{8b}$ each independently represent hydrogen or $C_{1-6}$ alkyl, or $R^{8a}$ and $R^{8b}$ may bond together to form 1,2-ethylene, 1,3-propylene or 2,3-dimethylbutan-2,3-diyl), or the formula:

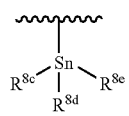

(wherein $R^{8c}$, $R^{8d}$ and $R^{8e}$ each independently represent $C_{1-6}$ alkyl)], a salt thereof or a hydrate of the foregoing;

<28> a Corticotropin-Releasing Factor (CRF) receptor antagonist comprising a compound according to <1>;

<29> a Corticotropin-Releasing Factor (CRF)-1 receptor or Corticotropin-Releasing Factor (CRF)-2 receptor antagonist comprising a compound according to <1>;

<30> a therapeutic or prophylactic agent for a disease associated with Corticotropin-Releasing Factor (CRF), comprising a compound according to <1>;

<31> a therapeutic or prophylactic agent for depression, depressive symptom, mania, anxiety, generalized anxiety disorder, panic disorder, phobias, obsessive-compulsive disorder, posttraumatic stress disorder, Tourette's syndrome, autism, affective disorder, dysthymia, bipolar disorder, cyclothymic personality or schizophrenia, comprising a compound according to <1>;

<32> a therapeutic or prophylactic agent for a depressive symptom which is major depression, single-episode depression, recurrent depression, depression-induced child abuse or postpartum depression, comprising a compound according to <1>;

<33> a therapeutic or prophylactic agent for peptic ulcer, irritable bowel syndrome, ulcerative colitis, Crohn's disease, diarrhea, constipation, postoperative ileus, stress-associated gastrointestinal disorders or nervous vomiting, comprising a compound according to <1>;

<34> a therapeutic or prophylactic agent for Alzheimer's disease, senile dementia of Alzheimer's type, neurodegenerative disease, multi-infarct dementia, senile dementia, anorexia nervosa, eating disorder, obesity, diabetes, alcohol dependence, pharmacophilia, drug withdrawal symptoms, alcohol withdrawal symptoms, sleep disorder, insomnia, migraine, stress-induced headache, muscle contraction induced headache, ischemic neuronal damage, excitotoxic neuronal damage, stroke, progressive supranuclear palsy, amyotrophic lateral sclerosis, multiple sclerosis, muscular spasm, chronic fatigue syndrome, psychosocial dwarfism, epilepsy, head trauma, spinal cord injury, cheirospasm, spasmodic torticollis, cervicobrachial syndrome, primary glaucoma, Meniere's syndrome, autonomic imbalance, alopecia, neurosis, hypertension, cardiovascular disorder, tachycardia, congestive heart failure, hyperventilation syndrome, bronchial asthma, apneusis, sudden infant death syndrome, inflammatory disorder, pain, allergosis, impotence, menopausal disorder, fertilization disorder, infertility, cancer, HIV infection-induced immune dysfunction, stress-induced immune dysfunction, hemorrhagic stress, Cushing's syndrome, thyroid function disorder, encephalomyelitis, acromegaly, incontinence or osteoporosis, comprising a compound according to <1>;

<35> the use of a compound according to <1> or a salt thereof for the manufacture of a Corticotropin-Releasing Factor (CRF) receptor antagonist;

<36> the use of a compound according to <1> or a salt thereof for the manufacture of a Corticotropin-Releasing Factor (CRF)-1 receptor antagonist or Corticotropin-Releasing Factor (CRF)-1 receptor antagonist;

<37> the use of a compound according to <1> or a salt thereof for the manufacture of a therapeutic or prophylactic agent for depression, depressive symptom, mania, anxiety, generalized anxiety disorder, panic disorder, phobia, obsessive-compulsive disorder, posttraumatic stress disorder, Tourette's syndrome, autism, affective disorder, dysthymia, bipolar disorder, cyclothymic personality, schizophrenia, peptic ulcer, irritable bowel syndrome, ulcerative colitis, Crohn's disease, diarrhea, constipation, postoperative ileus, stress-associated gastrointestinal disorders or nervous vomiting;

<38> a therapeutic or prophylactic method for a disease associated with Corticotropin-Releasing Factor (CRF) receptor, comprising single or multiple administration of a therapeutically effective dose of a compound according to <1> or a salt thereof to a patient with a disease associated with Corticotropin-Releasing Factor (CRF) receptor.

BEST MODE FOR CARRYING OUT THE INVENTION

The present invention will now be explained in greater detail.

Several of the structural formulas given for compounds throughout the present specification will represent a specific isomer for convenience, but the invention is not limited to such specific isomers and encompasses all isomers and isomer mixtures, including geometric isomers, asymmetric carbon-derived optical isomers, stereoisomers and tautomers, implied by the structures of the compounds, of which any isomer or mixture thereof may be used. The compounds of the invention therefore may include those having asymmetric carbons in their molecules and existing as optically active forms or racemic forms, and all such compounds are encompassed by the invention without restrictions. There are also no restrictions on any crystalline polymorphism of the compounds, and any crystal forms may be used alone or in mixtures, while the compounds of the invention also include anhydrides and hydrates. Metabolites of the compounds of the present invention, produced by degradation in the body, are also encompassed by the claims of the invention.

The symbols and terms used throughout the present specification will now be defined, with a more detailed description of the invention.

The term "CRF receptor antagonist" as used throughout the present specification refers to a substance capable of inactivating CRF receptors. Such substances also include those capable of attenuating or inhibiting the physiological activity of CRF.

As diseases included among "diseases associated with CRF" or "diseases associated with CRF receptors" according to the present specification there may be mentioned depression and depressive symptoms (major depression, single-episode depression, recurrent depression, depression-induced child abuse, postpartum depression, etc.), mania, anxiety, generalized anxiety disorder, panic disorder, phobias, obsessive-compulsive disorder, posttraumatic stress disorder, Tourette's syndrome, autism, affective disorder, dysthymia, bipolar disorder, cyclothymic personality, schizophrenia, peptic ulcer, irritable bowel syndrome, ulcerative colitis, Crohn's disease, diarrhea, constipation, postoperative ileus, stress-associated gastrointestinal disorders, nervous vomiting, Alzheimer's disease, senile dementia of Alzheimer's type, neurodegenerative disease, multi-infarct dementia, senile dementia, anorexia nervosa, eating disorder, obesity, diabetes, alcohol dependence, pharmacophilia, drug withdrawal symptoms, alcohol withdrawal symptoms, sleep disorder, insomnia, migraine, stress-induced headache, muscle contraction induced headache, ischemic neuronal damage, excitotoxic neuronal damage, stroke, progressive supranuclear palsy, amyotrophic lateral sclerosis, multiple sclerosis, muscular spasm, chronic fatigue syndrome, psychosocial dwarfism, epilepsy, head trauma, spinal cord injury, cheirospasm, spasmodic torticollis, cervicobrachial syndrome, primary glaucoma, Meniere's syndrome, autonomic imbalance, alopecia, neurosis, hypertension, cardiovascular disorder, tachycardia, congestive heart failure, hyperventilation syndrome, bronchial asthma, apneusis, sudden infant death syndrome, inflammatory disorder, pain, allergosis, impotence, menopausal disorder, fertilization disorder, infertility, cancer, HIV infection-related immune dysfunction, stress-induced immune dysfunction, hemorrhagic stress, Cushing's syndrome, thyroid function disorder, encephalomyelitis, acromegaly, incontinence, osteoporosis, and the like. The compounds of the invention are effective for treatment or prevention of the aforementioned diseases.

The term "neurodegenerative disease" as used throughout the present specification refers to either acute degenerative disease or chronic degenerative disease, and specifically it includes, for example, neuropathies such as subarachnoid hemorrhage, acute stage cerebrovascular disorder, etc. and Alzheimer's disease, Parkinson's disease, Huntington's chorea, amyotrophic lateral sclerosis, spinocerebellar degeneration, etc. The term "eating disorder" as used throughout the present specification refers to increased appetite, cibophobia and the like. The term "cardiovascular disorder" as used throughout the present specification refers to angina pectoris nervosa and the like. The term "inflammatory disorder" as used throughout the present specification refers to, for example, rheumatic arthritis, osteoarthritis, lumbago and the like, and the term "allergosis" refers to, for example, atopic dermatitis, eczema, hives, psoriasis and the like.

Throughout the present specification, "n-" signifies "normal", "sec-" signifies "secondary" and "tert-" and "t-" both signify "tertiary".

Halogen as used throughout the present specification refers to fluorine, chlorine, bromine, iodine and the like, with fluorine, chlorine or bromine being preferred.

The terms "$C_{1-6}$ alkyl" and "$C_{1-10}$ alkyl" used throughout the present specification refer respectively to a linear or branched alkyl group of 1 to 6 carbons and a linear or branched alkyl group of 1 to 10 carbons, and are preferably methyl, ethyl, n-propyl, iso-propyl, n-butyl, iso-butyl, sec-butyl, tert-butyl, n-pentyl, 1,1-dimethylpropyl, 1,2-dimethylpropyl, 2,2-dimethylpropyl, 1-ethylpropyl, 2-ethylpropyl, n-hexyl, 1-methyl-2-ethylpropyl, 1-ethyl-2-methylpropyl, 1,1,2-trimethylpropyl, 1-propylpropyl, 1-methylbutyl, 2-methylbutyl, 1,1-dimethylbutyl, 1,2-dimethylbutyl, 2,2-dimethylbutyl, 1,3-dimethylbutyl, 2,3-dimethylbutyl, 2-ethylbutyl, 2-methylpentyl, 3-methylpentyl, or the like, more preferably methyl, ethyl, n-propyl, iso-propyl or tert-butyl, and even more preferably methyl, ethyl or iso-propyl.

The terms "$C_{2-6}$ alkenyl" and "$C_{2-10}$ alkenyl" used throughout the present specification refer respectively to a linear or branched alkenyl group of 2 to 6 carbons and a linear or branched alkenyl group of 2 to 10 carbons, and preferred examples of such groups include vinyl, allyl, 1-propenyl, 2-propenyl, isopropenyl, 2-methyl-1-propenyl, 3-methyl-1-propenyl, 2-methyl-2-propenyl, 3-methyl-2-propenyl, 1-butenyl, 2-butenyl, 3-butenyl, 1-pentenyl, 1-hexenyl, 1,3-hexanedienyl and 1,6-hexanedienyl.

The terms "$C_{2-6}$ alkynyl" and "$C_{2-10}$ alkynyl" used throughout the present specification refer respectively to an alkynyl group of 2 to 6 carbons and an alkynyl group of 2 to 10 carbons, and preferred examples of such groups include ethynyl, 1-propynyl, 2-propynyl, 1-butynyl, 2-butynyl, 3-butynyl, 3-methyl-1-propynyl, 1-ethynyl-2propynyl, 2-methyl-3-propynyl, 1-pentynyl, 1-hexynyl, 1,3-hexanediynyl and 1,6-hexanediynyl.

The term "$C_{1-6}$ alkylene" used throughout the present specification refers to a divalent group derived by removing another hydrogen from any desired position of the aforementioned "$C_{1-6}$ alkyl", and as specific examples there may be mentioned methylene, ethylene, methylethylene, propylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene and hexamethylene, preferably methylene and 1,2-ethylene, and more preferably methylene.

The term "$C_{2-6}$ alkenylene" used through the present specification refers to a divalent group derived by removing another hydrogen from the aforementioned "$C_{2-6}$ alkenyl", and as specific examples there may be mentioned vinylene, propenylene, butenylene, pentenylene and hexenylene, preferably vinylene, propenylene, butenylene, pentenylene, even more preferably vinylene, propenylene and butenylene, and even more preferably 1,2-vinylene and 1,3-propenylene.

The term "$C_{2-6}$ alkynylene" used throughout the present specification refers to a divalent group derived by removing another hydrogen from the aforementioned "$C_{2-6}$ alkynyl", and as specific examples there may be mentioned ethynylene, propynylene, butynylene, pentynylene and hexynylene, preferably ethynylene, propynylene, butynylene and pentynylene, more preferably ethynylene, propynylene and butynylene, even more preferably ethynylene and propynylene, and most preferably ethynylene.

The term "$C_{3-8}$ cycloalkyl" used throughout the present specification refers to a cyclic aliphatic hydrocarbon group of 3 to 8 carbons, and as examples there may be mentioned cyclopropyl, cyclobutyl, cyclopentyl, cyclohexyl, cycloheptyl and cyclooctyl, preferably cyclopropyl, cyclobutyl and cyclopentyl, and more preferably cyclopropyl.

The term "$C_{5-8}$ cycloalkenyl" used throughout the present specification refers to a cycloalkenyl group composed of 5 to 8 carbons, and as examples there may be mentioned cyclopenten-3-yl, cyclohexen-1-yl and cyclohexen-3-yl.

The terms "$C_{1-6}$ alkoxy" and "$C_{1-10}$ alkoxy" used throughout the present specification refer respectively to an oxy group bonded with the aforementioned "$C_{1-6}$ alkyl" and an oxy group bonded with the aforementioned "$C_{1-10}$ alkyl", and as examples there may be mentioned methoxy, ethoxy, n-propoxy, iso-propoxy, sec-propoxy, n-butoxy, iso-butoxy, sec-butoxy, tert-butoxy, n-pentyloxy, iso-pentyloxy, sec-pentyloxy, n-hexoxy, iso-hexoxy, 1,1-dimethylpropyloxy, 1,2-dimethylpropyloxy, 2,2-dimethylpropyloxy, 2-ethylpropoxy, 1-methyl-2-ethylpropoxy, 1-ethyl-2-methylpropoxy, 1,1,2-trimethylpropoxy, 1,1,2-trimethylpropoxy, 1,1-dimethylbutoxy, 1,2-dimethylbutoxy, 2,2-dimethylbutoxy, 2,3-dimethylbutyloxy, 1,3-dimethylbutyloxy, 2-ethylbutoxy, 1,3-dimethylbutoxy, 2-methylpentoxy, 3-methylpentoxy and hexyloxy, preferably methoxy, ethoxy, n-propoxy, iso-propoxy, sec-propoxy, n-butoxy, iso-butoxy, sec-butoxy and tert-butoxy, and more preferably methoxy.

The terms "$C_{1-6}$ alkylthio" and "$C_{1-10}$ alkylthio" used throughout the present specification refer respectively to a thio group bonded with the aforementioned "$C_{1-6}$ alkyl" and a thio group bonded with the aforementioned "$C_{1-10}$ alkyl", and as examples there may be mentioned methylthio, ethylthio, n-propylthio, iso-propylthio, n-butylthio, iso-butylthio, sec-butylthio, tert-butylthio, n-pentylthio, 1,1-dimethylpropylthio, 1,2-dimethylpropylthio, 2,2-dimethylpropylthio, 1-ethylpropylthio, 2-ethylpropylthio, n-hexyl, 1-methyl-2-ethylpropylthio, 1-ethyl-2-methylpropylthio, 1,1,2-trimethylpropylthio, 1-propylpropylthio, 1-methylbutylthio, 2-methylbutylthio, 1,1-dimethylbutylthio, 1,2-dimethylbutylthio, 2,2-dimethylbutylthio, 1,3-dimethylbutylthio, 2,3-dimethylbutylthio, 2-ethylbutylthio, 2-methylpentylthio and 3-methylpentylthio.

The term "$C_{1-6}$ alkylsulfinyl" used throughout the present specification refers to a sulfinyl group bonded with the aforementioned "$C_{1-6}$ alkyl", and as examples there may be mentioned methylsulfinyl, ethylsulfinyl, n-propylsulfinyl and iso-propylsulfinyl.

The term "$C_{1-6}$ alkylsulfonyl" used throughout the present specification refers to a sulfonyl group bonded with the aforementioned "$C_{1-6}$ alkyl", and as examples there may be mentioned methylsulfonyl, ethylsulfonyl, n-propylsulfonyl and iso-propylsulfonyl.

The term "$C_{6-14}$ aryl" used throughout the present specification refers to an aromatic hydrocarbon ring group of 6 to 14 carbons, which may be a monocyclic, bicyclic or tricyclic fused ring. As preferred examples of such groups there may be mentioned phenyl, indenyl, 1-naphthyl, 2-naphthyl, azulenyl, heptalenyl, biphenyl, indacenyl, acenaphthyl, fluorenyl, phenalenyl, phenanthrenyl, anthracenyl, cyclopentacyclooctenyl and benzocyclooctenyl, preferably phenyl, 1-naphthyl or 2-naphthyl, and more preferably phenyl.

The term "5- to 14-membered heteroaryl group" used throughout the present specification refers to a 5- to 14-membered aromatic heterocycle group, which is monocyclic, bicyclic or tricyclic group containing at least one hetero atom selected from N, O and S. As specific examples of such groups there may be mentioned nitrogen-containing heteroaryl groups such as pyrrolyl, pyridyl, pyridazinyl, pyrimidinyl, pyrazinyl, triazolyl, tetrazolyl, benzotriazolyl, pyrazolyl, imidazolyl, benzimidazolyl, indolyl, isoindolyl, indolidinyl, purinyl, indazolyl, quinolyl, isoquinolyl, quinolidyl, phthalazyl, naphthylidinyl, quinoxalyl, quinazolinyl, cinnolinyl, pteridinyl, imidazotriazinyl, pyrazinopyridazinyl, acridinyl, phenanthridinyl, carbazolyl, carbazolinyl, pyrimidinyl, phenanthrolinyl, phenazinyl, imidazopyridinyl, imidazopyrimidinyl, pyrazolopyridinyl, and pyrazolopyridinyl; sulfur-containing heteroaryl groups such as thienyl and benzothienyl; oxygen-containing heteroaryl groups such as furyl, pyranyl, cyclopentapyranyl, benzofuryl and isobenzofuryl; and heteroaryl groups containing two or more different hetero atoms, such as thiazolyl, isothiazolyl, benzothiazolyl, benzothiadiazolyl, phenothiazinyl, isoxazolyl, furazanyl, phenoxazinyl, oxazolyl, isoxazoyl, benzoxazolyl, oxadiazolyl, pyrazolooxazolyl, imidazothiazolyl, thienofuranyl, furopyrrolyl, pyridoxazinyl and benzo[1,2,5]thiadiazolyl.

The "5- to 14-membered heteroaryl group" is preferably pyrrolyl, pyridyl, pyridazinyl, pyrimidinyl, pyrazinyl, triazolyl, tetrazolyl, pyrazolyl, imidazolyl, indolyl, thienyl, benzothienyl, furyl, benzofuranyl, thiazolyl, isothiazolyl, oxazolyl, isoxazolyl or oxadiazolyl, and more preferably pyridyl, thienyl, furyl, thiazolyl or oxazolyl.

The term "5- to 6-membered heteroaryl group" used throughout the present specification refers to a 5- to 6-membered heteroaryl group among the aforementioned 5- to 14-membered heteroaryl group, and as specific examples there may be mentioned pyrrolyl, pyridyl, pyridazinyl, pyrimidinyl, pyrazinyl, triazolyl, tetrazolyl, pyrazolyl, imidazolyl, thienyl, furyl, thiazolyl, isothiazolyl, oxazolyl, isoxazolyl and oxadiazolyl, and more preferably pyridyl, thienyl, furyl, thiazolyl or oxazolyl.

The term "9- to 11-membered benzene fused ring group" used throughout the present specification refers to a bicyclic group comprising a non-aromatic ring fused with a benzene ring, and having 9 to 11 atoms composing the ring of the ring group. The "9- to 11-membered benzene fused ring" of a "9- to 11-membered benzene fused ring group" is a ring represented by the following formula:

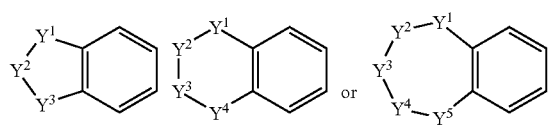

(wherein $Y^1$, $Y^2$, $Y^3$, $Y^4$ and $Y^5$ represent carbonyl, oxygen, sulfur, methylene or the formula —$NR^{31}$— (wherein $R^{31}$ represents hydrogen or $C_{1-6}$ alkyl), and such a "9- to 11-membered benzene fused ring" is preferably a ring represented by the formula:

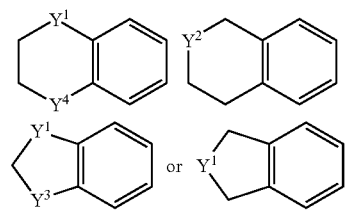

(wherein $Y^1$, $Y^2$, $Y^3$ and $Y^4$ have the same definitions as above), more preferably a ring represented by the formulas:

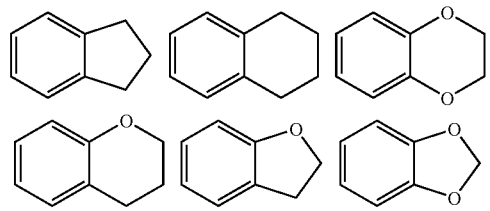

-continued

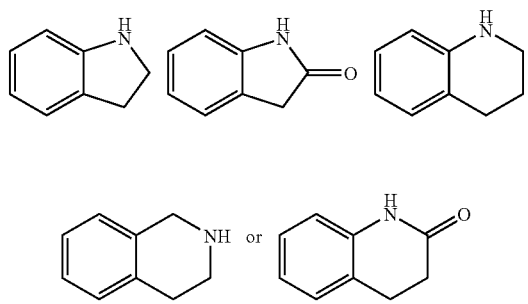

and even more preferably a ring represented by the formula:

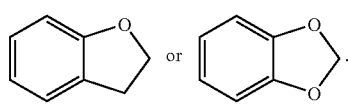

The term "9- to 11-membered benzene fused ring group" refers to a monovalent group derived by removing a hydrogen atom from any desired position of the "9- to 11-membered benzene fused ring".

The term "8- to 11-membered heteroaryl fused ring group" used throughout the present specification refers to a bicyclic group comprising a non-aromatic ring fused with "5- to 6-membered aromatic heterocycle" such as pyridine, thiophene or furan, and having 8 to 11 atoms composing the ring of the ring group.

The term "monocyclic 4- to 8-membered non-aromatic heterocyclic group" used throughout the present specification refers to:

[1] a monocyclic non-aromatic cyclic group,

[2] having 4 to 8 atoms in the ring of the cyclic group,

[3] containing 1 or 2 hetero atoms among the atoms of the ring of the cyclic group,

[4] optionally including 1 or 2 double bonds in the ring, and

[5] optionally including 1 to 3 carbonyl in the ring.

As specific examples of the "monocyclic 4- to 8-membered non-aromatic heterocycle" of a "monocyclic 4- to 8-membered non-aromatic heterocyclic group" there may be mentioned pyrrolidine, piperidine, azepane, pyridone, pyrazinone, tetrahydrofuran, tetrahydrothiophene, tetrahydropyran, morpholine, thiomorpholine, piperazine, thiazolidine, dioxane, imidazoline, thiazoline, azetidine, oxetane, thietane, dioxolane, piperidin-4-one, piperidin-3-one, piperidin-2-one, pyrrolidin-2-one, tetrahydrofuran-2-one and 3,4-dihydro-2H-pyran.

A "monocyclic 4- to 8-membered non-aromatic heterocyclic group" is a monovalent group derived by removing a hydrogen atom from any desired position of a "monocyclic 4- to 8-membered non-aromatic heterocycle".

The term "bicyclic 7- to 12-membered hydrocarbon ring" used throughout the present specification refers to a bicyclic hydrocarbon ring having 7 to 12 carbon atoms in the ring.

Specifically, it refers to

[1] a hydrocarbon ring represented by the formula:

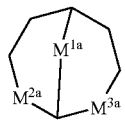

(wherein $M^{1a}$, $M^{2a}$ and $M^{3a}$ each independently represent the formula $-(CH_2)_{m1}-$ (wherein m1 is an integer of 0-2), with the proviso that $M^{1a}$, $M^{2a}$ and $M^{3a}$ are not all $-(CH_2)_0-$),

[2] a hydrocarbon ring represented by the formula:

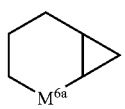

(wherein $M^{6a}$ represents the formula $-(CH_2)_{m3}-$ (wherein m3 is an integer of 0-3)), or

[3] a hydrocarbon ring represented by the formula:

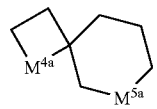

(wherein $M^{4a}$ and $M^{5a}$ each independently represent the formula $-(CH_2)_{m2}-$ (wherein m2 is an integer of 0-3)).

As specific examples of the "bicyclic 7- to 12-membered hydrocarbon ring" there may be mentioned bicyclo[3.1.0]hexane, bicyclo[4.1.0]heptane, spiro[2,4]heptane, spiro[2,5]octane, bicyclo[4.4.0]decane(decahydro-naphthalene), octahydro-indene(bicyclo[4.3.0]nonane), bicyclo[3.3.1]nonane, bicyclo[3.2.1]octane, spiro[4,5]decane, spiro[3,5]nonane, norbornane, adamantane, bicyclo[1.1.0]butane, spiro[2,2]pentane, bicyclo[2.1.0]pentane, bicyclo[3.1.0]hexane, bicyclo[4.1.0]heptane, nortricyclane, quadricyclane, bicyclo[3.3.0]octane, bicyclo[2.2.2]octane, perhydroquinacene, bicyclo[3.3.3]undecane and perhydroanthracene.

The "bicyclic 7- to 12-membered hydrocarbon cycle" is preferably bicyclo[4.4.0]decane(decahydro-naphthalene), octahydro-indene(bicyclo[4.3.0]nonane), bicyclo[3.3.1]nonane, bicyclo[3.2.1]octane, spiro[5,4]decane or spiro[3,5]nonane, and more preferably bicyclo[4.4.0]decane(decahydro-naphthalene) or octahydro-indene(bicyclo[4.3.0]nonane).

The term "bicyclic 7- to 12-membered hydrocarbon ring group" used throughout the present specification refers to a monovalent group derived by removing a hydrogen atom from any desired position of the aforementioned "bicyclic 7- to 12-membered hydrocarbon cycle".

The term "bicyclic 7- to 12-membered non-aromatic heterocyclic group" used throughout the present specification refers to

[1] a bicyclic non-aromatic cyclic group,

[2] having 7 to 12 atoms in the ring of the cyclic group,

[3] containing 1 to 3 hetero atoms among the atoms of the ring of the cyclic group,

[4] optionally including 1 to 3 double bonds in the ring, and

[5] optionally including 1 to 3 carbonyl in the ring.

That is, a "bicyclic 7- to 12-membered non-aromatic heterocyclic group" is a monovalent derived from the aforementioned "bicyclic 7- to 12-membered hydrocarbon cycle" by [1] replacing any 1 to 3 methine or methylene in the ring with oxygen, sulfur, nitrogen or —NH—, and then [2] removing a hydrogen atom at any desired position of the ring.

The term "4- to 14-membered heterocyclic group" used throughout the present specification has 4 to 14 members and refers to

[1] a monocyclic, bicyclic or tricyclic heterocyclic group,

[2] having 4 to 14 atoms in the ring of the cyclic group,

[3] containing 1 to 3 hetero atoms among the atoms of the ring of the cyclic group,

[4] optionally including 1 to 3 double bonds in the ring, and

[5] optionally including 1 to 3 carbonyl in the ring.

Specifically, for example, it refers the aforementioned "monocyclic 4- to 8-membered non-aromatic heterocyclic group" or "bicyclic 7- to 12-membered non-aromatic heterocyclic group".

The "14- to 14-membered heterocyclic group" is preferably a "4- to 7-membered heterocyclic group" as defined below, and more preferably there may be mentioned tetrahydrofuranyl, tetrahydrothiophenyl, tetrahydropyranyl, dioxoranyl, pyrrolidin-2-onyl, dihydrofuran-2-onyl and piperidinyl.

The term "4- to 7-membered heterocyclic group" used throughout the present specification refers to 4- to 7-membered heterocyclic groups among the groups referred by "4- to 14-membered heterocyclic group" as defined above. Specifically, it refers to a monovalent group derived by removing a hydrogen atom from any desired position of a ring represented by, for example, the formula:

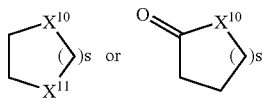

(wherein $X^{10}$ represents sulfur, oxygen or —$NX^{12}$ (wherein $X^{12}$ represents hydrogen or $C_{1-6}$ alkyl), $X^{11}$ represents methylene, sulfur, oxygen or —$NX^{13}$ (wherein $X^{13}$ represents hydrogen or $C_{1-6}$ alkyl), and s represents an integer of 1-3), and preferably there may be mentioned tetrahydrofuranyl, tetrahydrothiophenyl, tetrahydropyranyl, dioxoranyl, pyrrolidin-2-onyl, dihydrofuran-2-onyl and piperidinyl. The term "tetrahydrofuranyl" used throughout the present specification refers to a monovalent group derived by removing a hydrogen atom from any desired position of a tetrahydrofuran ring, and specifically there may be mentioned tetrahydrofuran-2-yl and tetrahydrofuran-3-yl.

The term "tetrahydrothiophenyl" used throughout the present specification refers to a monovalent group derived by removing a hydrogen atom from any desired position of a tetrahydrothiophene ring, and specifically there may be mentioned tetrahydrothiophen-2-yl and tetrahydrothiophen-3-yl.

The term "tetrahydropyranyl" used throughout the present specification refers to a monovalent group derived by removing a hydrogen atom from any desired position of a tetrahydropyran ring, and specifically there may be mentioned tetrahydropyran-2-yl, tetrahydropyran-3-yl and tetrahydropyran-4-yl.

The term "dioxolanyl" used throughout the present specification refers to a monovalent group derived by removing a hydrogen atom from any desired position of a dioxolane ring, and specifically there may be mentioned dioxolan-2-yl and dioxolan-4-yl.

The term "pyrrolidin-2-onyl" used throughout the present specification refers to a monovalent group derived by removing a hydrogen atom from any desired position of a pyrrolidin-2-one ring, and specifically there may be mentioned pyrrolidin-2-on-1-yl, pyrrolidin-2-on-3-yl, pyrrolidin-2-on-4-yl and pyrrolidin-2-on-5-yl.

The term "furanyl" used throughout the present specification refers to a monovalent group derived by removing a hydrogen atom from any desired position of a furan ring, and specifically there may be mentioned 2-furanyl and 3-furanyl.

The term "thienyl" used throughout the present specification refers to a monovalent group derived by removing a hydrogen atom from any desired position of a thiophene ring, and specifically there may be mentioned 2-thienyl and 3-thienyl.

The term "pyrrolidinyl" used throughout the present specification refers to a monovalent group derived by removing a hydrogen atom from any desired position of a pyrrolidine ring, and specifically there may be mentioned 1-pyrrolidinyl, 2-pyrrolidinyl and 3-pyrrolidinyl.

The term "piperidyl" used throughout the present specification refers to a monovalent group derived by removing a hydrogen atom from any desired position of a piperidine ring, and specifically there may be mentioned 1-pyrrolidinyl, 2-pyrrolidinyl and 3-pyrrolidinyl.

The term "oxazolyl" used throughout the present specification refers to a monovalent group derived by removing a hydrogen atom from any desired position of an oxazole ring, and specifically there may be mentioned 2-oxazolyl, 4-oxazolyl and 5-oxazolyl.

The term "isoxazolyl" used throughout the present specification refers to a monovalent group derived by removing a hydrogen atom from any desired position of an isoxazole ring, and specifically there may be mentioned 3-isoxazolyl, 4-isoxazolyl and 5-isoxazolyl.

The term "thiazolyl" used throughout the present specification refers to a monovalent group derived by removing a hydrogen atom from any desired position of a thiazole ring, and specifically there may be mentioned 2-thiazolyl, 4-thiazolyl and 5-thiazolyl.

The term "pyrrolyl" used throughout the present specification refers to a monovalent group derived by removing a hydrogen atom from any desired position of a pyrrole ring, and specifically there may be mentioned 1-pyrrolyl, 2-pyrrolyl and 3-pyrrolyl.

The term "pyrazolyl" used throughout the present specification refers to a monovalent group derived by removing a hydrogen atom from any desired position of a pyrazole ring, and specifically there may be mentioned 1-pyrazolyl, 3-pyrazolyl, 4-pyrazolyl and 5-pyrazolyl.

The term "morpholinyl" used throughout the present specification refers to a monovalent group derived by removing a hydrogen atom from any desired position of a morpholine ring, and specifically there may be mentioned 4-morpholinyl, 2-morpholinyl and 3-morpholinyl.

The term "pyridyl" used throughout the present specification refers to a monovalent group derived by removing a hydrogen atom from any desired position of a pyridine ring, and specifically there may be mentioned 2-pyridyl, 3-pyridyl and 4-pyridyl.

The term "dioxanyl" used throughout the present specification refers to a monovalent group derived by removing a hydrogen atom from any desired position of a 1,3-dioxane ring or 1,4-dioxane ring, and specifically there may be mentioned 1,3-dioxan-2-yl, 1,3-dioxan-4-yl, 1,3-dioxan-5-yl and 1,4-dioxan-2-yl.

The term "dihydropyranyl" used throughout the present specification refers to a monovalent group derived by removing a hydrogen atom from any desired position of a 3,4-dihydro-2H-pyran ring or 3,6-dihydro-2H-pyran ring, and specifically there may be mentioned 3,4-dihydro-2H-pyran-2-yl, 3,4-dihydro-2H-pyran-3-yl, 3,4-dihydro-2H-pyran-4-yl, 3,4-dihydro-2H-pyran-5-yl, 3,4-dihydro-2H-pyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl and 3,6-dihydro-2H-pyran-6-yl.

The term "dihydrofuran-2-onyl" used throughout the present specification refers to a monovalent group derived by removing a hydrogen atom from any desired position of a dihydrofuran-2-one ring, and specifically there may be mentioned dihydrofuran-2-on-3-yl, dihydrofuran-2-on-4-yl and dihydrofuran-2-on-5-yl.

A compound of general formula (I) above wherein "$R^2$ and $R^3$ or $R^3$ and $R^4$ may bond together to form a 5- to 7-membered ring optionally containing 1 to 4 hetero atoms in the ring and optionally containing carbonyl in the ring" is a compound in which the pyrazolo[1,5-a]pyridine in general formula (I) is fused with $M^1$ at the bonding positions of $R^2$ and $R^3$, as represented by the formula:

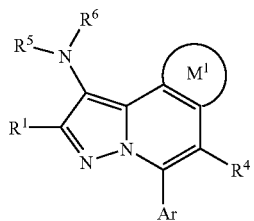

(wherein $R^1$, $R^4$, $R^5$, $R^6$ and Ar have the same definitions as above, ring $M^1$ is a 5- to 7-membered ring optionally having 1 to 4 hetero atoms and optionally having carbonyl in the ring, and ring $M^1$ also optionally has a substituent selected from Substituent Group A above), or a compound in which the pyrazolo[1,5-a]pyridine in general formula (I) is fused with $M^1$ at the bonding positions of $R^4$ and $R^3$, as represented by the formula:

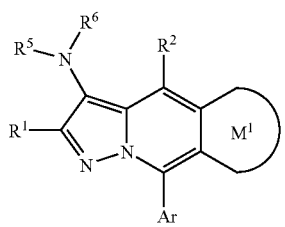

(wherein $R^1$, $R^2$, $R^5$, $R^6$ and Ar have the same definitions as above, ring $M^1$ is a 5- to 7-membered ring optionally having 1 to 4 hetero atoms and optionally having a carbonyl group in the ring, and ring $M^1$ also optionally has a substituent selected from Substituent Group A above).

As rings for "ring $M^1$" there may be mentioned as preferable pyridine optionally having a substituent selected from Substituent Group A, benzene optionally having a substituent selected from Substituent Group A, thiophene optionally having a substituent selected from Substituent Group A, cyclohexane optionally having a substituent selected from Substituent Group A, pyridine optionally having a substituent selected from Substituent Group A and piperidin-2-one optionally having a substituent selected from Substituent Group A.

A compound of general formula (I) above wherein "$R^5$ and $R^6$ may bond together to form a 5- to 10-membered ring optionally containing 1 to 4 hetero atoms in the ring and optionally containing carbonyl in the ring" is a compound wherein $R^5$ and $R^6$ in formula (I) bond together to form ring $M^2$, as represented by the formula:

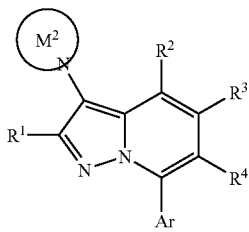

(wherein $R^1$, $R^2$, $R^3$, $R^4$ and Ar have the same definitions as above, ring $M^2$ is a 5- to 10-membered ring optionally having 1 to 4 hetero atoms and optionally having carbonyl in the ring, and ring $M^2$ also optionally has a substituent selected from Substituent Group A above.

As rings for "ring $M^2$" there may be mentioned as preferable "5- to 14-membered heteroaryl group" optionally having a substituent selected from Substituent Group A, "4- to 14-membered heterocyclic group" optionally having a substituent selected from Substituent Group A, "9- to 11-membered benzene fused ring group" optionally having a substituent selected from Substituent Group A, and "8- to 11-membered heteroaryl fused ring group" optionally having a substituent selected from Substituent Group A.

A compound of general formula (I) above wherein "$R^6$ and $R^2$ may bond together to form a 6- to 7-membered ring optionally containing 1 or 2 hetero atoms in the ring and optionally containing carbonyl in the ring" is a compound wherein $R^6$ and $R^2$ bond together as $M^3$ to form a ring, as represented by the formula:

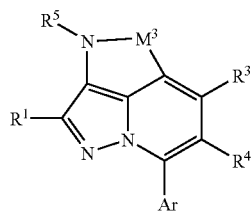

(wherein $R^1$, $R^3$, $R^4$, $R^5$ and Ar have the same definitions as above, and $M^3$ represents optionally substituted 1,2-ethylene, optionally substituted 1,3-propylene, optionally substituted 1,2-vinylene or optionally substituted amide.

The term "salt" used throughout the present specification is not particularly restricted so long as it is a salt formed with a compound of the present invention and is pharmacologically acceptable, and as preferred salts there may be mentioned hydrogen halide acid salt (for example, hydrofluoride, hydrochloride, hydrobromide and hydroiodide), inorganic acid salt (for example, sulfate, nitrate, perchlorate, phosphate, carbonate and bicarbonate), organic carboxylate (for example, acetate, trifluoroacetate, oxalate, maleate, tartarate, fumarate and citrate), organic sulfonate (for example, methanesulfonate, trifluoromethanesulfonate, ethanesulfonate, benzenesulfonate, toluenesulfonate and camphorsulfonate), amino acid salt (for example, aspartate and glutamate), quaternary amine salt, alkali metal salt (for example, sodium salt and potassium salt) or alkaline earth metal salt (for example, magnesium salt and calcium salt), and more preferred as "pharmacologically acceptable salt" are hydrochloride, oxalate, trifluoroacetate and the like.

Representative production schemes for compounds represented by formula (I) above according to the invention will now be presented. In the following production schemes, $R^1$, $R^2$, $R^3$, $R^4$, $R^5$, $R^6$, $R^{8a}$, $R^{8b}$, $R^{8c}$, $R^{8d}$ and Ar have the same respective definitions given above, X represents halogen (for example, fluorine, chlorine, bromine or iodine), and $X^{BS}$ represents boron substituted with $OR^{8a}$ and $OR^{8b}$ or tin substituted with $R^{8c}$, $R^{8d}$ and $R^{8e}$. Y represents $NR^y$, O, $S(O)_n$, and A represents NO or $NO_2$. A group represented by $Prot^N$ is an amino protecting group, and a group represented by $Prot^o$ is a hydroxyl protecting group. $A^X$ represents Ar or X [where Ar and X have the same respective definitions as given above], an Ar ring has the same definition for Ar given above, a Het ring represents an optionally substituted 5- to 14-membered heteroaryl or 9- to 11-membered benzene fused ring group, and $R^{1c}$ and $R^{1d}$ each represent optionally substituted $C_{1-6}$ alkyl, $C_{2-6}$ alkenyl, $C_{2-6}$ alkynyl, $C_{3-8}$ cycloalkyl or the like. $R^{ea}$ represents optionally substituted $C_{1-6}$ alkyl or the like, and Lev represents a leaving group such as halogen or trifluoromethanesulfonyl. $R^{ar}$ and $R^{het}$ each represent cyano, $C_{1-6}$ alkyl, $C_{2-6}$ alkenyl, $C_{2-6}$ alkynyl, halogenated $C_{1-6}$ alkyl, $C_{1-6}$ alkoxy, halogenated $C_{1-6}$ alkoxy, $C_{2-6}$ alkenyloxy, $C_{2-6}$ alkynyloxy, or the like. $R^{rr}$ represents cyano, $C_{1-6}$ alkoxy, optionally substituted aryl or optionally substituted 5- to 14-membered heteroaryl, and $R^{X1}$ represents $C_{1-6}$ alkyl, $C_{2-6}$ alkenyl, $C_{2-6}$ alkynyl, halogenated $C_{1-6}$ alkyl, benzyl, a substituent serving as a protective group for a Y atom such as Boc, or the like. $R^y$ and $R^{6o}$ each represent a substituent selected from Substituent Group A, n represents an integer of 0-2 and m represents an integer of 0-6. The term "room temperature" used below refers to a range of 0-40° C.

Production Scheme 1

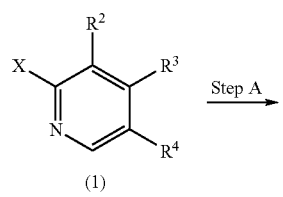

(1)

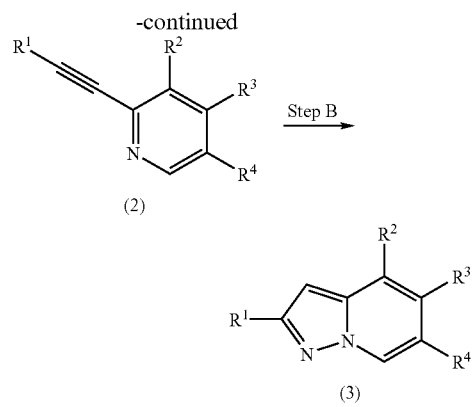

Step A: A halogenated compound (1) may be reacted in the presence of a catalyst such as a palladium catalyst or copper (I)iodide, in the presence of an acetylene derivative and a base and in an inert solvent at 0-250° C., to obtain an acetylene derivative (2). The solvent used will differ depending on the starting material, reagent, etc. and is not particularly restricted so long as it does not inhibit the reaction and dissolves the starting material to some extent, but preferably there may be mentioned benzene, toluene, xylene, anisole, N,N-dimethylformamide, 1,2-dimethoxyethane, tetrahydrofuran, dioxane, n-butanol, ethanol, methanol, 1-methyl-2-pyrrolidinone, water or mixtures thereof. The base used will differ depending on the starting material, solvent, etc. and is not particularly restricted so long as it does not inhibit the reaction, and as preferred bases there may be mentioned potassium carbonate, sodium carbonate, cesium fluoride, potassium fluoride, sodium hydrogencarbonate, triethylamine and diethylamine. These bases may also be used as solvents. When a palladium or nickel metal complex is used, its use will also differ depending on the starting material, solvent, etc. and is not particularly restricted so long as it does not inhibit the reaction, but $Pd(PPh_3)_4$, $Pd(OAc)_2/PPh_3$, $PdCl_2$, $PdCl_2(dppf)$, $Ni(dpp)_2Cl_2$ and the like are preferred.

Step B: The acetylene compound (2) may be treated with an N-amination agent (for example, hydroxylamine-O-sulfonic acid or O-mesitylenesulfonylhydroxylamine) in a solvent (for example, ethyl acetate, tetrahydrofuran, diethyl ether, dichloromethane, 1,2-dimethoxyethane, water, or the like) at a temperature of between −50° C. and room temperature to obtain an N-aminopyridinium salt, and this may be reacted in the presence of a base at a temperature of between 0° C. and 250° C. to obtain a closed ring compound (3). The solvent used will differ depending on the starting material, reagent, etc. and is not particularly restricted so long as it does not inhibit the reaction and dissolves the starting material to some extent, but preferably there may be mentioned benzene, toluene, xylene, anisole, N,N-dimethylformamide, 1,2-dimethoxyethane, tetrahydrofuran, dioxane, n-butanol, ethanol, methanol and 1-methyl-2-pyrrolidinone. The base used will differ depending on the starting material, solvent, etc. and is not particularly restricted so long as it does not inhibit the reaction, but as preferred bases there may be mentioned potassium carbonate, sodium carbonate, cesium fluoride, potassium fluoride, sodium hydrogencarbonate, triethylamine, sodium methoxide, sodium ethoxide, sodium tert-butoxide and potassium tert-butoxide.

Production Scheme 2

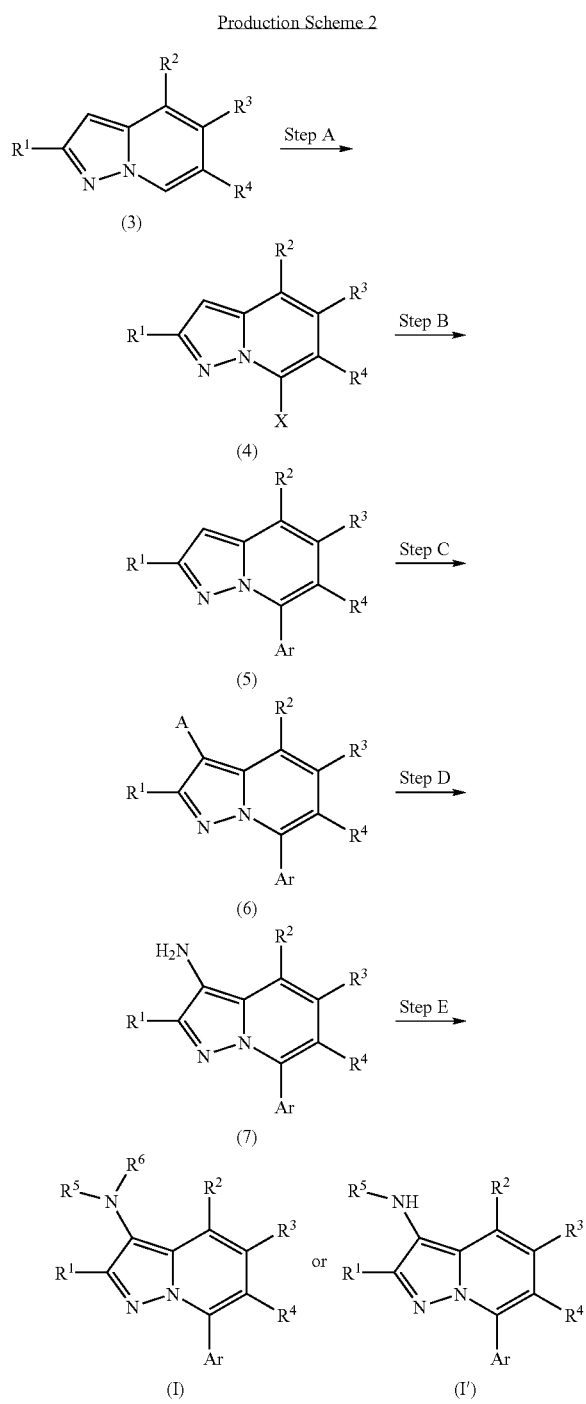

Step A: The pyrazolo[1,5-a]pyridine derivative (3) obtained in Production Scheme 1 may be treated with an alkyllithium reagent (for example, n-butyllithium, sec-butyllithium or tert-butyllithium) in an inert solvent at a temperature of between −78° C. and room temperature and then reacted with a halogenating agent to obtain a 7-halogenated compound (4). The halogenating agent used will differ depending on the starting material, solvent, etc. and is not particularly restricted so long as it does not inhibit the reaction, but preferably there may be mentioned bromine, iodine, N-chlorosuccinimide, N-bromosuccinimide, N-iodosuccinimide, hexachloroethane, 1,2-dibromoethane, 1,2-dibromo-1,1,2,2-tetrachloroethane and 1,2-diiodoethane. The solvent used will differ depending on the starting material, reagents, etc. and is not particularly restricted so long as it does not inhibit the reaction and dissolves the starting material to some extent, but preferably there may be mentioned hexane, pentane, tetrahydrofuran and diethyl ether.

Step B: The halogenated compound (4) may be reacted with a heteroaryl-boric acid or aryl-boric acid compound or an aryl-metal compound (for example, a heteroaryl-tin compound or aryl-tin compound) and a palladium or nickel complex, at a temperature of between 0° C. and 250° C., to obtain an aryl- or heteroaryl-substituted derivative (5). The solvent used will differ depending on the starting material, reagents, etc. and is not particularly restricted so long as it does not inhibit the reaction and dissolves the starting material to some extent, but preferably there may be mentioned benzene, toluene, xylene, mesitylene, anisole, N,N-dimethylformamide, 1,2-dimethoxyethane, tetrahydrofuran, 1,4-dioxane, n-butanol, ethanol, methanol, 1-methyl-2-pyrrolidinone, water and mixtures thereof. The base used will differ depending on the starting material, solvent, etc. and is not particularly restricted so long as it does not inhibit the reaction, but as preferred bases there may be mentioned potassium carbonate, sodium carbonate, barium hydroxide, cesium fluoride, potassium fluoride, sodium hydrogencarbonate and triethylamine. When a palladium or nickel complex is used, its use will also differ depending on the starting material, solvent, etc. and is not particularly restricted so long as it does not inhibit the reaction, but Pd(PPh$_3$)$_4$, Pd(OAc)$_2$/PPh$_3$, PdCl$_2$, PdCl$_2$(dppf), Ni(dpp)$_2$Cl$_2$ and the like are preferred.

Step C: The pyrazolo[1,5-a]pyridine derivative (5) may be reacted with a nitrating agent either in a solvent or without a solvent, to obtain a 3-nitro-pyrazolo[1,5-a]pyridine derivative (6). The solvent, if used, will differ depending on the starting material, reagent, etc. and is not particularly restricted so long as it does not inhibit the reaction and dissolves the starting material to some extent, but preferably there may be mentioned acetic anhydride, acetic acid, sulfuric acid, trifluoroacetic anhydride, trifluoroacetic acid, acetonitrile, 1,2-dimethoxyethane and tetrahydrofuran. The nitrating agent used will differ depending on the starting material, solvent, etc. and is not particularly restricted so long as it does not inhibit the reaction, but preferably there may be mentioned copper nitrate trihydrate, nitric acid, fuming nitric acid, sodium nitrate, BF$_4$NO$_2$, NH$_4$$^+$NO$_3$$^-$, and the like. The reaction temperature will normally be from −50° C. to 200° C.

Alternatively, the pyrazolo[1,5-a]pyridine derivative (5) may be reacted with a nitrosating agent to obtain a 3-nitroso-pyrazolo[1,5-a]pyridine derivative (6). This reaction may also be conducted either without a solvent or with a solvent, in which case the solvent will differ depending on the starting material, reagent, etc. and is not particularly restricted so long as it does not inhibit the reaction and dissolves the starting material to some extent, but preferably there may be mentioned solvents such as acetic anhydride, acetic acid, hydrochloric acid, sulfuric acid, trifluoroacetic anhydride, trifluoroacetic acid, acetonitrile, 1,2-dimethoxyethane and the like, or their mixtures with water or ethanol. The nitrosating agent used will differ depending on the starting material, solvent, etc. and is not particularly restricted so long as it does not inhibit the reaction, but preferably there may be mentioned sodium nitrite, BF$_4$NO and the like. The reaction temperature will normally be from −20° C. to 200° C.

Step D: The nitro derivative or nitroso derivative (6) may be reacted with a metal (powder) either in the presence or in the absence of an acid and either in a solvent or without a solvent, to obtain a 3-aminopyrazolo[1,5-a]pyridine derivative (7). The reaction temperature will normally be from −10° C. to 150° C. The acid, if used, will differ depending on the starting material, solvent, etc. and is not particularly restricted so long as it does not inhibit the reaction, but preferably there may be mentioned acetic acid, hydrochloric acid, sulfuric acid and the like. The solvent, if used, will differ depending on the starting material, reagent, etc. and is not particularly restricted so long as it does not inhibit the reaction and dissolves the starting material to some extent, but preferably there may be mentioned methanol, ethanol, n-butanol, water and the like, either alone or mixture thereof. The metal (powder) used may be Zn, Fe, $SnCl_2$, $NiCl_2$ or the like.

As an alternative method, the nitro or nitroso derivative (6) may be subjected to hydrogenation reaction under a hydrogen atmosphere to obtain a 3-amino-pyrazolo[1,5-a]pyridine derivative (7). The hydrogen pressure will normally be from 1 to 100 atmospheres, and the reaction temperature from 0-200° C. The reaction may be conducted either without a solvent or with a solvent, in which case the solvent will differ depending on the starting material, reagent, etc. and is not particularly restricted so long as it does not inhibit the reaction and dissolves the starting material to some extent, but preferably there may be mentioned methanol, ethanol, propanol, butanol, tetrahydrofuran, 1,4-dioxane, ethyl acetate, acetone, N,N-dimethylformamide and the like. The reaction may be conducted either in the presence or in the absence of an acid, and using a metal catalyst. The acid and metal catalyst used will differ depending on the starting material, solvent, etc. and is not particularly restricted so long as it does not inhibit the reaction, but as preferred acids there may be mentioned acetic acid and hydrochloric acid, while as preferred metal catalysts there may be mentioned Pd—C, $PtO_2$, Pt—C, Raney-Ni and the like. Also, ammonium formate or the like may be heated in a solvent such as methanol to generate hydrogen in the system during the reaction to obtain a 3-aminopyrazolo[1,5-a]pyridine derivative (7).

Step E: The 3-aminopyrazolo[1,5-a]pyridine derivative (7) may be reacted with a carbonyl derivative (for example, diethylketone) or an aldehyde derivative (for example, propionaldehyde) in the presence of a reducing agent to obtain a pyrazolo[1,5-a]pyridine derivative represented by formula (I) or (I'). Compound (I) or compound (I') may be obtained depending on the number of moles of the carbonyl derivative. The reaction may be conducted in the presence or in the absence of an acid, with or without a solvent, and in the presence or in the absence of an inorganic salt. The solvent, if used, will differ depending on the starting material, reagent, etc. and is not particularly restricted so long as it does not inhibit the reaction and dissolves the starting materials to some extent, but preferably there may be mentioned tetrahydrofuran, diethyl ether, 1,2-dichloroethane, dichloromethane, chloroform, acetonitrile, water and the like, which may be used alone or as mixed solvents. The acid, inorganic salt and reducing agent used will differ depending on the starting material, solvent, etc. and are not particularly restricted so long as they do not inhibit the reaction, but preferably there may be mentioned acetic acid, sulfuric acid and the like as acids, sodium sulfate and the like as inorganic salts, and sodium triacetoxyborohydride, sodium borohydride, sodium cyanoborohydride and the like as reducing agents. The reaction temperature will normally be from −10° C. to 150° C.

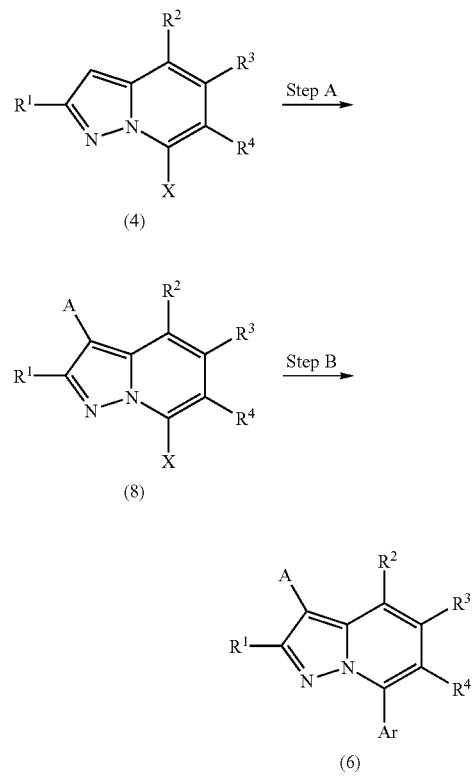

Production Scheme 3

Step A: The pyrazolo[1,5-a]pyridine derivative (4) may be subjected to nitration reaction or nitrosation reaction in the same manner as Step C of Production Scheme 2 above, to obtain compound (8).

Step B: The halogenated compound (8) may be subjected to cross-coupling reaction in the same manner as Step B of Production Scheme 2 above, to obtain an aryl- or heteroaryl-substituted derivative (6).

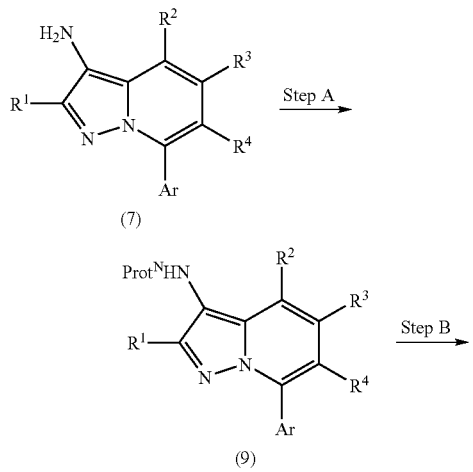

Production Scheme 4

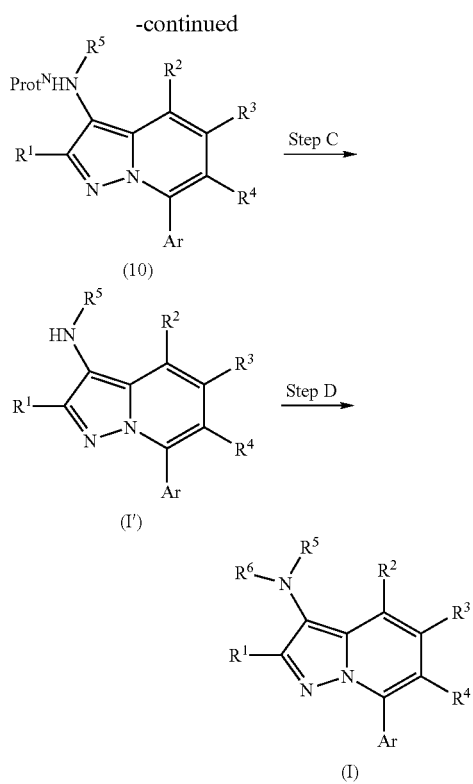

Step A: The 3-amino-pyrazolo[1,5-a]pyridine derivative (7) may be may be subjected to reaction with an amino-protecting reagent (for example, di-tert-butyl dicarbonate) to obtain a 3-aminopyrazolo[1,5-a]pyridine derivative (9) having the 3-position amino group protected with a carbamate group (for example, t-butoxycarbonyl). The reaction may be conducted with or without a solvent, and in the presence or in the absence of a base. The solvent, if used, will differ depending on the starting material, reagent, etc. and is not particularly restricted so long as it does not inhibit the reaction and dissolves the starting materials to some extent, but preferably there may be mentioned tetrahydrofuran, diethyl ether, 1,4-dioxane, dichloromethane, 1,2-dichloroethane, chloroform, N,N-dimethylformamide, and the like. The base, if used, will differ depending on the starting material, solvent, etc. and is not particularly restricted so long as it does not inhibit the reaction, but preferably there may be mentioned triethylamine, sodium hydride, potassium carbonate, sodium carbonate, cesium carbonate, sodium hydrogencarbonate, 4-(dimethylamino)pyridine, sodium bis(trimethylsilyl)amide, and the like. The reaction temperature will normally be from −70° C. to 150° C. As preferred examples of protecting groups ("Prot$^N$" in this scheme) there may be mentioned, in addition to Boc, also 9-fluorenylmethoxycarbonyl (Fmoc), 2,2,2-trichloroethoxycarbonyl (Troc), and the like, in which case the amino group is protected using a reagent and reaction suitable for that protecting group.

Step B: The 3-aminopyrazolo[1,5-a]pyridine derivative (9) may be reacted with an alkylating agent (for example, an optionally substituted alkyl halide), to obtain a pyrazolo[1,5-a]pyridine derivative (10). The reaction may be conducted with or without a solvent, and in the presence or in the absence of a base. The solvent, if used, will differ depending on the starting material, reagent, etc. and is not particularly restricted so long as it does not inhibit the reaction and dissolves the starting materials to some extent, but preferably there may be mentioned tetrahydrofuran, diethyl ether, N,N-dimethylformamide, dimethylsulfoxide, and the like. The base, if used, will differ depending on the starting material, solvent, etc. and is not particularly restricted so long as it does not inhibit the reaction, but preferably there may be mentioned sodium hydride, potassium hydride, potassium carbonate, sodium carbonate, cesium carbonate, potassium hydroxide, sodium hydroxide, and the like. The reaction temperature will normally be from −70° C. to 200° C.

Step C: The amino group-protected 3-amino-pyrazolo[1,5-a]pyridine derivative (10) may be subjected to deprotecting reaction to obtain a 3-monoalkylaminopyrazolo[1,5-a]pyridine derivative (I'). The reaction may be conducted either in the presence or in the absence of a deprotecting reagent. If used, the deprotecting reagent will differ depending on the starting material, solvent, etc. and is not particularly restricted so long as it does not inhibit the reaction, but preferably there may be mentioned hydrochloric acid, sulfuric acid, trifluoroacetic acid, methanesulfonic acid, iodotrimethylsilane, aluminum(III)chloride, trimethylsilyl triflate, and the like. When a group other than Boc (such as Fmoc, Troc or the like) is used as the protecting group, the deprotection is carried out using reagents and reaction suitable for that protecting group. The reaction may be conducted with or without a solvent, and if it is carried out with a solvent, the solvent is preferably ethyl acetate, tetrahydrofuran, diethyl ether, 1,4-dioxane, acetonitrile, dichloromethane, chloroform, nitromethane, phenol, anisole, thiophenol or the like. The solvent will depend on the starting material, reagent, etc. and is not particularly restricted so long as it does not inhibit the reaction and dissolves the starting materials to some extent. The reaction temperature will normally be from −70° C. to 200° C.

Step D: The pyrazolo[1,5-a]pyridine derivative (I') may be reacted with a carbonyl derivative (for example, diethylketone), an aldehyde derivative (for example, propionaldehyde) or a carbonyl-equivalent compound (for example, ((1-ethoxycyclopropyl)oxy)trimethylsilane), in the presence of a reducing agent, to obtain a pyrazolo[1,5-a]pyridine derivative (I). The reaction temperature will normally be from −10° C. to 150° C. The reaction may be conducted in the presence or in the absence of an acid, with or without a solvent, and in the presence or in the absence of an inorganic salt. The solvent, if used, will differ depending on the starting material, reagent, etc. and is not particularly restricted so long as it does not inhibit the reaction and dissolves the starting materials to some extent, but preferably there may be mentioned tetrahydrofuran, diethyl ether, 1,2-dichloroethane, dichloromethane, chloroform, acetonitrile, ethanol, methanol, water and the like, which may be used alone or as mixed solvents. The acid, inorganic salt and reducing agent used will differ depending on the starting material, solvent, etc. and are not particularly restricted so long as they do not inhibit the reaction, but preferably there may be mentioned acetic acid, sulfuric acid and the like as acids, sodium sulfate and the like as inorganic salts, and sodium triacetoxyborohydride, sodium borohydride, sodium cyanoborohydride and the like as reducing agents.

Alternatively, the pyrazolo[1,5-a]pyridine derivative (I') may be reacted with an acylating agent either in the presence or in the absence of a base, and with or without a solvent, to obtain a pyrazolo[1,5-a]pyridine derivative (I). The reaction temperature will normally be from −20° C. to 150° C. The solvent, if used, will differ depending on the starting material, reagent, etc. and is not particularly restricted so long as it does not inhibit the reaction and dissolves the starting materials to some extent, but preferably there may be mentioned tetrahydrofuran, diethyl ether, 1,2-dichloroethane, dichloromethane, acetonitrile, ethanol, methanol, water and the like, which may be used alone or as mixed solvents. The base, if used, will differ depending on the starting material, solvent, etc. and is not particularly restricted so long as it does not inhibit the reaction, but preferably there may be mentioned triethylamine, N,N-diisopropylethylamine, 4-(dimethylamino)pyridine, sodium carbonate, potassium carbonate, sodium hydroxide, potassium hydroxide, and the like.

which may be used alone or as mixed solvents. The metal (powder) used may be zinc, iron, $SnCl_2$, $NiCl_2$, or the like.

Step B: The 3-aminopyrazolo[1,5-a]pyridine derivative (11) may be subjected to reaction in the same manner as Step A of Production Scheme 4 above, and the amino group thereof protected, to obtain compound (12).

Step C: The halogenated compound (12) may be subjected to cross-coupling reaction using a palladium catalyst in the same manner as Step B of Production Scheme 2 above, to obtain compound (9).

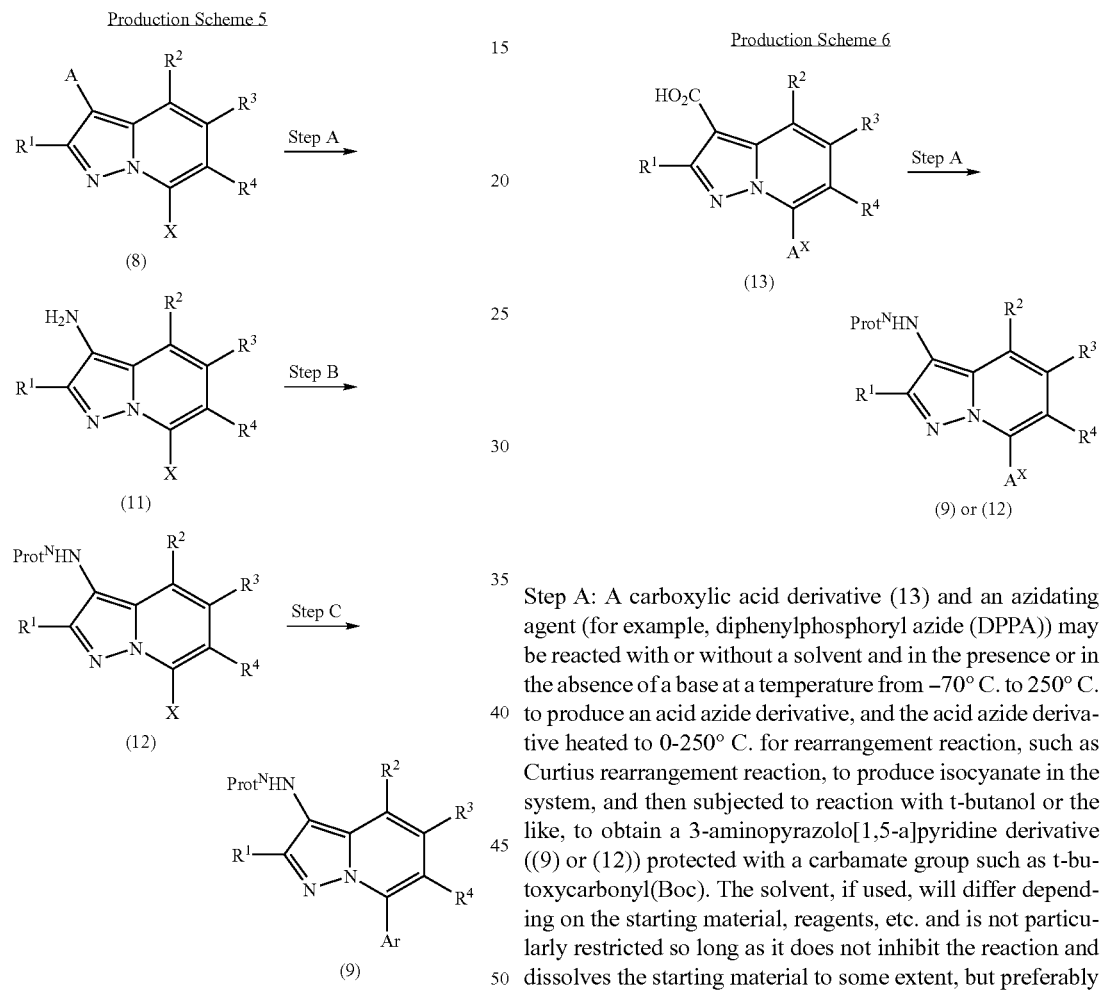

Step A: The nitro derivative or nitroso derivative (8) may be reacted with a metal (powder) to obtain a 3-aminopyrazolo[1,5-a]pyridine derivative (11). The reaction temperature will normally be from −10° C. to 150° C. The reaction may be conducted either in the presence or in the absence of an acid, and with or without a solvent. The acid, if used, will differ depending on the starting material, solvent, etc. and is not particularly restricted so long as it does not inhibit the reaction, but preferably there may be mentioned acetic acid, hydrochloric acid, sulfuric acid, and the like. The solvent, if used, will differ depending on the starting material, reagents, etc. and is not particularly restricted so long as it does not inhibit the reaction and dissolves the starting materials to some extent, but preferably there may be mentioned methanol, ethanol, n-butanol, tetrahydrofuran, water and the like, Step A: A carboxylic acid derivative (13) and an azidating agent (for example, diphenylphosphoryl azide (DPPA)) may be reacted with or without a solvent and in the presence or in the absence of a base at a temperature from −70° C. to 250° C. to produce an acid azide derivative, and the acid azide derivative heated to 0-250° C. for rearrangement reaction, such as Curtius rearrangement reaction, to produce isocyanate in the system, and then subjected to reaction with t-butanol or the like, to obtain a 3-aminopyrazolo[1,5-a]pyridine derivative ((9) or (12)) protected with a carbamate group such as t-butoxycarbonyl(Boc). The solvent, if used, will differ depending on the starting material, reagents, etc. and is not particularly restricted so long as it does not inhibit the reaction and dissolves the starting material to some extent, but preferably there may be mentioned benzene, toluene, xylene, diphenylether, t-butanol, tetrahydrofuran, dioxane, acetonitrile, N,N-dimethylformamide and the like, which may be used alone or as mixed solvents. The base, if used, will differ depending on the starting material, solvent, etc. and is not particularly restricted so long as it does not inhibit the reaction, but preferably there may be mentioned triethylamine, diisopropylethylamine, 4-(dimethylamino)pyridine, pyridine, and the like. As an alternative method for synthesis of the acid azide derivative, the carboxylic acid derivative (9) may be converted to an acid chloride or mixed acid anhydride and subjected to reaction with an azidating agent (for example, sodium azide, trimethylsilyl azide, etc.) to obtain the acid azide derivative. As yet alternative methods, the target compound ((9) or (12)) may also be obtained by Hofmann rearrangement or Schmidt rearrangement reaction.

Production Scheme 7

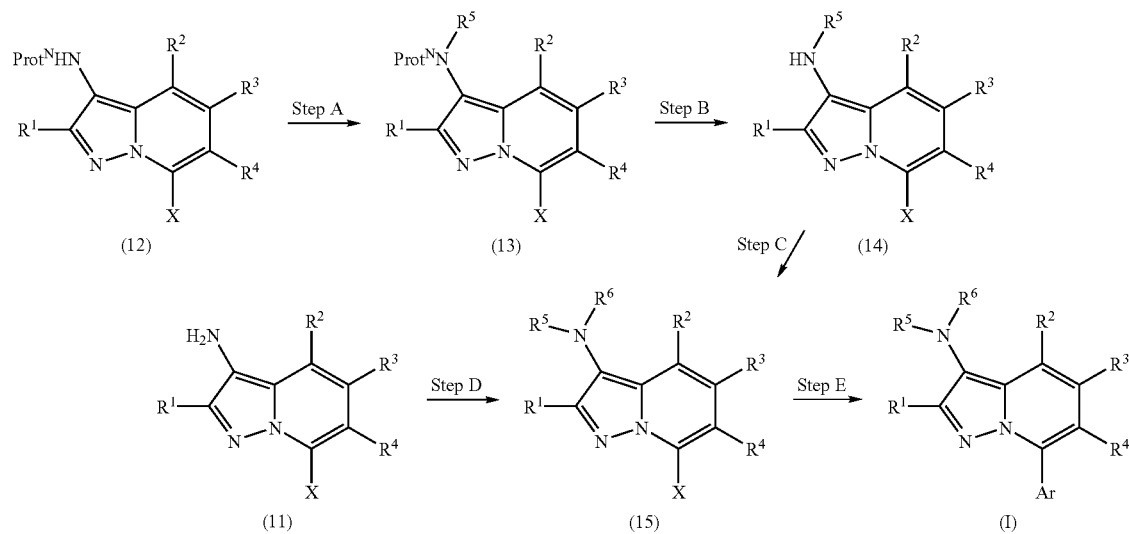

Step A: Compound (12) may be alkylated in the same manner as Step B of Production Scheme 4 to obtain Compound (13).

Step B: Compound (13) may be deprotected of the protecting group in the same manner as Step C of Production Scheme 4 to obtain Compound (14).

Step C: Compound (14) may be alkylated or acylated in the same manner as Step D of Production Scheme 4 to obtain Compound (15).

Step C: Compound (11) may be alkylated in the same manner as Step E of Production Scheme 2 to obtain Compound (15).

Step E: Compound (15) may be cross-coupled using a palladium complex or the like in the same manner as Step B of Production Scheme 2 to obtain Compound (I).

Production Scheme 8

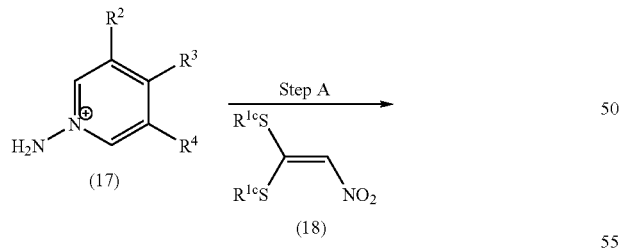

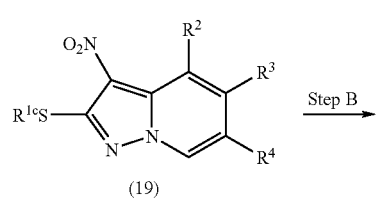

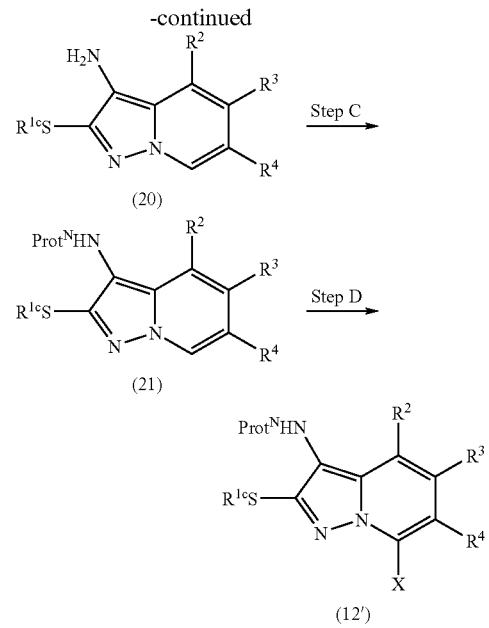

Step A: Compound (19) was produced according to the method disclosed in Heterocycles, 1977, 6, 379. Specifically, Compound (17) may be reacted with Compound (18), to obtain Compound (19).

Step B: Compound (20) may be obtained by reduction of Compound (19) according to Step D of Production Scheme 2.

Step C: Compound (21) having the 3-position amino group protected may be obtained from Compound (20) according to Step A of Production Scheme 4.

Step D: A halogenated compound (12') may be obtained from the 3-position amino group-protected Compound (21) by introducing a halogen at the 7-position according to Step A of Production Scheme 2.

Production Scheme 9

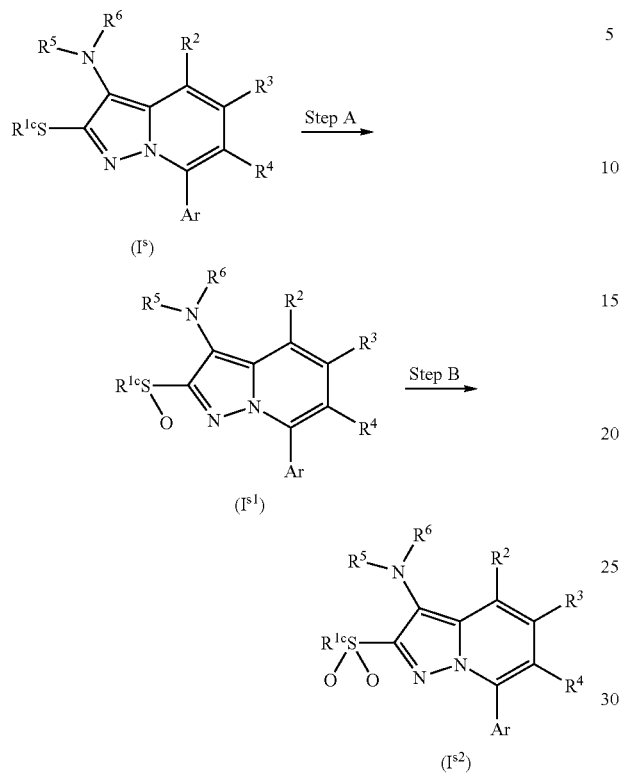

Production Scheme 10

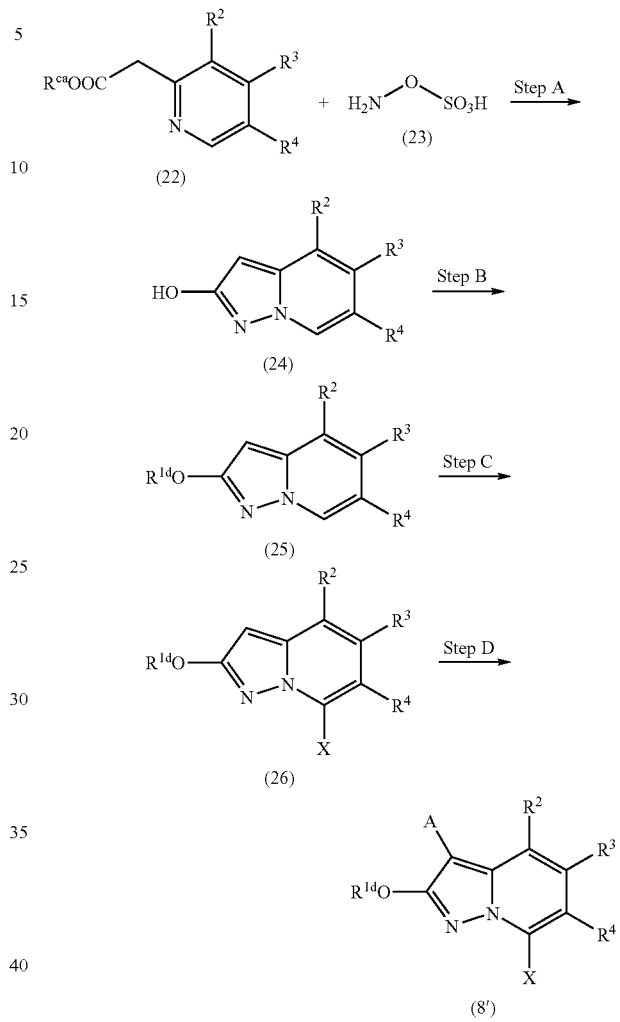

Step A: Compound (I$^s$) may be oxidized using an oxidizing agent such as m-chloroperbenzoic acid or the like, either with or without a solvent, to obtain a sulfoxide (I$^{s1}$). The reaction temperature will normally be from −70° C. to 150° C. The solvent, if used, will differ depending on the starting material, reagent, etc. and is not particularly restricted so long as it does not inhibit the reaction and dissolves the starting material to some extent, but preferably there may be mentioned acetone, acetic acid, trifluoroacetic acid, dichloromethane, chloroform, benzene, nitromethane, methanol, ethanol, water, and the like, which may be used alone or as mixed solvents. As oxidizing agents to be used there may be mentioned m-chloroperbenzoic acid, trifluoroperacetic acid, bis(trimethylsilyl) peroxy acid, sodium periodate, dinitrogen tetroxide, nitric acid/sulfuric acid mixture, chromic acid, and the like.

Step B: The sulfoxide (I$^{s1}$) may be oxidized using an oxidizing agent such as m-chloroperbenzoic acid or the like, either with or without a solvent, to obtain a sulfone (I$^{s2}$). The reaction temperature will normally be from −70° C. to 150° C. The solvent, if used, will differ depending on the starting material, reagent, etc. and is not particularly restricted so long as it does not inhibit the reaction and dissolves the starting material to some extent, but preferably there may be mentioned acetone, acetic acid, trifluoroacetic acid, dichloromethane, chloroform, benzene, methanol, ethanol, water, and the like, which may be used alone or as mixed solvents. As oxidizing agents to be used there may be mentioned m-chloroperbenzoic acid, chromic acid, osmium tetroxide, potassium permanganate, and the like.

Step A: A 2-pyridylacetic acid ester (22) and hydroxylamine-O-sulfonic acid (23) may be reacted in the presence or in the absence of a base, and with a solvent, to obtain a 2-hydroxypyrazolo[1,5-a]pyridine derivative (24). The reaction temperature will normally be from 0° C. to 100° C. The solvent used will differ depending on the starting materials, reagent, etc. and is not particularly restricted so long as it does not inhibit the reaction and dissolves the starting materials to some extent, but preferably there may be mentioned acetone, acetic acid, methanol, ethanol, water, and the like, which may be used alone or as mixed solvents.

Step B: A 2-hydroxypyrazolo[1,5-a]pyridine derivative (24) may be reacted with an alkylating agent either with or without a solvent, and in the presence or in the absence of a base, to obtain Compound (25). The reaction temperature will normally be from 0° C. to 100° C. The solvent, if used, will differ depending on the starting material, reagent, etc. and is not particularly restricted so long as it does not inhibit the reaction and dissolves the starting material to some extent, but preferably there may be mentioned acetone, methanol, ethanol, water, and the like, which may be used alone or as mixed solvents. As alkylating agents there may be mentioned dimethylsulfuric acid, alkyl halides, diazomethane, trimethylsilyldiazomethane, or the like. The base, if used, will differ depending on the starting material, solvent, etc. and is not particularly restricted so long as it does not inhibit the reaction, but preferably there may be mentioned calcium carbonate, sodium carbonate, sodium hydrogencarbonate, triethylamine, and the like.

Step C: Compound (25) may be used to obtain Compound (26) in the same manner as Step A of Production Scheme 2.

Step D: Compound (26) may be used to obtain Compound (8') in the same manner as Step C of Production Scheme 2.

Production Scheme 11

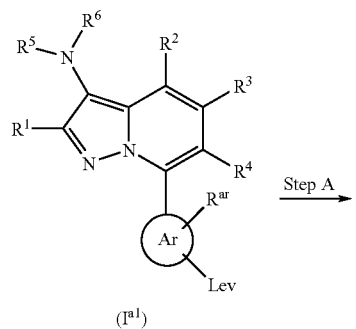

(I$^{a1}$)

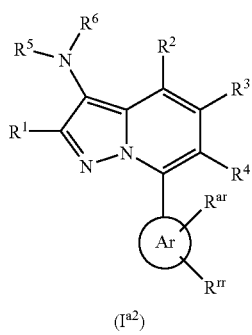

(I$^{a2}$)

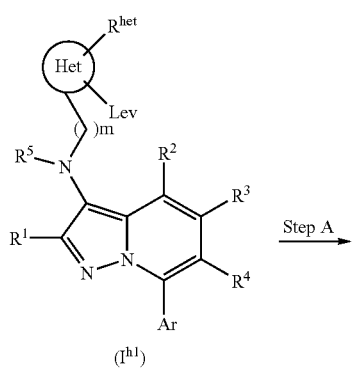

(I$^{h1}$)

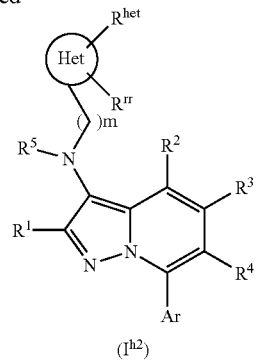

(I$^{h2}$)

Step A: A step of converting the leaving group Lev substituting at the 7-position or N atom at the 3-position of a pyrazolo[1,5-a]pyridine derivative represented by formula (I$^{a1}$) or formula (I$^{h1}$), to a desired substituent R$^{ar}$ or R$^{rr}$. The following reactions may be employed.

[1] A pyrazolo[1,5-a]pyridine derivative represented by formula (I$^{a1}$) or formula (I$^{h1}$) may be heated and reacted with a metal cyamide compound such as copper(I)cyamide, zinc cyamide or potassium cyamide, either with or without a solvent and in the presence or in the absence of a catalyst, to obtain a pyrazolo[1,5-a]pyridine derivative represented by formula (I$^{a2}$) or formula (I$^{h2}$). The reaction temperature will normally be from 40° C. to 250° C. The solvent, if used, will differ depending on the starting material, reagent, etc. and is not particularly restricted so long as it does not inhibit the reaction and dissolves the starting material to some extent, but preferably there may be mentioned N,N-dimethylformamide, 1-methyl-2-pyrrolidinone, 1,3-dimethyl-2-imidazolidinone, tetrahydrofuran, 1,4-dioxane, pyridine, quinoline, and the like, which may be used alone or as mixed solvents. The catalyst, if used, will differ depending on the starting material, solvent, etc. and is not particularly restricted so long as it does not inhibit the reaction, but preferably there may be mentioned crown ethers such as 18-crown-6.

[2] A pyrazolo[1,5-a]pyridine derivative represented by formula (I$^{a1}$) or formula (I$^{h1}$) may be reacted with an organic boric acid derivative, an organic tin derivative or a metal cyamide compound such as copper(I)cyamide, zinc cyamide or potassium cyamide, in the presence of a palladium or nickel complex, either with or without a solvent and in the presence or in the absence of a base, to obtain a pyrazolo[1,5-a]pyridine derivative represented by formula (I$^{a2}$) or formula (I$^{h2}$). The reaction temperature will normally be from 0° C. to 150° C. The solvent, if used, will differ depending on the starting material, reagent, etc. and is not particularly restricted so long as it does not inhibit the reaction and dissolves the starting material to some extent, but preferably there may be mentioned N,N-dimethylformamide, 1-methyl-2-pyrrolidinone, 1,3-dimethyl-2-imidazolidinone, tetrahydrofuran, 1,4-dioxane, 1,2-dimethoxyethane, benzene, toluene, xylene, ethanol, water, and the like, which may be used alone or as mixed solvents. As examples of palladium or nickel complexes to be used there may be mentioned Pd(PPh$_3$)$_4$, Pd(OAc)$_2$/PPh$_3$, Pd$_2$(dba)$_3$, PdCl$_2$, PdCl$_2$(dppf), Ni(dpp)$_2$Cl$_2$, and the like. The base, if used, will differ depending on the starting material, solvent, etc. and is not particularly restricted so long as it does not inhibit the reaction, but preferably there may be mentioned potassium carbonate, sodium carbonate, cesium fluoride, potassium fluoride, sodium hydrogencarbonate, barium hydroxide, triethylamine, and the like.

Production Scheme 12

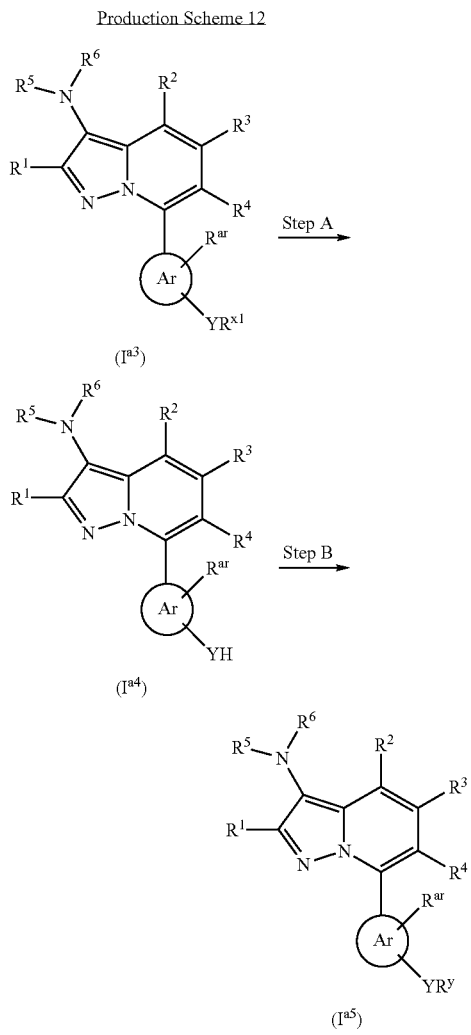

Step A: A step of removing $R^{x1}$ from a compound represented by formula ($I^{a3}$) having $YR^{x1}$, wherein $R^{x1}$ is considered to be a protecting group, under conditions for its deprotection. For example, when $YR^{x1}$ is a $C_{1-6}$ alkoxy group, it may be reacted with a deprotecting reagent such as boron tribromide, either with or without a solvent, to obtain a compound represented by formula ($I^{a4}$). The reaction may be conducted either in the presence or in the absence of a deprotecting agent. The deprotecting agent, if used, will differ depending on the starting material, reagent, etc., and preferably there may be mentioned boron tribromide, iodotrimethylsilane, boron trifluoride diethyl etherate, hydrochloric acid, and the like. The solvent used will differ depending on the starting material, reagent, etc. and is not particularly restricted so long as it does not inhibit the reaction and dissolves the starting material to some extent, but preferably there may be mentioned chloroform, dichloromethane, acetonitrile, ethyl acetate, methanol, ethanol, water, and the like, which may be used alone or as mixed solvents.

This step also includes deprotection of $R^{x1}$ considered as a protecting group when Y is $NR^y$ or $S(O)_n$.

Step B: For example, a compound represented by formula ($I^{a4}$) having a phenolic hydroxyl group may be reacted with an alkylating agent (for example, an optionally substituted alkyl halide), either in the presence or in the absence of a base, and with or without a solvent, to obtain a compound represented by formula ($I^{a5}$) having $R^y$ introduced therein. The reaction is conducted either with or without a solvent, and in the presence or in the absence of a base. The solvent, if used, will differ depending on the starting material, reagent, etc. and is not particularly restricted so long as it does not inhibit the reaction and dissolves the starting material to some extent, but preferably there may be mentioned tetrahydrofuran, diethyl ether, N,N-dimethylformamide, dimethylsulfoxide, acetone, ethanol, methanol, water, and the like. The base, if used, will differ depending on the starting material, solvent, etc. and is not particularly restricted so long as it does not inhibit the reaction, but preferably there may be mentioned sodium hydride, potassium hydride, potassium carbonate, sodium carbonate, cesium carbonate, potassium hydroxide, sodium hydroxide, and the like. The reaction temperature will normally be from −70° C. to 200° C.

As an alternative method, an optionally substituted alcohol derivative may be used for Mitsunobu reaction in the presence of a diazo compound such as diethyl azodicarboxylate and an organic phosphorus compound such as triphenylphosphine, with or without a solvent, at a reaction temperature of from −70° C. to 100° C., to obtain a compound represented by formula ($I^{a5}$) having $R^y$ introduced therein. The solvent, if used, will differ depending on the starting material, reagent, etc. and is not particularly restricted so long as it does not inhibit the reaction and dissolves the starting material to some extent, but preferably there may be mentioned tetrahydrofuran, diethyl ether, and the like.

The step may also include introduction of substituents by suitable substituent-introduction methods when Y is $NR^y$ or $S(O)_n$.

Production Scheme 13

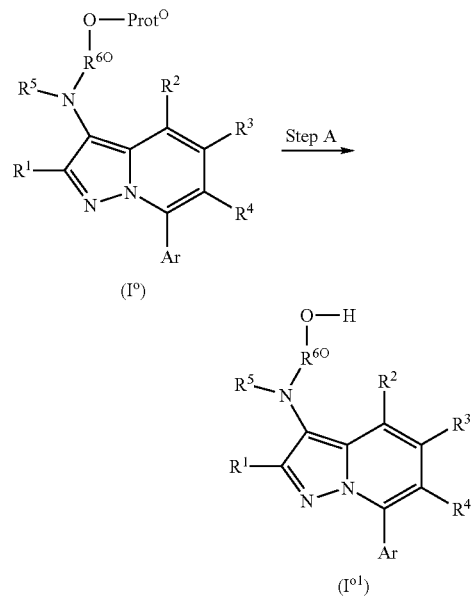

Step A: Compound (I°) having a hydroxyl group protected with a benzoate group or the like, on substituent $R^{6o}$ on N atom at the 3-position may be subjected to deprotecting reaction to obtain Compound ($I^{o1}$) having a hydroxyl group on the substituent $R^{6o}$ on N atom at the 3-position. The reaction may be conducted either in the presence or in the absence of a deprotecting agent. The deprotecting agent, if used, will differ depending on the starting material, solvent, etc. and is not particularly restricted so long as it does not inhibit the reaction, but preferably there may be mentioned sodium hydroxide, potassium hydroxide, sodium hydrogencarbonate, potassium carbonate, sodium carbonate, and the like. The reaction may also be conducted without or with a solvent, in which case the solvent is not particularly restricted so long as it does not inhibit the reaction and dissolves the starting material to some extent, but preferably there may be mentioned methanol, ethanol, n-butanol, water, and the like. The reaction temperature will normally be from 0° C. to 200° C. When a group other than a benzoate group (for example, methoxymethyl, benzyl, acetyl, etc.) is used as the protecting group, deprotection is carried out by reaction using a reagent suited for that protecting group.

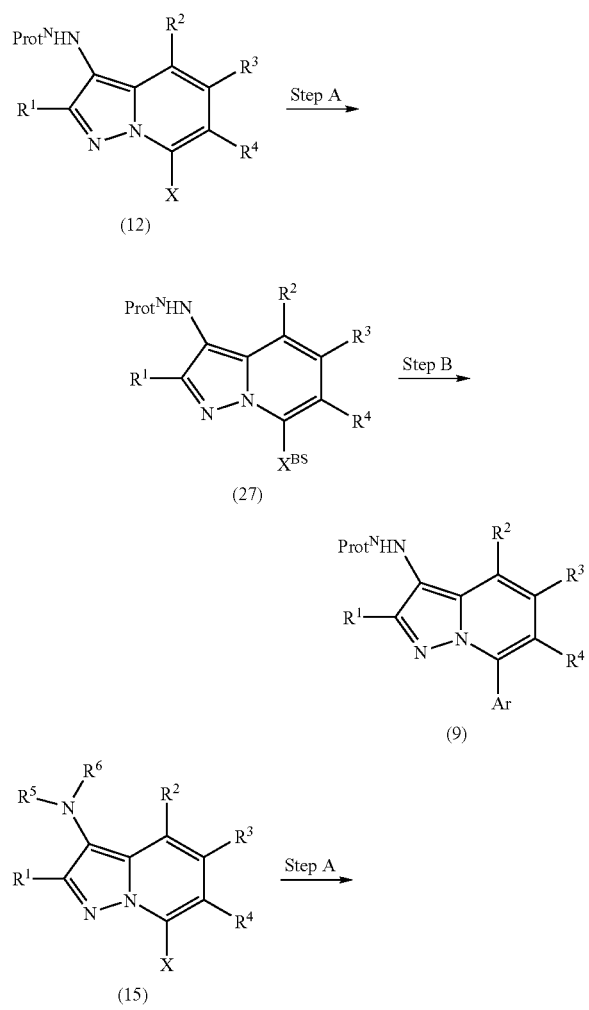

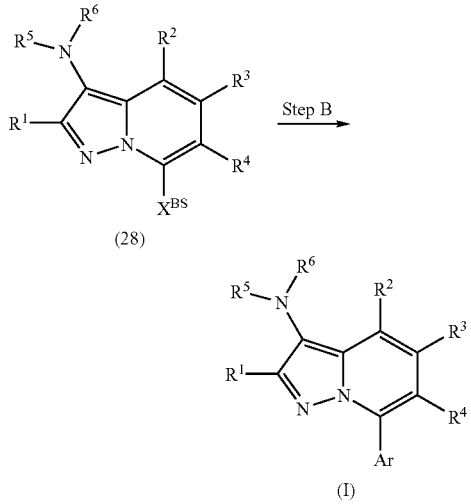

Step A: Compound (12) or (15) may be reacted with a boric acid ester derivative such as triethoxyborane or a halogenated organic tin compound such as trimethyltin chloride, either with or without a solvent, after using an organic lithium reagent such as n-butyllithium to convert the halogen atom to an anion, to obtain an organic boric acid derivative or organic tin derivative represented by formula (27) or (28). The reaction temperature will normally be from −100° C. to room temperature. The solvent used will differ depending on the starting material, reagent, etc. and is not particularly restricted so long as it does not inhibit the reaction and dissolves the starting material to some extent, but preferably there may be mentioned tetrahydrofuran, diethyl ether, n-hexane, n-pentane, and mixtures thereof. The organic lithium reagent used will differ depending on the starting material or solvent, but preferably there may be mentioned n-butyllithium, sec-butyllithium, tert-butyllithium, and the like. The boric acid ester used will also differ depending on the starting material, solvent, etc., but preferably there may be mentioned trimethoxyborane, triethoxyborane, triisopropyloxyborane, and the like. The organic tin compound used will likewise differ depending on the starting material, solvent, etc., but preferably there may be mentioned trimethyltin chloride, tributyltin chloride, tributyltin bromide, and the like. Instead of using an organic lithium reagent, the organic boric acid derivative or organic tin derivative represented by formula (27) or (28) may be obtained by the reaction of a Grignard reagent, which is converted from the halide by using metallic magnesium, and a boric acid ester, diborane compound or a halogenated organic tin reagent, either with or without a solvent.

As an alternative method, Compound (12) or (15) may be subjected to coupling reaction with a diborane such as bis(pinacolato)diborane or an organic tin compound such as hexamethylditin(IV), in the presence of a Pd catalyst such as tetrakis(triphenylphosphine)palladium(0) complex, in the presence or in the absence of a base and with or without a solvent, to obtain an organic boric acid derivative or organic tin derivative represented by formula (27) or (28). The reaction temperature will normally be from 0° C. to 200° C. The solvent used will differ depending on the starting material, reagent, etc. and is not particularly restricted so long as it does not inhibit the reaction and dissolves the starting material to some extent, but preferably there may be mentioned dioxane, toluene, 1,2-dimethoxyethane, and mixtures thereof.

Step B: Compound (27) or (28) may be subjected to coupling reaction in the same manner as Step B of Production Scheme 2 above, to obtain Compound (9) or (I).

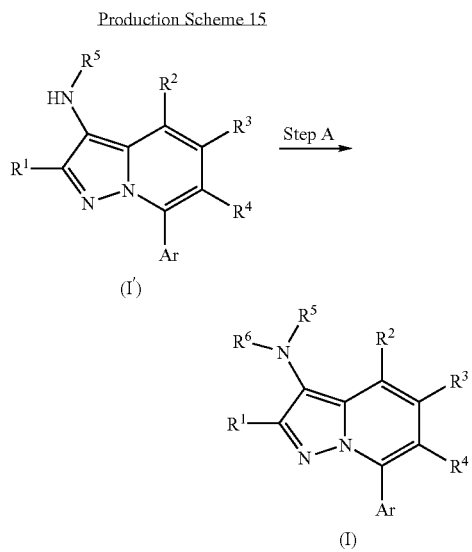

Production Scheme 15

Step A: A pyrazolo[1,5-a]pyridine derivative (I') may be reacted with an aryl halide (for example, bromobenzene) or a heteroaryl halide (for example, 2-bromopyridine), in the presence or in the absence of an organic phosphorus compound such as tri-t-butylphosphine, and in the presence of a Pd catalyst such as $Pd_2(dba)_3$, to obtain a pyrazolo[1,5-a] pyridine derivative (I) wherein $R^6$ is an aryl or heteroaryl group. The reaction temperature will normally be from 0° C. to 250° C. The reaction may be conducted in the presence or in the absence of a base, and with or without a solvent. The solvent, if used, will differ depending on the starting material, reagent, etc. and is not particularly restricted so long as it does not inhibit the reaction and dissolves the starting material to some extent, but preferably there may be mentioned toluene, xylene, mesitylene, tetrahydrofuran, diethyl ether, 1,2-dimethoxyethane, 1,4-dioxane, water, and the like, which may be used alone or as mixed solvents. The base, if used, will differ depending on the starting material, solvent, etc. and is not particularly restricted so long as it does not inhibit the reaction, but preferably there may be mentioned sodium t-butoxide, potassium t-butoxide, sodium carbonate, potassium carbonate, barium carbonate, cesium carbonate, and the like. As organic phosphorus compounds to be used there may be mentioned tri-t-butylphosphine, 2,2'-bis(diphenylphosphino)-1,1'-binaphthyl, di-t-butyl-o-biphenylphosphine, and the like. As Pd catalysts to be used there may be mentioned dichlorobis(tri-o-tolylphosphine)palladium complex, tetrakis(triphenylphosphine)palladium complex, $Pd_2(dba)_3$, $Pd_2(dba)_3CHCl_3$, $Pd(OAc)_2$, $PdCl_2(PPh_3)_2$, and the like.

Representative production schemes for compound (I) according to the present invention have been described above, but the starting compounds and reagents used for production of the compounds of the invention may also form salts or hydrates which will differ depending on the starting materials and solvent used, and these are not particularly restricted so long as the reaction is not inhibited. The solvents used will also differ depending on the starting materials and reagents, and they are not particularly restricted so long as they do not inhibit the reaction and dissolve the starting materials to some extent. When compound (I) of the present invention is obtained as a free compound, a common method may be used to convert it to a salt which compound (I) can form. The different isomers (for example, geometric isomers, and optical isomers, rotational isomers, stereoisomers and tautomers based on asymmetric carbons) obtained for compound (I) according to the invention may be purified and isolated using common separation means such as recrystallization, diastereomer salt methods, enzymatic separation methods and chromatography methods (for example, thin-layer chromatography, column chromatography, gas chromatography, etc.).

The compounds of the present invention represented by the formula (I) and their salts exhibit excellent antagonism against CRF receptors and particularly CRF1 receptor, as well as low toxicity and high safety, and are therefore highly useful as drugs. The compounds of the invention and their salts may therefore be used to obtain Corticotropin-Releasing Factor (CRF) receptor antagonists and Corticotropin-Releasing Factor (CRF)-1 receptor or Corticotropin-Releasing Factor (CRF)-1 receptor antagonists.

The compounds of the present invention and their salts may be used to obtain pharmaceutical compositions (formulations) as (i) therapeutic or prophylactic agents for diseases associated with Corticotropin-Releasing Factor (CRF), (ii) therapeutic or prophylactic agents for depression, depressive symptom, mania, anxiety, generalized anxiety disorder, panic disorder, phobias, obsessive-compulsive disorder, posttraumatic stress disorder, Tourette's syndrome, autism, affective disorder, dysthymia, bipolar disorder, cyclothymic personality and schizophrenia, (iii) therapeutic or prophylactic agents for depressive symptoms such as major depression, single-episode depression, recurrent depression, depression-induced child abuse or postpartum depression, (iv) therapeutic or prophylactic agents for peptic ulcer, irritable bowel syndrome, ulcerative colitis, Crohn's disease, diarrhea, constipation, postoperative ileus, stress-associated gastrointestinal disorders and nervous vomiting, and (v) therapeutic or prophylactic agents for Alzheimer's disease, senile dementia of Alzheimer's type, neurodegenerative disease, multi-infarct dementia, senile dementia, anorexia nervosa, eating disorder, obesity, diabetes, alcohol dependence, pharmacophilia, drug withdrawal symptoms, alcohol withdrawal symptoms, sleep disorder, insomnia, migraine, stress-induced headache, muscle contraction induced headache, ischemic neuronal damage, excitotoxic neuronal damage, stroke, progressive supranuclear palsy, amyotrophic lateral sclerosis, multiple sclerosis, muscular spasm, chronic fatigue syndrome, psychosocial dwarfism, epilepsy, head trauma, spinal cord injury, cheirospasm, spasmodic torticollis, cervicobrachial syndrome, primary glaucoma, Meniere's syndrome, autonomic imbalance, alopecia, neurosis, hypertension, cardiovascular disorder, tachycardia, congestive heart failure, hyperventilation syndrome, bronchial asthma, apneusis, sudden infant death syndrome, inflammatory disorder, pain, allergosis, impotence, menopausal disorder, fertilization disorder, infertility, cancer, HIV infection-related immune dysfunction, stress-induced immune dysfunction, hemorrhagic stress, Cushing's syndrome, thyroid function disorder, encephalomyelitis, acromegaly, incontinence and osteoporosis.

Treatment or prevention of a disease associated with Corticotropin-Releasing Factor (CRF) receptors is also possible by single or multiple administration of a therapeutically effective dose of a compound of the invention or salt thereof to a patient with the disease associated with CRF receptors.

Compounds represented by formula (I) according to the present invention and salts thereof or hydrates of the foregoing may be used directly or in admixture with publicly known pharmaceutically acceptable carriers, and formulated by common methods. As preferred dosage forms there may be mentioned tablets, powders, fine particles, granules, coated tablets, capsules, syrups, lozenges, inhalants, suppositories, injections, ointments, eye salves, eye drops, nasal drops, ear drops, paps, lotions and the like. For the formulation there may be employed any commonly used excipients, binders, disintegrators, lubricants, coloring agents, corrective coatings, and if necessary, stabilizers, emulsifiers, absorbefacients, surfactants, pH adjustors, preservatives, antioxidants, or the like, in combination with various components that are ordinarily used as starting materials for pharmaceutical formulations.

As such components there may be mentioned animal and vegetable oils such as soybean oil, beef tallow and synthetic glycerides; hydrocarbons such as liquid paraffin, squalane and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid esters, sorbitan fatty acid esters, glycerin fatty acid esters, polyoxyethylene sorbitan fatty acid esters, polyoxyethylene hydrogenated castor oil and polyoxyethylene-polyoxypropylene block copolymer; water-soluble polymers such as hydroxyethylcellulose, polyacrylic acid, carboxyvinyl polymer, polyethylene glycol, polyvinylpyrrolidone and methylcellulose; lower alcohols such as ethanol and isopropanol; polyhydric alcohols such as glycerin, propylene glycol, dipropylene glycol and sorbitol; sugars such as glucose and sucrose; inorganic powders such as silicic anhydride, magnesium aluminum silicate and aluminum silicate; purified water, and the like. Examples of excipients which may be used include lactose, corn starch, white soft sugar, glucose, mannitol, sorbit, crystalline cellulose and silicon dioxide; examples of binders which may be used include polyvinyl alcohol, polyvinyl ether, methylcellulose, ethylcellulose, gum arabic, tragacanth, gelatin, shellac, hydroxypropylcellulose, hydroxypropylmethyl cellulose, polyvinylpyrrolidone, polypropylene glycol/polyoxyethylene block polymer and meglumine, calcium citrate, dextrin pectin and carboxymethylcellulose calcium; examples of disintegrators which may be used include starch, agar, gelatin powder, crystalline cellulose, calcium carbonate, sodium hydrogencarbonate, calcium citrate, dextrin, pectin and carboxymethylcellulose calcium; examples of lubricants which may be used include magnesium stearate, talc, polyethylene glycol, silica and hydrogenated vegetable oils; examples of coloring agents which may be used include any of those approved for addition to drugs; examples of corrective coatings which may be used include cocoa powder, menthol, aromatic powders, mentha oil, borneol and powdered cinnamon; and examples of antioxidants which may be used include those approved for addition to drugs, such as ascorbic acid and alpha-tocopherol.

An oral formulation may be prepared by combining a compound of the present invention or salt thereof with an excipient, if necessary adding a binder, disintegrator, lubricant, coloring agent, corrective coating or the like, and forming a powder, fine particles, granules, tablets, coated tablets, capsules, etc. by a common method.

The tablets or granules may, of course, also be coated with a sugar coating, gelatin coating or other type of suitable coating if necessary.

In the case of a liquid formulation such as syrup, injection, eye drops or the like, a common method may be used for formulation with a pH adjustor, solubilizer, isotonizing agent or the like, as well as a solubilizing aid, stabilizer, buffering agent, suspending agent, antioxidant, etc. if necessary. In the case of a liquid formulation, it may also be lyophilized, and an injection may be administered intravenously, subcutaneously or intramuscularly. As preferred examples of suspending agents there may be mentioned methyl cellulose, polysorbate 80, hydroxyethyl cellulose, gum arabic, tragacanth powder, sodium carboxymethylcellulose, polyoxyethylene sorbitan monolaurate and the like; as preferred examples of solubilizing aids there may be mentioned polyoxyethylene hydrogenated castor oil, polysorbate 80, nicotinamide, polyoxyethylene sorbitan monolaurate and the like; as preferred examples of stabilizing agents there may be mentioned sodium sulfite, sodium metasulfite, ether and the like; and as preferred examples of preservatives there may be mentioned methyl paraoxybenzoate, ethyl paraoxybenzoate, sorbic acid, phenol, cresol, chlorocresol, and the like.

There are no particular restrictions on the method of preparing an external agent, and any common method may be employed. The base materials used may be any raw materials commonly employed in drugs, quasi drugs, cosmetics and the like, and as examples there may be mentioned raw materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water and the like, with addition of pH adjustors, antioxidants, chelating agents, antiseptics and fungicides, coloring agents, aromas and the like if necessary. Also, if necessary, there may also be included differentiation-inducing components, or other components such as circulation promoters, microbicides, antiphlogistic agents, cell activators, vitamins, amino acids, humectants, keratolytic agents and the like.

Drug formulations comprising the compounds of the present invention and salts thereof or hydrates of the foregoing as effective ingredients are useful for disease treatment or prevention in mammals (for example, humans, mice, rats, guinea pigs, rabbits, dogs, horses, monkeys, etc.), and especially for disease treatment or prevention in humans.

Although the dosage of a drug according to the present invention will differ depending on the patient's severity of symptoms, age, gender, body weight, the dosage form, type of salt, drug sensitivity and specific type of disease, etc., it will generally be from about 30 µp to 10 g, preferably from 100 µg to 500 mg, more preferably from 100 µg to 100 mg per day for adult humans in the case of oral administration or about 1-3000 µg/kg and preferably about 3-1000 µg/kg in the case of injection, administered once or divided over several times a day.

EXAMPLES

The following production examples, examples and test examples serve only for the purpose of illustration and are not intended to be restrictive on the compounds of the invention in any way. It will be apparent to those skilled in the art that various modifications may be added beyond these examples and within the scope of the claims of the invention in the present specification in order to maximize the effect of the invention, and such modifications are also encompassed within the claims.

Production Example 1

2-(1-Butynyl)pyridine

After dissolving 2-bromopyridine (50 g) in diethylamine (500 mL) and adding dichlorobis(triphenylphosphine)palladium(II) (2.2 g) and copper iodide (0.3 g), the mixture was stirred at room temperature for 4 hours while introducing 1-butyne (100 g) as a gas. After bubbling in nitrogen, extraction was performed with ethyl acetate. The insoluble portion was filtered out with celite, and then the organic layer was washed with water and brine. After drying over anhydrous magnesium sulfate and filtration, the solvent was concentrated under reduced pressure, the residue was purified by silica gel column chromatography, and the title compound (35 g) was obtained from the n-hexane:ethyl acetate (5:1) fraction as a brown oil.

$^1$H NMR (400 MHz, CDCl$_3$) δ 1.26 (t, J=7.6 Hz, 3H), 2.45 (q, J=7.6 Hz, 2H), 7.16-7.20 (m, 1H), 7.35-7.38 (m, 1H), 7.59-7.63 (m, 1H), 8.53-8.54 (m, 1H).

Production Example 2

2-Ethylpyrazolo[1,5-a]pyridine

After dissolving 2-(1-butynyl)pyridine (12.8 g) in dichloromethane (60 mL), a solution of O-mesitylenesulfonylhydroxyamine (Reference document: Synthesis, 1997, 1) (20 g) in dichloromethane (132 mL) was added dropwise while cooling on ice, and the mixture was stirred for 30 minutes. Diethyl ether (2 L) was added to the reaction mixture to precipitate crystals, which were collected by filtration and dried under reduced pressure to obtain N-amino-2-(1-butynyl)pyridinium mesitylenesulfonate (12.6 g) as colorless crystals.

A 6.1 g portion of the obtained N-amino-2-(1-butynyl)pyridinium mesitylenesulfonate was dissolved in tetrahydrofuran (600 mL), potassium tert-butoxide (3.55 g) was added at room temperature, and the mixture was vigorously stirred for 30 minutes. After adding ice water to the reaction mixture, extraction was performed with ethyl acetate. The aqueous layer was again extracted with ethyl acetate, the insoluble portion was filtered with a celite filter, and the organic layers were combined and washed with brine. After drying over anhydrous magnesium sulfate and filtration, the solvent was concentrated under reduced pressure, the residue was purified by silica gel column chromatography, and the title compound (0.63 g) was obtained from the n-hexane:ethyl acetate (10:1) fraction as a light yellow oil.

$^1$H NMR (400 MHz, CDCl$_3$) δ 1.36 (t, J=7.6 Hz, 3H), 2.86 (q, J=7.6 Hz, 2H), 6.30 (s, 1H), 6.65 (ddd, J=1.6, 6.8, 6.8 Hz, 1H), 7.04 (ddd, J=1.2, 6.8, 8.8 Hz, 1H), 7.41 (ddd, J=1.2, 1.2, 8.8 Hz, 1H), 8.37 (ddd, J=1.2, 1.2, 6.8 Hz, 1H).

Production Example 3

7-Bromo-2-ethylpyrazolo[1,5-a]pyridine

After dissolving 2-ethylpyrazolo[1,5-a]pyridine (80 mg) in tetrahydrofuran (1 mL), an n-butyllithiumhexane solution (1.6 M; 0.58 mL) was added dropwise at −78° C. under a nitrogen stream, and the mixture was stirred for 30 minutes. A solution of 1,2-dibromo-1,1,2,2-tetrachloroethane (196 mg) in tetrahydrofuran (0.5 mL) was added to the reaction mixture, and stirring was continued for 30 minutes. The temperature was increased to room temperature, water was added, extraction was performed with ethyl acetate and the organic layer washed with water and brine. After drying over anhydrous magnesium sulfate and filtration, the solvent was concentrated under reduced pressure, the residue was purified by silica gel column chromatography and the title compound (90 mg) was obtained from the n-hexane:ethyl acetate (20:1) fraction as a light brown oil.

$^1$H NMR (400 MHz, CDCl$_3$) δ 1.36 (t, J=7.6 Hz, 3H), 2.93 (q, J=7.6 Hz, 2H), 6.49 (s, 1H), 6.94 (dd, J=7.2, 8.4 Hz, 1H), 6.99 (dd, J=1.6, 7.2 Hz, 1H), 7.44 (dd, J=1.6, 8.4 Hz, 1H).

Production Example 4

7-(2,4-Dichlorophenyl)-2-ethylpyrazolo[1,5-a]pyridine

After dissolving 7-bromo-2-ethylpyrazolo[1,5-a]pyridine (300 mg) in ethanol (2 mL) and toluene (4 mL), 2,4-dichlorophenylboric acid (508 mg), tetrakis(triphenylphosphine)palladium(0) complex (154 mg) and 2M aqueous sodium carbonate (1.33 mL) were added and the mixture was heated and stirred at 80° C. for 3 hours under a nitrogen stream. Water was added to the reaction mixture, extraction was performed with ethyl acetate and the organic layer washed with brine. After drying over anhydrous magnesium sulfate and filtration, the solvent was concentrated under reduced pressure, the residue was purified by silica gel column chromatography, and the title compound (380 mg) was obtained from the n-hexane:ethyl acetate (100:1) fraction as a light yellow oil.

$^1$H NMR (400 MHz, CDCl$_3$) δ 1.30 (t, J=7.6 Hz, 3H), 2.82 (q, J=7.6 Hz, 2H), 6.42 (s, 1H), 6.64 (dd, J=1.6, 6.8 Hz, 1H), 7.12 (dd, J=6.8, 8.8 Hz, 1H), 7.38 (dd, J=2.0, 8.4 Hz, 1H), 7.48 (d, J=8.4 Hz, 1H), 7.51 (dd, J=1.6, 8.8 Hz, 1H), 7.55 (d, J=2.0 Hz, 1H).

Production Example 5

7-(2,4-Dichlorophenyl)-2-ethyl-3-nitropyrazolo[1,5-a]pyridine

After dissolving 7-(2,4-dichlorophenyl)-2-ethylpyrazolo[1,5-a]pyridine (280 mg) in acetonitrile (20 mL), nitronium tetrafluoroborate (255 mg) was added 4 times at 30 minute intervals while stirring on ice. The reaction mixture was added to ice water, extraction was performed with ethyl acetate and the extract washed with water and brine. After drying over anhydrous magnesium sulfate and filtration, the solvent was concentrated under reduced pressure, the residue was purified by silica gel column chromatography, and the title compound (115 mg) was obtained from the n-hexane:ethyl acetate (20:1) fraction as yellow crystals.

$^1$H NMR (400 MHz, CDCl$_3$) δ 1.30 (t, J=7.6 Hz, 3H), 3.15 (q, J=7.6 Hz, 2H), 7.07 (dd, J=1.6, 7.2 Hz, 1H), 7.43 (d, J=1.2 Hz, 1H), 7.60 (t, J=1.2 Hz, 1H), 7.70 (dd, J=7.2, 8.8 Hz, 1H), 8.44 (dd, J=1.6, 8.8 Hz, 1H).

Production Example 6

7-Bromo-2-ethyl-3-nitropyrazolo[1,5-a]pyridine

After dissolving 7-bromo-2-ethylpyrazolo[1,5-a]pyridine (1.1 g) in acetonitrile (20 mL), nitronium tetrafluoroborate (1.3 g) was added while stirring on ice, and stirring was continued for 30 minutes. The reaction mixture was added to ice water, extraction was performed with ethyl acetate and the extract washed with water and brine. After drying over anhydrous magnesium sulfate and filtration, the solvent was concentrated under reduced pressure, the residue was purified by silica gel column chromatography, and the title compound (670 mg) was obtained from the n-hexane:ethyl acetate (10:1) fraction as yellow crystals.

$^1$H NMR (400 MHz, CDCl$_3$) δ 1.42 (t, J=7.6 Hz, 3H), 3.27 (q, J=7.6 Hz, 2H), 7.39 (dd, J=1.2, 7.6 Hz, 1H), 7.50 (dd, J=7.6, 8.8 Hz, 1H), 8.38 (dd, J=1.2, 8.8 Hz, 1H).

Production Example 7

7-(2-Chloro-4-methoxyphenyl)-2-ethyl-3-nitropyrazolo[1,5-a]pyridine

After dissolving 7-bromo-2-ethyl-3-nitropyrazolo[1,5-a]pyridine (100 mg) in 1,2-dimethoxyethane (6 mL) and water (1 mL), 2-chloro-4-methoxyphenylboric acid (138 mg), tetrakis(triphenylphosphine)palladium(0) complex (86 mg) and barium hydroxide octahydrate (233 mg) were added and the mixture was heated and stirred at 80° C. for 3 hours under a nitrogen stream. Water was added to the reaction mixture, extraction was performed with ethyl acetate and the extract washed with saturated aqueous sodium hydrogencarbonate and brine, in that order. After drying over anhydrous magnesium sulfate and filtration, the solvent was concentrated under reduced pressure, the residue was purified by silica gel column chromatography, and the title compound (90 mg) was obtained from the n-hexane:ethyl acetate (30:1) fraction as yellow crystals.

$^1$H NMR (400 MHz, CDCl$_3$) δ 1.30 (t, J=7.6 Hz, 3H), 3.15 (q, J=7.6 Hz, 2H), 3.90 (s, 3H), 6.96 (dd, J=2.4, 8.4 Hz, 1H), 7.07 (dd, J=1.6, 7.2 Hz, 1H), 7.10 (d, J=2.4 Hz, 1H), 7.40 (d, J=8.4 Hz, 1H), 7.68 (dd, J=7.2, 8.8 Hz, 1H), 8.40 (dd, J=1.6, 8.8 Hz, 1H).

Production Example 8

2-Ethyl-4-methoxypyrazolo[1,5-a]pyridine

After adding dichlorobis(triphenylphosphine)palladium (II) (671 mg) and copper iodide (91 mg) to a solution of 2-bromo-3-methoxypyridine (18.0 g) in diethylamine (250 mL), 1-butyne (15.5 g) was bubbled through at room temperature, and the mixture was stirred for 20 hours. Upon completion of the reaction, the solvent was distilled off under reduced pressure. Water was added to the obtained residue, extraction was performed with ethyl acetate, the extract was washed with brine and dried over magnesium sulfate, and the solvent was distilled off under reduced pressure. The obtained residue was subjected to silica gel column chromatography (500 g), and 2-(1-butynyl)-4-methoxypyridine (10.0 g) was obtained from the n-hexane:ethyl acetate (2:1) fraction as a brown oil.

To a solution of the obtained 2-(1-butynyl)-4-methoxypyridine (10.0 g) in dichloromethane (100 mL) there was added dropwise a solution of O-mesitylenesulfonylhydroxyamine (16.0 g) in dichloromethane (100 mL) at 0° C., and the mixture was stirred for 1 hour. Diethyl ether (250 mL) was added to the reaction mixture, and the precipitated solid was suction filtered and dried to obtain N-amino-2-(1-butynyl)-4-methoxypyridinium mesitylenesulfonate as a white salt (20.7 g).

Potassium tert-butoxide (11.1 g) was added to a solution of N-amino-2-(1-butynyl)-4-methoxypyridinium mesitylenesulfonate (20.7 g) in tetrahydrofuran (300 mL) and N,N-dimethylformamide (15 mL), and the mixture was stirred at room temperature for 1 hour. Water was added while cooling on ice, extraction was performed with ethyl acetate, the extract washed with brine and dried over magnesium sulfate, and the solvent was distilled off under reduced pressure. The residue was subjected to silica gel column chromatography (200 g), and the title compound (6.44 g) was obtained from the n-hexane:ethyl acetate (3:1) fraction as a yellow oil.

$^1$H NMR (400 MHz, CDCl$_3$) δ 1.35 (t, J=7.6 Hz, 3H), 2.84 (q, J=7.6 Hz, 2H), 3.93 (s, 3H), 6.32 (d, J=7.7 Hz, 1H), 6.42 (s, 1H), 6.57 (t, J=7.5 Hz, 1H), 8.03 (dd, J=0.7, 7.0 Hz, 1H).

Production Example 9

7-Bromo-2-ethyl-4-methoxypyrazolo[1,5-a]pyridine n-Butyllithium (1.31 mL) was slowly added dropwise to a solution of 2-ethyl-4-methoxypyrazolo[1,5-a]pyridine (303 mg) in tetrahydrofuran (15 mL) at −78° C. After stirring the mixture at −78° C. for 1 hour, 1,2-dibromoethane (0.18 mL) was added and stirring was continued for 1 hour. Saturated aqueous ammonium chloride was added, extraction was performed with ethyl acetate, the extract washed with brine and dried over magnesium sulfate, and the solvent was distilled off under reduced pressure. The residue was subjected to silica gel column chromatography (20 g), and the title compound (282 mg) was obtained from the n-hexane:ethyl acetate (5:1) fraction as a colorless oil.

$^1$H NMR (400 MHz, CDCl$_3$) δ 1.35 (t, J=7.7 Hz, 3H), 2.91 (q, J=7.7 Hz, 2H), 3.93 (s, 3H), 6.28 (d, J=8.1 Hz, 1H), 6.61 (s, 1H), 6.85 (d, J=8.1 Hz, 1H).

Production Example 10

7-Bromo-2-ethyl-4-methoxy-3-nitropyrazolo[1,5-a]pyridine

After adding nitronium tetrafluoroborate (176 mg) to a solution of 7-bromo-2-ethyl-4-methoxypyrazolo[1,5-a]pyridine (282 mg) in acetonitrile (20 mL) at 0° C., the mixture was stirred for 20 minutes. Upon completion of the reaction, water was added, extraction was performed with ethyl acetate, the extract washed with saturated aqueous sodium hydrogencarbonate and brine and dried over magnesium sulfate, and the solvent was distilled off under reduced pressure. The residue was subjected to silica gel column chromatography (20 g), and the title compound (159 mg) was obtained from the n-hexane:ethyl acetate (3:1) fraction as yellow crystals.

$^1$H NMR (400 MHz, CDCl$_3$) δ 1.39 (t, J=7.5 Hz, 3H), 3.13 (q, J=7.5 Hz, 2H), 3.99 (s, 3H), 6.72 (d, J=8.4 Hz, 1H), 7.19 (d, J=8.3 Hz, 1H).

Production Example 11

2-Ethyl-4-methoxy-7-(2-methoxy-4,6-dimethylphenyl)-3-nitropyrazolo[1,5-a]pyridine After adding 4,6-dimethyl-2-methoxyphenylboric acid (191 mg), barium hydroxide octahydrate (334 mg) and tetrakis(triphenylphosphine)palladium(0) complex (123 mg) to a solution of 7-bromo-2-ethyl-4-methoxy-3-nitropyrazolo[1,5-a]pyridine (159 mg) in a mixture of ethyleneglycol diethyl ether (15 mL) and water (7.5 mL), the mixture was heated at 80° C. for 30 minutes. Water was added, extraction was performed with ethyl acetate, the extract was washed with saturated aqueous sodium hydrogencarbonate and brine and dried over magnesium sulfate, and the solvent was distilled off under reduced pressure. The residue was subjected to silica gel column chromatography (20 g), and the title compound (185 mg) was obtained from the n-hexane:ethyl acetate (5:1) fraction as yellow crystals.

$^1$H NMR (400 MHz, CDCl$_3$) δ 1.24 (t, J=7.5 Hz, 3H), 1.98 (s, 3H), 2.40 (s, 3H), 2.99 (q, J=7.5 Hz, 2H), 3.66 (s, 3H), 4.03 (s, 3H), 6.68 (s, 1H), 6.78 (s, 1H), 6.81 (d, J=8.1 Hz, 1H), 6.90 (d, J=8.1 Hz, 1H).

Production Example 12 tert-Butyl N-[2-methylthiopyrazolo[1,5-a]pyridin-3-yl]carbamate

2-Methylthio-3-nitropyrazolo[1,5-a]pyridine (Reference document: Heterocycles, 1977, 6, 379) (400 mg) was suspended in ethanol (20 mL), and then water (10 mL), acetic acid (2 mL) and zinc powder (800 mg) were added and the mixture was heated and stirred at 80° C. for 30 minutes. The reaction mixture was filtered, water was added to the filtrate, extraction was performed with ethyl acetate and the extract washed with saturated aqueous sodium hydrogencarbonate and brine. After drying over anhydrous magnesium sulfate and filtration, the solvent was concentrated under reduced pressure to obtain 2-methylthiopyrazolo[1,5-a]pyridin-3-yl] amine as a crude product. This was then dissolved in dichloromethane (5 mL), triethylamine (0.4 mL) was added, di-tert-butyl dicarbonate (625 mg) was further added while cooling on ice, and the mixture was stirred overnight at room temperature. After adding water to the reaction mixture, extraction was performed twice with ethyl acetate and the organic layer washed with water and brine. After drying over anhydrous magnesium sulfate and filtration, the solvent was concentrated under reduced pressure, the residue was purified by silica gel column chromatography, and the title compound (230 mg) was obtained from the n-hexane:ethyl acetate (5:1) fraction as a yellow oil.

$^1$H NMR (400 MHz, CDCl$_3$) δ 1.53 (br s, 9H), 2.60 (s, 3H), 6.00-6.15 (m, 1H), 6.69 (t, J=6.8 Hz, 1H), 7.11 (t, J=8.0 Hz, 1H), 7.40-7.50 (m, 1H), 8.83 (d, J=6.8 Hz, 1H).

Production Example 13 tert-Butyl N-[7-iodo-2-methylthiopyrazolo[1,5-a]pyridin-3-yl]carbamate

After dissolving tert-butyl N-[2-methylthiopyrazolo[1,5-a]pyridin-3-yl]carbamate (21.6 g) in tetrahydrofuran (1 L), a solution of n-butyllithium in hexane (1.6 M; 130 mL) was added dropwise at −78° C. under a nitrogen stream, and the mixture was stirred for 30 minutes. A solution of 1,2-diiodoethane (24 g) in tetrahydrofuran (50 mL) was added to the reaction mixture, and stirring was continued for 1 hour. Saturated aqueous ammonium chloride was added to the reaction mixture, the temperature was raised to room temperature, extraction was performed with ethyl acetate and the extract washed with water and brine. After drying over anhydrous magnesium sulfate and filtration, the solvent was concentrated under reduced pressure, the residue was purified by silica gel column chromatography, and the title compound was obtained from the n-hexane:ethyl acetate (5:1) fraction as yellow crystals.

$^1$H NMR (400 MHz, CDCl$_3$) δ 1.52 (s, 9H), 2.64 (s, 3H), 6.02-6.10 (m, 1H), 6.81 (dd, J=7.2, 8.8 Hz, 1H), 7.22 (dd, J=1.2, 7.2 Hz, 1H), 7.42-7.50 (m, 1H).

Production Example 14

7-Bromo-2-methoxypyrazolo[1,5-a]pyridine

A solution of 2-methoxypyrazolo[1,5-a]pyridine (7.15 g) [CAS No. 59942-88-0] in tetrahydrofuran (140 mL) was cooled to −78° C. under a nitrogen stream, and then a solution of n-butyllithium in hexane (1.6 M; 46 mL) was added dropwise and the mixture was stirred for 30 minutes. A solution of 1,2-dibromo-1,1,2,2-tetrachloroethane (18.9 g) in tetrahydrofuran (30 mL) was added dropwise at −78° C., and stirring was continued for 1 hour. After increasing the temperature of the reaction mixture to room temperature and adding water, extraction was performed with ethyl acetate and the extract washed with brine. After drying the obtained organic layer over anhydrous magnesium sulfate and filtering it, the solvent was concentrated under reduced pressure, the residue was purified by silica gel column chromatography, and the title compound (7.1 g) was obtained from the n-hexane:ethyl acetate (50:1) fraction as a yellow oil.

$^1$H NMR (400 MHz, CDCl$_3$) δ 4.03 (s, 3H), 6.02 (s, 1H), 6.91-6.97 (m, 2H), 7.31 (dd, J=2.4, 7.6 Hz, 1H).

Production Example 15

2-Methoxy-7-(2-methoxy-4,6-dimethylphenyl)-3-nitrosopyrazolo[1,5-a]pyridine

After dissolving 7-bromo-2-methoxypyrazolo[1,5-a]pyridine (400 mg) in acetic acid (4 mL), an aqueous solution (2 mL) containing sodium nitrite (134 mg) was added and the mixture was stirred at room temperature for 30 minutes. The precipitated crystals were collected by filtration and washed with water. After dissolving the obtained crude 7-bromo-2-methoxy-3-nitrosopyrazolo[1,5-a]pyridine, without further purification, in 1,2-dimethoxyethane (40 mL) and water (20 mL), 4,6-dimethyl-2-methoxyphenylboric acid (475 mg), tetrakis(triphenylphosphine)palladium(0) complex (203 mg) and barium hydroxide octahydrate (829 mg) were added and the mixture was heated and stirred at 80° C. for 1 hour. Water was added to the reaction mixture, extraction was performed with ethyl acetate, the organic layer washed with brine, dried over anhydrous magnesium sulfate and filtered, and the solvent was concentrated under reduced pressure. The obtained residue was purified by silica gel column chromatography, and the title compound (200 mg) was obtained from the n-hexane:ethyl acetate (5:1) fraction as a brown oil.

$^1$H NMR (400 MHz, CDCl$_3$) δ 2.05 (s, 3H), 2.43 (s, 3H), 3.70 (s, 3H), 4.20 (s, 3H), 6.70 (s, 1H), 6.79 (s, 1H), 6.08 (dd, J=1.6, 7.2 Hz, 1H), 7.80 (dd, J=7.2, 8.4 Hz, 1H), 8.30 (dd, J=1.6, 8.4 Hz, 1H).

Production Example 16

7-Bromo-2-methoxypyrazolo[1,5-a]pyridine-3-amine

After dissolving 7-bromo-2-methoxypyrazolo[1,5-a]pyridine (1 g) in acetic acid (10 mL), an aqueous solution (5 mL) containing sodium nitrite (334 mg) was added and the mixture was stirred at room temperature for 20 minutes. After adding ethanol (60 mL) and water (30 mL) to the reaction mixture, zinc powder (1 g) was added and the mixture was heated and stirred at 60° C. for 30 minutes. The insoluble residue was filtered out, water was added, and extraction was performed with ethyl acetate. After washing the organic layer with brine, drying it over anhydrous magnesium sulfate and filtering it, the solvent was concentrated under reduced pressure, the residue was purified by silica gel column chromatography, and the title compound (750 mg) was obtained from the n-hexane:ethyl acetate (3:1) fraction as brown crystals.

$^1$H NMR (400 MHz, CDCl$_3$) δ 4.13 (s, 3H), 6.78 (dd, J=1.6, 6.8 Hz, 1H), 6.81 (dd, J=6.8, 8.4 Hz, 1H), 7.24 (dd, J=1.6, 8.4 Hz, 1H).

Production Example 17 tert-Butyl N-(7-bromo-2-methoxypyrazolo[1,5-a]pyridin-3-yl)carbamate

After dissolving 7-bromo-2-methoxypyrazolo[1,5-a]pyridine-3-amine (810 mg) in dichloromethane (20 mL), triethylamine (0.7 mL) was added, di-tert-butyl dicarbonate (923 µL) was further added while cooling on ice, and the mixture was stirred overnight at room temperature. After adding water to the reaction mixture, extraction was performed with ethyl acetate and the organic layer was washed with brine. After drying over anhydrous magnesium sulfate and filtration, the solvent was concentrated under reduced pressure, the residue was purified by silica gel column chromatography, and the title compound (1.05 g) was obtained from the n-hexane:ethyl acetate (10:1) fraction as yellow crystals.

$^1$H NMR (400 MHz, CDCl$_3$) δ 1.49 (s, 9H), 4.12 (s, 3H), 6.89 (dd, J=1.2, 7.6 Hz, 1H), 6.94 (dd, J=7.6, 8.8 Hz, 1H), 7.30-7.39 (m, 1H).

Production Example 18

3-[(tert-Butoxycarbonyl)amino]-2-(methylsulfanyl)pyrazolo[1,5-a]pyridin-7-ylboric acid After dissolving tert-butyl N-(7-iodo-2-(methylsulfanyl)pyrazolo[1,5-a]pyridin-3-yl)carbamate (200 mg) in tetrahydrofuran (2 mL), the mixture was cooled to −78° C. and n-butyllithium (1.6 M; 0.66 mL) was added dropwise. The mixture was stirred for 1 hour at the same temperature, triethoxyborane (109 µL) was added and the temperature was increased to room temperature. Saturated aqueous ammonium chloride was added to the obtained reaction mixture, and extraction was performed with ethyl acetate. The obtained organic layer washed with brine and dried over anhydrous magnesium sulfate, and the solvent was distilled off under reduced pressure to obtain the title compound (106 mg) as grayish white crystals.

$^1$H NMR (400 MHz, CDCl$_3$) δ 1.53 (br s, 9H), 2.59 (s, 3H), 6.05 (br s, 1H), 6.66 (ddd, J=1.6, 1.6, 6.8 Hz, 1H), 7.04-7.12 (m, 1H), 7.44 (br s, 2H), 8.27 (ddd, J=1.6, 1.6, 7.2 Hz, 1H).

Example 1 tert-Butyl N-[7-(2,4-dichlorophenyl)-2-ethylpyrazolo[1,5-a]pyridin-3-yl]carbamate After dissolving [7-(2,4-dichlorophenyl)-2-ethylpyrazolo[1,5-a]pyridin-3-yl]amine (60 mg) and triethylamine (0.041 mL) in dichloromethane, di-tert-butyl dicarbonate (71 mg) was added while cooling on ice, and the mixture was stirred overnight at room temperature. Water was added to the reaction mixture, extraction was performed with ethyl acetate and the organic layer washed with water and brine. After drying over anhydrous magnesium sulfate and filtration, the solvent was concentrated under reduced pressure, the residue was purified by silica gel column chromatography, and the title compound (59 mg) was obtained from the n-hexane:ethyl acetate (10:1) fraction as a light yellow oil.

$^1$H NMR (400 MHz, CDCl$_3$) δ 1.26 (t, J=7.6 Hz, 3H), 1.68 (s, 9H), 2.79 (q, J=7.6 Hz, 2H), 6.70 (dd, J=1.6, 6.8 Hz, 1H), 7.20 (dd, J=6.8, 8.8 Hz, 1H), 7.39 (dd, J=2.0, 8.4 Hz, 1H), 7.44-7.50 (m, 2H), 7.56 (d, J=2.0 Hz, 1H).

Example 2

N-[7-(2,4-Dichlorophenyl)-2-ethylpyrazolo[1,5-a]pyridin-3-yl]-N,N-dipropylamine 7-(2,4-Dichlorophenyl)-2-ethyl-3-nitropyrazolo[1,5-a]pyridine (110 mg) was suspended in ethanol (6 mL), and then water (3 mL), acetic acid (1 mL) and zinc powder (220 mg) were added and the mixture was heated and stirred at 60° C. for 1 hour. The reaction mixture was filtered, water was added to the filtrate, extraction was performed with ethyl acetate and the extract washed with saturated aqueous sodium hydrogencarbonate and brine. After drying over anhydrous magnesium sulfate and filtration, the solvent was concentrated under reduced pressure to obtain [7-(2,4-dichlorophenyl)-2-ethylpyrazolo[1,5-a]pyridin-3-yl]amine (90 mg) as crude crystals. These were dissolved in tetrahydrofuran (1 mL), and after adding propionaldehyde (0.059 mL) and 3 M aqueous sulfuric acid (0.294 mL), sodium borohydride (22.2 mg) was added in five portions while vigorously stirring on ice, and stirring was continued for 30 minutes. Water was added to the reaction mixture, extraction was performed with diethyl ether and the extract washed with saturated sodium hydrogencarbonate and brine. After drying over anhydrous magnesium sulfate and filtration, the solvent was concentrated under reduced pressure, the residue was purified by silica gel column chromatography, and the title compound (59 mg) was obtained from the n-hexane:ethyl acetate (100:1) fraction as a yellow oil.

$^1$H NMR (400 MHz, CDCl$_3$) δ 0.88 (t, J=7.6 Hz, 6H), 1.23 (t, J=7.6 Hz, 3H), 1.34-1.44 (m, 4H), 2.75 (q, J=7.6 Hz, 2H), 3.02 (t, J=7.2 Hz, 4H), 6.57 (dd, J=1.2, 6.8 Hz, 1H), 7.01 (dd, J=6.8, 8.8 Hz, 1H), 6.57 (dd, J=2.0, 8.0 Hz, 1H), 7.50 (d, J=8.0 Hz, 1H), 7.51 (dd, J=1.2, 8.8 Hz, 1H), 7.54 (d, J=2.0 Hz, 1H).

Example 3

N-[7-(2-Chloro-4-methoxyphenyl)-2-ethylpyrazolo[1,5-a]pyridin-3-yl]-N,N-dipropylamine 7-(2-Chloro-4-methoxyphenyl)-2-ethyl-3-nitropyrazolo[1,5-a]pyridine (5 mg) was suspended in ethanol (2 mL), and then water (1 mL), acetic acid (0.5 mL) and zinc powder (10 mg) were added and the mixture was heated and stirred at 80° C. for 30 minutes. The reaction mixture was filtered, water was added to the filtrate, extraction was performed with ethyl acetate and the extract washed with saturated aqueous sodium hydrogencarbonate and brine. After drying over anhydrous magnesium sulfate and filtration, the solvent was concentrated under reduced pressure to obtain [7-(2-chloro-4-methoxyphenyl)-2-ethylpyrazolo[1,5-a]pyridin-3-yl]amine as crude crystals. These were dissolved in tetrahydrofuran (1 mL) without further purification, and after adding propionaldehyde (0.015 mL) and 3 M aqueous sulfuric acid (0.071 mL), sodium borohydride (5.4 mg) was added in five portions while vigorously stirring on ice, and stirring was continued for 30 minutes. Water was added to the reaction mixture, extraction was performed with diethyl ether and the extract washed with saturated sodium hydrogencarbonate and brine. After drying over anhydrous magnesium sulfate and filtration, the solvent was concentrated under reduced pressure and the residue was purified by preparative TLC [n-hexane:ethyl acetate (5:1), Rf=0.5] to obtain the title compound (6 mg) as a light yellow oil.

¹H NMR (400 MHz, CDCl₃) δ 0.88 (t, J=7.6 Hz, 6H), 1.23 (t, J=7.6 Hz, 3H), 1.34-1.44 (m, 4H), 2.76 (q, J=7.6 Hz, 2H), 3.02 (t, J=7.6 Hz, 4H), 3.87 (s, 3H), 6.56 (dd, J=1.6, 6.4 Hz, 1H), 6.92 (dd, J=2.8, 8.6 Hz, 1H), 6.99 (dd, J=6.4, 8.6 Hz, 1H), 7.06 (d, J=2.8 Hz, 1H), 7.32 (d, J=8.6 Hz, 1H), 7.45 (dd, J=1.6, 8.6 Hz, 1H).

The compounds of Examples 4 to 22 were synthesized according to the production methods of Examples 1, 2 and 3.

Example 4

N-[2-Ethyl-7-(2-methoxy-4,6-dimethylphenyl)pyrazolo[1,5-a]pyridin-3-yl]-N,N-dipropylamine (Light Yellow Crystals)
¹H NMR (400 MHz, CDCl₃) δ 0.87 (t, J=7.6 Hz, 6H), 1.19 (t, J=7.6 Hz, 3H), 1.34-1.44 (m, 4H), 1.98 (s, 3H), 2.39 (s, 3H), 2.74 (q, J=7.6 Hz, 2H), 3.02 (t, J=7.6 Hz, 4H), 3.68 (s, 3H), 6.49 (dd, J=1.2, 6.8 Hz, 1H), 6.68 (s, 1H), 6.76 (s, 1H), 6.99 (dd, J=6.8, 8.8 Hz, 1H), 6.99 (dd, J=1.2, 8.8 Hz, 1H).

Example 5

N-[7-(2,6-Dimethoxy-4-methylphenyl)-2-ethylpyrazolo[1,5-a]pyridin-3-yl]-N,N-dipropylamine (Light Yellow Oil)
¹H NMR (400 MHz, CDCl₃) δ 0.87 (t, J=7.6 Hz, 6H), 1.21 (t, J=7.6 Hz, 3H), 1.34-1.44 (m, 4H), 2.43 (s, 3H), 2.74 (q, J=7.6 Hz, 2H), 3.01 (t, J=7.6 Hz, 4H), 3.70 (s, 6H), 6.51 (s, 2H), 6.57 (dd, J=1.2, 6.8 Hz, 1H), 6.99 (dd, J=6.8, 8.8 Hz, 1H), 6.99 (dd, J=1.2, 8.8 Hz, 1H).

Example 6

N-[7-(2,4-Dimethoxyphenyl)-2-ethylpyrazolo[1,5-a]pyridin-3-yl]-N,N-dipropylamine (Light Yellow Oil)
¹H NMR (400 MHz, CDCl₃) δ 0.87 (t, J=7.6 Hz, 6H), 1.24 (t, J=7.6 Hz, 3H), 1.34-1.44 (m, 4H), 2.75 (q, J=7.6 Hz, 2H), 3.01 (t, J=7.6 Hz, 4H), 3.75 (s, 3H), 3.87 (s, 3H), 6.58-6.62 (m, 3H), 6.98 (dd, J=6.8, 9.2 Hz, 1H), 7.42 (dd, J=1.6, 8.8 Hz, 1H), 7.49 (d, J=9.2 Hz, 1H).

Example 7

N-[2-Ethyl-7-(4-methoxy-2-methylphenyl)pyrazolo[1,5-a]pyridin-3-yl]-N,N-dipropylamine (Light Yellow Oil)
¹H NMR (400 MHz, CDCl₃) δ 0.88 (t, J=7.6 Hz, 6H), 1.23 (t, J=7.6 Hz, 3H), 1.34-1.44 (m, 4H), 2.10 (s, 3H), 2.75 (q, J=7.6 Hz, 2H), 3.01 (t, J=7.6 Hz, 4H), 3.86 (s, 3H), 6.49 (dd, J=1.6, 6.8 Hz, 1H), 6.82 (dd, J=2.8, 8.4 Hz, 1H), 6.86 (d, J=2.8 Hz, 1H), 6.99 (dd, J=6.8, 8.8 Hz, 1H), 7.32 (d, J=8.4 Hz, 1H), 7.45 (dd, J=1.6, 8.8 Hz, 1H).

Example 8

N,N-Dicyclopropylmethyl-N-[2-ethyl-7-(2-methoxy-4,6-dimethylphenyl)pyrazolo[1,5-a]pyridin-3-yl]amine (Colorless Crystals)
¹H NMR (400 MHz, CDCl₃) δ −0.02-0.04 (m, 4H), 0.30-0.36 (m, 4H), 0.80-0.90 (m, 2H), 1.22 (t, J=7.6 Hz, 4H), 1.97 (s, 3H), 2.39 (s, 3H), 2.72-2.84 (m, 2H), 2.99 (d, J=6.4 Hz, 2H), 3.68 (s, 3H), 6.48 (dd, J=1.2, 6.8 Hz, 1H), 6.69 (s, 1H), 6.77 (s, 1H), 6.99 (dd, J=6.8, 8.8 Hz, 1H), 7.46 (dd, J=1.2, 8.8 Hz, 1H).

Example 9

N,N-Dicyclopropylmethyl-N-[2-ethyl-7-(4-methoxy-2-methylphenyl)pyrazolo[1,5-a]pyridin-3-yl]amine (Yellow Oil)
¹H NMR (400 MHz, CDCl₃) δ −0.02-0.06 (m, 4H), 0.30-0.38 (m, 4H), 0.78-0.90 (m, 2H), 1.26 (t, J=7.5 Hz, 3H), 2.08 (s, 3H), 2.81 (q, J=7.5 Hz, 2H), 3.00 (d, J=6.6 Hz, 4H), 3.86 (s, 3H), 6.49 (dd, J=1.4, 6.7 Hz, 1H), 6.80-6.90 (m, 2H), 6.99 (dd, J=6.8, 9.0 Hz, 1H), 7.34 (d, J=8.2 Hz, 1H), 7.48 (dd, J=1.4, 8.9 Hz, 1H).

MS (ESI) m/z 390 MH⁺

Example 10

N-[7-(4-Chloro-2-methoxyphenyl)-2-ethylpyrazolo[1,5-a]pyridin-3-yl]-N,N-dicyclopropylmethylamine (Yellow Oil)
¹H NMR (400 MHz, CDCl₃) δ −0.02-0.06 (m, 4H), 0.30-0.37 (m, 4H), 0.76-0.88 (m, 2H), 1.25 (t, J=7.5 Hz, 3H), 2.79 (q, J=7.5 Hz, 2H), 2.98 (d, J=6.6 Hz, 4H), 3.75 (s, 3H), 6.57 (dd, J=1.3, 6.8 Hz, 1H), 6.97 (dd, J=6.8, 8.8 Hz, 1H), 7.01 (d, J=2.0 Hz, 1H), 7.05 (dd, J=2.0, 8.1 Hz, 1H), 7.46 (d, J=1.6 Hz, 1H), 7.48 (d, J=1.3 Hz, 1H).

MS (ESI) m/z 410 MH⁺

Example 11

N,N-Dicyclopropylmethyl-N-[2-ethyl-7-(4-methoxy-2,6-dimethylphenyl)pyrazolo[1,5-a]pyridin-3-yl]amine (Yellow Crystals)
¹H NMR (400 MHz, CDCl₃) δ −0.02-0.06 (m, 4H), 0.30-0.40 (m, 4H), 0.81-0.94 (m, 2H), 1.24 (t, J=7.5 Hz, 3H), 2.04 (s, 6H), 2.81 (q, J=7.5 Hz, 2H), 3.03 (d, J=6.6 Hz, 4H), 3.87 (s, 3H), 6.45 (dd, J=1.5, 6.8 Hz, 1H), 6.73 (s, 2H), 7.02 (dd, J=6.8, 8.8 Hz, 1H), 7.49 (dd, J=1.4, 8.9 Hz, 1H).

MS (ESI) m/z 404 MH⁺

Example 12

N,N-Dicyclopropylmethyl-N-[7-(2,6-dimethoxy-4-methylphenyl)-2-ethylpyrazolo[1,5-a]pyridin-3-yl]amine (Yellow Oil)
¹H NMR (400 MHz, CDCl₃) δ 0.00-0.04 (m, 4H), 0.30-0.36 (m, 4H), 0.80-0.90 (m, 2H), 1.23 (t, J=7.6 Hz, 3H), 2.43 (s, 3H), 2.78 (q, J=7.6 Hz, 2H), 2.98 (d, J=6.8 Hz, 4H), 3.69 (s, 6H), 6.51 (s, 2H), 6.56 (dd, J=1.6, 6.8 Hz, 1H), 6.98 (dd, J=6.8, 8.8 Hz, 1H), 7.44 (dd, J=1.6, 8.8 Hz, 1H).

Example 13

N,N-Dicyclopropylmethyl-N-[7-(2,4-dimethoxy-6-methylphenyl)-2-ethylpyrazolo[1,5-a]pyridin-3-yl]amine (Colorless Crystals)

$^1$H NMR (400 MHz, CDCl$_3$) δ −0.02-−0.03 (m, 2H), 0.29-0.35 (m, 2H), 0.80-0.90 (m, 1H), 1.23 (t, J=7.6 Hz, 3H), 2.00 (s, 3H), 2.74-2.84 (m, 2H), 2.99 (d, J=6.4 Hz, 2H), 3.67 (s, 3H), 3.86 (s, 3H), 6.44 (d, J=2.0 Hz, 1H), 6.47-6.50 (m, 2H), 6.98 (dd, J=6.8, 8.8 Hz, 1H), 7.45 (dd, J=1.6, 8.8 Hz, 1H).

Example 14

N,N-Dicyclopropylmethyl-N-[2-ethyl-7-(2,4,6-trimethoxyphenyl)pyrazolo[1,5-a]pyridin-3-yl]amine (Light Yellow Crystals)

$^1$H NMR (400 MHz, CDCl$_3$) δ 0.00-0.04 (m, 4H), 0.30-0.36 (m, 4H), 0.80-0.90 (m, 2H), 1.23 (t, J=7.6 Hz, 3H), 2.79 (q, J=7.6 Hz, 2H), 2.99 (d, J=6.8 Hz, 4H), 3.69 (s, 6H), 3.88 (s, 3H), 6.25 (s, 2H), 6.55 (dd, J=1.6, 6.8 Hz, 1H), 6.98 (dd, J=6.8, 8.8 Hz, 1H), 7.43 (dd, J=1.6, 8.8 Hz, 1H).

Example 15

N,N-Dicyclopropylmethyl-N-[7-(2,4-dimethoxyphenyl)-2-ethylpyrazolo[1,5-a]pyridin-3-yl]amine (Yellow Oil)

$^1$H NMR (400 MHz, CDCl$_3$) δ 0.00-0.05 (m, 4H), 0.32-0.38 (m, 4H), 0.80-0.90 (m, 2H), 1.26 (t, J=7.6 Hz, 3H), 2.80 (q, J=7.6 Hz, 2H), 2.98 (d, J=6.8 Hz, 4H), 3.74 (s, 3H), 3.87 (s, 3H), 6.57-6.63 (m, 3H), 6.97 (dd, J=6.8, 8.8 Hz, 1H), 7.44 (dd, J=1.6, 8.8 Hz, 1H), 7.48 (dd, J=1.2, 7.6 Hz, 1H).

Example 16

N,N-Dicyclopropylmethyl-N-[2-ethyl-7-(2-methoxy-4-methylphenyl)pyrazolo[1,5-a]pyridin-3-yl]amine (Yellow Oil)

$^1$H NMR (400 MHz, CDCl$_3$) δ 0.00-0.05 (m, 4H), 0.32-0.38 (m, 4H), 0.80-0.90 (m, 2H), 1.26 (t, J=7.6 Hz, 3H), 2.43 (s, 3H), 2.80 (q, J=7.6 Hz, 2H), 2.99 (d, J=6.8 Hz, 4H), 3.75 (s, 3H), 6.59 (dd, J=0.8, 6.8 Hz, 1H), 6.86 (s, 1H), 6.89 (br d, J=7.6 Hz, 1H), 6.98 (dd, J=6.8, 8.8 Hz, 1H), 7.41 (d, J=7.6 Hz, 1H), 7.45 (dd, J=0.8, 8.8 Hz, 1H).

Example 17

N,N-Dicyclopropylmethyl-N-[2-ethyl-7-(2-methoxy-4-trifluoromethylphenyl)pyrazolo[1,5-a]pyridin-3-yl]amine (Yellow Oil)

$^1$H NMR (400 MHz, CDCl$_3$) δ 0.01-0.06 (m, 4H), 0.32-0.37 (m, 4H), 0.78-0.80 (m, 2H), 1.26 (t, J=7.6 Hz, 3H), 2.80 (q, J=7.6 Hz, 2H), 2.99 (d, J=6.8 Hz, 4H), 3.81 (s, 3H), 6.61 (dd, J=1.2, 6.8 Hz, 1H), 7.00 (dd, J=6.8, 8.8 Hz, 1H), 7.24 (br s, 1H), 7.34 (br d J=7.6 Hz, 1H), 7.51 (dd, J=1.2, 8.8 Hz, 1H), 7.65 (d, J=7.6 Hz, 1H).

Example 18

N-[7-(4-Chloro-2,6-dimethoxyphenyl)-2-ethylpyrazolo[1,5-a]pyridin-3-yl]-N,N-dicyclopropylmethylamine (Yellow Oil)

$^1$H NMR (400 MHz, CDCl$_3$) δ −0.02-0.06 (m, 4H), 0.30-0.38 (m, 4H), 0.78-0.91 (m, 2H), 1.23 (t, J=7.5 Hz, 3H), 2.79 (q, J=7.5 Hz, 2H), 2.99 (d, J=6.6 Hz, 4H), 3.70 (s, 6H), 6.54 (dd, J=1.5, 6.8 Hz, 1H), 6.69 (s, 2H), 6.98 (dd, J=6.8, 8.8 Hz, 1H), 7.46 (dd, J=1.5, 8.8 Hz, 1H).

MS (ESI) m/z 440 MH$^+$

Example 19

N-[7-(2-Chloro-4-methoxyphenyl)-2-ethylpyrazolo[1,5-a]pyridin-3-yl]-N,N-dicyclopropylmethylamine (Yellow Oil)

$^1$H NMR (400 MHz, CDCl$_3$) δ −0.02-0.06 (m, 4H), 0.30-0.38 (m, 4H), 0.77-0.90 (m, 2H), 1.26 (t, J=7.5 Hz, 3H), 2.80 (q, J=7.5 Hz, 2H), 2.99 (d, J=6.6 Hz, 4H), 3.86 (s, 3H), 6.55 (dd, J=1.3, 6.8 Hz, 1H), 6.92 (dd, J=2.6, 8.6 Hz, 1H), 6.99 (dd, J=6.8, 9.0 Hz, 1H), 7.06 (d, J=2.4 Hz, 1H), 7.47 (d, J=8.4 Hz, 1H), 7.49 (dd, J=1.3, 8.8 Hz, 1H).

MS (ESI) m/z 410 MH$^+$

Example 20

N,N-Dicyclopropylmethyl-N-[7-(2,4-dichloro-6-methoxyphenyl)-2-ethylpyrazolo[1,5-a]pyridin-3-yl]amine (White Crystals)

$^1$H NMR (400 MHz, CDCl$_3$) δ −0.02-0.06 (m, 4H), 0.30-0.40 (m, 4H), 0.79-0.92 (m, 2H), 1.24 (t, J=7.5 Hz, 3H), 2.80 (dq, J=2.2, 7.5 Hz, 2H), 3.00 (d, J=6.8 Hz, 4H), 3.72 (s, 3H), 6.55 (dd, J=1.5, 6.8 Hz, 1H), 6.94 (d, J=1.8 Hz, 1H), 7.01 (dd, J=6.8, 8.8 Hz, 1H), 7.17 (d, J=1.8 Hz, 1H), 7.52 (dd, J=1.4, 8.9 Hz, 1H).

MS (ESI) m/z 444 MH$^+$

Example 21

N,N-Dicyclopropylmethyl-N-[2-ethyl-7-(4-methoxy-2-trifluoromethylphenyl)pyrazolo[1,5-a]pyridin-3-yl]amine (Yellow Oil)

$^1$H NMR (400 MHz, CDCl$_3$) δ −0.03-0.03 (m, 4H), 0.30-0.36 (m, 4H), 0.78-0.86 (m, 2H), 1.21 (t, J=7.6 Hz, 3H), 2.70-2.82 (m, 2H, 2.98 (d, J=6.4 Hz, 4H), 3.91 (s, 3H), 6.49 (d, J=6.0 Hz, 1H), 6.98 (dd, J=6.8, 8.8 Hz, 1H), 7.16 (dd, J=2.8, 8.8 Hz, 1H), 7.26-7.32 (m, 1H), 7.45-7.51 (m, 2H).

Example 22

N-[7-(2-Chloro-6-methoxy-4-methylphenyl)-2-ethylpyrazolo[1,5-a]pyridin-3-yl]-N,N-dicyclopropylmethylamine (Light Yellow Crystals)
$^1$H NMR (400 MHz, CDCl$_3$) δ 0.00-0.04 (m, 4H), 0.32-0.36 (m, 4H), 0.80-0.92 (m, 2H), 1.23 (t, J=8.0 Hz, 3H), 2.42 (s, 3H), 2.76-2.84 (m, 2H), 3.00 (d, J=6.4 Hz, 4H), 3.70 (s, 3H), 6.55 (dd, J=1.6, 6.8 Hz, 1H), 6.76 (br s, 1H), 6.98 (br s, 1H), 7.01 (dd, J=6.8, 8.8 Hz, 1H), 7.50 (dd, J=1.6, 8.8 Hz, 1H).

Example 23

N-[7-(2,4-Dichlorophenyl)-2-ethylpyrazolo[1,5-a]pyridin-3-yl]-N-(3-hexyl)amine

After dissolving [7-(2,4-dichlorophenyl)-2-ethylpyrazolo[1,5-a]pyridin-3-yl]amine (30 mg) in acetic acid (1 mL), 3-hexanone (0.024 mL) and sodium sulfate (139 mg) were added and the mixture was stirred at room temperature for 30 minutes. Sodium triacetoxyborohydride (41.5 mg) was then added, and stirring was continued for 2 hours. Water was added to the reaction mixture, extraction was performed with ethyl acetate and the extract washed with saturated aqueous sodium hydrogencarbonate and brine. After drying the obtained organic layer over anhydrous magnesium sulfate and filtering it, the solvent was concentrated under reduced pressure, the residue was purified by silica gel column chromatography, and the title compound (21 mg) was obtained from the n-hexane:ethyl acetate (30:1) fraction as a yellow oil.

$^1$H NMR (400 MHz, CDCl$_3$) δ 0.86-0.93 (m, 3H), 0.97 (t, J=7.6 Hz, 3H), 1.22-1.30 (m, 5H), 1.40-1.54 (m, 4H), 2.72-2.80 (m, 2H), 2.94-3.02 (m, 1H), 6.54-6.60 (m, 1H), 6.98-7.06 (m, 1H), 7.25-7.27 (m, 1H), 7.36 (dd, J=2.0, 8.4 Hz, 1H), 7.48 (d, J=8.4 Hz, 1H), 7.54 (d, J=2.0 Hz, 1H).

Example 24

N-[7-(2,4-Dichlorophenyl)-2-ethylpyrazolo[1,5-a]pyridin-3-yl]-N-(2-methoxyethyl)amine After dissolving tert-butyl N-[7-(2,4-dichlorophenyl)-2-ethylpyrazolo[1,5-a]pyridin-3-yl]carbamate (57 mg) in N,N-dimethylformamide (2 mL), sodium hydride (60%, 7.3 mg) was added while cooling on ice, and then 2-bromoethyl methyl ether (0.015 mL) was added and the mixture was stirred for 1 hour. Water was added to the reaction mixture, extraction was performed with ethyl acetate and the extract washed with brine. The obtained organic layer was dried over anhydrous magnesium sulfate and filtered, and then the solvent was concentrated under reduced pressure to obtain a crude product. This was dissolved in ethyl acetate (1 mL) without purification, a 4 N hydrochloric acid/ethyl acetate solution (2 mL) was added, and the mixture was stirred at room temperature for 1 hour. The reaction mixture was neutralized with 5 N aqueous sodium hydroxide while cooling on ice, and then extraction was performed with ethyl acetate and the organic layer washed with water and brine. After drying over anhydrous magnesium sulfate and filtration, the solvent was concentrated under reduced pressure, the residue was purified by silica gel column chromatography, and the title compound (46 mg) was obtained from the n-hexane:ethyl acetate (5:1) fraction as a yellow oil.

$^1$H NMR (400 MHz, CDCl$_3$) δ 1.26 (t, J=7.6 Hz, 3H), 2.77 (q, J=7.6 Hz, 2H), 3.25 (t, J=4.8 Hz, 2H), 3.41 (s, 3H), 3.50 (t, J=4.8 Hz, 2H), 6.57 (dd, J=1.6, 6.8 Hz, 1H), 7.03 (dd, J=6.8, 8.8 Hz, 1H), 7.37 (dd, J=2.0, 8.4 Hz, 1H), 7.47 (d, J=8.4 Hz, 1H), 7.50-7.53 (m, 1H), 7.54 (d, J=2.0 Hz, 1H).

Example 25

N-[7-(2,4-Dichlorophenyl)-2-ethylpyrazolo[1,5-a]pyridin-3-yl]-N-(2-methoxyethyl)-N-propylamine N-[7-(2,4-Dichlorophenyl)-2-ethylpyrazolo[1,5-a]pyridin-3-yl]-N-(2-methoxyethyl)amine (14 mg) was dissolved in tetrahydrofuran (1 mL), and after adding propionaldehyde (0.016 mL) and 3 M aqueous sulfuric acid (0.77 mL), sodium borohydride (5.8 mg) was added in five portions while vigorously stirring on ice, and stirring was continued for 30 minutes. Water was added to the reaction mixture, extraction was performed with diethyl ether and the extract washed with saturated aqueous sodium hydrogencarbonate and brine. After drying over anhydrous magnesium sulfate and filtration, the solvent was concentrated under reduced pressure and the residue was purified by preparative TLC [n-hexane:ethyl acetate (5:1), Rf=0.5] to obtain the title compound (9.5 mg) as a light yellow oil.

$^1$H NMR (400 MHz, CDCl$_3$) δ 0.87 (t, J=7.6 Hz, 3H), 1.23 (t, J=7.6 Hz, 3H), 1.34-1.44 (m, 2H), 2.75 (q, J=7.6 Hz, 2H), 3.08 (dd, J=6.4, 7.2 Hz, 2H), 3.28 (t, J=6.0 Hz, 2H), 3.29 (s, 3H), 3.35 (t, J=6.0 Hz, 2H), 6.59 (dd, J=1.6, 6.8 Hz, 1H), 7.03 (dd, J=6.8, 8.8 Hz, 1H), 7.37 (dd, J=2.0, 8.4 Hz, 1H), 7.50 (d, J=8.4 Hz, 1H), 7.52 (dd, J=1.6, 8.8 Hz, 1H), 7.54 (d, J=2.0 Hz, 1H).

The compounds of Examples 26 to 39 were synthesized according to the production method of Example 25.

Example 26

N-Cyclopropylmethyl-N-[7-(2,4-dichlorophenyl)-2-ethylpyrazolo[1,5-a]pyridin-3-yl]-N-(2-methoxyethyl)amine (Light Yellow Oil)
$^1$H NMR (400 MHz, CDCl$_3$) δ 0.01-0.03 (m, 2H), 0.34-0.38 (m, 2H), 0.80-0.90 (m, 1H), 1.25 (t, J=7.6 Hz, 3H), 2.77 (q, J=7.6 Hz, 2H), 2.98 (d, J=6.4 Hz, 2H), 3.29 (s, 3H), 3.37 (br s, 4H), 6.58 (dd, J=1.6, 6.8 Hz, 1H), 7.03 (dd, J=6.8, 9.2 Hz, 1H), 7.38 (dd, J=2.0, 8.4 Hz, 1H), 7.50 (d, J=8.4 Hz, 1H), 7.53 (dd, J=1.6, 9.2 Hz, 1H), 7.55 (d, J=2.0 Hz, 1H).

Example 27

N-[7-(2,4-Dichlorophenyl)-2-ethylpyrazolo[1,5-a]pyridin-3-yl]-N-isobutyl-N-(2-methoxyethyl)amine (Light Yellow Oil)
$^1$H NMR (400 MHz, CDCl$_3$) δ 0.91 (d, J=6.8 Hz, 6H), 1.24 (t, J=7.6 Hz, 3H), 1.52-1.62 (m, 1H), 2.76 (q, J=7.6 Hz, 2H), 2.92 (d, J=7.2 Hz, 2H), 3.23 (t, J=6.0 Hz, 2H), 3.29 (s, 3H), 3.37 (t, J=6.0 Hz, 2H), 6.57-6.60 (m, 1H), 7.04 (dd, J=6.8, 8.8 Hz, 1H), 7.37 (dd, J=2.0, 8.4 Hz, 1H), 7.50 (d, J=8.4 Hz, 1H), 7.52-7.55 (m, 1H), 7.54 (d, J=2.0 Hz, 1H).

Example 28

N-[2-Ethyl-7-(2-methoxy-4,6-dimethylphenyl)pyrazolo[1,5-a]pyridin-3-yl]-N-isobutyl-N-(2-methoxyethyl)amine (Light Yellow Oil)
$^1$H NMR (400 MHz, CDCl$_3$) δ 0.85-0.95 (m, 6H), 1.16-1.26 (m, 3H), 1.52-1.62 (m, 1H), 1.97 (s, 3H), 2.39 (s, 3H), 2.70-2.80 (m, 2H), 2.87-2.95 (m, 2H), 3.20-3.40 (m, 4H), 3.68 (s, 3H), 6.47-6.54 (m, 1H), 6.69 (s, 1H), 6.77 (s, 1H), 6.98-7.06 (m, 1H), 7.42-7.50 (m, 1H).

Example 29

N-[2-Ethyl-7-(2-methoxy-4,6-dimethylphenyl)pyrazolo[1,5-a]pyridin-3-yl]-N-isobutyl-N-(2-methoxyethyl)amine (Light Yellow Oil)
MS (ESI) m/z 396 MH$^+$

Example 30

N-[2-Ethyl-7-(2-methoxy-4,6-dimethylphenyl)pyrazolo[1,5-a]pyridin-3-yl]-N-(3-fluoropropyl)-N-propylamine (Light Yellow Oil)
$^1$H NMR (400 MHz, CDCl$_3$) δ 0.88 (t, J=7.6 Hz, 3H), 1.20 (t, J=7.6 Hz, 3H), 1.38-1.46 (m, 2H), 1.68-1.82 (m, 2H), 1.98 (s, 3H), 2.39 (s, 3H), 2.73 (q, J=7.6 Hz, 2H), 3.00-3.05 (m, 2H), 3.22 (t, J=6.8 Hz, 2H), 3.68 (s, 3H), 4.52 (td, J=6.0, 47.6 Hz, 2H), 6.52 (dd, J=1.6, 6.8 Hz, 1H), 6.69 (s, 1H). 6.77 (s, 1H), 7.02 (dd, J=6.8, 8.8 Hz, 1H), 7.42 (dd, J=1.6, 8.8 Hz, 1H).

Example 31

N-[2-Ethyl-7-(2-methoxy-4,6-dimethylphenyl)pyrazolo[1,5-a]pyridin-3-yl]-N-propyl-N-tetrahydro-2-furanylmethylamine (Light Yellow Oil)
MS (ESI) m/z 422 MH$^+$

Example 32

N-Cyclopropylmethyl-N-[2-ethyl-7-(2-methoxy-4,6-dimethylphenyl)pyrazolo[1,5-a]pyridin-3-yl]-N-propylamine (Light Yellow Oil)
MS (ESI) m/z 392 MH$^+$

Example 33

N-Cyclopropylmethyl-N-[2-ethyl-7-(2-methoxy-4,6-dimethylphenyl)pyrazolo[1,5-a]pyridin-3-yl]-N-(2-methoxyethyl)amine (Light Yellow Oil)
MS (ESI) m/z 408 MH$^+$

Example 34

N-Cyclopropylmethyl-N-[2-ethyl-7-(2-methoxy-4,6-dimethylphenyl)pyrazolo[1,5-a]pyridin-3-yl]-N-(3-fluoropropyl)amine (Light Yellow Oil)
$^1$H NMR (400 MHz, CDCl$_3$) δ −0.02-0.02 (m, 2H), 0.32-0.38 (m, 2H), 0.80-0.90 (m, 2H), 1.20 (t, J=7.6 Hz, 3H), 1.70-1.82 (m, 2H), 1.97 (s, 3H), 2.39 (s, 3H), 2.74 (q, J=7.6 Hz, 2H), 2.92 (d, J=6.8 Hz, 2H), 3.30 (t, J=6.8 Hz, 2H), 3.68 (s, 3H), 4.55 (td, J=6.0, 47.2 Hz, 2H), 6.51 (dd, J=1.2, 6.8 Hz, 1H), 6.69 (s, 1H). 6.77 (s, 1H), 7.02 (dd, J=6.8, 8.8 Hz, 1H), 7.44 (dd, J=1.2, 8.8 Hz, 1H).

Example 35

N-Cyclopropylmethyl-N-[2-ethyl-7-(2-methoxy-4,6-dimethylphenyl)pyrazolo[1,5-a]pyridin-3-yl]-N-tetrahydro-2-furanylmethylamine (Light Yellow Oil)
MS (ESI) m/z 434 MH$^+$

Example 36

N-Cyclopropylmethyl-N-[2-ethyl-7-(2-methoxy-4,6-dimethylphenyl)pyrazolo[1,5-a]pyridin-3-yl]-N-tetrahydro-3-furanylmethylamine (Yellow Oil)
$^1$H NMR (400 MHz, CDCl$_3$) δ −0.02-0.03 (m, 2H), 0.33-0.40 (m, 2H), 0.80-0.90 (m, 1H), 1.21 (t, J=7.2 Hz, 3H), 1.60-1.70 (m, 1H), 1.88-1.98 (m, 1H), 1.99 (s, 3H), 2.23-2.32 (m, 1H), 2.40 (s, 3H), 2.76 (q, J=7.2 Hz, 2H), 2.92 (d, J=6.4 Hz, 2H), 3.06-3.13 (m, 1H), 3.21-3.28 (m, 1H), 3.60-3.65 (m, 1H), 3.66-3.72 (m, 4H), 3.73-3.86 (m, 2H), 6.52 (br d, J=6.8 Hz, 1H), 6.70 (s, 1H), 6.78 (s, 1H), 7.03 (dd, J=6.8, 8.8 Hz, 1H), 7.45 (br d, J=8.8 Hz, 1H).

Example 37

N-Cyclopropylmethyl-N-[7-(2,6-dimethoxy-4-methylphenyl)-2-ethylpyrazolo[1,5-a]pyridin-3-yl]-N-tetrahydro-3-furanylmethylamine (Yellow Oil)
$^1$H NMR (400 MHz, CDCl$_3$) δ −0.02-0.04 (m, 2H), 0.34-0.40 (m, 2H), 0.80-0.90 (m, 1H), 1.21 (t, J=7.2 Hz, 3H), 1.55-1.67 (m, 1H), 1.86-1.96 (m, 1H), 2.43 (s, 3H), 2.74 (q, J=7.2 Hz, 2H), 2.90 (d, J=6.8 Hz, 2H), 3.04-3.11 (m, 1H), 3.20-3.26 (m, 1H), 3.58-3.84 (m, 7H), 6.51 (s, 2H), 6.57-6.60 (m, 1H), 6.98-7.04 (m, 1H), 7.40-7.44 (m, 1H).

Example 38

N-Cyclopropylmethyl-N-[7-(2,6-dimethoxy-4-methylphenyl)-2-ethylpyrazolo[1,5-a]pyridin-3-yl]-N-tetrahydro-2-furanylmethylamine (Light Yellow Oil)
$^1$H NMR (400 MHz, CDCl$_3$) δ −0.01-0.04 (m, 2H), 0.32-0.38 (m, 2H), 0.80-0.90 (m, 1H), 1.22 (t, J=7.6 Hz, 3H), 1.62-1.70 (m, 1H), 1.75-1.95 (m, 3H), 2.43 (s, 3H), 2.77 (q, J=7.6 Hz, 2H), 2.96 (d, J=6.8 Hz, 2H), 3.03-3.10 (m, 1H), 3.40-3.46 (m, 1H), 3.64-3.72 (m, 4H), 3.80-3.90 (m, 2H), 6.51 (s, 2H), 6.57 (dd, J=1.2, 6.8 Hz, 1H), 7.00 (dd, J=6.8, 8.8 Hz, 1H), 7.46 (dd, J=1.2, 8.8 Hz, 1H).

Example 39

N-Cyclopropyl-N-[7-(2,6-dimethoxy-4-methylphenyl)-2-ethylpyrazolo[1,5-a]pyridin-3-yl]-N-(1,3-dioxolan-2-ylmethyl)amine (Yellow Oil)
$^1$H NMR (400 MHz, CDCl$_3$) δ −0.02-0.04 (m, 2H), 0.32-0.38 (m, 2H), 0.80-0.90 (m, 1H), 1.22 (t, J=7.6 Hz, 3H), 2.41 (s, 3H), 2.77 (q, J=7.6 Hz, 2H), 3.01 (d, J=7.2 Hz, 2H), 3.35 (d, J=4.4 Hz, 2H), 3.68 (s, 6H), 3.78-3.84 (m, 2H), 3.94-3.98 (m, 2H), 4.90 (t, J=4.4 Hz, 1H), 6.49 (s, 2H), 6.56 (dd, J=1.2, 6.8 Hz, 1H), 7.00 (dd, J=6.8, 8.8 Hz, 1H), 7.44 (dd, J=1.2, 8.8 Hz, 1H).

Example 40

N-Cyclopropylmethyl-N-[7-(2,4-dimethoxy-6-methylphenyl)-2-ethylpyrazolo[1,5-a]pyridin-3-yl]-N-tetrahydro-3-furanylmethylamine After dissolving N-(7-bromo-2-ethylpyrazolo[1,5-a]pyridin-3-yl)-N-cyclopropylmethyl-N-tetrahydro-3-furanylmethylamine (150 mg) in 1,2-dimethoxyethane (20 mL) and water (10 mL), 2,4-dimethoxy-6-methylphenylboric acid (155 mg), tetrakis(triphenylphosphine)palladium(0) complex (92 mg) and barium hydroxide octahydrate (250 mg) were added and the mixture was heated and stirred at 80° C. for 1 hour. Water was added to the reaction mixture, extraction was performed with ethyl acetate, the organic layer washed with brine, dried over anhydrous magnesium sulfate and filtered, and the solvent was concentrated under reduced pressure. The obtained residue was purified by silica gel column chromatography, and the title compound (88 mg) was obtained from the n-hexane:ethyl acetate (6:1) fraction as a yellow oil.
$^1$H NMR (400 MHz, CDCl$_3$) δ −0.02-0.04 (m, 2H), 0.32-0.41 (m, 2H), 0.80-0.92 (m, 1H), 1.23 (t, J=7.5 Hz, 3H), 1.58-1.70 (m, 1H), 1.87-2.00 (m, 1H), 2.02 (s, 3H), 2.22-2.34 (m, 1H), 2.76 (dq, J=1.8, 7.5 Hz, 2H), 2.92 (dd, J=1.7, 6.8 Hz, 2H), 3.06-3.14 (m, 1H), 3.20-3.29 (m, 1H), 3.60-3.65 (m, 1H), 3.66-3.88 (m, 3H), 3.68 (s, 3H), 3.87 (s, 3H), 6.45 (d, J=2.4 Hz, 1H), 6.49 (d, J=2.2 Hz, 1H), 6.52 (dd, J=0.9, 6.8 Hz, 1H), 7.03 (dd, J=6.8, 8.8 Hz, 1H), 7.42-7.48 (m, 1H).

The compounds of Examples 41 to 46 were synthesized according to the production method of Example 40.

Example 41

N-Cyclopropylmethyl-N-[2-ethyl-7-(4-methoxy-2,6-dimethylphenyl)pyrazolo[1,5-a]pyridin-3-yl]-N-tetrahydro-3-furanylmethylamine (Yellow Crystals)
$^1$H NMR (400 MHz, CDCl$_3$) δ −0.03-0.06 (m, 2H), 0.33-0.42 (m, 2H), 0.80-0.92 (m, 1H), 1.23 (t, J=7.5 Hz, 3H), 1.60-1.73 (m, 1H), 1.90-2.02 (m, 1H), 2.04 (s, 6H), 2.24-2.38 (m, 1H), 2.78 (q, J=7.5 Hz, 2H), 2.94 (d, J=6.8 Hz, 2H), 3.13 (dd, J=8.6, 12.0 Hz, 1H), 3.27 (dd, J=6.6, 12.0 Hz, 1H), 3.64 (dd, J=5.5, 8.6 Hz, 1H), 3.68-3.90 (m, 3H), 3.87 (s, 3H), 6.48 (dd, J=1.3, 6.6 Hz, 1H), 6.74 (s, 2H), 7.05 (dd, J=6.6, 8.8 Hz, 1H), 7.48 (dd, J=1.3, 8.8 Hz, 1H).

Example 42

N-[7-(4-Chloro-2-methoxyphenyl)-2-ethylpyrazolo[1,5-a]pyridin-3-yl]-N-cyclopropylmethyl-N-tetrahydro-3-furanylmethylamine (Light Brown Oil)
$^1$H NMR (400 MHz, CDCl$_3$) δ −0.02-0.06 (m, 2H), 0.34-0.42 (m, 2H), 0.78-0.90 (m, 1H), 1.25 (t, J=7.5 Hz, 3H), 1.58-1.69 (m, 1H), 1.85-1.96 (m, 1H), 2.18-2.32 (m, 1H), 2.76 (q, J=7.5 Hz, 2H), 2.90 (d, J=6.8 Hz, 2H), 3.08 (dd, J=8.6, 12.0 Hz, 1H), 3.23 (dd, J=6.8, 12.0 Hz, 1H), 3.58-3.86 (m, 4H), 3.76 (s, 3H), 6.61 (dd, J=1.3, 6.8 Hz, 1H), 6.98-7.04 (m, 2H), 7.06 (dd, J=1.9, 8.1 Hz, 1H), 7.45 (dd, J=1.3, 8.9 Hz, 1H), 7.46 (d, J=8.1 Hz, 1H).

Example 43

N-Cyclopropylmethyl-N-[2-ethyl-7-(2-[2-(fluoromethoxy)-4,6-dimethylbenzyl]oxy-4,6-dimethylphenyl)pyrazolo[1,5-a]pyridin-3-yl]-N-tetrahydro-3-furanylmethylamine (Yellow Oil)
$^1$H NMR (400 MHz, CDCl$_3$) δ −0.08-0.02 (m, 2H), 0.28-0.36 (m, 2H), 0.72-0.85 (m, 1H), 1.17 (t, J=7.5 Hz, 3H), 1.56-1.70 (m, 1H), 1.84-1.96 (m, 1H), 1.88 (s, 3H), 1.96 (s, 3H), 2.23 (s, 3H), 2.16-2.26 (m, 1H), 2.40 (s, 3H), 2.64-2.78 (m, 2H), 2.80-2.94 (m, 2H), 3.02-3.10 (m, 1H), 3.14-3.25 (m, 1H), 3.56-3.86 (m, 4H), 4.87 (d, J=11.0 Hz, 1H), 5.03 (d, J=11.0 Hz, 1H), 5.38 (s, 1H), 5.52 (s, 1H), 6.42 (dd, J=1.4, 6.9 Hz, 1H), 6.60 (s, 1H), 6.70 (s, 1H), 6.78 (s, 1H), 6.91 (s, 1H), 6.90-6.97 (m, 1H), 7.37 (dd, J=1.3, 8.8 Hz, 1H).

Example 44

N-[7-(2-Chloro-6-methoxy-4-methylphenyl)-2-ethylpyrazolo[1,5-a]pyridin-3-yl]-N-cyclopropylmethyl-N-tetrahydro-3-furanylmethylamine (Yellow Oil)
$^1$H NMR (400 MHz, CDCl$_3$) δ −0.02-0.06 (m, 2H), 0.32-0.42 (m, 2H), 0.78-0.92 (m, 1H), 1.22 (t, J=7.6 Hz, 3H), 1.58-1.70 (m, 1H), 1.86-1.98 (m, 1H), 2.22-2.34 (m, 1H), 2.42 (s, 3H), 2.70-2.82 (m, 2H), 2.91 (dd, J=1.6, 6.8 Hz, 2H), 3.04-3.14 (m, 1H), 3.24 (dd, J=6.7, 12.0 Hz, 1H), 3.59-3.87 (m, 4H), 3.70 (s, 3H), 6.58 (dd, J=1.3, 6.8 Hz, 1H), 6.75 (s, 1H), 6.98 (s, 1H), 7.04 (dd, J=6.8, 8.9 Hz, 1H), 7.44-7.51 (m, 1H).

Example 45

N-Cyclopropylmethyl-N-2-ethyl-7-[2-(fluoromethoxy)-4,6-dimethylphenyl]pyrazolo[1,5-a]pyridin-3-yl-N-tetrahydro-3-furanylmethylamine (Yellow Oil)
$^1$H NMR (400 MHz, CDCl$_3$) δ −0.03-0.08 (m, 2H), 0.33-0.44 (m, 2H), 0.80-0.94 (m, 1H), 1.23 (t, J=7.6 Hz, 3H), 1.60-1.74 (m, 1H), 1.89-2.01 (m, 1H), 2.08 (s, 3H), 2.22-2.36 (m, 1H), 2.43 (s, 3H), 2.72-2.83 (m, 2H), 2.93 (d, J=6.8 Hz, 2H), 3.08-3.16 (m, 1H), 3.22-3.31 (m, 1H), 3.58-3.92 (m, 4H), 5.32 (d, J=2.6 Hz, 0.5H), 5.45 (d, J=2.7 Hz, 0.5H), 5.54 (d, J=2.7 Hz, 0.5H), 5.68 (d, J=2.7 Hz, 0.5H), 6.56 (dd, J=1.3, 6.8 Hz, 1H), 6.97 (s, 1H), 7.01 (s, 1H), 7.07 (dd, J=6.8, 8.8 Hz, 1H), 7.49 (dd, J=1.3, 8.8 Hz, 1H).

Example 46

N-[7-(2,6-Dimethoxy-4-methylphenyl)-2-ethylpyrazolo[1,5-a]pyridin-3-yl]-N-propyl-N-tetrahydro-3-furanylmethylamine (Yellow Oil)

$^1$H NMR (400 MHz, CDCl$_3$) δ 0.88 (t, J=7.3 Hz, 3H), 1.21 (t, J=7.5 Hz, 3H), 1.34-1.46 (m, 2H), 1.54-1.68 (m, 1H), 1.85-1.96 (m, 1H), 2.18-2.32 (m, 1H), 2.43 (s, 3H), 2.73 (q, J=7.5 Hz, 2H), 2.94-3.05 (m, 3H), 3.14 (dd, J=6.6, 12.0 Hz, 1H), 3.58 (dd, J=5.5, 8.4 Hz, 1H), 3.62-3.85 (m, 3H), 3.69 (s, 6H), 6.51 (s, 2H), 6.59 (dd, J=1.5, 6.8 Hz, 1H), 7.01 (dd, J=6.8, 8.8 Hz, 1H), 7.40 (dd, J=1.3, 8.8 Hz, 1H).

MS (ESI) m/z 438 MH$^+$

Example 47

N-Cyclopropylmethyl-N-[2-ethyl-7-(2-methoxy-4,6-dimethylphenyl)pyrazolo[1,5-a]pyridin-3-yl]-N-tetrahydro-2H-4-pyranylmethylamine After dissolving N-cyclopropylmethyl-N-[2-ethyl-7-(2-methoxy-4,6-dimethylphenyl)pyrazolo[1,5-a]pyridin-3-yl] amine (255 mg) in tetrahydrofuran (2 mL), tetrahydro-2H-4-pyrancarbaldehyde (173 mg) [CAS No. 50675-18-8] and sodium triacetoxyborohydride (241 mg) were added, and the mixture was stirred at room temperature for 1 hour. Saturated aqueous sodium hydrogencarbonate was added to the reaction mixture, extraction was performed with ethyl acetate, and the extract washed with brine. After drying over anhydrous magnesium sulfate and filtration, the solvent was concentrated under reduced pressure, the residue was purified by silica gel column chromatography, and the title compound (134 mg) was obtained from the n-hexane:ethyl acetate (5:1) fraction as a yellow oil.

$^1$H NMR (400 MHz, CDCl$_3$) δ -0.04-0.00 (m, 2H), 0.31-0.35 (m, 2H), 0.76-0.88 (m, 1H), 1.20 (t, J=7.6 Hz, 3H), 1.24-1.34 (m, 2H), 1.54-1.65 (m, 1H), 1.72-1.80 (m, 2H), 1.98 (s, 3H), 2.39 (s, 3H), 2.74 (dq, J=1.6, 7.6 Hz, 2H), 2.88 (d, J=6.8 Hz, 2H), 3.04 (d, J=6.8 Hz, 2H), 3.31 (dt, J=2.0, 11.6 Hz, 2H), 3.68 (s, 3H), 3.92-3.98 (m, 2H), 6.51 (dd, J=1.6, 6.8 Hz, 1H), 6.69 (s, 1H), 6.77 (s, 1H), 7.01 (dd, J=6.8, 8.8 Hz, 1H), 7.44 (dd, J=1.6, 8.8 Hz, 1H).

The compounds of Examples 48 to 61 were synthesized according to the production method of Example 47.

Example 48

N-Cyclopropylmethyl-N-[2-ethyl-7-(4-methoxy-2,6-dimethylphenyl)pyrazolo[1,5-a]pyridin-3-yl]-N-tetrahydro-2H-4-pyranylamine (White Crystals)

$^1$H NMR (400 MHz, CDCl$_3$) δ -0.02-0.05 (m, 2H), 0.34-0.42 (m, 2H), 0.78-0.90 (m, 1H), 1.31 (t, J=7.5 Hz, 3H), 1.56-1.70 (m, 2H), 1.88-1.98 (m, 2H), 2.12 (s, 6H), 2.86 (q, J=7.5 Hz, 2H), 3.10 (d, J=6.8 Hz, 2H), 3.33-3.44 (m, 1H), 3.50 (dt, J=2.0, 12.0 Hz, 2H), 3.95 (s, 3H), 4.04-4.12 (m, 2H), 6.56 (dd, J=1.4, 6.7 Hz, 1H), 6.82 (s, 2H), 7.13 (dd, J=6.8, 8.8 Hz, 1H), 7.53 (dd, J=1.4, 8.8 Hz, 1H).

MS (ESI) m/z 434 MH$^+$

Example 49

N-[7-(4-Chloro-2,6-dimethoxyphenyl)-2-ethylpyrazolo[1,5-a]pyridin-3-yl]-N-cyclopropylmethyl-N-tetrahydro-2H-4-pyranylamine (Yellow Oil)

$^1$H NMR (400 MHz, CDCl$_3$) δ -0.02-0.06 (m, 2H), 0.30-0.40 (m, 2H), 0.75-0.88 (m, 1H), 1.29 (t, J=7.5 Hz, 3H), 1.51-1.64 (m, 2H), 1.83-1.92 (m, 2H), 2.83 (q, J=7.5 Hz, 2H), 3.05 (d, J=6.6 Hz, 2H), 3.26-3.38 (m, 1H), 3.44 (dt, J=2.0, 12.0 Hz, 2H), 3.77 (s, 6H), 3.98-4.06 (m, 2H), 6.64 (dd, J=1.4, 6.9 Hz, 1H), 6.76 (s, 2H), 7.08 (dd, J=6.9, 8.8 Hz, 1H), 7.48 (dd, J=1.4, 8.8 Hz, 1H).

MS (ESI) m/z 470 MH$^+$

Example 50

N-[2-Ethyl-7-(4-methoxy-2,6-dimethylphenyl)pyrazolo[1,5-a]pyridin-3-yl]-N-propyl-N-tetrahydro-2H-4-pyranylamine (White Crystals)

$^1$H NMR (400 MHz, CDCl$_3$) δ 0.85 (t, J=7.4 Hz, 3H), 1.19 (t, J=7.5 Hz, 3H), 1.25-1.38 (m, 2H), 1.46-1.60 (m, 2H), 1.74-1.83 (m, 2H), 2.01 (s, 6H), 2.72 (q, J=7.4 Hz, 2H), 3.08 (t, J=7.2 Hz, 2H), 3.11-3.22 (m, 1H), 3.37 (dt, J=2.0, 12.0 Hz, 2H), 3.84 (s, 3H), 3.92-4.00 (m, 2H), 6.45 (dd, J=1.4, 6.6 Hz, 1H), 6.70 (s, 2H), 7.02 (dd, J=6.8, 8.8 Hz, 1H), 7.41 (dd, J=1.4, 8.9 Hz, 1H).

MS (ESI) m/z 422 MH$^+$

Example 51

N-[7-(4-Chloro-2,6-dimethoxyphenyl)-2-ethylpyrazolo[1,5-a]pyridin-3-yl]-N-propyl-N-tetrahydro-2H-4-pyranylamine (Yellow Crystals)

$^1$H NMR (400 MHz, CDCl$_3$) δ 0.84 (t, J=7.3 Hz, 3H), 1.20 (t, J=7.5 Hz, 3H), 1.23-1.37 (m, 2H), 1.46-1.60 (m, 2H), 1.74-1.84 (m, 2H), 2.73 (q, J=7.5 Hz, 2H), 3.07 (t, J=7.3 Hz, 2H), 3.10-3.21 (m, 1H), 3.36 (dt, J=1.8, 12.0 Hz, 2H), 3.70 (s, 6H), 3.90-3.99 (m, 2H), 6.57 (dd, J=1.4, 6.9 Hz, 1H), 6.69 (s, 2H), 7.01 (dd, J=6.9, 8.9 Hz, 1H), 7.40 (dd, J=1.4, 8.9 Hz, 1H).

MS (ESI) m/z 458 MH$^+$

Example 52

N-Cyclopropylmethyl-N-[2-ethyl-7-(2-methoxy-4,6-dimethylphenyl)pyrazolo[1,5-a]pyridin-3-yl]-N-tetrahydro-2H-4-pyranylamine (Yellow Oil)

$^1$H NMR (400 MHz, CDCl$_3$) δ -0.10--0.04 (m, 2H), 0.24-0.32 (m, 2H), 0.70-0.80 (m, 1H), 1.21 (t, J=7.6 Hz, 3H), 1.46-1.60 (m, 2H), 1.76-1.84 (m, 2H), 1.97 (s, 3H), 2.40 (s, 3H), 2.70-2.80 (m, 2H), 2.98 (d, J=6.4 Hz, 2H), 3.22-3.30 (m, 1H), 3.34-3.42 (m, 2H), 3.68 (s, 3H), 3.92-3.99 (m, 2H), 6.51 (dd, J=1.2, 6.8 Hz, 1H), 6.69 (s, 1H), 6.77 (s, 1H), 7.02 (dd, J=6.8, 9.2 Hz, 1H), 7.40 (dd, J=1.2, 9.2 Hz, 1H).

Example 53

N-[2-Ethyl-7-(2-methoxy-4,6-dimethylphenyl)pyrazolo[1,5-a]pyridin-3-yl]-N-(3-fluoropropyl)-N-tetrahydro-2H-4-pyranylamine (Yellow Oil)

$^1$H NMR (400 MHz, CDCl$_3$) δ 1.19 (t, J=7.2 Hz, 3H), 1.48-1.60 (m, 2H), 1.60-1.74 (m, 2H), 1.76-1.84 (m, 2H), 1.97 (s, 3H), 2.40 (s, 3H), 2.68-2.76 (m, 2H), 3.12-3.20 (m, 1H), 3.29 (t, J=6.4 Hz, 2H), 3.36 (dt, J=1.6, 11.6 Hz, 2H), 3.69 (s, 3H), 3.94-4.00 (m, 2H), 4.51 (td, J=5.6, 47.6 Hz, 2H), 6.54 (dd, J=1.2, 6.8 Hz, 1H), 6.69 (s, 1H), 6.77 (s, 1H), 7.05 (dd, J=6.8, 8.8 Hz, 1H), 7.39 (dd, J=1.2, 8.8 Hz, 1H).

Example 54

[2-Ethyl-7-(2-methoxy-4,6-dimethylphenyl)pyrazolo[1,5-a]pyridin-3-yl]-N-(2-methoxyethyl)-N-tetrahydro-2H-4-pyranylamine (Yellow Oil)

$^1$H NMR (400 MHz, CDCl$_3$) δ 1.20 (t, J=7.6 Hz, 3H), 1.47-1.58 (m, 2H), 1.77-1.84 (m, 2H), 1.98 (s, 3H), 2.40 (s, 3H), 2.68-2.76 (m, 2H), 3.16-3.25 (m, 1H), 3.26 (s, 3H), 3.27-3.40 (m, 6H), 3.69 (s, 3H), 3.92-3.99 (m, 2H), 6.53 (dd, J=1.2, 6.8 Hz, 1H), 6.70 (s, 1H), 6.77 (s, 1H), 7.05 (dd, J=6.8, 8.8 Hz, 1H), 7.40 (dd, J=1.2, 8.8 Hz, 1H).

Example 55

N-Cyclopropylmethyl-N-[7-(2,6-dimethoxy-4-methylphenyl)-2-ethylpyrazolo[1,5-a]pyridin-3-yl]-N-tetrahydro-2H-4-pyranylamine (Yellow Oil)

$^1$H NMR (400 MHz, CDCl$_3$) δ −0.06--0.01 (m, 2H), 0.26-0.32 (m, 2H), 0.70-0.80 (m, 1H), 1.22 (t, J=7.6 Hz, 3H), 1.46-1.62 (m, 2H), 1.76-1.84 (m, 2H), 2.43 (s, 3H), 2.75 (q, J=7.6 Hz, 2H), 2.97 (d, J=6.8 Hz, 2H), 3.22-3.30 (m, 1H), 3.32-3.40 (m, 2H), 3.69 (s, 6H), 3.92-3.98 (m, 2H), 6.51 (s, 2H), 6.58 (dd, J=1.6, 6.8 Hz, 1H), 7.01 (dd, J=6.8, 8.8 Hz, 1H), 7.39 (dd, J=1.6, 8.8 Hz, 1H).

Example 56

N-[7-(2,6-Dimethoxy-4-methylphenyl)-2-ethylpyrazolo[1,5-a]pyridin-3-yl]-N-(3-fluoropropyl)-N-tetrahydro-2H-4-pyranylamine (Yellow Oil)

$^1$H NMR (400 MHz, CDCl$_3$) δ 1.20 (t, J=7.2 Hz, 3H), 1.49-1.60 (m, 2H), 1.61-1.74 (m, 2H), 1.77-1.84 (m, 2H), 2.43 (s, 3H), 2.72 (q, J=7.2 Hz, 2H), 3.12-3.20 (m, 1H), 3.28 (t, J=6.8 Hz, 2H), 3.36 (dt, J=2.0, 12.4 Hz, 2H), 3.70 (s, 6H), 3.93-3.99 (m, 2H), 4.50 (td, J=6.0, 47.2 Hz, 2H), 6.51 (s, 2H), 6.62 (dd, J=1.2, 6.8 Hz, 1H), 7.04 (dd, J=6.8, 8.8 Hz, 1H), 7.38 (dd, J=1.2, 8.8 Hz, 1H).

Example 57

N-[7-(2,6-Dimethoxy-4-methylphenyl)-2-ethylpyrazolo[1,5-a]pyridin-3-yl]-N-(2-methoxyethyl)-N-tetrahydro-2H-4-pyranylamine (Yellow Oil)

$^1$H NMR (400 MHz, CDCl$_3$) δ 1.21 (t, J=7.6 Hz, 3H), 1.47-1.59 (m, 2H), 1.77-1.84 (m, 2H), 2.43 (s, 3H), 2.72 (q, J=7.6 Hz, 2H), 3.15-3.24 (m, 1H), 3.26 (s, 3H), 3.27-3.40 (m, 6H), 3.70 (s, 3H), 3.92-3.98 (m, 2H), 6.51 (s, 2H), 6.61 (dd, J=1.6, 6.8 Hz, 1H), 7.04 (dd, J=6.8, 8.8 Hz, 1H), 7.38 (dd, J=1.6, 8.8 Hz, 1H).

Example 58

N-Cyclopropylmethyl-N-[7-(2,4-dimethoxy-6-methylphenyl)-2-ethylpyrazolo[1,5-a]pyridin-3-yl]-N-tetrahydro-2H-4-pyranylamine (Yellow Oil)

$^1$H NMR (400 MHz, CDCl$_3$) δ −0.10--0.01 (m, 2H), 0.23-0.32 (m, 2H), 0.70-0.80 (m, 1H), 1.22 (t, J=7.6 Hz, 3H), 1.46-1.58 (m, 2H), 1.77-1.85 (m, 2H), 2.00 (s, 3H), 2.68-2.82 (m, 2H), 2.98 (d, J=7.6 Hz, 2H), 3.22-3.31 (m, 1H), 3.38 (dt, J=2.0, 12.0 Hz, 2H), 3.68 (s, 3H), 3.86 (s, 3H), 3.73-4.00 (m, 2H), 6.44 (d, J=2.0 Hz, 1H), 6.48 (d, J=2.0 Hz, 1H), 6.51 (dd, J=1.2, 6.8 Hz, 1H), 7.01 (dd, J=6.8, 8.8 Hz, 1H), 7.40 (dd, J=1.2, 8.8 Hz, 1H).

Example 59

N-[7-(2,4-Dimethoxy-6-methylphenyl)-2-ethylpyrazolo[1,5-a]pyridin-3-yl]-N-(3-fluoropropyl)-N-tetrahydro-2H-4-pyranylamine (Yellow Oil)

$^1$H NMR (400 MHz, CDCl$_3$) δ 1.20 (t, J=7.6 Hz, 3H), 1.48-1.60 (m, 2H), 1.60-1.74 (m, 2H), 1.76-1.84 (m, 2H), 2.00 (s, 3H), 2.72 (q, J=7.6 Hz, 2H), 3.12-3.20 (m, 1H), 3.29 (t, J=6.8 Hz, 2H), 3.36 (dt, J=2.0, 12.0 Hz, 2H), 3.68 (s, 3H), 3.86 (s, 3H), 3.93-4.00 (m, 2H), 4.51 (td, J=6.0, 47.2 Hz, 2H), 6.44 (d, J=2.0 Hz, 1H), 6.48 (d, J=2.0 Hz, 1H), 6.54 (dd, J=1.6, 6.8 Hz, 1H), 7.04 (dd, J=6.8, 8.8 Hz, 1H), 7.38 (dd, J=1.6, 8.8 Hz, 1H).

Example 60

N-Cyclopropylmethyl-N-[2-ethyl-7-(2-methoxy-4,6-dimethylphenyl)pyrazolo[1,5-a]pyridin-3-yl]-N-tetrahydro-2H-3-pyranylamine (Yellow Oil)

$^1$H NMR (400 MHz, CDCl$_3$) δ −0.02-0.06 (m, 2H), 0.32-0.42 (m, 2H), 0.78-0.88 (m, 1H), 1.30 (t, J=7.6 Hz, 3H), 1.30-1.44 (m, 1H), 1.66-1.76 (m, 2H), 2.06 (s, 3H), 2.06-2.18 (m, 1H), 2.49 (s, 3H), 2.83 (q, J=7.6 Hz, 2H), 3.06 (d, J=6.8 Hz, 2H), 3.18-3.38 (m, 3H), 3.77 (s, 3H), 3.86-3.96 (m, 1H), 4.12-4.20 (m, 1H), 6.61 (dd, J=1.2, 6.8 Hz, 1H), 6.78 (s, 1H), 6.86 (s, 1H), 7.12 (dd, J=6.8, 8.8 Hz, 1H), 7.48 (dd, J=1.2, 8.8 Hz, 1H).

Example 61

N-Cyclopropylmethyl-N-[7-(2,6-dimethoxy-4-methylphenyl)-2-ethylpyrazolo[1,5-a]pyridin-3-yl]-N-tetrahydro-2H-4-pyranylmethylamine (Yellow Oil)

$^1$H NMR (400 MHz, CDCl$_3$) δ −0.01-0.03 (m, 2H), 0.34-0.40 (m, 2H), 0.80-0.90 (m, 1H), 1.23 (t, J=7.6 Hz, 3H), 1.20-1.34 (m, 2H), 1.56-1.62 (m, 1H), 1.74-1.80 (m, 2H), 2.45 (s, 3H), 2.77 (q, J=7.6 Hz, 2H), 2.89 (d, J=6.4 Hz, 2H), 3.06 (d, J=6.8 Hz, 2H), 3.32 (dt, J=2.0, 11.6 Hz, 2H), 3.71 (s, 6H), 3.92-3.98 (m, 2H), 6.53 (s, 2H), 6.60 (dd, J=1.2, 6.8 Hz, 1H), 7.01 (dd, J=6.8, 8.8 Hz, 1H), 7.45 (dd, J=1.2, 8.8 Hz, 1H).

Example 62

N,N-Dicyclopropylmethyl-N-[2-ethyl-4-methoxy-7-(2-methoxy-4,6-dimethylphenyl)pyrazolo[1,5-a]pyridin-3-yl]amine 2-Ethyl-4-methoxy-7-(2-methoxy-4,6-dimethylphenyl)-3-nitropyrazolo[1,5-a]pyridine (185 mg) was dissolved in a mixture of ethanol (7 mL) and water (7.5 mL), and then acetic acid (0.3 mL) and zinc powder (185 mg) were added and the reaction mixture was heated at 60° C. for 20 minutes. The reaction mixture was filtered with celite, and the obtained filtrate was concentrated under reduced pressure. Water was added, extraction was performed with ethyl acetate, the extract washed with saturated aqueous sodium hydrogencarbonate and brine and dried over magnesium sulfate, and the solvent was distilled off under reduced pressure to obtain 2-ethyl-4-methoxy-7-(2-methoxy-4,6-dimethylphenyl)pyrazolo[1,5-a]pyridin-3-amine as a crude product.

To a solution of the obtained crude 2-ethyl-4-methoxy-7-(2-methoxy-4,6-dimethylphenyl)pyrazolo[1,5-a]pyridin-3-amine in tetrahydrofuran (10 mL) there were added cyclopropanecarboxyaldehyde (0.20 mL) and 3 M sulfuric acid (0.87 mL), and then sodium borohydride (79 mg) was slowly added at 0° C. and the mixture was stirred at room temperature for 30 minutes. A 5 N aqueous sodium hydroxide solution was added while cooling on ice to make the reaction mixture basic, and then extraction was performed with ethyl acetate, the extract washed with saturated aqueous sodium hydrogencarbonate and brine and dried over magnesium sulfate, and the solvent was distilled off under reduced pressure. The residue was subjected to silica gel column chromatography (20 g), and the title compound (185 mg) was obtained from the n-hexane:ethyl acetate (6:1) fraction as white crystals.

$^1$H NMR (400 MHz, CDCl$_3$) δ −0.32-0.46 (m, 8H), 0.70-0.88 (m, 2H), 1.20 (t, J=7.5 Hz, 3H), 1.97 (s, 3H), 2.38 (s, 3H), 2.74-2.97 (m, 6H), 3.67 (s, 3H), 3.93 (s, 3H), 6.34 (d, J=7.7 Hz, 1H), 6.38 (d, J=7.7 Hz, 1H), 6.68 (s, 1H), 6.75 (s, 1H).

MS (ESI) m/z 434 MH$^+$

Example 63

N-[2-Ethyl-4-methoxy-7-(2-methoxy-4,6-dimethylphenyl)pyrazolo[1,5-a]pyridin-3-yl]-N-(1-ethylpropyl)amine To a solution of 2-ethyl-4-methoxy-7-(2-methoxy-4,6-dimethylphenyl)pyrazolo[1,5-a]pyridin-3-amine (100 mg) in acetic acid (10 mL) there was added 3-pentanone (0.04 mL), and then sodium triacetoxyborohydride (85.0 mg) was slowly added at room temperature and the mixture was stirred for 3 hours. A 5 N aqueous sodium hydroxide solution was added while cooling on ice, and then extraction was performed with ethyl acetate, the organic layer washed with saturated aqueous sodium hydrogencarbonate and brine and dried over magnesium sulfate, and the solvent was distilled off under reduced pressure. The obtained residue was subjected to silica gel column chromatography (10 g), and the title compound (69 mg) was obtained from the n-hexane:ethyl acetate (5:1) fraction as yellow crystals.

$^1$H NMR (400 MHz, CDCl$_3$) δ 0.94 (t, J=7.5 Hz, 3H), 0.96 (t, J=7.5 Hz, 3H), 1.21 (t, J=7.5 Hz, 3H), 1.42-1.55 (m, 4H), 1.98 (s, 3H), 2.38 (s, 3H), 2.70 (q, J=7.5 Hz, 2H), 2.87-2.96 (m, 1H), 3.67 (s, 3H), 3.92 (s, 3H), 6.20 (d, J=7.7 Hz, 1H), 6.28 (d, J=7.5 Hz, 1H), 6.67 (s, 1H), 6.74 (s, 1H).

MS (ESI) m/z 396 MH$^+$

Example 64 tert-Butyl N-[7-(2,4-dichlorophenyl)-2-methylthiopyrazolo[1,5-a]pyridin-3-yl]carbamate After dissolving tert-butyl N-[2-methylthiopyrazolo[1,5-a]pyridin-3-yl]carbamate (220 mg) in tetrahydrofuran (3 mL), a solution of n-butyllithium in hexane (1.6 M; 1.51 mL) was added dropwise at −78° C. under a nitrogen stream, and the mixture was stirred for 30 minutes. A solution of 1,2-dibromo-1,1,2,2-tetrachloroethane (384 mg) in tetrahydrofuran (2 mL) was added to the reaction mixture, and stirring was continued for 30 minutes. Saturated aqueous ammonium chloride was added to the reaction mixture, the temperature was raised to room temperature, extraction was performed with ethyl acetate and the extract washed with water and brine. After drying over anhydrous magnesium sulfate and filtration, the solvent was concentrated under reduced pressure, the residue was purified by silica gel column chromatography, and tert-butyl N-[7-bromo-2-methylthiopyrazolo[1,5-a]pyridin-3-yl]carbamate was obtained from the n-hexane:ethyl acetate (10:1) fraction as yellow crystals. After dissolving this in 1,2-dimethoxyethane (6 mL) and water (1 mL), 2,4-dichlorophenylboric acid (191 mg), tetrakis(triphenylphosphine)palladium(0) complex (116 mg) and barium hydroxide octahydrate (315 mg) were added and the mixture was heated and stirred at 80° C. for 4 hours under a nitrogen stream. Water was added to the reaction mixture, extraction was performed with ethyl acetate and the extract washed with brine. After drying over anhydrous magnesium sulfate and filtration, the solvent was concentrated under reduced pressure, the residue was purified by silica gel column chromatography, and the title compound (160 mg) was obtained from the n-hexane:ethyl acetate (20:1) fraction as a yellow oil.

$^1$H NMR (400 MHz, CDCl$_3$) δ 1.58 (s, 9H), 2.46 (s, 3H), 6.67 (m, 1H), 7.16 (dd, J=6.8, 8.8 Hz, 1H), 7.36 (dd, J=2.0, 8.4 Hz, 1H), 7.43 (d, J=8.4 Hz, 1H), 7.54 (d, J=2.0 Hz, 1H).

Example 65 tert-Butyl N-[7-(2-methoxy-4,6-dimethylphenyl)-2-(methylsulfanyl)pyrazolo[1,5-a]pyridin-3-yl]carbamate After dissolving tert-butyl N-[7-iodo-2-(methylsulfanyl)pyrazolo[1,5-a]pyridin-3-yl]carbamate (2.0 g) in 1,2-dimethoxyethane (60 mL) and water (30 mL), 4,6-dimethyl-2-methoxyphenylboric acid (1.33 g), tetrakis(triphenylphosphine)palladium(0) complex (865 mg) and barium hydroxide octahydrate (2.34 g) were added and the mixture was heated and stirred at 80° C. for 3 hours. Water was added to the reaction mixture, extraction was performed with ethyl acetate and the extract washed with brine. After drying over anhydrous magnesium sulfate and filtration, the solvent was concentrated under reduced pressure, the residue was purified by silica gel column chromatography, and the title compound (2.1 g) was obtained from the n-hexane:ethyl acetate (20:1) fraction as yellow amorphous.

¹H NMR (400 MHz, CDCl₃) δ 1.54 (br s, 9H), 1.98 (s, 3H), 2.39 (s, 3H), 2.42 (s, 3H), 3.64 (s, 3H), 6.02-6.12 (m, 1H), 6.58 (dd, J=1.6, 6.8 Hz, 1H), 7.13 (dd, J=6.8, 9.2 Hz, 1H), 7.42-7.48 (m, 1H).

Example 66

N-Cyclopropylmethyl-N-[7-(2-methoxy-4,6-dimethylphenyl)-2-(methylsulfanyl)pyrazolo[1,5-a]pyridin-3-yl]amine After dissolving tert-butyl N-[7-(2-methoxy-4,6-dimethylphenyl)-2-(methylsulfanyl)pyrazolo[1,5-a]pyridin-3-yl] carbamate (400 mg) in N,N-dimethylformamide (5 mL), sodium hydride (60%, 58 mg) was added while cooling on ice, and then (bromomethyl)cyclopropane (111 μL) was added and the mixture was stirred for 1 hour at 40° C. Water was added to the reaction mixture, extraction was performed with ethyl acetate and the extract washed with brine. After drying the obtained organic layer over anhydrous magnesium sulfate and filtering it, the solvent was concentrated under reduced pressure to obtain crude tert-butyl N-cyclopropylmethyl-N-[7-(2-methoxy-4,6-dimethylphenyl)-2-(methylsulfanyl)pyrazolo[1,5-a]pyridin-3-yl]carbamate. This was dissolved in ethyl acetate (10 mL) without purification, a 4 N hydrochloric acid/ethyl acetate solution (20 mL) was added, and the mixture was stirred at 40° C. for 1 hour. The reaction mixture was neutralized with 5 N aqueous sodium hydroxide while cooling on ice, and then extraction was performed with ethyl acetate and the organic layer was washed with brine. After drying over anhydrous magnesium sulfate and filtration, the solvent was distilled off under reduced pressure to obtain the title compound (368 mg) as a yellow oil.

¹H NMR (400 MHz, CDCl₃) δ 0.18-0.23 (m, 2H), 1.50-0.55 (m, 1H), 1.1.04-1.13 (m, 1H), 1.98 (s, 3H), 2.38 (s, 3H), 2.39 (s, 3H), 2.99 (d, J=6.8 Hz, 2H), 3.66 (s, 3H), 6.51 (dd, J=1.2, 6.8 Hz, 1H), 6.66 (br s, 1H), 6.74 (br s, 1H), 7.00 (dd, J=6.8, 8.8 Hz, 1H), 7.42 (dd, J=1.6, 8.8 Hz, 1H).

Example 67

N-[7-(2-Methoxy-4,6-dimethylphenyl)-2-(methylsulfanyl)pyrazolo[1,5-a]pyridin-3-yl]-N,N-dipropylamine tert-Butyl N-[7-(2-methoxy-4,6-dimethylphenyl)-2-(methylsulfanyl)pyrazolo[1,5-a]pyridin-3-yl]carbamate (50 mg) was dissolved in a 4 N hydrochloric acid/ethyl acetate solution (2 mL), and the mixture was stirred at room temperature for 1 hour. The reaction mixture was neutralized with 5 N aqueous sodium hydroxide and extracted with ethyl acetate, and the organic layer was concentrated to obtain 7-(2-methoxy-4,6-dimethylphenyl)-2-(methylsulfanyl)pyrazolo[1,5-a]pyridine-3-amine. This was dissolved in tetrahydrofuran (1 mL), and after adding propionaldehyde (0.078 mL) and 3 M aqueous sulfuric acid (0.363 mL), sodium borohydride (27 mg) was added in five portions at a time while vigorously stirring on ice, and stirring was continued for 30 minutes. After adding saturated aqueous sodium hydrogencarbonate to neutralize the reaction mixture, extraction was performed with ethyl acetate and the organic layer was concentrated. The residue was purified by silica gel column chromatography, and the title compound (20.6 mg) was obtained from the n-hexane:ethyl acetate (7:1) fraction as a light yellow oil.

¹H NMR (400 MHz, CDCl₃) δ 0.88 (t, J=7.6 Hz, 6H), 1.34-1.44 (m, 4H), 1.99 (s, 3H), 2.40 (s, 3H), 2.43 (s, 3H), 3.01-3.06 (m, 4H), 3.63 (s, 3H), 6.49 (dd, J=1.2, 6.8 Hz, 1H), 6.67 (s, 1H). 6.75 (s, 1H), 7.03 (dd, J=6.8, 8.8 Hz, 1H), 7.39 (dd, J=1.2, 8.8 Hz, 1H).

The compounds of Examples 68 to 101 were synthesized according to the production method of Example 67.

Example 68

N-[7-(2,6-Dimethoxy-4-methylphenyl)-2-(methylsulfanyl)pyrazolo[1,5-a]pyridin-3-yl]-N,N-dipropylamine (Light Yellow Oil)
¹H NMR (400 MHz, CDCl₃) δ 0.84-0.92 (m, 6H), 1.34-1.44 (m, 4H), 2.40-2.48 (m, 6H), 3.00-3.10 (m, 4H), 3.70 (s, 6H), 6.49 (s, 2H), 6.56-6.60 (m, 1H), 6.99-7.05 (m, 1H), 7.35-7.42 (m, 1H).

Example 69

N-[7-(2,6-Dimethoxy-3-pyridyl)-2-(methylsulfanyl)pyrazolo[1,5-a]pyridin-3-yl]-N,N-dipropylamine (Light Yellow Oil)
¹H NMR (400 MHz, CDCl₃) δ 0.88 (t, J=6.8 Hz, 6H), 1.33-1.42 (m, 4H), 2.50 (s, 3H), 2.95-3.06 (m, 4H), 3.93 (s, 3H), 3.99 (s, 3H), 6.42 (d, J=8.4 Hz, 1H), 6.67-6.74 (m, 1H), 6.98-7.06 (m, 1H), 7.34-7.42 (m, 1H), 7.98 (d, J=8.4 Hz, 1H).

Example 70

N-[7-(6-Methoxy-2-methyl-3-pyridyl)-2-(methylsulfanyl)pyrazolo[1,5-a]pyridin-3-yl]-N,N-dipropylamine (Light Yellow Oil)
¹H NMR (400 MHz, CDCl₃) δ 0.88 (t, J=7.2 Hz, 6H), 1.32-1.42 (m, 4H), 2.30 (s, 3H), 2.47 (s, 3H), 3.00-3.06 (m, 4H), 4.00 (s, 3H), 6.48 (d, J=6.8 Hz, 1H), 6.66 (d, J=8.4 Hz, 1H), 7.03 (dd, J=6.8, 8.4 Hz, 1H), 7.42 (d, J=8.4 Hz, 1H), 7.61 (d, J=8.4 Hz, 1H).

Example 71

N3,N3-Dipropyl-7-[6-(dimethylamino)-4-methyl-3-pyridyl]-2-(methylsulfanyl)pyrazolo[1,5-a]pyridin-3-amine (Light Yellow Oil)
¹H NMR (400 MHz, CDCl₃) δ 0.82 (t, J=7.6 Hz, 6H), 1.19-1.70 (m, 4H), 2.06 (s, 3H), 2.42 (s, 3H), 2.90-3.00 (m, 4H), 3.13 (s, 6H), 6.40-6.47 (m, 2H), 6.92-7.02 (m, 1H), 7.30-7.40 (m, 1H), 8.08 (s, 1H).
MS (ESI) m/z 398 MH⁺

Example 72

N,N-Dicyclopropylmethyl-N-[7-(2-methoxy-4,6-dimethylphenyl)-2-(methylsulfanyl)pyrazolo[1,5-a] pyridin-3-yl]amine (Light Yellow Oil)
¹H NMR (400 MHz, CDCl₃) δ 0.00-0.04 (m, 4H), 0.28-0.34 (m, 4H), 0.80-0.90 (m, 2H), 1.99 (s, 3H), 2.40 (s, 3H), 2.44 (s, 3H), 2.97-3.04 (m, 4H), 3.68 (s, 3H), 6.49 (dd, J=1.2, 6.8 Hz, 1H), 6.67 (s, 1H). 6.76 (s, 1H), 7.03 (dd, J=6.8, 8.8 Hz, 1H), 7.46 (dd, J=1.2, 8.8 Hz, 1H).

Example 73

N,N-Diisobutyl-N-[7-(2-methoxy-4,6-dimethylphenyl)-2-(methylsulfanyl)pyrazolo[1,5-a]pyridin-3-yl]amine (Light Yellow Oil)
MS (ESI) m/z 426 MH+

Example 74

N-[7-(2,4-Dimethoxy-6-methylphenyl)-2-(methylsulfanyl)pyrazolo[1,5-a]pyridin-3-yl]-N,N-dipropylamine (Light Yellow Oil)
$^1$H NMR (400 MHz, CDCl$_3$) δ 0.88 (t, J=7.2 Hz, 6H), 1.35-1.44 (m, 4H), 2.02 (s, 3H), 2.43 (s, 3H), 3.03 (t, J=7.6 Hz, 4H), 3.67 (s, 3H), 3.86 (s, 3H), 6.42 (br s, 1H), 6.46 (br s, 1H), 6.47-6.51 (m, 1H), 7.00-7.05 (m, 1H), 7.37-7.40 (m, 1H).

Example 75

N-[7-(2-Methoxy-4-methylphenyl)-2-(methylsulfanyl)pyrazolo[1,5-a]pyridin-3-yl]-N,N-dipropylamine (Light Yellow Oil)
$^1$H NMR (400 MHz, CDCl$_3$) δ 0.88 (t, J=7.6 Hz, 6H), 1.35-1.44 (m, 4H), 2.44 (s, 3H), 2.47 (s, 3H), 3.03 (t, J=7.6 Hz, 4H), 3.77 (s, 3H), 6.61 (dd, J=1.2, 6.8 Hz, 1H), 6.84 (s, 1H), 7.02 (dd, J=6.8, 8.8 Hz, 1H), 7.37-7.40 (m, 1H), 7.43 (d, J=7.6 Hz, 1H).

Example 76

N,N-Dicyclopropylmethyl-N-[7-(2,6-dimethoxy-4-methylphenyl)-2-(methylsulfanyl)pyrazolo[1,5-a]pyridin-3-yl]amine (Colorless Oil)
$^1$H NMR (400 MHz, CDCl$_3$) δ −0.01-0.05 (m, 4H), 0.28-0.34 (m, 4H), 0.80-0.92 (m, 2H), 2.43 (m, 3H), 2.46 (s, 3H), 3.00 (d, J=6.4 Hz, 2H), 3.69 (s. 6H), 6.49 (s, 2H), 6.57 (dd, J=1.6, 6.8 Hz, 1H), 7.02 (dd, J=6.8, 8.8 Hz, 1H), 7.44 (dd, J=1.6, 8.8 Hz, 1H).

Example 77

N-[7-(4-Chloro-2-methoxyphenyl)-2-(methylsulfanyl)pyrazolo[1,5-a]pyridin-3-yl]-N,N-dicyclopropylmethylamine (Light Yellow Oil)
$^1$H NMR (400 MHz, CDCl$_3$) δ 0.02-0.06 (m, 4H), 0.30-0.34 (m, 4H), 0.80-0.90 (m, 2H), 2.48 (s, 3H), 2.99 (d, J=6.4 Hz, 4H), 3.76 (s, 3H), 6.59 (dd, J=1.6, 6.8 Hz, 1H), 7.00-7.03 (m, 21H), 7.06 (dd, J=2.0, 8.0 Hz, 1H), 7.46-7.50 (m, 2H).

Example 78

N-[7-(2-Chloro-4-methoxyphenyl)-2-(methylsulfanyl)pyrazolo[1,5-a]pyridin-3-yl]-N,N-dicyclopropylmethylamine (Light Yellow Oil)
$^1$H NMR (400 MHz, CDCl$_3$) δ 0.01-0.06 (m, 4H), 0.28-0.35 (m, 4H), 0.80-0.90 (m, 2H), 2.49 (s, 3H), 2.99 (d, J=6.4 Hz, 4H), 3.88 (s, 3H), 6.55-6.58 (m, 1H), 6.90-6.94 (m, 1H), 7.01-7.07 (m, 2H), 7.45-7.53 (m, 2H).

Example 79

N,N-Dicyclopropylmethyl-N-[7-(4-methoxy-2-methylphenyl)-2-(methylsulfanyl)pyrazolo[1,5-a]pyridin-3-yl]amine (Light Yellow Oil)
$^1$H NMR (400 MHz, CDCl$_3$) δ 0.00-0.04 (m, 4H), 0.28-0.34 (m, 4H), 0.78-0.88 (m, 2H), 2.10 (s, 3H), 2.48 (s, 3H), 2.99 (d, J=6.8 Hz, 4H), 3.87 (s, 3H), 6.47-6.51 (m, 1H), 6.81-6.86 (m, 1H), 7.03 (dd, J=6.8, 8.8 Hz, 1H), 7.33 (d, J=8.0 Hz, 1H), 7.45-7.49 (m, 1H).

Example 80

N-[7-(4-Methoxy-2,6-dimethylphenyl)-2-(methylsulfanyl)pyrazolo[1,5-a]pyridin-3-yl]-N,N-dipropylamine (Light Yellow Crystals)
$^1$H NMR (400 MHz, CDCl$_3$) δ 0.89 (t, J=7.3 Hz, 6H), 1.30-1.46 (m, 4H), 2.01 (s, 6H), 2.41 (s, 3H), 3.03 (t, J=7.1 Hz, 4H), 3.84 (s, 3H), 6.43 (br d, J=6.4 Hz, 1H), 6.69 (s, 2H), 6.98-7.07 (m, 1H), 7.40 (br d, J=9.3 Hz, 1H).
MS (ESI) m/z 398 MH+

Example 81

N,N-Dicyclopropylmethyl-N-[7-(4-methoxy-2,6-dimethylphenyl)-2-(methylsulfanyl)pyrazolo[1,5-a]pyridin-3-yl]amine (Light Yellow Crystals)
$^1$H NMR (400 MHz, CDCl$_3$) δ −0.06-0.10 (m, 4H), 0.22-0.36 (m, 4H), 0.80-0.94 (m, 2H), 2.01 (s, 6H), 2.44 (s, 3H), 3.01 (d, J=6.4 Hz, 4H), 3.85 (s, 3H), 6.44 (br d, J=6.4 Hz, 1H), 6.70 (s, 2H), 7.00-7.09 (m, 1H), 7.47 (br d, J=8.6 Hz, 1H).
MS (ESI) m/z 422 MH+

Example 82

N,N-Dicyclopropylmethyl-N-[7-[4-methoxy-2-(trifluoromethyl)phenyl]-2-(methylsulfanyl)pyrazolo[1,5-a]pyridin-3-yl]amine (Yellow Oil)
$^1$H NMR (400 MHz, CDCl$_3$) δ 0.00-0.04 (m, 4H), 0.27-0.32 (m, 4H), 0.80-0.90 (m, 2H), 2.42 (s, 3H), 2.95-3.05 (m, 4H), 3.93 (s, 3H), 6.50 (dd, J=1.6, 6.8 Hz, 1H), 7.02 (dd, J=6.8, 8.8 Hz, 1H), 7.15 (dd, J=2.4, 8.4 Hz, 1H), 7.29 (d, J=2.4 Hz, 1H), 7.45 (d, J=8.4 Hz, 1H), 7.49 (dd, J=1.6, 8.8 Hz, 1H).

Example 83

N-[7-[2-Chloro-4-(trifluoromethoxy)phenyl]-2-(methylsulfanyl)pyrazolo[1,5-a]pyridin-3-yl]-N,N-dicyclopropylmethylamine (Yellow Oil)

$^1$H NMR (400 MHz, CDCl$_3$) δ 0.00-0.04 (m, 4H), 0.28-0.34 (m, 4H), 0.80-0.90 (m, 2H), 2.48 (s, 3H), 3.00 (d, J=6.4 Hz, 4H), 6.58 (dd, J=1.6, 6.8 Hz, 1H), 7.05 (dd, J=6.8, 8.8 Hz, 1H), 7.23-7.27 (m, 1H), 7.40-7.42 (m, 1H), 7.54 (dd, J=1.6, 8.8 Hz, 1H), 7.59 (dd, J=8.4 Hz, 1H).

Example 84

N,N-Dicyclopropylmethyl-N-[7-(4-methyl-1,3-benzodioxol-5-yl)-2-(methylsulfanyl)pyrazolo[1,5-a]pyridin-3-yl]amine (Yellow Crystals)

$^1$H NMR (400 MHz, CDCl$_3$) δ 0.00-0.04 (m, 4H), 0.28-0.33 (m, 4H), 0.80-0.90 (m, 2H), 1.95 (s, 3H), 2.50 (s, 3H), 3.00 (d, J=6.8 Hz, 4H), 6.04 (s, 2H), 6.50 (dd, J=1.2, 6.8 Hz, 1H), 6.76 (d, J=8.4 Hz, 1H), 6.93 (d, J=8.4 Hz, 1H), 7.48 (dd, J=1.2, 8.8 Hz, 1H).

Example 85

N-[7-(2,4-Dimethoxyphenyl)-2-(methylsulfanyl)pyrazolo[1,5-a]pyridin-3-yl]-N,N-dipropylamine (Yellow Oil)

$^1$H NMR (400 MHz, CDCl$_3$) δ 0.88 (t, J=7.3 Hz, 6H), 1.30-1.45 (m, 4H), 2.48 (s, 3H), 3.02 (t, J=7.3 Hz, 4H), 3.76 (s, 3H), 3.88 (s, 3H), 6.56-6.64 (m, 3H), 7.01 (dd, J=6.9, 8.9 Hz, 1H), 7.37 (dd, J=1.4, 8.8 Hz, 1H), 7.49 (d, J=8.9 Hz, 1H).

Example 86

N,N-Dicyclopropylmethyl-N-[7-(2,4-dimethoxyphenyl)-2-(methylsulfanyl)pyrazolo[1,5-a]pyridin-3-yl]amine (Yellow Oil)

$^1$H NMR (400 MHz, CDCl$_3$) δ −0.02-0.08 (m, 4H), 0.25-0.34 (m, 4H), 0.75-0.88 (m, 2H), 2.47 (s, 3H), 2.97 (d, J=6.8 Hz, 4H), 3.72 (s, 3H), 3.86 (s, 3H), 6.54-6.60 (m, 3H), 6.99 (dd, J=6.8, 8.8 Hz, 1H), 7.41 (dd, J=1.4, 8.8 Hz, 1H), 7.47 (dd, J=0.8, 8.0 Hz, 1H).

Example 87

N-[7-(4-Chloro-2,6-dimethoxyphenyl)-2-(methylsulfanyl)pyrazolo[1,5-a]pyridin-3-yl]-N,N-dipropylamine (Yellow Crystals)

$^1$H NMR (400 MHz, CDCl$_3$) δ 0.88 (t, J=7.3 Hz, 6H), 1.33-1.45 (m, 4H), 2.43 (s, 3H), 3.02 (t, J=7.3 Hz, 4H), 3.70 (s, 6H), 6.54 (dd, J=1.4, 6.9 Hz, 1H), 6.67 (s, 2H), 7.02 (dd, J=6.9, 8.9 Hz, 1H), 7.40 (dd, J=1.5, 8.8 Hz, 1H).

MS (ESI) m/z 434 MH$^+$

Example 88

N-[7-(4-Chloro-2,6-dimethoxyphenyl)-2-(methylsulfanyl)pyrazolo[1,5-a]pyridin-3-yl]-N,N-dicyclopropylmethylamine (Yellow Crystals)

$^1$H NMR (400 MHz, CDCl$_3$) δ −0.02-0.06 (m, 4H), 0.26-0.34 (m, 4H), 0.77-0.91 (m, 2H), 2.45 (s, 3H), 2.99 (d, J=6.6 Hz, 4H), 3.69 (s, 6H), 6.54 (dd, J=1.5, 6.8 Hz, 1H), 6.66 (s, 2H), 7.02 (dd, J=6.8, 8.8 Hz, 1H), 7.45 (dd, J=1.4, 8.9 Hz, 1H).

MS (ESI) m/z 458 MH$^+$

Example 89

N-[7-(2-Chloro-6-methoxy-4-methylphenyl)-2-(methylsulfanyl)pyrazolo[1,5-a]pyridin-3-yl]-N,N-dipropylamine (Yellow Crystals)

$^1$H NMR (400 MHz, CDCl$_3$) δ 0.88 (t, J=7.4 Hz, 6H), 1.33-1.45 (m, 4H), 2.41 (s, 3H), 2.43 (s, 3H), 3.03 (t, J=7.4 Hz, 4H), 3.70 (s, 3H), 6.55 (dd, J=1.3, 6.8 Hz, 1H), 6.72 (s, 1H), 6.95 (s, 1H), 7.04 (dd, J=6.9, 8.9 Hz, 1H), 7.43 (dd, J=1.4, 8.9 Hz, 1H).

MS (ESI) m/z 418 MH$^+$

Example 90

N-[7-(2-Chloro-6-methoxy-4-methylphenyl)-2-(methylsulfanyl)pyrazolo[1,5-a]pyridin-3-yl]-N,N-dicyclopropylmethylamine (Yellow Crystals)

$^1$H NMR (400 MHz, CDCl$_3$) δ −0.02-0.08 (m, 4H), 0.26-0.36 (m, 4H), 0.78-0.92 (m, 2H), 2.41 (s, 3H), 2.45 (s, 3H), 3.00 (d, J=6.6 Hz, 4H), 3.69 (s, 3H), 6.55 (dd, J=1.5, 6.8 Hz, 1H), 6.73 (s, 1H), 6.96 (s, 1H), 7.04 (dd, J=6.8, 9.0 Hz, 1H), 7.49 (dd, J=1.4, 8.9 Hz, 1H).

MS (ESI) m/z 442 MH$^+$

Example 91

N,N-Dicyclopropylmethyl-N-[2-(methylsulfanyl)-7-(2,4,6-trimethoxyphenyl)pyrazolo[1,5-a]pyridin-3-yl]amine (Light Yellow Crystals)

$^1$H NMR (400 MHz, CDCl$_3$) δ 0.00-0.06 (m, 4H), 0.28-0.34 (m, 4H), 0.80-0.90 (m, 2H), 2.46 (s, 3H), 2.99 (d, J=6.4 Hz, 4H), 3.69 (s, 6H), 3.89 (s, 3H), 6.23 (s, 2H), 6.56 (dd, J=1.2, 6.8 Hz, 1H), 7.02 (dd, J=6.8, 8.8 Hz, 1H), 7.43 (dd, J=1.2, 8.8 Hz, 1H).

Example 92

N,N-Dicyclopropylmethyl-N-[7-(2,4-dimethoxy-6-methylphenyl)-2-(methylsulfanyl)pyrazolo[1,5-a]pyridin-3-yl]amine (Yellow Oil)

$^1$H NMR (400 MHz, CDCl$_3$) δ −0.01-0.04 (m, 4H), 0.28-0.34 (m, 4H), 0.80-0.92 (m, 2H), 2.02 (m, 3H), 2.45 (s, 3H), 2.96-3.04 (m, 4H), 3.67 (s, 3H), 3.87 (s. 6H), 6.42 (d, J=2.0 Hz, 2H), 6.47 (d, J=2.0 Hz, 2H), 6.49 (dd, J=1.6, 6.8 Hz, 1H), 7.03 (dd, J=6.8, 8.8 Hz, 1H), 7.46 (dd, J=1.6, 8.8 Hz, 1H).

Example 93

N3,N3-Dicyclopropylmethyl-7-[6-(dimethylamino)-2-methyl-3-pyridyl]-2-(methylsulfanyl)pyrazolo[1,5-a]pyridin-3-amine (Yellow Oil)

$^1$H NMR (400 MHz, CDCl$_3$) δ 0.00-0.40 (m, 4H), 0.29-0.33 (m, 4H), 0.80-0.90 (m, 2H), 2.23 (s, 3H), 2.51 (s, 3H), 2.99 (d, J=6.8 Hz, 4H), 3.15 (s, 6H), 6.42-6.48 (m, 2H), 7.00-7.04 (m, 1H), 7.44 (dd, J=1.6, 8.8 Hz, 1H), 7.52 (d, J=8.8 Hz, 1H).

Example 94

N3,N3-Dicyclopropylmethyl-7-[6-(dimethylamino)-2,4-dimethyl-3-pyridyl]-2-(methylsulfanyl)pyrazolo[1,5-a]pyridin-3-amine (Yellow Oil)

$^1$H NMR (400 MHz, CDCl$_3$) δ −0.01-0.02 (m, 4H), 0.26-0.32 (m, 4H), 0.80-0.90 (m, 2H), 1.95 (s, 3H), 2.15 (s, 3H), 2.45 (s, 3H), 3.00 (d, J=6.8 Hz, 4H), 3.13 (s, 6H), 6.30 (s, 1H), 6.43 (dd, J=1.6, 6.8 Hz, 1H), 7.01 (dd, J=6.8, 8.8 Hz, 1H), 7.46 (dd, J=1.6, 8.8 Hz, 1H).

Example 95

N3,N3-Dicyclopropylmethyl-7-[6-(dimethylamino)-3-pyridyl]-2-(methylsulfanyl)pyrazolo[1,5-a]pyridin-3-amine (Yellow Oil)

$^1$H NMR (400 MHz, CDCl$_3$) δ 0.00-0.70 (m, 4H), 0.29-0.34 (m, 4H), 0.80-0.85 (m, 2H), 2.61 (s, 3H), 2.95 (d, J=6.8 Hz, 4H), 3.17 (s, 6H), 6.60-6.64 (m, 2H), 7.01-7.05 (m, 1H), 7.39-7.42 (m, 1H), 8.28-8.31 (m, 1H), 8.71-8.72 (m, 1H).

Example 96

N,N-Dicyclopropylmethyl-N-[7-(4-methoxy-6-methyl-3-pyridyl)-2-(methylsulfanyl)pyrazolo[1,5-a]pyridin-3-yl]amine (Yellow Oil)

$^1$H NMR (400 MHz, CDCl$_3$) δ −0.04-0.08 (m, 4H), 0.26-0.37 (m, 4H), 0.74-0.93 (m, 2H), 2.46 (s, 3H), 2.79 (s, 3H), 2.97 (d, J=6.8 Hz, 4H), 3.88 (s, 3H), 6.60 (dd, J=1.3, 6.8 Hz, 1H), 6.90 (s, 1H), 7.02 (dd, J=6.8, 8.9 Hz, 1H), 7.53 (dd, J=1.4, 8.9 Hz, 1H), 8.80 (s, 1H).

Example 97

N,N-Dicyclopropylmethyl-N-[7-(4,6-dimethyl-3-pyridyl)-2-(methylsulfanyl)pyrazolo[1,5-a]pyridin-3-yl]amine (Brown Oil)

$^1$H NMR (400 MHz, CDCl$_3$) δ −0.04-0.08 (m, 4H), 0.24-0.36 (m, 4H), 0.76-0.98 (m, 2H), 2.11 (s, 3H), 2.46 (s, 3H), 2.60 (s, 3H), 2.98 (d, J=6.8 Hz, 4H), 6.52 (dd, J=1.3, 6.8 Hz, 1H), 7.05 (dd, J=6.8, 8.8 Hz, 1H), 7.12 (s, 1H), 7.52 (dd, J=1.5, 8.9 Hz, 1H), 8.46 (s, 1H).

Example 98

N3,N3-Dicyclopropylmethyl-7-[6-(dimethylamino)-4-methyl-3-pyridyl]-2-(methylsulfanyl)pyrazolo[1,5-a]pyridin-3-amine (Light Yellow Oil)

$^1$H NMR (400 MHz, CDCl$_3$) δ −0.02-0.08 (m, 4H), 0.26-0.36 (m, 4H), 0.78-0.90 (m, 2H), 2.09 (s, 3H), 2.50 (s, 3H), 2.99 (d, J=6.5 Hz, 4H), 3.15 (s, 6H), 6.45 (s, 1H), 6.50 (dd, J=1.6, 6.8 Hz, 1H), 7.03 (dd, J=6.8, 8.8 Hz, 1H), 7.47 (dd, J=1.6, 8.9 Hz, 1H), 8.15 (s, 1H).

Example 99

N-[7-(2-Methoxy-4,6-dimethylphenyl)-2-(methylsulfanyl)pyrazolo[1,5-a]pyridin-3-yl]-N,N-ditetrahydro-3-furanylmethylamine (Yellow Oil)

$^1$H NMR (400 MHz, CDCl$_3$) δ 1.55-1.66 (m, 2H), 1.89-1.98 (m, 2H), 1.98-2.01 (m, 3H), 2.18-2.28 (m, 2H), 2.40 (s, 3H), 2.43 (s, 3H), 2.96-3.03 (m, 2H), 3.11-3.19 (m, 2H), 3.56-3.61 (m, 2H), 3.64-3.70 (m, 5H), 3.74-3.84 (m, 4H), 6.53 (d, J=1.6, 6.8 Hz, 1H), 6.67 (s, 1H), 6.76 (s, 1H), 7.08 (dd, J=6.8, 8.8 Hz, 1H), 7.31 (dd, J=1.6, 8.8 Hz, 1H).

Example 100

N,N-Di(3-furylmethyl)-N-[7-(4-methoxy-2,6-dimethylphenyl)-2-(methylsulfanyl)pyrazolo[1,5-a]pyridin-3-yl]amine (Yellow Oil)

$^1$H NMR (400 MHz, CDCl$_3$) δ 1.97 (s, 6H), 2.42 (s, 3H), 3.84 (s, 3H), 4.12 (s, 4H), 6.28-6.33 (m, 2H), 6.39 (dd, J=1.3, 8.1 Hz, 1H), 6.68 (s, 2H), 6.95 (dd, J=6.8, 8.9 Hz, 1H), 7.13 (dd, J=1.4, 8.9 Hz, 1H), 7.20-7.25 (m, 2H), 7.26-7.32 (m, 2H).

Example 101

N-[7-(4-Bromo-2-methoxyphenyl)-2-(methylsulfanyl)pyrazolo[1,5-a]pyridin-3-yl]-N,N-dicyclopropylmethylamine (Yellow Oil)

$^1$H NMR (400 MHz, CDCl$_3$) δ 0.00-0.08 (m, 4H), 0.28-0.46 (m, 4H), 0.78-0.89 (m, 2H), 2.48 (s, 3H), 2.95-3.03 (m, 4H), 3.76 (s, 3H), 6.59 (dd, J=1.3, 6.8 Hz, 1H), 7.02 (dd, J=6.8, 8.8 Hz, 1H), 7.16 (s, 1H), 7.21 (d, J=8.0 Hz, 1H), 7.42 (d, J=8.0 Hz, 1H), 7.48 (dd, J=1.3, 8.8 Hz, 1H).

Example 102

N-[7-(2,4-Dichlorophenyl)-2-methylthiopyrazolo[1,5-a]pyridin-3-yl]-N-propylamine After dissolving tert-butyl N-[7-(2,4-dichlorophenyl)-2-methylthiopyrazolo[1,5-a]pyridin-3-yl]carbamate (150 mg) in N,N-dimethylformamide (3 mL), sodium hydride (60%, 21 mg) was added while cooling on ice, and then 1-iodopropane (0.041 mL) was added and the mixture was stirred for 30 minutes. Water was added to the reaction mixture, extraction was performed with ethyl acetate and the extract washed with brine. The obtained organic layer was dried over anhydrous magnesium sulfate and filtered, and then the solvent was distilled off under reduced pressure to obtain a crude product. This was dissolved in ethyl acetate (1 mL) without purification, a 4 N hydrochloric acid/ethyl acetate solution (4 mL) was added, and the mixture was stirred at room temperature for 2 hours. The reaction mixture was neutralized with 5 N aqueous sodium hydroxide while cooling on ice, and then extraction was performed with ethyl acetate and the organic layer washed with water and brine. After drying over anhydrous magnesium sulfate and filtration, the solvent was concentrated under reduced pressure, the residue was purified by silica gel column chromatography, and the title compound (60 mg) was obtained from the n-hexane:ethyl acetate (20:1) fraction as a yellow oil.

$^1$H NMR (400 MHz, CDCl$_3$) δ 0.99 (t, J=7.6 Hz, 3H), 1.63-1.72 (m, 2H), 2.45 (s, 3H), 3.20 (t, J=7.6 Hz, 2H), 6.62 (br d, J=6.4 Hz, 1H), 7.06 (dd, J=6.4, 8.4 Hz, 1H), 7.36 (dd, J=2.0, 8.4 Hz, 1H), 7.44 (d, J=8.4 Hz, 1H), 7.53 (d, J=2.0 Hz, 1H), 7.63-7.69 (m, 1H).

Example 103

N-[7-(2,4-Dichlorophenyl)-2-methylthiopyrazolo[1,5-a]pyridin-3-yl]-N,N-dipropylamine N-[7-(2,4-dichlorophenyl)-2-methylthiopyrazolo[1,5-a]pyridin-3-yl]-N-propylamine (59 mg) was dissolved in tetrahydrofuran (1 mL), and after adding propionaldehyde (0.035 mL) and 3 M aqueous sulfuric acid (0.16 mL), sodium borohydride (12 mg) was added in five portions while vigorously stirring on ice, and stirring was continued for 30 minutes. Water was added to the reaction mixture, extraction was performed with diethyl ether and the extract washed with saturated aqueous sodium hydrogencarbonate and brine. After drying over anhydrous magnesium sulfate and filtration, the solvent was concentrated under reduced pressure, the residue was purified by silica gel column chromatography, and the title compound (49 mg) was obtained from the n-hexane:ethyl acetate (100:1) fraction as a yellow oil.

$^1$H NMR (400 MHz, CDCl$_3$) δ 0.88 (t, J=7.6 Hz, 6H), 1.33-1.44 (m, 4H), 2.46 (s, 3H), 3.02 (t, J=7.6 Hz, 2H), 6.56 (br d, J=6.4 Hz, 1H), 7.03 (dd, J=6.4, 8.4 Hz, 1H), 7.36 (dd, J=2.0, 8.4 Hz, 1H), 7.45 (d, J=8.4 Hz, 1H), 7.49 (d, J=8.4 Hz, 1H), 7.54 (d, J=2.0 Hz, 1H).

The compounds of Examples 104 to 158 were synthesized according to the production method of Examples 102 and 103.

Example 104

N-Isobutyl-N-[7-(2-methoxy-4,6-dimethylphenyl)-2-(methylsulfanyl)pyrazolo[1,5-a]pyridin-3-yl]-N-propylamine (Light Yellow Oil)
$^1$H NMR (400 MHz, CDCl$_3$) δ 0.85-0.95 (m, 9H), 1.35-1.45 (m, 2H), 1.50-1.60 (m, 1H), 1.99 (s, 3H), 2.40 (s, 3H), 2.42 (s, 3H), 2.86 (d, J=6.8 Hz, 2H), 2.98 (t, J=6.8 Hz, 2H), 3.68 (s, 3H), 6.47-6.51 (m, 1H), 6.67 (s, 1H), 6.75 (s, 1H), 7.00-7.06 (m, 1H), 7.38-7.43 (m, 1H).

Example 105

N-Cyclopropylmethyl-N-[7-(2-methoxy-4,6-dimethylphenyl)-2-(methylsulfanyl)pyrazolo[1,5-a]pyridin-3-yl]-N-propylamine (Yellow Oil)
$^1$H NMR (400 MHz, CDCl$_3$) δ −0.03-0.01 (m, 2H), 0.27-0.32 (m, 2H), 0.80-0.90 (m, 1H), 0.90 (t, J=7.6 Hz, 3H), 1.35-1.45 (m, 2H), 1.99 (s, 3H), 2.40 (s, 3H), 2.43 (s, 3H), 2.93 (d, J=6.8 Hz, 2H), 3.10-3.15 (m, 2H), 3.68 (s, 3H), 6.49 (dd, J=1.2, 6.8 Hz, 1H), 6.67 (s, 1H). 6.75 (s, 1H), 7.03 (dd, J=6.8, 8.8 Hz, 1H), 7.43 (dd, J=1.2, 8.8 Hz, 1H).

Example 106

N-[7-(2-Methoxy-4,6-dimethylphenyl)-2-(methylsulfanyl)pyrazolo[1,5-a]pyridin-3-yl]-N-(2-methoxyethyl)-N-propylamine (Light Yellow Oil)
$^1$H NMR (400 MHz, CDCl$_3$) δ 0.88 (t, J=7.2 Hz, 3H), 1.30-1.44 (m, 2H), 1.99 (s, 3H), 2.40 (s, 3H), 2.43 (s, 3H), 3.06-3.12 (m, 2H), 3.28 (s, 3H), 3.28-3.32 (m, 2H), 3.35-3.40 (m, 2H), 3.68 (s, 3H), 6.51 (dd, J=1.2, 6.8 Hz, 1H), 6.67 (s, 1H). 6.75 (s, 1H), 7.05 (dd, J=6.8, 8.8 Hz, 1H), 7.41 (dd, J=1.6, 8.8 Hz, 1H).

Example 107

N-Cyclopropylmethyl-N-[7-(2-methoxy-4,6-dimethylphenyl)-2-(methylsulfanyl)pyrazolo[1,5-a]pyridin-3-yl]-N-(2-methoxyethyl)amine (Light Yellow Oil)
$^1$H NMR (400 MHz, CDCl$_3$) δ −0.02-0.02 (m, 2H), 0.28-0.32 (m, 2H), 0.82-0.92 (m, 2H), 1.99 (s, 3H), 2.40 (s, 3H), 2.44 (s, 3H), 2.98 (d, J=6.8 Hz, 2H), 3.29 (s, 3H), 3.36-3.42 (m, 4H), 3.68 (s, 3H), 6.51 (dd, J=1.2, 6.8 Hz, 1H), 6.67 (s, 1H). 6.76 (s, 1H), 7.05 (dd, J=6.8, 8.8 Hz, 1H), 7.44 (dd, J=1.2, 8.8 Hz, 1H).

Example 108

N-Isobutyl-N-[7-(2-methoxy-4,6-dimethylphenyl)-2-(methylsulfanyl)pyrazolo[1,5-a]pyridin-3-yl]-N-(2-methoxyethyl)amine (Light Yellow Oil)
MS (ESI) m/z 428 MH$^+$ Example 109

N-(3-Fluoropropyl)-N-[7-(2-methoxy-4,6-dimethylphenyl)-2-(methylsulfanyl)pyrazolo[1,5-a]pyridin-3-yl]-N-propylamine (Light Yellow Oil)
$^1$H NMR (400 MHz, CDCl$_3$) δ 0.89 (t, J=7.2 Hz, 3H), 1.36-1.45 (m, 2H), 1.68-1.82 (m, 2H), 1.99 (s, 3H), 2.40 (s, 3H), 2.43 (s, 3H), 3.01-3.06 (m, 2H), 3.23 (t, J=6.8 Hz, 2H), 3.68 (s, 3H), 4.56 (td, J=6.0, 47.6 Hz, 2H), 6.51 (dd, J=1.6, 6.8

Hz, 1H), 6.67 (s, 1H). 6.75 (s, 1H), 7.06 (dd, J=6.8, 8.8 Hz, 1H), 7.37 (dd, J=1.6, 8.8 Hz, 1H).

Example 110

N-Cyclopropylmethyl-N-(3-fluoropropyl)-N-[7-(2-methoxy-4,6-dimethylphenyl)-2-(methylsulfanyl)pyrazolo[1,5-a]pyridin-3-yl]amine (Light Yellow Oil)

$^1$H NMR (400 MHz, CDCl$_3$) δ −0.02-0.02 (m, 2H), 0.28-0.36 (m, 2H), 0.80-0.92 (m, 1H), 1.70-1.84 (m, 2H), 1.99 (s, 3H), 2.40 (s, 3H), 2.43 (s, 3H), 2.93 (d, J=6.8 Hz, 2H), 3.31 (t, J=7.6 Hz, 2H), 3.68 (s, 3H), 4.57 (td, J=6.0, 47.2 Hz, 2H), 6.50 (dd, J=1.6, 6.8 Hz, 1H), 6.67 (s, 1H), 6.76 (s, 1H), 7.05 (dd, J=6.8, 8.8 Hz, 1H), 7.40 (dd, J=1.6, 8.8 Hz, 1H).

Example 111

N-(3-Fluoropropyl)-N-isobutyl-N-[7-(2-methoxy-4,6-dimethylphenyl)-2-(methylsulfanyl)pyrazolo[1,5-a]pyridin-3-yl]amine (Light Yellow Oil)
MS (ESI) m/z 430 MH$^+$

Example 112

N-Cyclopropylmethyl-N-[7-(2-methoxy-4,6-dimethylphenyl)-2-(methylsulfanyl)pyrazolo[1,5-a]pyridin-3-yl]-N-tetrahydro-2-furanylmethylamine (Light Yellow Oil)
MS (ESI) m/z 452 MH$^+$

Example 113

N-Isobutyl-N-[7-(2-methoxy-4,6-dimethylphenyl)-2-(methylsulfanyl)pyrazolo[1,5-a]pyridin-3-yl]-N-tetrahydro-2-furanylmethylamine (Light Yellow Oil)
MS (ESI) m/z 454 MH$^+$

Example 114

N-[7-(2-Methoxy-4,6-dimethylphenyl)-2-(methylsulfanyl)pyrazolo[1,5-a]pyridin-3-yl]-N-(2-morpholinoethyl)-N-propylamine (Light Yellow Oil)
MS (ESI) m/z 469 MH$^+$

Example 115

N1-[7-(2-Methoxy-4,6-dimethylphenyl)-2-(methylsulfanyl)pyrazolo[1,5-a]pyridin-3-yl]-N2,N2-dimethyl-N1-propyl-1,2-ethanediamine (Light Yellow Oil)
MS (ESI) m/z 427 MH$^+$

Example 116

N-[7-(2-Methoxy-4,6-dimethylphenyl)-2-(methylsulfanyl)pyrazolo[1,5-a]pyridin-3-yl]-N-propyl-N-(2-tetrahydro-1H-1-pyrrolylethyl)amine (Light Yellow Oil)
MS (ESI) m/z 453 MH$^+$

Example 117

N-[7-(2-Methoxy-4,6-dimethylphenyl)-2-(methylsulfanyl)pyrazolo[1,5-a]pyridin-3-yl]-N-propyl-N-(2-pyridylmethyl)amine (Light Yellow Oil)
MS (ESI) m/z 447 MH$^+$

Example 118

N-Cyclopropylmethyl-N-[7-(4-methoxy-2,6-dimethylphenyl)-2-(methylsulfanyl)pyrazolo[1,5-a]pyridin-3-yl]-N-propylamine (Yellow Oil)

$^1$H NMR (400 MHz, CDCl$_3$) δ −0.04-0.05 (m, 2H), 0.26-0.37 (m, 2H), 0.82-0.98 (m, 1H), 0.96 (t, J=7.3 Hz, 3H), 1.38-1.52 (m, 2H), 2.06 (s, 6H), 2.47 (s, 3H), 2.98 (d, J=6.8 Hz, 2H), 3.12-3.20 (m, 2H), 3.90 (s, 3H), 6.44-6.50 (m, 1H), 6.74 (s, 2H), 7.03-7.12 (m, 1H), 7.44-7.52 (m, 1H).
MS (ESI) m/z 410 MH$^+$

Example 119

N-Isobutyl-N-[7-(4-methoxy-2,6-dimethylphenyl)-2-(methylsulfanyl)pyrazolo[1,5-a]pyridin-3-yl]-N-propylamine (Yellow Crystals)

$^1$H NMR (400 MHz, CDCl$_3$) δ 0.89 (t, J=7.4 Hz, 3H), 0.93 (d, J=6.6 Hz, 6H), 1.33-1.45 (m, 2H), 1.52-1.64 (m, 1H), 2.01 (s, 6H), 2.41 (s, 3H), 2.87 (d, J=7.1 Hz, 2H), 2.98 (t, J=7.4 Hz, 2H), 3.84 (s, 3H), 6.42 (dd, J=1.3, 6.8 Hz, 1H), 6.69 (s, 2H), 7.03 (dd, J=6.8, 8.8 Hz, 1H), 7.42 (dd, J=1.3, 8.8 Hz, 1H).
MS (ESI) m/z 412 MH$^+$

Example 120

N-Cyclopropylmethyl-N-isobutyl-N-[7-(4-methoxy-2,6-dimethylphenyl)-2-(methylsulfanyl)pyrazolo[1,5-a]pyridin-3-yl]amine (Yellow Crystals)

$^1$H NMR (400 MHz, CDCl$_3$) δ −0.02-0.05 (m, 2H), 0.32-0.39 (m, 2H), 0.87-0.99 (m, 1H), 1.01 (d, J=6.6 Hz, 6H), 1.60-1.74 (m, 1H), 2.10 (s, 6H), 2.49 (s, 3H), 2.96 (d, J=6.8 Hz, 2H), 3.02 (d, J=7.1 Hz, 2H), 3.93 (s, 3H), 6.50 (dd, J=1.5, 6.8 Hz, 1H), 6.77 (s, 2H), 7.11 (dd, J=6.8, 9.0 Hz, 1H), 7.54 (dd, J=1.4, 8.8 Hz, 1H).
MS (ESI) m/z 424 MH$^+$

Example 121

N-Cyclopropylmethyl-N-[7-(2-methoxy-4,6-dimethylphenyl)-2-(methylsulfanyl)pyrazolo[1,5-a]pyridin-3-yl]-N-[(3-methyl-3-oxetanyl)methyl]amine (Light Yellow Oil)

$^1$H NMR (400 MHz, CDCl$_3$) δ −0.04-0.04 (m, 2H), 0.30-0.40 (m, 2H), 0.76-0.86 (m, 1H), 0.87 (s, 3H), 1.97 (s, 1.5H), 1.98 (s, 1.5H), 2.40 (s, 3H), 2.45 (s, 3H), 2.86-3.01 (m, 2H), 3.20-3.25 (m, 1H), 3.52-3.74 (m, 8H), 6.55 (dd, J=1.2, 6.8 Hz, 1H), 6.67 (s, 1H), 6.76 (s, 1H), 7.11 (dd, J=6.8, 8.8 Hz, 1H), 7.44-7.48 (m, 1H).

Example 122

N-Cyclopropylmethyl-N-[7-(2,6-dimethoxy-4-methylphenyl)-2-(methylsulfanyl)pyrazolo[1,5-a]pyridin-3-yl]-N-tetrahydro-2-furanylmethylamine (Yellow Oil)

$^1$H NMR (400 MHz, CDCl$_3$) δ −0.02-0.02 (m, 2H), 0.29-0.34 (m, 2H), 0.80-0.90 (m, 1H), 1.62-1.72 (m, 1H), 1.75-1.85 (m, 2H), 1.86-1.96 (m, 1H), 2.43 (m, 3H), 2.44 (s, 3H), 2.96 (d, J=6.8 Hz, 2H), 3.05-3.11 (m, 1H), 3.40-3.45 (m, 1H), 3.65-3.72 (m, 4H), 3.80-3.90 (m, 2H), 6.49 (s, 2H), 6.57 (dd, J=1.6, 6.8 Hz, 1H), 7.04 (dd, J=6.8, 8.8 Hz, 1H), 7.44 (dd, J=1.6, 8.8 Hz, 1H).

Example 123

N-Cyclopropylmethyl-N-[7-(2-methoxy-4,6-dimethylphenyl)-2-(methylsulfanyl)pyrazolo[1,5-a]pyridin-3-yl]-N-tetrahydro-3-furanylmethylamine (Yellow Oil)

$^1$H NMR (400 MHz, CDCl$_3$) δ −0.04-0.02 (m, 2H), 0.28-0.34 (m, 2H), 0.80-0.88 (m, 1H), 1.60-1.70 (m, 1H), 1.88-1.98 (m, 1H), 1.98 (s, 1.5H), 1.99 (s, 1.5H), 2.20-2.30 (m, 1H), 2.40 (s, 3H), 2.43 (s, 3H), 2.88-2.92 (m, 2H), 3.04-3.10 (m, 1H), 3.20-3.26 (m, 1H), 3.60-3.64 (m, 1H), 3.65-3.70 (m, 4H), 3.74-3.84 (m, 2H), 6.50 (dd, J=1.2, 6.8 Hz, 1H), 6.67 (s, 1H), 6.75 (s, 1H), 7.05 (dd, J=6.8, 8.8 Hz, 1H), 7.39-7.41 (m, 1H).

Example 124

N-Ethyl-N-[7-(2-methoxy-4,6-dimethylphenyl)-2-(methylsulfanyl)pyrazolo[1,5-a]pyridin-3-yl]-N-tetrahydro-3-furanylmethylamine (Light Yellow Oil)

$^1$H NMR (400 MHz, CDCl$_3$) δ 0.97 (t, J=7.2 Hz, 3H), 1.55-1.66 (m, 1H), 1.87-1.97 (m, 1H), 1.98 (s, 1.5H), 1.99 (s, 1.5H), 2.20-2.28 (m, 1H), 2.40 (s, 3H), 2.43 (s, 3H), 3.02 (dd, J=8.4, 12.0 Hz, 1H), 3.10 (q, J=7.2 Hz, 2H), 3.19 (dd, J=6.4, 12.0 Hz, 1H), 3.57 (dd, J=5.6, 8.4 Hz, 1H), 3.63-3.71 (m, 4H), 3.72-3.84 (m, 2H), 6.51 (dd, J=1.2, 6.8 Hz, 1H), 6.67 (s, 1H), 6.75 (s, 1H), 7.05 (dd, J=6.8, 9.2 Hz, 1H), 7.35 (dd, J=1.6, 9.2 Hz, 1H).

Example 125

N-Cyclopropylmethyl-N-[7-(2,6-dimethoxy-4-methylphenyl)-2-(methylsulfanyl)pyrazolo[1,5-a]pyridin-3-yl]-N-tetrahydro-3-furanylmethylamine (Light Yellow Oil)

$^1$H NMR (400 MHz, CDCl$_3$) δ 0.00-0.05 (m, 2H), 0.30-0.38 (m, 2H), 0.80-0.90 (m, 1H), 1.55-1.70 (m, 1H), 1.86-1.96 (m, 1H), 2.22-2.30 (m, 1H), 2.44 (s, 3H), 2.45 (s, 3H), 2.90 (d, J=6.4 Hz, 2H), 3.04-3.10 (m, 1H), 3.21-3.26 (m, 1H), 3.60-3.68 (m, 2H), 3.70 (s, 6H), 3.73-3.84 (m, 2H), 6.49 (s, 2H), 6.57-6.60 (m, 1H), 7.02-7.07 (m, 1H), 7.36-7.40 (m, 1H).

Example 126

1-(2-(Cyclopropylmethyl)[7-(2-methoxy-4,6-dimethylphenyl)-2-(methylsulfanyl)pyrazolo[1,5-a]pyridin-3-yl]aminoethyl)-2-pyrrolidinone (Light Yellow Oil)

$^1$H NMR (400 MHz, CDCl$_3$) δ −0.07-0.03 (m, 2H), 0.27-0.47 (m, 2H), 0.78-0.88 (m, 1H), 1.86-1.96 (m, 2H), 1.99 (s, 3H), 2.28-2.36 (m, 2H), 2.40 (s, 3H), 2.43 (s, 3H), 2.88-2.98 (m, 2H), 3.32-3.43 (m, 6H), 3.68 (s, 3H), 6.51 (dd, J=1.3, 6.8 Hz, 1H), 6.67 (s, 1H), 6.76 (s, 1H), 7.05 (dd, J=6.8, 8.8 Hz, 1H), 7.39 (dd, J=1.3, 8.8 Hz, 1H).

Example 127

N-[7-(2,6-Dimethoxy-4-methylphenyl)-2-(methylsulfanyl)pyrazolo[1,5-a]pyridin-3-yl]-N-propyl-N-tetrahydro-3-furanylmethylamine (White Crystals)

$^1$H NMR (400 MHz, CDCl$_3$) δ 0.89 (t, J=7.3 Hz, 3H), 1.39 (ddq, J=7.3, 7.3, 7.3 Hz, 2H), 1.57-1.67 (m, 1H), 1.87-1.97 (m, 1H), 2.18-2.31 (m, 1H), 2.44 (s, 3H), 2.44 (s, 3H), 2.97-3.04 (m, 1H), 3.01 (dd, J=7.3, 7.3 Hz, 2H), 3.12-3.20 (m, 1H), 3.55-3.84 (m, 4H), 3.70 (s, 6H), 6.49 (s, 2H), 6.58 (dd, J=1.3, 6.8 Hz, 1H), 7.05 (dd, J=6.8, 8.8 Hz, 1H), 7.35 (dd, J=1.3, 8.8 Hz, 1H).

Example 128

N-[7-(4-Methoxy-2,6-dimethylphenyl)-2-(methylsulfanyl)pyrazolo[1,5-a]pyridin-3-yl]-N-propyl-N-tetrahydro-3-furanylmethylamine (Yellow Oil)

$^1$H NMR (400 MHz, CDCl$_3$) δ 0.90 (t, J=7.3 Hz, 3H), 1.32-1.45 (m, 2H), 1.56-1.68 (m, 1H), 1.87-2.00 (m, 1H), 2.01 (s, 6H), 2.15-2.30 (m, 1H), 2.42 (s, 3H), 2.96-3.06 (m, 3H), 3.17 (dd, J=6.6, 12.0 Hz, 1H), 3.59 (dd, J=5.7, 8.4 Hz, 1H), 3.62-3.71 (m, 1H), 3.72-3.84 (m, 2H), 3.85 (s, 3H), 6.45 (dd, J=1.4, 6.8 Hz, 1H), 6.69 (s, 2H), 7.05 (dd, J=6.8, 8.8 Hz, 1H), 7.36 (dd, J=1.3, 8.9 Hz, 1H).

Example 129

N-Cyclopropylmethyl-N-[7-(4-methoxy-2,6-dimethylphenyl)-2-(methylsulfanyl)pyrazolo[1,5-a]pyridin-3-yl]-N-tetrahydro-3-furanylmethylamine (Yellow Oil)

$^1$H NMR (400 MHz, CDCl$_3$) δ −0.03-0.05 (m, 2H), 0.30-0.38 (m, 2H), 0.82-0.94 (m, 1H), 1.62-1.75 (m, 1H), 1.92-2.04 (m, 1H), 2.05 (s, 3H), 2.06 (s, 3H), 2.24-2.37 (m, 1H), 2.46 (s, 3H), 2.95 (d, J=6.8 Hz, 2H), 3.12 (dd, J=8.7, 12.0 Hz, 1H), 3.29 (dd, J=6.6, 12.0 Hz, 1H), 3.66 (dd, J=5.7, 8.6 Hz, 1H), 3.71 (dd, J=7.4, 8.4 Hz, 1H), 3.81 (dd, J=7.2, 8.8 Hz, 1H), 3.84-3.90 (m, 1H), 3.89 (s, 3H), 6.49 (dd, J=1.5, 6.8 Hz, 1H), 6.74 (s, 2H), 7.09 (dd, J=6.8, 8.8 Hz, 1H), 7.44 (dd, J=1.5, 8.8 Hz, 1H).

Example 130

N-[7-(4-Methoxy-2,6-dimethylphenyl)-2-(methylsulfanyl)pyrazolo[1,5-a]pyridin-3-yl]-N-propyl-N-tetrahydro-2-furanylmethylamine (Yellow Oil)
$^1$H NMR (400 MHz, CDCl$_3$) δ 0.89 (t, J=7.4 Hz, 3H), 1.32-1.46 (m, 2H), 1.58-1.70 (m, 1H), 1.74-1.99 (m, 3H), 2.00 (s, 3H), 2.01 (s, 3H), 2.41 (s, 3H), 3.01 (dd, J=6.8, 12.0 Hz, 1H), 3.09 (t, J=7.5 Hz, 2H), 3.33 (dd, J=5.6, 12.0 Hz, 1H), 3.64-3.74 (m, 1H), 3.77-3.90 (m, 2H), 3.85 (s, 3H), 6.44 (dd, J=1.5, 6.8 Hz, 1H), 6.69 (s, 2H), 7.05 (dd, J=6.8, 8.8 Hz, 1H), 7.43 (dd, J=1.4, 8.8 Hz, 1H).

Example 131

N-Cyclopropylmethyl-N-[7-(4-methoxy-2,6-dimethylphenyl)-2-(methylsulfanyl)pyrazolo[1,5-a]pyridin-3-yl]-N-tetrahydro-2-furanylmethylamine (Yellow Oil)
$^1$H NMR (400 MHz, CDCl$_3$) δ −0.02-0.05 (m, 2H), 0.28-0.38 (m, 2H), 0.80-0.97 (m, 1H), 1.67-1.78 (m, 1H), 1.79-2.06 (m, 3H), 2.05 (s, 3H), 2.06 (s, 3H), 2.46 (s, 3H), 3.02 (d, J=6.8 Hz, 2H), 3.14 (dd, J=7.0, 13.0 Hz, 1H), 3.47 (dd, J=5.5, 13.0 Hz, 1H), 3.70-3.80 (m, 1H), 3.82-3.98 (m, 2H), 3.89 (s, 3H), 6.48 (dd, J=1.5, 6.8 Hz, 1H), 6.74 (s, 2H), 7.09 (dd, J=6.8, 8.8 Hz, 1H), 7.51 (dd, J=1.4, 8.8 Hz, 1H).

Example 132

N-[7-(4-Chloro-2,6-dimethoxyphenyl)-2-(methylsulfanyl)pyrazolo[1,5-a]pyridin-3-yl]-N-propyl-N-tetrahydro-2-furanylmethylamine (Yellow Crystals)
$^1$H NMR (400 MHz, CDCl$_3$) δ 0.88 (t, J=7.1 Hz, 3H), 1.30-1.46 (m, 2H), 1.54-1.70 (m, 1H), 1.72-2.00 (m, 3H), 2.43 (s, 3H), 2.95-3.12 (m, 3H), 3.25-3.38 (m, 1H), 3.62-3.76 (m, 1H), 3.70 (s, 6H), 3.77-3.90 (m, 2H), 6.55 (dd, J=1.4, 6.8 Hz, 1H), 6.67 (s, 2H), 7.04 (dd, J=6.8, 8.9 Hz, 1H), 7.43 (dd, J=1.4, 8.9 Hz, 1H).

Example 133

N-[7-(4-Chloro-2,6-dimethoxyphenyl)-2-(methylsulfanyl)pyrazolo[1,5-a]pyridin-3-yl]-N-cyclopropylmethyl-N-tetrahydro-2-furanylmethylamine (Yellow Oil)
$^1$H NMR (400 MHz, CDCl$_3$) δ −0.02-0.05 (m, 2H), 0.28-0.36 (m, 2H), 0.77-0.92 (m, 1H), 1.62-1.72 (m, 1H), 1.73-1.99 (m, 3H), 2.44 (s, 3H), 2.96 (t, J=7.2 Hz, 2H), 3.00-3.12 (m, 1H), 3.35-3.46 (m, 1H), 3.62-3.76 (m, 1H), 3.70 (s, 6H), 3.77-3.92 (m, 2H), 6.55 (dd, J=1.3, 6.8 Hz, 1H), 6.67 (s, 2H), 7.04 (dd, J=6.9, 8.8 Hz, 1H), 7.46 (dd, J=1.3, 8.8 Hz, 1H).

Example 134

N-(3-Furylmethyl)-N-[7-(4-methoxy-2,6-dimethylphenyl)-2-(methylsulfanyl)pyrazolo[1,5-a]pyridin-3-yl]-N-propylamine (Light Yellow Oil)
$^1$H NMR (400 MHz, CDCl$_3$) δ 0.88 (t, J=7.3 Hz, 3H), 1.34-1.46 (m, 2H), 1.99 (s, 6H), 2.42 (s, 3H), 3.07 (t, J=7.4 Hz, 2H), 3.84 (s, 3H), 4.09 (s, 2H), 6.32 (d, J=1.1 Hz, 1H), 6.41 (dd, J=1.3, 6.8 Hz, 1H), 6.68 (s, 2H), 7.00 (dd, J=6.8, 8.9 Hz, 1H), 7.23 (s, 1H), 7.25-7.30 (m, 2H).

Example 135

N-Cyclopropylmethyl-N-(3-furylmethyl)-N-[7-(4-methoxy-2,6-dimethylphenyl)-2-(methylsulfanyl)pyrazolo[1,5-a]pyridin-3-yl]amine (Yellow Oil)
$^1$H NMR (400 MHz, CDCl$_3$) δ −0.02-0.08 (m, 2H), 0.30-0.40 (m, 2H), 0.82-0.96 (m, 1H), 2.04 (s, 6H), 2.48 (s, 3H), 3.00 (d, J=6.6 Hz, 2H), 3.89 (s, 3H), 4.24 (s, 2H), 6.42 (s, 1H), 6.47 (dd, J=1.3, 6.8 Hz, 1H), 6.74 (s, 2H), 7.06 (dd, J=6.8, 8.9 Hz, 1H), 7.30-7.36 (m, 2H), 7.41 (dd, J=1.3, 8.9 Hz, 1H).

Example 136

N-(3-Furylmethyl)-N-[7-(2-methoxy-4,6-dimethylphenyl)-2-(methylsulfanyl)pyrazolo[1,5-a]pyridin-3-yl]-N-propylamine (Yellow Oil)
$^1$H NMR (400 MHz, CDCl$_3$) δ 0.87 (t, J=7.4 Hz, 3H), 1.33-1.46 (m, 2H), 1.97 (s, 3H), 2.39 (s, 3H), 2.43 (s, 3H), 3.06 (t, J=7.3 Hz, 2H), 3.67 (s, 3H), 4.09 (s, 2H), 6.32-6.38 (m, 1H), 6.48 (dd, J=1.3, 6.8 Hz, 1H), 6.66 (s, 1H), 6.75 (s, 1H), 7.00 (dd, J=6.8, 8.8 Hz, 1H), 7.20-7.32 (m, 3H).

Example 137

N-Cyclopropylmethyl-N-(3-furylmethyl)-N-[7-(2-methoxy-4,6-dimethylphenyl)-2-(methylsulfanyl)pyrazolo[1,5-a]pyridin-3-yl]amine (Yellow Oil)
$^1$H NMR (400 MHz, CDCl$_3$) δ −0.03-0.06 (m, 2H), 0.28-0.38 (m, 2H), 0.80-0.93 (m, 1H), 2.00 (s, 3H), 2.42 (s, 3H), 2.46 (s, 3H), 2.97 (dd, J=2.1, 6.7 Hz, 2H), 3.69 (s, 3H), 4.22 (s, 2H), 6.38-6.42 (m, 1H), 6.51 (dd, J=1.5, 6.8 Hz, 1H), 6.69 (s, 1H), 6.78 (s, 1H), 7.05 (dd, J=6.8, 8.8 Hz, 1H), 7.26-7.34 (m, 2H), 7.39 (dd, J=1.5, 8.8 Hz, 1H).

Example 138

N-[7-(2,6-Dimethoxy-4-methylphenyl)-2-(methylsulfanyl)pyrazolo[1,5-a]pyridin-3-yl]-N-propyl-N-tetrahydro-2-furanylmethylamine (White Crystals)
$^1$H NMR (400 MHz, CDCl$_3$) δ 0.87 (t, J=7.3 Hz, 3H), 1.40 (ddq, J=7.3, 7.3, 7.3 Hz, 2H), 1.58-1.68 (m, 1H), 1.72-1.98 (m, 3H), 2.44 (s, 3H), 2.44 (s, 3H), 2.96-3.04 (m, 1H), 3.07 (dd, J=7.3, 7.3 Hz, 2H), 3.31-3.38 (m, 1H), 3.63-3.73 (m, 1H), 3.69 (s, 6H), 3.78-3.89 (m, 2H), 6.49 (s, 2H), 6.57 (dd, J=1.3, 6.8 Hz, 1H), 7.04 (dd, J=6.8 Hz, 1H), 7.41 (dd, J=1.3, 8.8 Hz, 1H).

Example 139

3-(Cyclopropylmethyl)[7-(2-methoxy-4,6-dimethylphenyl)-2-(methylsulfanyl)pyrazolo[1,5-a]pyridin-3-yl]aminotetrahydro-2-furanone (White Crystals)

$^1$H NMR (400 MHz, CDCl$_3$) δ −0.03-0.08 (m, 2H), 0.23-0.34 (m, 2H), 0.80-0.92 (m, 1H), 1.98 (s, 3H), 2.21-2.47 (m, 2H), 2.40 (s, 3H), 2.43 (s, 3H), 3.15-3.23 (m, 1H), 3.25-3.33 (m, 1H), 3.67 (s, 3H), 4.08-4.21 (m, 3H), 6.54 (dd, J=1.3, 6.8 Hz, 1H), 6.67 (s, 1H), 6.76 (s, 1H), 7.10 (dd, J=6.8, 8.8 Hz, 1H), 7.65 (dd, J=1.3, 8.8 Hz, 1H).

Example 140

N-Cyclopropylmethyl-N-[7-(2,4-dimethoxy-6-methylphenyl)-2-(methylsulfanyl)pyrazolo[1,5-a]pyridin-3-yl]-N-tetrahydro-3-furanylmethylamine (Yellow Oil)

$^1$H NMR (400 MHz, CDCl$_3$) δ −0.02-0.01 (m, 2H), 0.30-0.35 (m, 2H), 0.80-0.90 (m, 1H), 1.60-1.70 (m, 1H), 1.88-1.98 (m, 2H), 2.01 (s, 1.5H), 2.02 (s, 1.5H), 2.20-2.30 (m, 1H), 2.43 (s, 3H), 2.88-2.92 (m, 2H), 3.04-3.10 (m, 1H), 3.20-3.27 (m, 1H), 3.60-3.65 (m, 1H), 3.65-3.70 (m, 4H), 3.74-3.85 (m, 2H), 3.84 (s. 3H), 6.42 (d, J=2.0 Hz, 1H), 6.46 (d, J=2.0 Hz, 1H), 6.50 (dd, J=1.2, 6.8 Hz, 1H), 7.05 (dd, J=6.8, 8.8 Hz, 1H), 7.37-7.40 (m, 1H).

Example 141

N-[7-(2,4-Dimethoxy-6-methylphenyl)-2-(methylsulfanyl)pyrazolo[1,5-a]pyridin-3-yl]-N-propyl-N-tetrahydro-3-furanylmethylamine (Yellow Oil)

$^1$H NMR (400 MHz, CDCl$_3$) δ 0.89 (t, J=7.6 Hz, 3H), 1.34-1.44 (m, 2H), 1.58-1.66 (m, 1H), 1.88-1.96 (m, 1H), 2.01 (s, 1.5H), 2.02 (s, 1.5H), 2.20-2.30 (m, 1H), 2.43 (s, 3H), 2.97-3.04 (m, 3H), 3.14-3.20 (m, 2H), 3.56-3.60 (m, 1H), 3.63-3.70 (m, 4H), 3.74-3.83 (m, 2H), 3.87 (s, 3H), 6.42 (d, J=2.0 Hz, 1H), 6.46 (d, J=2.0 Hz, 1H), 6.50 (dd, J=1.2, 6.8 Hz, 1H), 7.05 (dd, J=6.8, 8.8 Hz, 1H), 7.35 (dd, J=1.2, 8.8 Hz, 1H).

Example 142

N-Cyclopropylmethyl-N-[7-(2,4-dimethoxy-6-methylphenyl)-2-(methylsulfanyl)pyrazolo[1,5-a]pyridin-3-yl]-N-tetrahydro-2-furanylamine (Light Yellow Crystals)

$^1$H NMR (400 MHz, CDCl$_3$) δ −0.06-0.00 (m, 2H), 0.26-0.35 (m, 2H), 0.82-0.90 (m, 1H), 1.57-1.72 (m, 1H), 1.74-1.88 (m, 2H), 1.90-1.99 (m, 1H), 2.01 (s, 1.5H), 2.02 (s, 1.5H), 2.44 (s, 3H), 2.97 (d, J=6.8 Hz, 2H), 3.05-3.12 (m, 1H), 3.38-3.45 (m, 1H), 3.66 (s, 1.5H), 3.67 (s, 1.5H), 3.67-3.72 (m, 2H), 3.80-3.92 (m, 5H), 6.42 (d, J=2.0 Hz, 1H), 6.46 (d, J=2.0 Hz, 1H), 6.48-6.52 (m, 1H), 7.04 (dd, J=6.8, 8.8 Hz, 1H), 7.42-7.47 (m, 1H).

Example 143

N-[7-(2,4-Dimethoxy-6-methylphenyl)-2-(methylsulfanyl)pyrazolo[1,5-a]pyridin-3-yl]-N-propyl-N-tetrahydro-2-furanylamine (Light Yellow Crystals)

$^1$H NMR (400 MHz, CDCl$_3$) δ 0.88 (t, J=7.6 Hz, 3H), 1.35-1.44 (m, 2H), 1.58-1.68 (m, 1H), 1.76-1.87 (m, 2H), 1.88-1.99 (m, 1H), 2.01 (s, 1.5H), 2.02 (s, 1.5H), 2.43 (s, 3H), 2.98-3.04 (m, 1H), 3.05-3.10 (m, 2H), 3.30-3.36 (m, 1H), 3.66 (s, 3H), 3.66-3.72 (m, 1H), 3.80-3.86 (m, 2H), 3.87 (s, 3H), 6.42 (d, J=2.0 Hz, 1H), 6.46 (d, J=2.0 Hz, 1H), 6.50 (dd, J=1.6, 6.8 Hz, 1H), 7.04 (dd, J=6.8, 8.8 Hz, 1H), 7.40-7.44 (m, 1H).

Example 144

N-Cyclopropylmethyl-N-[7-(2,6-dimethoxy-4-methylphenyl)-2-(methylsulfanyl)pyrazolo[1,5-a]pyridin-3-yl]-N-(3-furylmethyl)-amine (Yellow Oil)

$^1$H NMR (400 MHz, CDCl$_3$) δ −0.02-0.04 (m, 2H), 0.30-0.37 (m, 2H), 0.80-0.92 (m, 1H), 2.44 (s, 3H), 2.46 (s, 3H), 2.95 (d, J=6.8 Hz, 2H), 3.69 (s, 6H), 4.21 (s, 2H), 6.38-6.42 (m, 1H), 6.49 (s, 2H), 6.57 (dd, J=1.3, 6.8 Hz, 1H), 7.02 (dd, J=6.8, 8.8 Hz, 1H), 7.28-7.32 (m, 2H), 7.37 (dd, J=1.5, 8.8 Hz, 1H).

Example 145

N-[7-(2-Methoxy-4,6-dimethylphenyl)-2-(methylsulfanyl)pyrazolo[1,5-a]pyridin-3-yl]-N-propyl-N-tetrahydro-3-furanylmethylamine (Yellow Oil)

$^1$H NMR (400 MHz, CDCl$_3$) δ 0.89 (t, J=7.2 Hz, 3H), 1.34-1.43 (m, 2H), 1.55-1.66 (m, 1H), 1.88-1.98 (m, 1H), 1.99 (s, 1.5H), 2.00 (s, 1.5H), 2.20-2.30 (m, 1H), 2.40 (s, 3H), 2.42 (s, 3H), 2.96-3.05 (m, 3H), 3.14-3.20 (m, 1H), 3.58 (dd, J=5.6, 8.4 Hz, 1H), 3.63-3.70 (m, 1H), 3.68 (s, 3H), 3.74-3.84 (m, 2H), 6.51 (dd, J=1.6, 6.8 Hz, 1H), 6.67 (s, 1H), 6.75 (s, 1H), 7.05 (dd, J=6.8, 8.8 Hz, 1H), 7.35 (dd, J=1.6, 6.8 Hz, 1H).

Example 146

N-Cyclopropylmethyl-N-[7-(2-methoxy-4,6-dimethylphenyl)-2-(methylsulfanyl)pyrazolo[1,5-a]pyridin-3-yl]-N-(2-tetrahydro-2-furanylethyl)amine (Yellow Oil)

$^1$H NMR (400 MHz, CDCl$_3$) δ −0.03-0.00 (m, 2H), 0.26-0.32 (m, 2H), 0.80-0.90 (m, 1H), 1.38-1.50 (m, 1H), 1.50-1.60 (m, 1H), 1.64-1.76 (m, 1H), 1.80-1.90 (m, 1H), 1.91-1.98 (m, 1H), 1.98 (s, 1.5H), 1.99 (s, 1.5H), 2.40 (s, 3H), 2.43 (s, 3H), 2.93 (d, J=6.8 Hz, 2H), 3.20-3.34 (m, 2H), 3.66-3.73 (m, 1H), 3.68 (s, 3H), 3.80-3.86 (m, 1H), 3.88-3.96 (m, 1H), 6.49 (dd, J=1.6, 6.8 Hz, 1H), 6.67 (s, 1H), 6.75 (s, 1H), 7.03 (dd, J=6.8, 8.8 Hz, 1H), 7.42 (dd, J=1.6, 8.8 Hz, 1H).

Example 147

N-Cyclopropylmethyl-N-[7-(2-methoxy-4,6-dimethylphenyl)-2-(methylsulfanyl)pyrazolo[1,5-a]pyridin-3-yl]-N-(3-pyridylmethyl)amine (Yellow Oil)

$^1$H NMR (400 MHz, CDCl$_3$) δ −0.04-0.01 (m, 2H), 0.28-0.35 (m, 2H), 0.80-0.89 (m, 1H), 1.94 (s, 3H), 2.39 (s, 3H), 2.44 (s, 3H), 2.87-2.97 (m, 2H), 3.65 (s, 3H), 4.36 (s, 2H), 6.48 (dd, J=1.3, 6.8 Hz, 1H), 6.66 (s, 1H), 6.74 (s, 1H), 7.03 (dd, J=6.8, 8.8 Hz, 1H), 7.17 (dd, J=4.8, 8.0 Hz, 1H), 7.38 (dd, J=1.3, 8.8 Hz, 1H), 7.74 (d, J=8.0 Hz, 1H), 8.42 (d, J=4.8 Hz, 1H), 8.61 (s, 1H).

Example 148

N-Cyclopropylmethyl-N-[7-(2,6-dimethoxy-4-methylphenyl)-2-(methylsulfanyl)pyrazolo[1,5-a]pyridin-3-yl]-N-(2-furylmethyl)amine (Yellow Oil)
$^1$H NMR (400 MHz, CDCl$_3$) δ –0.04-0.06 (m, 2H), 0.28-0.36 (m, 2H), 0.80-0.93 (m, 1H), 2.42 (s, 3H), 2.45 (s, 3H), 3.00 (d, J=6.8 Hz, 2H), 3.68 (s, 6H), 4.31 (s, 2H), 6.08-6.12 (m, 1H), 6.24 (dd, J=1.8, 3.1 Hz, 1H), 6.48 (s, 2H), 6.55 (dd, J=1.4, 6.8 Hz, 1H), 6.99 (dd, J=6.8, 8.9 Hz, 1H), 7.24 (dd, J=1.3, 8.8 Hz, 1H), 7.32 (dd, J=0.7, 1.8 Hz, 1H).

Example 149

N-Cyclopropylmethyl-N-[7-(2,6-dimethoxy-4-methylphenyl)-2-(methylsulfanyl)pyrazolo[1,5-a]pyridin-3-yl]-N-[(5-methyl-2-furyl)methyl]amine (Yellow Oil)
$^1$H NMR (400 MHz, CDCl$_3$) δ –0.02-0.06 (m, 2H), 0.28-0.36 (m, 2H), 0.80-0.93 (m, 1H), 2.22 (s, 3H), 2.42 (s, 3H), 2.45 (s, 3H), 3.00 (d, J=6.8 Hz, 2H), 3.68 (s, 6H), 4.25 (s, 2H), 5.78-5.82 (m, 1H), 5.97 (d, J=3.1 Hz, 1H), 6.48 (s, 2H), 6.55 (dd, J=1.4, 6.9 Hz, 1H), 6.98 (dd, J=6.8, 8.9 Hz, 1H), 7.25 (dd, J=1.4, 8.9 Hz, 1H).

Example 150

N-Cyclopropylmethyl-N-[7-(2-methoxy-4,6-dimethylphenyl)-2-(methylsulfanyl)pyrazolo[1,5-a]pyridin-3-yl]-N-(1H-3-pyrrolylmethyl)amine (Yellow Oil)
$^1$H NMR (400 MHz, CDCl$_3$) δ –0.06-–0.03 (m, 2H), 0.28-0.34 (m, 2H), 0.78-0.88 (m, 1H), 1.97 (s, 3H), 2.39 (s, 3H), 2.44 (s, 3H), 2.88 (d, J=6.4 Hz, 2H), 3.66 (s, 3H), 4.34 (s, 2H), 6.07-6.10 (m, 1H), 6.09 (dd, J=2.4, 5.6 Hz, 1H), 6.50 (dd, J=1.6, 6.8 Hz, 1H), 6.66 (s, 1H), 6.70-6.72 (m, 1H), 6.74 (s, 1H), 7.04 (dd, J=6.8, 8.8 Hz, 1H), 7.35 (dd, J=1.6, 8.8 Hz, 1H), 8.70-8.80 (m, 1H).

Example 151

N-Cyclopropylmethyl-N-[7-(2-methoxy-4,6-dimethylphenyl)-2-(methylsulfanyl)pyrazolo[1,5-a]pyridin-3-yl]-N-(1H-4-pyrazolylmethyl)amine (Yellow Oil)
$^1$H NMR (400 MHz, CDCl$_3$) δ 0.00-0.02 (m, 2H), 0.33-0.39 (m, 2H), 0.82-0.92 (m, 1H), 1.98 (s, 3H), 2.41 (s, 3H), 2.47 (s, 3H), 2.95 (d, J=6.8 Hz, 2H), 3.67 (s, 3H), 4.49 (s, 2H), 6.14 (d, J=1.6 Hz, 1H), 6.53 (dd, J=1.2, 6.8 Hz, 1H), 6.68 (s, 1H), 6.70 (s, 1H), 7.08 (dd, J=6.8, 8.8 Hz, 1H), 7.39 (dd, J=1.2, 8.8 Hz, 1H), 7.48 (d, J=1.2 Hz, 1H).

Example 152

N-Cyclopropylmethyl-N-[7-(2-methoxy-4,6-dimethylphenyl)-2-(methylsulfanyl)pyrazolo[1,5-a]pyridin-3-yl]-N-(4-pyridylmethyl)amine (Yellow Oil)
$^1$H NMR (400 MHz, CDCl$_3$) δ –0.06-–0.02 (m, 2H), 0.29-0.36 (m, 2H), 0.81-0.90 (m, 1H), 1.95 (s, 3H), 2.39 (s, 3H), 2.44 (s, 3H), 2.83-2.95 (m, 2H), 3.65 (s, 3H), 4.37 (s, 2H), 6.49 (dd, J=1.3, 6.8 Hz, 1H), 6.65 (s, 1H), 6.73 (s, 1H), 7.05 (dd, J=6.8, 8.8 Hz, 1H), 7.39 (d, J=6.0 Hz, 2H), 7.43 (dd, J=1.3, 8.8 Hz, 1H), 8.47 (d, J=6.0 Hz, 2H).

Example 153

N-Cyclopropylmethyl-N-(2,2-difluoroethyl)-N-[7-(2-methoxy-4,6-dimethylphenyl)-2-(methylsulfanyl)pyrazolo[1,5-a]pyridin-3-yl]amine (Yellow Oil)
$^1$H NMR (400 MHz, CDCl$_3$) δ –0.02-0.04 (m, 2H), 0.28-0.38 (m, 2H), 0.78-0.90 (m, 1H), 1.97 (s, 3H), 2.38 (s, 3H), 2.42 (s, 3H), 2.99 (dd, J=1.6, 6.8 Hz, 2H), 3.49 (dd, J=4.4, 9.6 Hz, 2H), 3.66 (s, 3H), 5.76 (tt, J=4.6, 56.4 Hz, 1H), 6.52 (dd, J=1.6, 7.2 Hz, 1H), 6.65 (s, 1H), 6.74 (s, 1H), 7.08 (dd, J=6.8, 8.8 Hz, 1H), 7.41 (dd, J=1.6, 8.8 Hz, 1H).

Example 154

N-(2,2-Difluoroethyl)-N-[7-(2-methoxy-4,6-dimethylphenyl)-2-(methylsulfanyl)pyrazolo[1,5-a]pyridin-3-yl]-N-tetrahydro-3-furanylmethylamine (Yellow Oil)
$^1$H NMR (400 MHz, CDCl$_3$) δ 1.58-1.66 (m, 1H), 1.90-1.98 (m, 1H), 1.99 (s, 3H), 2.18-2.26 (m, 1H), 2.40 (s, 3H), 2.44 (s, 3H), 3.06-3.14 (m, 1H), 3.22-3.28 (m, 1H), 3.36-3.46 (m, 2H), 3.56-3.62 (m, 1H), 3.64-3.72 (m, 1H), 3.68 (s, 3H), 3.72-3.84 (m, 2H), 5.74 (tt, J=4.4, 56.4 Hz, 1H), 6.56 (dd, J=1.6, 6.8 Hz, 1H), 6.67 (s, 1H), 6.76 (s, 1H), 7.12 (dd, J=6.8, 8.8 Hz, 1H), 7.36 (dd, J=1.2, 8.8 Hz, 1H).

Example 155

N-Cyclopropylmethyl-N-[7-[2-(fluoromethoxy)-4,6-dimethylphenyl]-2-(methylsulfanyl)pyrazolo[1,5-a]pyridin-3-yl]-N-tetrahydro-3-furanylmethylamine (Light Yellow Oil)
$^1$H NMR (400 MHz, CDCl$_3$) δ –0.06-0.01 (m, 2H), 0.28-0.35 (m, 2H), 0.78-0.88 (m, 1H), 1.59-1.70 (m, 1H), 1.88-1.98 (m, 1H), 2.04 (s, 3H), 2.20-2.30 (m, 1H), 2.40 (s, 3H), 2.41 (s, 3H), 2.84-2.94 (m, 2H), 3.02-3.10 (m, 1H), 3.20-3.27 (m, 1H), 3.58-3.70 (m, 2H), 3.72-3.85 (m, 2H), 5.40 (dd, J=2.4, 75 Hz, 1H), 5.53 (dd, J=2.4, 75 Hz, 1H), 6.50 (dd, J=1.3, 6.8 Hz, 1H), 6.91 (s, 1H), 6.94 (s, 1H), 7.05 (dd, J=6.8, 8.8 Hz, 1H), 7.40 (dd, J=1.3, 8.8 Hz, 1H).

Example 156

N-Cyclopropylmethyl-N-[7-(2-methoxy-4,6-dimethylphenyl)-2-(methylsulfanyl)pyrazolo[1,5-a]pyridin-3-yl]-N-[(1-methyl-1H-2-imidazolyl)methyl]amine (Light Yellow Amorphous)
$^1$H NMR (400 MHz, CDCl$_3$) δ –0.08-0.02 (m, 2H), 0.23-0.33 (m, 2H), 0.75-0.85 (m, 1H), 1.98 (s, 3H), 2.40 (s, 3H), 2.43 (s, 3H), 2.85-2.91 (m, 2H), 3.65 (s, 3H), 3.66 (s, 3H), 4.43 (s, 2H), 6.49 (dd, J=1.3, 6.8 Hz, 1H), 6.66 (s, 1H), 6.74 (s, 1H), 6.79 (d, J=1.2 Hz, 1H), 6.91 (d, J=1.2 Hz, 1H), 7.02 (dd, J=6.8, 8.8 Hz, 1H), 7.26 (dd, J=1.3, 8.8 Hz, 1H).

Example 157

N3-Cyclopropylmethyl-N3-[6-(dimethylamino)-3-pyridyl]methyl-7-(2-methoxy-4,6-dimethylphenyl)-2-(methylsulfanyl)pyrazolo[1,5-a]pyridin-3-amine (Light Yellow Amorphous)
$^1$H NMR (400 MHz, CDCl$_3$) δ −0.12-−0.02 (m, 2H), 0.22-0.32 (m, 2H), 0.75-0.86 (m, 1H), 1.95 (s, 3H), 2.39 (s, 3H), 2.43 (s, 3H), 2.80-2.92 (m, 2H), 3.04 (s, 6H), 3.65 (s, 3H), 4.19 (s, 2H), 6.44 (d, J=8.0 Hz, 1H), 6.47 (dd, J=1.3, 6.8 Hz, 1H), 6.65 (s, 1H), 6.73 (s, 1H), 7.00 (dd, J=6.8, 8.8 Hz, 1H), 7.40 (dd, J=1.3, 8.8 Hz, 1H), 7.53 (dd, J=2.4, 8.0 Hz, 1H), 8.11 (d, J=2.4 Hz, 1H).

Example 158

2-[7-(2-Methoxy-4,6-dimethylphenyl)-2-(methylsulfanyl)pyrazolo[1,5-a]pyridin-3-yl]amino-1-methyl-ethyl benzoate (Yellow Oil)
$^1$H NMR (400 MHz, CDCl$_3$) δ 1.41-1.49 (m, 3H), 1.96 (s, 3H), 2.35 (s, 3H), 2.39 (s, 3H), 3.35-3.49 (m, 2H), 3.66 (s, 3H), 5.25-5.36 (m, 1H), 6.52 (dd, J=6.8 Hz, 1H), 6.66 (s, 1H), 6.75 (s, 1H), 7.01 (dd, J=6.8, 8.8 Hz, 1H), 7.38 (d, J=8.0 Hz, 1H), 7.46 (dd, J=8.0, 8.0 Hz, 1H), 7.46 (d, J=8.8 Hz, 1H), 7.57 (dd, J=8.0, 8.0 Hz, 1H), 8.07 (d, J=8.0 Hz, 2H).

Example 159

N-Cyclopropylmethyl-N-[7-(2-methoxy-4,6-dimethylphenyl)-2-(methylsulfanyl)pyrazolo[1,5-a]pyridin-3-yl]-N-tetrahydro-2H-4-pyranylmethylamine After dissolving N-cyclopropylmethyl-N-[7-(2-methoxy-4,6-dimethylphenyl)-2-(methylsulfanyl)pyrazolo[1,5-a]pyridin-3-yl]amine (100 mg) in tetrahydrofuran (2 mL), tetrahydro-2H-4-pyrancarbaldehyde (78 mg) [CAS No. 50675-18-8] and sodium triacetoxyborohydride (87 mg) were added, and the mixture was stirred for 1 hour. Saturated aqueous sodium hydrogencarbonate was added to the reaction mixture, extraction was performed with ethyl acetate, and the extract washed with brine. After drying over anhydrous magnesium sulfate and filtration, the solvent was concentrated under reduced pressure, the residue was purified by silica gel column chromatography, and the title compound (70 mg) was obtained from the n-hexane:ethyl acetate (7:1) fraction as a yellow oil.
$^1$H NMR (400 MHz, CDCl$_3$) δ −0.05-0.00 (m, 2H), 0.27-0.35 (m, 2H), 0.80-0.90 (m, 1H), 1.22-1.33 (m, 2H), 1.50-1.62 (m, 1H), 1.75-1.82 (m, 2H), 2.00 (s, 3H), 2.40 (s, 3H), 2.43 (s, 3H), 2.88 (d, J=6.4 Hz, 2H), 3.05 (d, J=7.2 Hz, 2H), 3.28-3.35 (m, 2H), 3.69 (s, 3H), 3.90-3.96 (m, 2H), 6.50 (dd, J=1.2, 6.8 Hz, 1H), 6.68 (s, 1H), 6.76 (s, 1H), 7.04 (dd, J=6.8, 8.8 Hz, 1H), 7.40 (dd, J=1.2, 8.8 Hz, 1H).

The compounds of Examples 160 to 198 were synthesized according to the production method of Example 159.

Example 160

N-[7-(4-Chloro-2,6-dimethoxyphenyl)-2-(methylsulfanyl)pyrazolo[1,5-a]pyridin-3-yl]-N-cyclopropylmethyl-N-tetrahydro-2H-4-pyranylamine (Yellow Oil)
$^1$H NMR (400 MHz, CDCl$_3$) δ −0.02-0.06 (m, 2H), 0.26-0.36 (m, 2H), 0.72-0.88 (m, 1H), 1.50-1.65 (m, 2H), 1.84-1.94 (m, 2H), 2.49 (s, 3H), 3.04 (d, J=6.6 Hz, 2H), 3.30-3.39 (m, 1H), 3.44 (dt, J=1.5, 12.0 Hz, 2H), 3.75 (s, 6H), 3.96-4.04 (m, 2H), 6.61 (br d, J=6.8 Hz, 1H), 6.73 (s, 2H), 7.10 (dd, J=6.9, 8.9 Hz, 1H), 7.45 (br d, J=8.8 Hz, 1H).
MS (ESI) m/z 488 MH$^+$ Example 161

N-Cyclopropylmethyl-N-[7-(2-methoxy-4,6-dimethylphenyl)-2-(methylsulfanyl)pyrazolo[1,5-a]pyridin-3-yl]-N-tetrahydro-2H-4-pyranylamine (Light Yellow Amorphous)
$^1$H NMR (400 MHz, CDCl$_3$) δ −0.08-−0.04 (m, 2H), 0.22-0.26 (m, 2H), 0.70-0.80 (m, 1H), 1.46-1.60 (m, 2H), 1.80-1.86 (m, 2H), 1.99 (s, 3H), 2.40 (s, 3H), 2.43 (s, 3H), 2.99 (d, J=6.4 Hz, 2H), 3.26-3.34 (m, 1H), 3.35-3.43 (m, 2H), 3.68 (s, 3H), 3.92-3.98 (m, 2H), 6.50 (dd, J=1.2, 6.8 Hz, 1H), 6.67 (s, 1H), 6.75 (s, 1H), 7.05 (dd, J=6.8, 8.8 Hz, 1H), 7.38 (dd, J=1.2, 8.8 Hz, 1H).

Example 162

N-[7-(2-Methoxy-4,6-dimethylphenyl)-2-(methylsulfanyl)pyrazolo[1,5-a]pyridin-3-yl]-N-propyl-N-tetrahydro-2H-4-pyranylamine (Light Yellow Crystals)
$^1$H NMR (400 MHz, CDCl$_3$) δ 0.87 (t, J=7.2 Hz, 3H), 1.26-1.36 (m, 2H), 1.50-1.60 (m, 2H), 1.80-1.86 (m, 2H), 2.40 (s, 3H), 2.42 (s, 3H), 3.09 (t, J=6.4 Hz, 2H), 3.16-3.24 (m, 1H), 3.38 (t, J=11.6 Hz, 2H), 3.69 (s, 3H), 3.92-3.98 (m, 2H), 6.49-6.52 (m, 1H), 6.67 (s, 1H), 6.75 (s, 1H), 7.02-7.08 (m, 1H), 7.34-7.38 (m, 1H).

Example 163

N-(3-Fluoropropyl)-N-[7-(2-methoxy-4,6-dimethylphenyl)-2-(methylsulfanyl)pyrazolo[1,5-a]pyridin-3-yl]-N-tetrahydro-2H-4-pyranylamine (Light Yellow Crystals)
$^1$H NMR (400 MHz, CDCl$_3$) δ 1.50-1.73 (m, 4H), 1.80-1.86 (m, 2H), 1.99 (s, 3H), 3.14-3.23 (m, 1H), 3.30 (t, J=6.8 Hz, 2H), 3.37 (dt, J=2.0, 12.0 Hz, 2H), 3.69 (s, 3H), 3.92-4.00 (m, 2H), 4.55 (td, J=5.6, 47.6 Hz, 2H), 6.53 (dd, J=1.2, 6.8 Hz, 1H), 6.67 (s, 1H), 6.75 (s, 1H), 7.07 (dd, J=6.8, 8.8 Hz, 1H), 7.33 (dd, J=1.2, 8.8 Hz, 1H).

Example 164

N-Cyclopropylmethyl-N-[7-(2,6-dimethoxy-4-methylphenyl)-2-(methylsulfanyl)pyrazolo[1,5-a]pyridin-3-yl]-N-tetrahydro-2H-4-pyranylamine (Light Yellow Amorphous)
$^1$H NMR (400 MHz, CDCl$_3$) δ −0.04-0.00 (m, 2H), 0.24-0.30 (m, 2H), 0.70-0.80 (m, 1H), 1.48-1.62 (m, 2H), 1.80-1.86 (m, 2H), 2.44 (s, 3H), 2.45 (s, 3H), 2.99 (d, J=6.8 Hz, 2H), 3.25-3.40 (m, 2H), 3.69 (s, 6H), 3.90-3.98 (m, 2H), 6.49 (s, 2H), 6.58 (dd, J=1.2, 6.8 Hz, 1H), 7.04 (dd, J=6.8, 8.8 Hz, 1H), 7.37 (dd, J=1.2, 8.8 Hz, 1H).

Example 165

N-[7-(2,6-Dimethoxy-4-methylphenyl)-2-(methylsulfanyl)pyrazolo[1,5-a]pyridin-3-yl]-N-propyl-N-tetrahydro-2H-4-pyranylamine (Light Yellow Crystals)
$^1$H NMR (400 MHz, CDCl$_3$) δ 0.86 (t, J=7.2 Hz, 3H), 1.28-1.36 (m, 2H), 1.49-1.60 (m, 2H), 1.80-1.86 (m, 2H), 2.43 (s, 6H), 3.09 (t, J=7.2 Hz, 2H), 3.15-3.24 (m, 1H), 3.33-3.40 (m, 2H), 3.70 (s, 6H), 3.92-3.98 (m, 2H), 6.49 (s, 2H), 6.57-6.60 (m, 1H), 7.02-7.06 (m, 1H), 7.32-7.36 (m, 1H).

Example 166

N-[7-(2,6-Dimethoxy-4-methylphenyl)-2-(methylsulfanyl)pyrazolo[1,5-a]pyridin-3-yl]-N-(3-fluoropropyl)-N-tetrahydro-2H-4-pyranylamine (Light Yellow Crystals)
$^1$H NMR (400 MHz, CDCl$_3$) δ 1.50-1.73 (m, 4H), 1.80-1.86 (m, 2H), 2.42 (s, 1.5H), 2.43 (s, 1.5H), 2.44 (s, 3H), 3.14-3.23 (m, 1H), 3.29 (t, J=6.4 Hz, 2H), 3.37 (t, J=12.0 Hz, 2H), 3.70 (s, 6H), 3.92-3.99 (m, 2H), 4.54 (td, J=5.6, 47.6 Hz, 2H), 6.49 (s, 2H), 6.58-6.62 (m, 1H), 7.04-7.08 (m, 1H), 7.29-7.33 (m, 1H).

Example 167

N-[7-(4-Methoxy-2,6-dimethylphenyl)-2-(methylsulfanyl)pyrazolo[1,5-a]pyridin-3-yl]-N-propyl-N-tetrahydro-2H-4-pyranylamine (Yellow Oil)
$^1$H NMR (400 MHz, CDCl$_3$) δ 0.87 (t, J=7.3 Hz, 3H), 1.24-1.37 (m, 2H), 1.46-1.60 (m, 2H), 1.78-1.86 (m, 2H), 2.01 (s, 6H), 2.40 (s, 3H), 3.09 (t, J=7.2 Hz, 2H), 3.15-3.25 (m, 1H), 3.38 (dt, J=2.0, 12.0 Hz, 2H), 3.85 (s, 3H), 3.92-3.99 (m, 2H), 6.44 (dd, J=1.5, 6.8 Hz, 1H), 6.69 (s, 2H), 7.05 (dd, J=6.8, 9.0 Hz, 1H), 7.37 (dd, J=1.4, 8.9 Hz, 1H).
MS (ESI) m/z 440 MH$^+$

Example 168

N-Cyclopropylmethyl-N-[7-(4-methoxy-2,6-dimethylphenyl)-2-(methylsulfanyl)pyrazolo[1,5-a]pyridin-3-yl]-N-tetrahydro-2H-4-pyranylamine (Yellow Crystals)
$^1$H NMR (400 MHz, CDCl$_3$) δ −0.02-0.06 (m, 2H), 0.28-0.37 (m, 2H), 0.78-0.90 (m, 1H), 1.55-1.68 (m, 2H), 1.89-1.98 (m, 2H), 2.11 (s, 6H), 2.51 (s, 3H), 3.09 (d, J=6.6 Hz, 2H), 3.35-3.45 (m, 1H), 3.49 (dt, J=2.0, 12.0 Hz, 2H), 3.95 (s, 3H), 4.02-4.09 (m, 2H), 6.54 (dd, J=1.4, 6.6 Hz, 1H), 6.79 (s, 2H), 7.15 (dd, J=6.7, 8.9 Hz, 1H), 7.49 (dd, J=1.4, 8.9 Hz, 1H).
MS (ESI) m/z 452 MH$^+$

Example 169

N-(3-Fluoropropyl)-N-[7-(4-methoxy-2,6-dimethylphenyl)-2-(methylsulfanyl)pyrazolo[1,5-a]pyridin-3-yl]-N-tetrahydro-2H-4-pyranylamine (Light Brown Oil)
$^1$H NMR (400 MHz, CDCl$_3$) δ 1.48-1.65 (m, 2H), 1.66-1.74 (m, 2H), 1.78-1.87 (m, 2H), 2.01 (s, 6H), 2.40 (s, 3H), 3.14-3.24 (m, 1H), 3.29 (t, J=6.6 Hz, 2H), 3.37 (dt, J=2.0, 12.0 Hz, 2H), 3.85 (s, 3H), 3.92-4.00 (m, 2H), 4.49 (t, J=5.8 Hz, 1H), 4.61 (t, J=5.8 Hz, 1H), 6.46 (dd, J=1.5, 6.8 Hz, 1H), 6.69 (s, 2H), 7.07 (dd, J=6.8, 8.8 Hz, 1H), 7.34 (dd, J=1.4, 8.8 Hz, 1H).
MS (ESI) m/z 458 MH$^+$

Example 170

N-[7-(4-Chloro-2,6-dimethoxyphenyl)-2-(methylsulfanyl)pyrazolo[1,5-a]pyridin-3-yl]-N-(3-fluoropropyl)-N-tetrahydro-2H-4-pyranylamine (Yellow Crystals)
$^1$H NMR (400 MHz, CDCl$_3$) δ 1.48-1.65 (m, 2H), 1.66-1.74 (m, 2H), 1.78-1.87 (m, 2H), 2.42 (s, 3H), 3.16-3.23 (m, 1H), 3.28 (t, J=6.6 Hz, 2H), 3.36 (dt, J=1.8, 12.0 Hz, 2H), 3.70 (s, 6H), 3.90-4.00 (m, 2H), 4.48 (t, J=5.8 Hz, 1H), 4.60 (t, J=5.8 Hz, 1H), 6.57 (dd, J=1.4, 6.9 Hz, 1H), 6.67 (s, 2H), 7.06 (dd, J=6.8, 8.8 Hz, 1H), 7.33 (dd, J=1.4, 8.8 Hz, 1H).

Example 171

N-[7-(4-Chloro-2,6-dimethoxyphenyl)-2-(methylsulfanyl)pyrazolo[1,5-a]pyridin-3-yl]-N-propyl-N-tetrahydro-2H-4-pyranylamine (Yellow Crystals)
$^1$H NMR (400 MHz, CDCl$_3$) δ 0.86 (t, J=7.4 Hz, 3H), 1.25-1.38 (m, 2H), 1.47-1.60 (m, 2H), 1.78-1.87 (m, 2H), 2.42 (s, 3H), 3.08 (t, J=7.3 Hz, 2H), 3.14-3.24 (m, 1H), 3.37 (dt, J=2.0, 12.0 Hz, 2H), 3.70 (s, 6H), 3.91-3.99 (m, 2H), 6.55 (dd, J=1.4, 6.9 Hz, 1H), 6.67 (s, 2H), 7.04 (dd, J=6.8, 8.8 Hz, 1H), 7.36 (dd, J=1.4, 8.8 Hz, 1H).
MS (ESI) m/z 476 MH$^+$

Example 172

N-[7-(2-Chloro-6-methoxy-4-methylphenyl)-2-(methylsulfanyl)pyrazolo[1,5-a]pyridin-3-yl]-N-cyclopropylmethyl-N-tetrahydro-2H-4-pyranylamine (Light Green Crystals)
$^1$H NMR (400 MHz, CDCl$_3$) δ −0.05-0.00 (m, 2H), 0.20-0.26 (m, 2H), 0.70-0.90 (m, 1H), 1.50-1.62 (m, 2H), 1.80-1.88 (m, 2H), 2.42 (s, 3H), 2.43 (s, 3H), 2.99 (d, J=6.8 Hz, 2H), 3.25-3.44 (m, 3H), 3.70 (s, 3H), 3.90-3.95 (m, 2H), 6.56 (dd, J=1.6, 7.2 Hz, 1H), 6.73 (s, 1H), 6.96 (d, J=0.8 Hz, 1H), 7.06 (dd, J=7.2, 9.2 Hz, 1H), 7.42 (dd, J=1.6, 8.8 Hz, 1H).

Example 173

N-[7-(2-Chloro-6-methoxy-4-methylphenyl)-2-(methylsulfanyl)pyrazolo[1,5-a]pyridin-3-yl]-N-propyl-N-tetrahydro-2H-4-pyranylamine (Light Yellow Crystals)
$^1$H NMR (400 MHz, CDCl$_3$) δ 0.86 (t, J=7.2 Hz, 3H), 1.25-1.36 (m, 2H), 1.50-1.70 (m, 2H), 1.78-1.88 (m, 2H), 2.41 (s, 3H), 2.42 (s, 3H), 3.09 (t, J=7.6 Hz, 2H), 3.15-3.22 (m, 1H), 3.34-3.40 (m, 2H), 3.70 (s, 3H), 3.93-3.96 (m, 2H), 6.56 (dd, J=1.2, 6.8 Hz, 1H), 6.73 (s, 1H), 6.96 (br s, 1H), 7.06 (dd, J=7.2, 9.2 Hz, 1H), 7.39 (dd, J=1.6, 8.8 Hz, 1H).

Example 174

N-Cyclopropylmethyl-N-[7-(4-methoxy-2,6-dimethylphenyl)-2-(methylsulfanyl)pyrazolo[1,5-a]pyridin-3-yl]-N-(1-methyl-4-piperidyl)amine (Yellow Crystals)
$^1$H NMR (400 MHz, CDCl$_3$) δ −0.02-0.06 (m, 2H), 0.27-0.36 (m, 2H), 0.78-0.92 (m, 1H), 1.56-1.68 (m, 2H), 1.83-1.93 (m, 1H), 1.98-2.10 (m, 3H), 2.11 (s, 6H), 2.33 (s, 3H), 2.51 (s, 3H), 2.88-2.97 (m, 2H), 3.10 (d, J=6.6 Hz, 2H), 3.12-3.22 (m, 1H), 3.95 (s, 3H), 6.53 (dd, J=1.4, 6.7 Hz, 1H), 6.79 (s, 2H), 7.13 (dd, J=6.8, 8.8 Hz, 1H), 7.49 (dd, J=1.4, 8.8 Hz, 1H).
MS (ESI) m/z 465 MH$^+$ Example 175

1-(4-(Cyclopropylmethyl)[7-(4-methoxy-2,6-dimethylphenyl)-2-(methylsulfanyl)pyrazolo[1,5-a]pyridin-3-yl]aminopiperidino)-1-ethanone (Light Yellow Oil)
$^1$H NMR (400 MHz, CDCl$_3$) δ −0.02-0.06 (m, 2H), 0.28-0.38 (m, 2H), 0.78-0.90 (m, 1H), 1.43-1.56 (m, 2H), 1.97-2.08 (m, 2H), 2.11 (s, 3H), 2.13 (s, 3H), 2.15 (s, 3H), 2.52 (s, 3H), 2.86 (dt, J=2.8, 14.0 Hz, 1H), 3.09 (d, J=6.6 Hz, 2H), 3.19 (dt, J=2.8, 14.0 Hz, 1H), 3.38-3.50 (m, 1H), 3.82-3.92 (m, 1H), 3.95 (s, 3H), 4.48-4.58 (m, 1H), 6.56 (dd, J=1.5, 6.8 Hz, 1H), 6.80 (s, 2H), 7.16 (dd, J=6.8, 8.8 Hz, 1H), 7.47 (dd, J=1.5, 8.8 Hz, 1H).
MS (ESI) m/z 493 MH$^+$ Example 176

N-Cyclopropylmethyl-N-[7-(2-methoxy-4,6-dimethylphenyl)-2-(methylsulfanyl)pyrazolo[1,5-a]pyridin-3-yl]-N-tetrahydro-2-thiophenylamine (Light Yellow Oil)
$^1$H NMR (400 MHz, CDCl$_3$) δ −0.04-0.06 (m, 2H), 0.26-0.36 (m, 2H), 0.78-0.88 (m, 1H), 1.85-1.95 (m, 1H), 2.03 (s, 1.5H), 2.04 (s, 1.5H), 2.15-2.25 (m, 1H), 2.46 (s, 3H), 2.49 (s, 3H), 2.76-2.84 (m, 1H), 2.85-2.92 (m, 2H), 2.93-3.01 (m, 1H), 3.02-3.08 (m, 2H), 3.74 (s, 3H), 4.01-4.12 (m, 1H), 6.57 (dd, J=1.4, 6.8 Hz, 1H), 6.73 (s, 1H), 6.81 (s, 1H), 7.12 (dd, J=6.8, 8.8 Hz, 1H), 7.46 (dd, J=1.4, 8.8 Hz, 1H).

Example 177

N-Cyclopropylmethyl-N-[7-(2-methoxy-4,6-dimethylphenyl)-2-(methylsulfanyl)pyrazolo[1,5-a]pyridin-3-yl]-N-tetrahydro-2H-3-pyranylamine (Yellow Solid)
$^1$H NMR (400 MHz, CDCl$_3$) δ −0.02-0.04 (m, 2H), 0.26-0.36 (m, 2H), 0.78-0.88 (m, 1H), 1.32-1.44 (m, 1H), 1.62-1.78 (m, 2H), 2.06 (s, 3H), 2.04-2.18 (m, 1H), 2.48 (s, 3H), 2.50 (s, 3H), 2.98-3.10 (m, 2H), 3.20-3.38 (m, 3H), 3.76 (s, 3H), 3.82-3.92 (m, 1H), 4.12-4.22 (m, 1H), 6.60 (dd, J=1.6, 7.2 Hz, 1H), 6.75 (s, 1H), 6.83 (s, 1H), 7.15 (dd, J=7.2, 8.8 Hz, 1H), 7.45 (dd, J=1.6, 8.8 Hz, 1H).
MS (ESI) m/z 452 MH$^+$ Example 178

N-(3-Furylmethyl)-N-[7-(4-methoxy-2,6-dimethylphenyl)-2-(methylsulfanyl)pyrazolo[1,5-a]pyridin-3-yl]-N-tetrahydro-2H-4-pyranylamine (Yellow Oil)
$^1$H NMR (400 MHz, CDCl$_3$) δ 1.50-1.66 (m, 2H), 1.84-1.94 (m, 2H), 1.97 (s, 6H), 2.40 (s, 3H), 3.24-3.34 (m, 1H), 3.39 (t, J=12.0 Hz, 2H), 3.84 (s, 3H), 3.92-4.02 (m, 2H), 4.20 (s, 2H), 6.28 (s, 1H), 6.42 (d, J=6.6 Hz, 1H), 6.68 (s, 2H), 7.03 (dd, J=6.8, 8.7 Hz, 1H), 7.17-7.30 (m, 3H).

Example 179

N-(3-Furylmethyl)-N-[7-(2-methoxy-4,6-dimethylphenyl)-2-(methylsulfanyl)pyrazolo[1,5-a]pyridin-3-yl]-N-tetrahydro-2H-4-pyranylamine (Yellow Amorphous)
$^1$H NMR (400 MHz, CDCl$_3$) δ 1.50-1.66 (m, 2H), 1.82-1.94 (m, 2H), 1.95 (s, 3H), 2.39 (s, 3H), 2.41 (s, 3H), 3.22-3.33 (m, 1H), 3.38 (br t, J=12.0 Hz, 2H), 3.66 (s, 3H), 3.90-4.02 (m, 2H), 4.20 (s, 2H), 6.28-6.33 (m, 1H), 6.49 (dd, J=1.3, 6.8 Hz, 1H), 6.66 (s, 1H), 6.74 (s, 1H), 7.03 (dd, J=6.8, 8.9 Hz, 1H), 7.18-7.30 (m, 3H).

Example 180

N-[7-(2,6-Dimethoxy-4-methylphenyl)-2-(methylsulfanyl)pyrazolo[1,5-a]pyridin-3-yl]-N-tetrahydro-2-furanylmethyl-N-tetrahydro-2H-4-pyranylamine (White Crystals)
$^1$H NMR (400 MHz, CDCl$_3$) δ 1.47-1.66 (m, 4H), 1.73-1.94 (m, 4H), 2.43 (s, 3H), 2.44 (s, 3H), 2.97-3.05 (m, 1H), 3.15-3.25 (m, 1H), 3.30-3.47 (m, 3H), 3.62-3.85 (m, 3H), 3.70 (s, 6H), 3.90-3.99 (m, 2H), 6.49 (s, 2H), 6.59 (dd, J=1.3, 6.8 Hz, 1H), 7.05 (dd, J=6.8, 8.8 Hz, 1H), 7.35 (dd, J=1.3, 8.8 Hz, 1H).

Example 181

N-Cyclopropylmethyl-N-[7-(2-methoxy-4,6-dimethylphenyl)-2-(methylsulfanyl)pyrazolo[1,5-a]pyridin-3-yl]-N-tetrahydro-3-furanylamine (White Solid)
$^1$H NMR (400 MHz, CDCl$_3$) δ −0.15-−0.03 (m, 2H), 0.18-0.31 (m, 2H), 0.70-0.81 (m, 1H), 1.78-2.05 (m, 2H), 1.98 (s, 3H), 2.40 (s, 3H), 2.44 (s, 3H), 2.80-2.98 (m, 2H), 3.55-3.67 (m, 1H), 3.68 (s, 3H), 3.75-3.95 (m, 3H), 4.08-4.18 (m, 1H), 6.52 (d, J=6.8 Hz, 1H), 6.68 (s, 1H), 6.76 (s, 1H), 7.07 (dd, J=6.8, 8.8 Hz, 1H), 7.44 (d, J=8.8 Hz, 1H).

Example 182

N-[7-(2-Methoxy-4,6-dimethylphenyl)-2-(methylsulfanyl)pyrazolo[1,5-a]pyridin-3-yl]-N-tetrahydro-3-furanyl-N-tetrahydro-3-furanylmethylamine (White Solid)

$^1$H NMR (400 MHz, CDCl$_3$) δ 1.54-1.68 (m, 1H), 1.76-2.18 (m, 4H), 1.98 (s, 3H), 2.40 (s, 3H), 2.44 (s, 3H), 2.98-3.24 (m, 2H), 3.49-4.07 (m, 9H), 3.68 (s, 3H), 6.54 (d, J=6.8 Hz, 1H), 6.67 (s, 1H), 6.76 (s, 1H), 7.09 (dd, J=6.8, 8.8 Hz, 1H), 7.34 (d, J=8.8 Hz, 1H).

Example 183

N-Cyclopropylmethyl-N-[7-(2,6-dimethoxy-4-methylphenyl)-2-(methylsulfanyl)pyrazolo[1,5-a]pyridin-3-yl]-N-tetrahydro-2H-3-pyranylamine (Yellow Oil)

$^1$H NMR (400 MHz, CDCl$_3$) δ −0.02-0.04 (m, 2H), 0.28-0.34 (m, 2H), 0.74-0.84 (m, 1H), 1.28-1.38 (m, 1H), 1.60-1.70 (m, 2H), 2.04-2.12 (m, 1H), 2.48 (s, 3H), 2.49 (s, 3H), 2.98-3.06 (m, 2H), 3.20-3.34 (m, 3H), 3.74 (s, 6H), 3.80-3.86 (m, 1H), 4.10-4.18 (m, 1H), 6.54 (s, 2H), 6.64 (dd, J=1.2, 6.8 Hz, 1H), 7.10 (dd, J=6.8, 8.8 Hz, 1H), 7.40 (dd, J=1.2, 8.8 Hz, 1H).

Example 184

N-Cyclopropylmethyl-N-[7-(2,4-dimethoxy-6-methylphenyl)-2-(methylsulfanyl)pyrazolo[1,5-a]pyridin-3-yl]-N-tetrahydro-2H-3-pyranylamine (Yellow Oil)

$^1$H NMR (400 MHz, CDCl$_3$) δ −0.02-0.04 (m, 2H), 0.28-0.34 (m, 2H), 0.76-0.86 (m, 1H), 1.30-1.42 (m, 1H), 1.60-1.74 (m, 2H), 2.06-2.16 (m, 1H), 2.50 (s, 3H), 3.00-3.10 (m, 2H), 3.20-3.38 (m, 3H), 3.74 (s, 3H), 3.84-3.90 (m, 1H), 3.94 (s, 3H), 4.12-4.20 (m, 1H), 6.50 (s, 1H), 6.53 (s, 1H), 6.58 (dd, J=1.2, 7.2 Hz, 1H), 7.12 (dd, J=7.2, 8.8 Hz, 1H), 7.43 (dd, J=1.2, 8.8 Hz, 1H).

Example 185

N-Cyclopropylmethyl-N-[7-(2,4-dimethoxy-6-methylphenyl)-2-(methylsulfanyl)pyrazolo[1,5-a]pyridin-3-yl]-N-tetrahydro-2H-4-pyranylamine (Yellow Oil)

$^1$H NMR (400 MHz, CDCl$_3$) δ −0.02-0.04 (m, 2H), 0.26-0.34 (m, 2H), 0.78-0.88 (m, 1H), 1.52-1.68 (m, 2H), 1.86-1.96 (m, 2H), 2.09 (s, 3H), 2.51 (s, 3H), 3.02-3.10 (m, 2H), 3.32-3.40 (m, 1H), 3.40-3.50 (m, 2H), 3.75 (s, 3H), 3.94 (s, 3H), 3.98-4.08 (m, 2H), 6.49 (s, 1H), 6.54 (s, 1H), 6.58 (dd, J=1.2, 6.8 Hz, 1H), 7.12 (dd, J=6.8, 8.8 Hz, 1H), 7.46 (dd, J=1.2, 8.8 Hz, 1H).

Example 186

N-Cyclopropylmethyl-N-[7-(4-methoxy-2,6-dimethylphenyl)-2-(methylsulfanyl)pyrazolo[1,5-a]pyridin-3-yl]-N-tetrahydro-2H-3-pyranylamine (Yellow Oil)

$^1$H NMR (400 MHz, CDCl$_3$) δ −0.02-0.04 (m, 2H), 0.28-0.36 (m, 2H), 0.78-0.88 (m, 1H), 1.32-1.44 (m, 1H), 1.66-1.78 (m, 2H), 2.10 (s, 6H), 2.10-2.18 (m, 1H), 2.50 (s, 3H), 3.02-3.12 (m, 2H), 3.24-3.40 (m, 3H), 3.84-3.94 (m, 1H), 3.94 (s, 3H), 4.14-4.20 (m, 1H), 6.50 (dd, J=1.2, 6.8 Hz, 1H), 6.78 (s, 2H), 7.15 (dd, J=6.8, 8.8 Hz, 1H), 7.48 (dd, J=1.2, 8.8 Hz, 1H).

Example 187

N-Cyclopropylmethyl-N-[7-(2,6-dimethoxy-4-methylphenyl)-2-(methylsulfanyl)pyrazolo[1,5-a]pyridin-3-yl]-N-tetrahydro-2H-4-pyranylmethylamine (Yellow Oil)

$^1$H NMR (400 MHz, CDCl$_3$) δ −0.02-0.00 (m, 2H), 0.32-0.38 (m, 2H), 0.82-0.92 (m, 1H), 1.24-1.35 (m, 2H), 1.55-1.60 (m, 1H), 1.87-1.95 (m, 2H), 2.46 (s, 6H), 2.90 (d, J=6.8 Hz, 2H), 3.06 (d, J=7.2 Hz, 2H), 3.32 (dt, J=2.0, 12.0 Hz, 2H), 3.72 (s, 6H), 3.92-3.98 (m, 2H), 6.52 (s, 2H), 6.60 (dd, J=1.6, 6.8 Hz, 1H), 7.05 (dd, J=6.8, 8.8 Hz, 1H), 7.41 (dd, J=1.6, 8.8 Hz, 1H).

Example 188

N-[7-(2-Methoxy-4,6-dimethylphenyl)-2-(methylsulfanyl)pyrazolo[1,5-a]pyridin-3-yl]-N-tetrahydro-3-furanylmethyl-N-tetrahydro-2H-4-pyranylamine (White Amorphous)

$^1$H NMR (400 MHz, CDCl$_3$) δ 1.48-1.65 (m, 2H), 1.74-1.95 (m, 4H), 1.99 (s, 3H), 2.09-2.19 (m, 1H), 2.40 (s, 3H), 2.42 (s, 3H), 3.01-3.25 (m, 3H), 3.31-3.41 (m, 2H), 3.54-3.84 (m, 4H), 3.69 (s, 3H), 3.91-4.00 (m, 2H), 6.52 (dd, J=1.3, 6.8 Hz, 1H), 6.67 (s, 1H), 6.76 (s, 1H), 7.07 (dd, J=6.8, 8.8 Hz, 1H), 7.31 (dd, J=1.3, 8.8 Hz, 1H).

Example 189

N-Cyclopropylmethyl-N-(3,4-dihydro-2H-2-pyranylmethyl)-N-[7-(2-methoxy-4,6-dimethylphenyl)-2-(methylsulfanyl)pyrazolo[1,5-a]pyridin-3-yl]amine (Yellow Oil)

$^1$H NMR (400 MHz, CDCl$_3$) δ −0.05-0.00 (m, 2H), 0.28-0.34 (m, 2H), 0.83-0.92 (m, 1H), 1.58-1.70 (m, 1H), 1.90-2.04 (m, 2H), 1.99 (s, 1.5H), 2.01 (s, 1.5H), 2.04-2.13 (m, 1H), 2.40 (s, 3H), 2.42 (s, 3H), 2.97 (d, J=6.8 Hz, 2H), 3.17-3.23 (m, 1H), 3.46-3.52 (m, 1H), 3.69 (s, 1.5H), 3.70 (s, 1.5H), 3.77-3.83 (m, 1H), 4.60-4.65 (m, 1H), 6.33 (br d, J=6.4 Hz, 1H), 6.50-6.53 (m, 1H), 6.65 (br s, 1H), 6.74 (br s, 1H), 7.03-7.08 (m, 1H), 7.43-7.47 (m, 1H).

Example 190

N-Cyclopropylmethyl-N-[7-(2-methoxy-4,6-dimethylphenyl)-2-(methylsulfanyl)pyrazolo[1,5-a]pyridin-3-yl]-N-[(2-methoxy-3-pyridyl)methyl]amine (Yellow Oil)

$^1$H NMR (400 MHz, CDCl$_3$) δ −0.08-0.02 (m, 2H), 0.27-0.37 (m, 2H), 0.82-0.93 (m, 1H), 1.96 (s, 3H), 2.39 (s, 3H), 2.43 (s, 3H), 2.88-3.00 (m, 2H), 3.66 (s, 3H), 3.92 (s, 3H), 4.34 (s, 2H), 6.48 (dd, J=1.3, 6.8 Hz, 1H), 6.66 (s, 1H), 6.74

(s, 1H), 6.82 (dd, J=4.8, 7.2 Hz, 1H), 7.02 (dd, J=6.8, 8.8 Hz, 1H), 7.41 (dd, J=1.3, 8.8 Hz, 1H), 7.86 (dd, J=2.0, 7.2 Hz, 1H), 7.99 (dd, J=2.0, 4.8 Hz, 1H).

Example 191

N-[7-(2,6-Dimethoxy-4-methylphenyl)-2-(methylsulfanyl)pyrazolo[1,5-a]pyridin-3-yl]-N-tetrahydro-2H-4-pyranyl-N-tetrahydro-2H-4-pyranylmethylamine (White Amorphous)

$^1$H NMR (400 MHz, CDCl$_3$) δ 1.16-1.28 (m, 2H), 1.39-1.65 (m, 3H), 1.71-1.86 (m, 4H), 2.43 (s, 3H), 2.44 (s, 3H), 2.98-3.15 (m, 3H), 3.22-3.40 (m, 4H), 3.71 (s, 6H), 3.86-3.99 (m, 4H), 6.50 (s, 2H), 6.60 (d, J=6.8 Hz, 1H), 7.05 (dd, J=6.8, 8.8 Hz, 1H), 7.31 (d, J=8.8 Hz, 1H).

Example 192

N-(2,2-Difluoroethyl)-N-[7-(2-methoxy-4,6-dimethylphenyl)-2-(methylsulfanyl)pyrazolo[1,5-a]pyridin-3-yl]-N-tetrahydro-2H-4-pyranylamine (White Solid)

$^1$H NMR (400 MHz, CDCl$_3$) δ 1.44-1.58 (m, 2H), 1.80-1.86 (m, 2H), 1.99 (s, 3H), 2.40 (s, 3H), 2.43 (s, 3H), 3.18-3.28 (m, 1H), 3.32-3.42 (m, 2H), 3.44-3.54 (m, 2H), 3.68 (s, 3H), 3.92-3.98 (m, 2H), 5.67 (tt, J=4.4, 56.4 Hz, 1H), 6.56 (dd, J=1.6, 6.8 Hz, 1H), 6.67 (s, 1H), 6.76 (s, 1H), 7.12 (dd, J=6.8, 8.8 Hz, 1H), 7.35 (dd, J=1.6, 8.8 Hz, 1H).

Example 193

N-(2,2-Difluoroethyl)-N-[7-(2-methoxy-4,6-dimethylphenyl)-2-(methylsulfanyl)pyrazolo[1,5-a]pyridin-3-yl]-N-tetrahydro-2H-4-pyranylmethylamine (Brown Oil)

$^1$H NMR (400 MHz, CDCl$_3$) δ 1.20-1.32 (m, 2H), 1.50-1.62 (m, 1H), 1.76-1.82 (m, 2H), 2.00 (s, 3H), 2.41 (s, 3H), 2.45 (s, 3H), 3.06 (d, J=7.2, 2H), 3.28-3.48 (m, 4H), 3.69 (s, 3H), 3.92-3.98 (m, 2H), 5.74 (tt, J=4.4, 56.4 Hz, 1H), 6.56 (dd, J=1.6, 6.8 Hz, 1H), 6.67 (s, 1H), 6.76 (s, 1H), 7.11 (dd, J=6.8, 8.8 Hz, 1H), 7.36 (dd, J=1.2, 8.8 Hz, 1H).

Example 194

N-Butyl-N-[7-(2,6-dimethoxy-4-methylphenyl)-2-ethylpyrazolo[1,5-a]pyridin-3-yl]-N-tetrahydro-2H-4-pyranylmethylamine (Yellow Oil)

$^1$H NMR (400 MHz, CDCl$_3$) δ 0.85 (t, J=7.2 Hz, 3H), 1.19-1.40 (m, 6H), 1.48-1.60 (m, 1H), 1.74-1.80 (m, 2H), 2.43 (s, 6H), 2.95 (d, J=6.8 Hz, 2H), 3.01 (t, J=6.8 Hz, 2H), 3.30 (dt, J=2.0, 11.6 Hz, 2H), 3.70 (s, 3H), 3.88-3.95 (m, 2H), 6.48 (s, 2H), 6.57 (dd, J=1.6, 7.2 Hz, 1H), 7.02 (dd, J=7.2, 8.8 Hz, 1H), 7.33 (dd, J=1.6, 8.8 Hz, 1H).

Example 195

N-Cyclobutylmethyl-N-[7-(2,6-dimethoxy-4-methylphenyl)-2-ethylpyrazolo[1,5-a]pyridin-3-yl]-N-tetrahydro-2H-4-pyranylmethylamine (Yellow Oil)

$^1$H NMR (400 MHz, CDCl$_3$) δ 1.18-1.29 (m, 2H), 1.48-1.63 (m, 3H), 1.70-1.80 (m, 4H), 1.81-1.90 (m, 2H), 2.30-2.40 (m, 1H), 2.43 (s, 3H), 2.44 (s, 3H), 2.93 (d, J=6.8 Hz, 2H), 3.04 (d, J=7.0 Hz, 2H), 3.30 (dt, J=2.0, 12.0 Hz, 2H), 3.69 (s, 6H), 3.89-3.94 (m, 2H), 6.48 (s, 2H), 6.57 (dd, J=1.6, 6.8 Hz, 1H), 7.02 (dd, J=6.8, 8.8 Hz, 1H), 7.31 (dd, J=1.6, 8.8 Hz, 1H).

Example 196

N-Cyclopropylmethyl-N-[7-(2-methoxy-4,6-dimethylphenyl)-2-(methylsulfanyl)pyrazolo[1,5-a]pyridin-3-yl]-N-tetrahydro-2H-3-pyranylmethylamine (Yellow Oil)

$^1$H NMR (400 MHz, CDCl$_3$) δ −0.02-0.06 (m, 2H), 0.28-0.42 (m, 2H), 0.82-0.92 (m, 1H), 1.22-1.32 (m, 1H), 1.52-1.66 (m, 2H), 1.72-1.80 (m, 1H), 1.86-1.94 (m, 1H), 2.04 (br s, 3H), 2.45 (br s, 3H), 2.47 (br s, 3H), 2.86-2.94 (m, 2H), 2.96-3.04 (m, 1H), 3.14-3.22 (m, 1H), 3.24-3.30 (m, 1H), 3.40-3.46 (m, 1H), 3.72 (br s, 3H), 3.84-3.90 (m, 1H), 4.12-4.18 (m, 1H), 6.54 (dd, J=1.6, 6.8 Hz, 1H), 6.71 (s, 1H), 6.79 (s, 1H), 7.07 (dd, J=6.8, 8.8 Hz, 1H), 7.44 (dd, J=1.6, 8.8 Hz, 1H).

MS (ESI) m/z 466 MH$^+$

Example 197

N-Cyclopropylmethyl-N-[7-(2,6-dimethoxy-4-methylphenyl)-2-(methylsulfanyl)pyrazolo[1,5-a]pyridin-3-yl]-N-tetrahydro-2H-3-pyranylmethylamine (Yellow Oil)

$^1$H NMR (400 MHz, CDCl$_3$) δ −0.02-0.04 (m, 2H), 0.30-0.36 (m, 2H), 0.80-0.90 (m, 1H), 1.18-1.28 (m, 1H), 1.52-1.60 (m, 2H), 1.66-1.76 (m, 1H), 1.82-1.90 (m, 1H), 2.45 (s, 6H), 2.84-2.92 (m, 2H), 2.94-2.98 (m, 1H), 3.10-3.18 (m, 1H), 3.18-3.26 (m, 1H), 3.36-3.44 (m, 1H), 3.70 (s, 6H), 3.80-3.86 (m, 1H), 4.08-4.12 (m, 1H), 6.49 (s, 2H), 6.57 (dd, J=1.6, 8.8 Hz, 1H), 7.03 (dd, J=6.8, 8.8 Hz, 1H), 7.39 (dd, J=1.6, 8.8 Hz, 1H).

Example 198

N-Cyclopropylmethyl-N-(5,6-dihydro-2H-3-pyranylmethyl)-N-[7-(2-methoxy-4,6-dimethylphenyl)-2-(methylsulfanyl)pyrazolo[1,5-a]pyridin-3-yl]amine (Yellow Oil)

$^1$H NMR (400 MHz, CDCl$_3$) δ −0.02-0.04 (m, 2H), 0.28-0.38 (m, 2H), 0.80-0.88 (m, 1H), 2.01 (s, 3H), 2.06-2.14 (m, 2H), 2.44 (s, 3H), 2.47 (s, 3H), 2.84-2.96 (m, 2H), 3.71 (s, 3H), 3.71-3.76 (m, 4H), 4.30-4.34 (m, 2H), 5.75 (br s, 1H), 6.53 (dd, J=1.6, 6.8 Hz, 1H), 6.70 (s, 1H), 6.78 (s, 1H), 7.07 (dd, J=6.8, 8.8 Hz, 1H), 7.44 (dd, J=1.6, 8.8 Hz, 1H).

MS (ESI) m/z 464 MH$^+$

Example 199

N-[7-(2-Methoxy-4,6-dimethylphenyl)-2-(methylsulfanyl)pyrazolo[1,5-a]pyridin-3-yl]-N-(2-oxetanylmethyl)amine After dissolving tert-butyl N-[7-(2-methoxy-4,6-dimethylphenyl)-2-(methylsulfanyl)pyrazolo[1,5-a]pyridin-3-yl]carbamate (100 mg) in N,N-dimethylformamide (2 mL), sodium hydride (60%, 15 mg) was added while cooling on ice, the mixture was stirred for 30 minutes, 2-oxetanylmethyl 4-methyl-1-benzenesulfonate (70 mg) was added and the mixture was stirred for 1 hour at 40° C. 2-Oxetanylmethyl 4-methyl-1-benzenesulfonate (23 mg) [CAS No. 115845-51-7] and sodium hydride (60%, 5 mg) were again added, and the mixture was stirred for 1 hour. Water was added to the reaction mixture, extraction was performed with ethyl acetate and the extract washed with brine. After drying the obtained organic layer over anhydrous magnesium sulfate and filtering it, the solvent was concentrated under reduced pressure to obtain crude tert-butyl N-[7-(2-methoxy-4,6-dimethylphenyl)-2-(methylsulfanyl)pyrazolo[1,5-a]pyridin-3-yl]-N-(2-oxetanylmethyl)carbamate. This was dissolved in ethyl acetate (2 mL) without purification, a 4 N hydrochloric acid/ethyl acetate solution (1 mL) was added, and the mixture was stirred at room temperature for 1 hour. The reaction mixture was neutralized with 5 N aqueous sodium hydroxide while cooling on ice, and then extraction was performed with ethyl acetate and the organic layer was washed with brine. After drying the obtained organic layer over anhydrous magnesium sulfate and filtering it, the solvent was concentrated under reduced pressure, the residue was purified by silica gel column chromatography, and the title compound (8 mg) was obtained from the n-hexane:ethyl acetate (3:1) fraction as a yellow oil.

$^1$H NMR (400 MHz, CDCl$_3$) δ 1.94-2.04 (m, 1H), 2.00 (s, 3H), 2.24-2.34 (m, 1H), 2.40 (s, 3H), 2.44 (s, 3H), 3.24-3.35 (m, 2H), 3.49-3.62 (m, 2H), 4.46-4.54 (m, 1H), 6.48-6.54 (m, 1H), 6.67 (s, 1H), 6.75 (s, 1H), 7.00-7.06 (m, 1H), 7.44-7.50 (m, 1H).

MS (ESI) m/z 383 MH$^+$

Example 200

N-Cyclopropylmethyl-N-[7-(2-methoxy-4,6-dimethylphenyl)-2-(methylsulfanyl)pyrazolo[1,5-a]pyridin-3-yl]-N-(2-oxetanylmethyl)amine After dissolving N-[7-(2-methoxy-4,6-dimethylphenyl)-2-(methylsulfanyl)pyrazolo[1,5-a]pyridin-3-yl]-N-(2-oxetanylmethyl)amine (8 mg) in N,N-dimethylformamide (2 mL), sodium hydride (60%, 1.6 mg) was added while cooling on ice, and then cyclopropylmethyl bromide (3.8 μL) was added and the mixture was stirred at room temperature for 12 hours. Water was added to the reaction mixture, extraction was performed with ethyl acetate and the extract washed with brine. After drying over anhydrous magnesium sulfate and filtration, the solvent was concentrated under reduced pressure, the residue was purified by silica gel column chromatography, and the title compound (1.8 mg) was obtained from the n-hexane:ethyl acetate (10:1) fraction as a yellow oil.

$^1$H NMR (400 MHz, CDCl$_3$) δ 0.22-0.26 (m, 2H), 0.54-0.60 (m, 2H), 1.06-1.16 (m, 1H), 1.99 (s, 1.5H), 2.00 (s, 1.5H), 2.00-2.08 (m, 1H), 2.16-2.26 (m, 1H), 2.39 (s, 3H), 2.43 (br s, 3H), 3.28-3.40 (m, 4H), 3.44-3.50 (m, 1H), 3.56-3.64 (m, 1H), 3.67 (s, 3H), 4.20-4.26 (m, 1H), 6.45-6.52 (m, 1H), 6.66 (s, 1H), 6.75 (s, 1H), 6.97-7.04 (m, 1H), 7.50-7.56 (m, 1H).

The compound of Example 201 was synthesized according to the production method of Examples 199 and 200.

Example 201

N-Cyclopropylmethyl-N-(1,3-dioxolan-2-ylmethyl)-N-[7-(2-methoxy-4,6-dimethylphenyl)-2-(methylsulfanyl)pyrazolo[1,5-a]pyridin-3-yl]amine (Yellow Oil)

$^1$H NMR (400 MHz, CDCl$_3$) δ −0.02-0.04 (m, 2H), 0.24-0.36 (m, 2H), 0.82-0.94 (m, 1H), 2.00 (s, 3H), 2.41 (s, 3H), 2.45 (s, 3H), 3.00-3.08 (m, 2H), 3.39 (d, J=4.0 Hz, 2H), 3.68 (s, 3H), 3.80-3.90 (m, 2H), 3.92-4.00 (m, 2H), 5.00 (t, J=4.0 Hz, 1H), 6.51 (dd, J=1.2, 6.8 Hz, 1H), 6.67 (s, 1H), 6.75 (s, 1H), 7.06 (dd, J=6.8, 8.8 Hz, 1H), 7.47 (dd, J=1.6, 8.8 Hz, 1H).

MS (ESI) m/z 454 MH$^+$

Example 202

1-(Cyclopropylmethyl)[7-(2-methoxy-4,6-dimethylphenyl)-2-(methylsulfanyl)pyrazolo[1,5-a]pyridin-3-yl]amino-2-propanol (Yellow Oil)

Cyclopropanecarboxyaldehyde (0.047 mL) and 3 M sulfuric acid (0.21 mL) were added to a solution of 2-[7-(2-methoxy-4,6-dimethylphenyl)-2-(methylsulfanyl)pyrazolo[1,5-a]pyridin-3-yl]amino-1-methylethyl benzoate (100 mg) in tetrahydrofuran (0.7 mL) while cooling on ice, and then sodium borohydride (16 mg) was slowly added thereto at the same temperature. The mixture was stirred for 30 minutes at room temperature, and then 5 N aqueous sodium hydroxide (0.3 mL) was added while cooling on ice to make the reaction mixture basic. Methanol (2.1 mL) was added to the reaction mixture, and after heating to reflux for 1 hour, it was returned to room temperature, extraction was performed with ethyl acetate, and the extract washed with brine, dried over anhydrous magnesium sulfate and concentrated under reduced pressure. The residue was purified by silica gel column chromatography (ethyl acetate:n-hexane=1:5) to obtain the title compound (80 mg) as a yellow oil.

$^1$H NMR (400 MHz, CDCl$_3$) δ −0.03-0.07 (m, 2H), 0.32-0.45 (m, 2H), 0.83-0.92 (m, 1H), 1.08-1.14 (m, 3H), 1.98 (s, 3H), 2.40 (s, 3H), 2.44 (s, 3H), 2.69-2.78 (m, 1H), 2.83-2.91 (m, 1H), 2.96-3.04 (m, 1H), 3.42-3.50 (m, 1H), 3.56-3.68 (m, 1H), 3.68 (s, 3H), 6.54 (dd, J=1.3, 6.8 Hz, 1H), 6.67 (s, 1H), 6.76 (s, 1H), 7.09 (dd, J=6.8, 8.8 Hz, 1H), 7.39 (dd, J=1.3, 8.8 Hz, 1H).

Example 203

1-(Cyclopropylmethyl)[7-(2-methoxy-4,6-dimethylphenyl)-2-(methylsulfanyl)pyrazolo[1,5-a]pyridin-3-yl]amino-3-fluoro-2-propanol (Brownish Oil)

p-Toluenesulfonic acid hydrate (40 mg) and epifluorohydrin (0.15 mL) [CAS No. 503-09-3] were added to a solution of N-cyclopropylmethyl-N-[7-(2-methoxy-4,6-dimethylphenyl)-2-(methylsulfanyl)pyrazolo[1,5-a]pyridin-3-yl]

amine (50 mg) in 1,2-dimethoxyethane (0.40 mL), and the mixture was heated to reflux for 3 hours. After cooling to room temperature, the solvent was distilled off under reduced pressure. The obtained residue was purified by basic silica gel column chromatography (ethyl acetate:n-hexane=1:5) to obtain the title compound (24 mg) as a brownish oil.

$^1$H NMR (400 MHz, CDCl$_3$) δ −0.03-0.09 (m, 2H), 0.34-0.46 (m, 2H), 0.84-0.94 (m, 1H), 1.99 (s, 3H), 2.40 (s, 3H), 2.44 (s, 3H), 2.87-2.94 (m, 1H), 2.97-3.04 (m, 1H), 3.06-3.14 (m, 1H), 3.48-3.55 (m, 1H), 3.68 (s, 3H), 3.68-3.79 (m, 2H), 4.30-4.57 (m, 2H), 6.55 (dd, J=1.3, 6.8 Hz, 1H), 6.68 (s, 1H), 6.76 (s, 1H), 7.11 (dd, J=6.8, 8.8 Hz, 1H), 7.39 (dd, J=1.3, 8.8 Hz, 1H).

The compounds of Examples 204 to 206 were synthesized according to the production methods of Examples 202 and 203.

Example 204

1-(Cyclopropylmethyl)[7-(2-methoxy-4,6-dimethylphenyl)-2-(methylsulfanyl)pyrazolo[1,5-a]pyridin-3-yl]amino-3-methoxy-2-propanol (Yellow Oil)

$^1$H NMR (400 MHz, CDCl$_3$) δ −0.05-0.07 (m, 2H), 0.32-0.44 (m, 2H), 0.84-0.93 (m, 1H), 1.98 (s, 3H), 2.40 (s, 3H), 2.43 (s, 3H), 2.86-2.93 (m, 1H), 2.96-3.06 (m, 2H), 3.35 (s, 3H), 3.36-3.51 (m, 3H), 3.67 (s, 3H), 6.54 (dd, J=1.3, 6.8 Hz, 1H), 6.67 (s, 1H), 6.76 (s, 1H), 7.08 (dd, J=6.8, 8.8 Hz, 1H), 7.40 (dd, J=1.3, 8.8 Hz, 1H).

Example 205

(2S)-1-(Cyclopropylmethyl)[7-(2-methoxy-4,6-dimethylphenyl)-2-(methylsulfanyl)pyrazolo[1,5-a]pyridin-3-yl]amino-3-methoxypropan-2-ol (Yellow Oil)

$^1$H NMR (400 MHz, CDCl$_3$) δ −0.05-0.07 (m, 2H), 0.32-0.44 (m, 2H), 0.84-0.93 (m, 1H), 1.98 (s, 3H), 2.40 (s, 3H), 2.43 (s, 3H), 2.86-2.93 (m, 1H), 2.96-3.06 (m, 2H), 3.35 (s, 3H), 3.36-3.51 (m, 3H), 3.67 (s, 3H), 6.54 (dd, J=1.3, 6.8 Hz, 1H), 6.67 (s, 1H), 6.76 (s, 1H), 7.08 (dd, J=6.8, 8.8 Hz, 1H), 7.40 (dd, J=1.3, 8.8 Hz, 1H).

Example 206

4-(Cyclopropylmethyl)[7-(2-methoxy-4,6-dimethylphenyl)-2-(methylsulfanyl)pyrazolo[1,5-a]pyridin-3-yl]amino-2-butanol (Light Yellow Oil)

$^1$H NMR (400 MHz, CDCl$_3$) δ −0.01-0.11 (m, 2H), 0.27-0.39 (m, 2H), 0.72-0.83 (m, 1H), 1.17-1.21 (m, 3H), 1.47-1.68 (m, 2H), 1.99 (s, 3H), 2.41 (s, 3H), 2.45 (s, 3H), 2.88-3.02 (m, 2H), 3.18-3.28 (m, 1H), 3.61-3.75 (m, 1H), 3.68 (s, 3H), 4.02-4.12 (m, 1H), 6.54 (d, J=6.8 Hz, 1H), 6.68 (s, 1H), 6.76 (s, 1H), 7.09 (dd, J=6.8, 8.8 Hz, 1H), 7.50 (d, J=8.8 Hz, 1H).

Example 207

4-[3-[Di(cyclopropylmethyl)amino]-2-(methylsulfanyl)pyrazolo[1,5-a]pyridin-7-yl]-3-methoxybenzonitrile After dissolving N-[7-(4-bromo-2-methoxyphenyl)-2-(methylsulfanyl)pyrazolo[1,5-a]pyridin-3-yl]-N,N-dicyclopropylmethylamine (60 mg) in N,N-dimethylformamide (0.26 mL), zinc cyamide (31 mg) and tetrakis (triphenylphosphine)palladium(0) complex (23 mg) were added, the mixture was heated and stirred at 95° C. for 12 hours and then cooled to room temperature, and ethyl acetate was added. After filtering out the precipitated insoluble portion, extraction was performed with ethyl acetate. The obtained organic layer washed with water and dried over magnesium sulfate, and the solvent was distilled off under reduced pressure. The obtained residue was purified by silica gel column chromatography (ethyl acetate:n-hexane=1:8) to obtain the title compound (32 mg) as a yellow oil.

$^1$H NMR (400 MHz, CDCl$_3$) δ 0.00-0.07 (m, 4H), 0.28-0.35 (m, 4H), 0.78-0.87 (m, 2H), 2.46 (s, 3H), 2.95-3.02 (m, 4H), 3.80 (s, 3H), 6.62 (dd, J=1.3, 6.8 Hz, 1H), 7.04 (dd, J=6.8, 8.8 Hz, 1H), 7.25 (d, J=1.1 Hz, 1H), 7.38 (dd, J=1.1, 7.7 Hz, 1H), 7.52 (dd, J=1.3, 8.8 Hz, 1H), 7.67 (d, J=7.7 Hz, 1H).

The compounds of Examples 208 to 210 were synthesized according to the production method of Example 207.

Example 208

4-[3-[(Cyclopropylmethyl)(tetrahydro-3-furanylmethyl)amino]-2-(methylsulfanyl)pyrazolo[1,5-a]pyridin-7-yl]-3-methoxybenzonitrile (Yellow Amorphous)

$^1$H NMR (400 MHz, CDCl$_3$) δ −0.03-0.08 (m, 2H), 0.30-0.41 (m, 2H), 0.78-0.88 (m, 1H), 1.60-1.70 (m, 1H), 1.87-1.98 (m, 1H), 2.16-2.29 (m, 1H), 2.45 (s, 3H), 2.84-2.94 (m, 2H), 3.02-3.10 (m, 1H), 3.20-3.28 (m, 1H), 3.59-3.87 (m, 4H), 3.81 (s, 3H), 6.64 (dd, J=1.9, 6.8 Hz, 1H), 7.07 (dd, J=6.8, 8.8 Hz, 1H), 7.26 (d, J=1.1 Hz, 1H), 7.38 (dd, J=1.1, 7.8 Hz, 1H), 7.45 (dd, J=1.9, 8.8 Hz, 1H), 7.66 (d, J=7.8 Hz, 1H).

Example 209

4-[3-[Di(cyclopropylmethyl)amino]-2-(methylsulfanyl)pyrazolo[1,5-a]pyridin-7-yl]-3-methoxy-5-methylbenzonitrile (Light Yellow Crystals)

$^1$H NMR (400 MHz, CDCl$_3$) δ −0.03-0.08 (m, 4H), 0.25-0.37 (m, 4H), 0.78-0.91 (m, 2H), 2.06 (s, 3H), 2.41 (s, 3H), 2.94-3.06 (m, 4H), 3.72 (s, 3H), 6.48 (d, J=6.8 Hz, 1H), 7.06 (dd, J=6.8, 8.8 Hz, 1H), 7.09 (s, 1H), 7.25 (s, 1H), 7.52 (d, J=8.8 Hz, 1H).

Example 210

4-[3-[(Cyclopropylmethyl)(tetrahydro-3-furanylmethyl)amino]-2-(methylsulfanyl)pyrazolo[1,5-a]pyridin-7-yl]-3-methoxy-5-methylbenzonitrile (Light Yellow Crystals)

$^1$H NMR (400 MHz, CDCl$_3$) δ −0.06-0.03 (m, 2H), 0.27-0.36 (m, 2H), 0.78-0.88 (m, 1H), 1.58-1.70 (m, 1H), 1.88-1.98 (m, 1H), 2.06 (s, 3H), 2.19-2.32 (m, 1H), 2.40 (s, 3H), 2.84-2.96 (m, 2H), 3.02-3.10 (m, 1H), 3.21-3.29 (m, 1H), 3.58-3.86 (m, 4H), 3.72 (s, 3H), 6.49 (dd, J=1.3, 6.8 Hz, 1H), 7.07 (dd, J=6.8, 8.8 Hz, 1H), 7.09 (s, 1H), 7.25 (s, 1H), 7.44 (dd, J=1.3, 8.8 Hz, 1H).

Example 211

5-(((Cyclopropylmethyl)[7-(2,6-dimethoxy-4-methylphenyl)-2-(methylsulfanyl)pyrazolo[1,5-a]pyridin-3-yl]aminomethyl)-2-furonitrile Zinc cyamide (31 mg) and tetrakis(triphenylphosphine)palladium(0) complex (52 mg) were added to a solution of N-[(5-bromo-2-furyl)methyl]-N-cyclopropylmethyl-N-[7-(2,6-dimethoxy-4-methylphenyl)-2-(methylsulfanyl)pyrazolo[1,5-a]pyridin-3-yl]amine (122 mg) in a mixture of N,N-dimethylformamide (3 mL) and N-methyl-2-pyrrolidinone (3 mL), and the mixture was heated at 155° C. for 4 hours. The reaction mixture was cooled to room temperature, water was added, extraction was performed with ethyl acetate, the extract washed with saturated aqueous sodium hydrogencarbonate and brine and dried over magnesium sulfate, and the solvent was distilled off under reduced pressure. The residue was subjected to silica gel column chromatography, and the title compound (23 mg) was obtained from the n-hexane:ethyl acetate (1:4) fraction as a yellow oil.
$^1$H NMR (400 MHz, CDCl$_3$) δ 0.01-0.08 (m, 2H), 0.33-0.40 (m, 2H), 0.80-0.93 (m, 1H), 2.43 (s, 3H), 2.45 (s, 3H), 3.00 (d, J=6.8 Hz, 2H), 3.68 (s, 6H), 4.37 (s, 2H), 6.27 (d, J=3.7 Hz, 1H), 6.48 (s, 2H), 6.59 (dd, J=1.5, 7.0 Hz, 1H), 6.95 (d, J=3.5 Hz, 1H), 7.05 (dd, J=7.0, 8.8 Hz, 1H), 7.29 (dd, J=1.4, 8.9 Hz, 1H).

Example 212

N,N-Dicyclopropylmethyl-N-[7-[2-methoxy-6-methyl-4-(1,3-thiazol-2-yl)phenyl]-2-(methylsulfanyl)pyrazolo[1,5-a]pyridin-3-yl]amine After dissolving N-[7-(4-bromo-2-methoxy-6-methylphenyl)-2-(methylsulfanyl)pyrazolo[1,5-a]pyridin-3-yl]-N,N-dicyclopropylmethylamine (45 mg) in toluene (0.60 mL), tributylstannylthiazole (52 mg) and tetrakis (triphenylphosphine)palladium(0) complex (9 mg) were added, the mixture was heated and stirred at 120° C. for 2 hours and then cooled to room temperature, and ethyl acetate was added. After filtering out the precipitated insoluble portion, the solvent was distilled off under reduced pressure. The obtained residue was purified by silica gel column chromatography (ethyl acetate: n-hexane=1:5) to obtain the title compound (30 mg) as white crystals.
$^1$H NMR (400 MHz, CDCl$_3$) δ −0.03-0.08 (m, 4H), 0.25-0.38 (m, 4H), 0.80-0.92 (m, 2H), 2.10 (s, 3H), 2.43 (s, 3H), 2.95-3.07 (m, 4H), 3.79 (s, 3H), 6.53 (d, J=6.8 Hz, 1H), 7.06 (dd, J=6.8, 8.8 Hz, 1H), 7.38 (d, J=3.2 Hz, 1H), 7.48 (d, J=8.8 Hz, 1H), 7.49 (s, 1H), 7.52 (s, 1H), 7.91 (d, J=3.2 Hz, 1H).

The compound of Example 213 was synthesized according to the production method of Example 212.

Example 213

N,N-Dicyclopropylmethyl-N-[7-[2-methoxy-6-methyl-4-(3-pyridyl)phenyl]-2-(methylsulfanyl)pyrazolo[1,5-a]pyridin-3-yl]amine (Light Yellow Solid)
$^1$H NMR (400 MHz, CDCl$_3$) δ −0.02-0.08 (m, 4H), 0.28-0.38 (m, 4H), 0.81-0.92 (m, 2H), 2.11 (s, 3H), 2.45 (s, 3H), 2.96-3.08 (m, 4H), 3.77 (s, 3H), 6.55 (d, J=6.8 Hz, 1H), 7.04 (s, 1H), 7.07 (dd, J=6.8, 8.8 Hz, 1H), 7.15 (s, 1H), 7.40 (dd, J=4.8, 8.0 Hz, 1H), 7.50 (d, J=8.8 Hz, 1H), 7.95 (d, J=8.0 Hz, 1H), 8.63 (d, J=4.8 Hz, 1H), 8.92 (s, 1H).

Example 214

3-(((Cyclopropylmethyl)[7-(2-methoxy-4,6-dimethylphenyl)-2-(methylsulfanyl)pyrazolo[1,5-a]pyridin-3-yl]aminomethyl)-2-pyridinol (White Crystals)
After dissolving N-cyclopropylmethyl-N-[7-(2-methoxy-4,6-dimethylphenyl)-2-(methylsulfanyl)pyrazolo[1,5-a]pyridin-3-yl]-N-[(2-methoxy-3-pyridyl)methyl]amine (63 mg) in ethanol (1 mL), a 4 N hydrochloric acid/ethyl acetate solution (1 mL) was added at room temperature and the mixture was heated to reflux for 3 hours. Saturated aqueous sodium hydrogencarbonate was added to the reaction mixture for neutralization while cooling on ice, and extraction was performed with ethyl acetate. The obtained organic layer was washed with water and dried over magnesium sulfate, and the solvent was distilled off under reduced pressure. The obtained residue was purified by silica gel column chromatography (ethyl acetate) to obtain the title compound (49 mg) as white crystals.
$^1$H NMR (400 MHz, CDCl$_3$) δ −0.05-0.06 (m, 2H), 0.27-0.38 (m, 2H), 0.84-0.97 (m, 1H), 1.97 (s, 3H), 2.40 (s, 3H), 2.44 (s, 3H), 2.91-3.03 (m, 2H), 3.66 (s, 3H), 4.36 (s, 2H), 6.27 (dd, J=6.4, 6.4 Hz, 1H), 6.50 (d, J=6.8 Hz, 1H), 6.68 (s, 1H), 6.76 (s, 1H), 7.05 (dd, J=6.8, 8.8 Hz, 1H), 7.23 (d, J=6.4 Hz, 1H), 7.52 (d, J=8.8 Hz, 1H), 7.85 (d, J=6.4 Hz, 1H).

The compound of Example 215 was synthesized according to the production method of Example 214.

Example 215

3-(((Cyclopropylmethyl)[7-(2-methoxy-4,6-dimethylphenyl)-2-(methylsulfanyl)pyrazolo[1,5-a]pyridin-3-yl]aminomethyl)-2-pyrazinol (Light Yellow Crystals)
$^1$H NMR (400 MHz, CDCl$_3$) δ 0.00-0.09 (m, 2H), 0.30-0.49 (m, 2H), 0.78-0.91 (m, 1H), 1.97 (s, 3H), 2.40 (s, 3H), 2.47 (s, 3H), 2.94-3.03 (m, 2H), 3.66 (s, 3H), 4.69 (s, 2H), 6.57 (dd, J=1.3, 6.8 Hz, 1H), 6.66 (s, 1H), 6.74 (s, 1H), 7.14 (dd, J=6.8, 8.8 Hz, 1H), 7.55 (dd, J=1.3, 8.8 Hz, 1H), 7.83 (br s, 2H).

Example 216

2-[3-[Di(cyclopropylmethyl)amino]-2-(methylsulfanyl)pyrazolo[1,5-a]pyridin-7-yl]-3,5-dimethylphenol A 1 M boron tribromide/dichloromethane solution (0.42 mL) was added to a solution of N,N-dicyclopropylmethyl-N-[7-(2-methoxy-4,6-dimethylphenyl)-2-(methylsulfanyl)pyrazolo[1,5-a]pyridin-3-yl]amine (35 mg) in dichloromethane (10 mL) at room temperature under a nitrogen atmosphere, and the mixture was stirred for 10 minutes. The reaction mixture was added to ice water, extraction was performed with ethyl acetate, and the organic layer was washed with brine, dried over anhydrous magnesium sulfate and concentrated under reduced pressure. The obtained residue was subjected to silica gel column chromatography, and the title compound (17 mg) was obtained from the n-hexane:ethyl acetate (6:1) fraction as white crystals.
$^1$H NMR (400 MHz, CDCl$_3$) δ −0.02-0.02 (m, 4H), 0.24-0.30 (m, 4H), 0.74-0.82 (m, 2H), 2.23 (s, 3H), 2.32 (s, 3H), 2.50 (s, 3H), 2.88-3.00 (m, 4H), 6.64 (d, J=6.8 Hz, 1H), 6.76 (s, 1H), 7.09 (dd, J=6.8, 8.0 Hz, 1H), 7.48 (d, J=8.8 Hz, 1H), 7.65 (s, 1H).
MS (ESI) m/z 408 MH$^+$

Example 217

N,N-Dicyclopropylmethyl-N-[7-(2-ethoxy-4,6-dimethylphenyl)-2-(methylsulfanyl)pyrazolo[1,5-a]pyridin-3-yl]amine After adding ethanol (2 μL), triphenylphosphine (15 mg) and diethyl azodicarboxylate (9 μL) to a solution of 2-[3-[di(cyclopropylmethyl)amino]-2-(methylsulfanyl)pyrazolo[1,5-a]pyridin-7-yl]-3,5-dimethylphenol (15 mg) in tetrahydrofuran (0.45 mL) under a nitrogen atmosphere, the mixture was stirred at room temperature overnight. The reaction mixture was added to water, extraction was performed with ethyl acetate, and the organic layer washed with brine, dried over anhydrous magnesium sulfate and concentrated under reduced pressure. The obtained residue was subjected to silica gel column chromatography, and the title compound (3.7 mg) was obtained from the n-hexane:ethyl acetate (9:1) fraction as a yellow oil.

$^1$H NMR (400 MHz, CDCl$_3$) δ −0.02-0.04 (m, 4H), 0.26-0.32 (m, 4H), 0.80-0.92 (m, 2H), 1.06 (t, J=6.8 Hz, 3H), 2.04 (s, 3H), 2.39 (s, 3H), 2.45 (s, 3H), 3.02 (d, J=6.4 Hz, 4H), 3.84-4.04 (m, 2H), 6.51 (dd, J=0.8, 8.4 Hz, 1H), 6.67 (s, 1H), 6.76 (s, 1H), 7.04 (dd, J=6.8, 8.8 Hz, 1H), 7.47 (dd, J=0.8, 8.8 Hz, 1H).

The compounds of Examples 218 to 223 were synthesized according to the production method of Example 217.

Example 218

N,N-Dicyclopropylmethyl-N-[7-[2-(2-fluoroethoxy)-4,6-dimethylphenyl]-2-(methylsulfanyl)pyrazolo[1,5-a]pyridin-3-yl]amine (Yellow Oil)

$^1$H NMR (400 MHz, CDCl$_3$) δ −0.02-0.04 (m, 4H), 0.26-0.34 (m, 4H), 0.82-0.92 (m, 2H), 2.04 (s, 3H), 2.40 (s, 3H), 2.44 (s, 3H), 3.02 (d, J=6.4 Hz, 4H), 3.94-4.50 (m, 4H), 6.53 (dd, J=0.8, 7.2 Hz, 1H), 6.70 (s, 1H), 6.82 (s, 1H), 7.05 (dd, J=7.2, 8.8 Hz, 1H), 7.47 (d, J=8.8 Hz, 1H).

Example 219

N-[7-[2-(Cyclopropylmethoxy)-4,6-dimethylphenyl]-2-(methylsulfanyl)pyrazolo[1,5-a]pyridin-3-yl]-N,N-dicyclopropylmethylamine (Yellow Oil)

$^1$H NMR (400 MHz, CDCl$_3$) δ −0.02-0.08 (m, 6H), 0.28-0.38 (m, 6H), 0.86-0.96 (m, 3H), 2.07 (s, 3H), 2.42 (s, 3H), 2.48 (s, 3H), 3.05 (d, J=6.8 Hz, 4H), 3.71 (dd, J=6.4, 10.0 Hz, 1H), 3.81 (dd, J=6.4, 10.0 Hz, 1H), 6.55 (dd, J=1.6, 6.8 Hz, 1H), 6.71 (s, 1H), 6.80 (s, 1H), 7.08 (dd, J=6.8, 8.8 Hz, 1H), 7.51 (dd, J=1.6, 8.8 Hz, 1H).

Example 220

N,N-Dicyclopropylmethyl-N-[7-[2-(2-methoxyethoxy)-4,6-dimethylphenyl]-2-(methylsulfanyl)pyrazolo[1,5-a]pyridin-3-yl]amine (Yellow Oil)

$^1$H NMR (400 MHz, CDCl$_3$) δ −0.02-0.04 (m, 4H), 0.26-0.34 (m, 4H), 0.78-0.88 (m, 2H), 2.02 (s, 3H), 2.38 (s, 3H), 2.44 (s, 3H), 3.00 (d, J=7.2 Hz, 4H), 3.11 (s, 3H), 3.28-3.36 (m, 1H), 3.38-3.44 (m, 1H), 3.90-3.96 (m, 1H), 3.44-4.10 (m, 1H), 6.50 (dd, J=1.2, 7.2 Hz, 1H), 6.69 (s, 1H), 6.77 (s, 1H), 7.02 (dd, J=6.8, 8.8 Hz, 1H), 7.45 (dd, J=1.2, 8.8 Hz, 1H).

MS (ESI) m/z 466 MH$^+$

Example 221

N,N-Dicyclopropylmethyl-N-[7-(2-isopropoxy-4,6-dimethylphenyl)-2-(methylsulfanyl)pyrazolo[1,5-a]pyridin-3-yl]amine (Yellow Oil)

$^1$H NMR (400 MHz, CDCl$_3$) δ −0.02-0.02 (m, 4H), 0.26-0.34 (m, 4H), 0.82-0.92 (m, 2H), 0.96 (d, J=6.4 Hz, 3H), 1.15 (d, J=6.0 Hz, 3H), 2.04 (s, 3H), 2.41 (s, 3H), 2.46 (s, 3H), 2.98-3.08 (m, 4H), 4.24-4.36 (m, 1H), 6.51 (d, J=6.8 Hz, 1H), 6.71 (s, 1H), 6.77 (s, 1H), 7.05 (dd, J=7.2, 8.8 Hz, 1H), 7.47 (dd, J=1.2, 8.8 Hz, 1H).

MS (ESI) m/z 450 MH$^+$

Example 222

2-[3-[Di(cyclopropylmethyl)amino]-2-(methylsulfanyl)pyrazolo[1,5-a]pyridin-7-yl]-3,5-dimethylphenoxymethylcyanide (Yellow Oil)

$^1$H NMR (400 MHz, CDCl$_3$) δ −0.02-0.04 (m, 4H), 0.26-0.34 (m, 4H), 0.80-0.92 (m, 2H), 2.02 (s, 3H), 2.43 (s, 3H), 2.44 (s, 3H), 3.01 (d, J=6.4 Hz, 4H), 4.57 (dd, J=16.0, 25.6 Hz, 2H), 6.50 (dd, J=1.6, 6.8 Hz, 1H), 6.81 (s, 1H), 6.92 (s, 1H), 7.06 (dd, J=6.8, 8.8 Hz, 1H), 7.50 (dd, J=1.6, 8.8 Hz, 1H).

MS (ESI) m/z 447 MH$^+$

Example 223

N,N-Dicyclopropylmethyl-N-[7-[2,4-dimethyl-6-(2-tetrahydro-1H-1-pyrrolylethoxy)phenyl]-2-(methylsulfanyl)pyrazolo[1,5-a]pyridin-3-yl]amine (Yellow Oil)

$^1$H NMR (400 MHz, CDCl$_3$) δ −0.02-0.04 (m, 4H), 0.24-0.34 (m, 4H), 0.78-0.88 (m, 2H), 1.56-1.64 (m, 4H), 2.01 (s, 3H), 2.20-2.32 (m, 4H), 2.37 (s, 3H), 2.42 (s, 3H), 2.42-2.58 (m, 2H), 2.94-3.04 (m, 4H), 3.92-4.06 (m, 2H), 6.47 (dd, J=1.6, 7.2 Hz, 1H), 6.64 (s, 1H), 6.74 (s, 1H), 7.00 (dd, J=7.2, 9.2 Hz, 1H), 7.44 (dd, J=1.6, 8.8 Hz, 1H).

MS (ESI) m/z 505 MH$^+$

Example 224

N-Cyclopropyl-N-cyclopropylmethyl-N-[7-(2-methoxy-4,6-dimethylphenyl)-2-(methylsulfanyl)pyrazolo[1,5-a]pyridin-3-yl]amine After dissolving N-cyclopropylmethyl-N-[7-(2-methoxy-4,6-dimethylphenyl)-2-(methylsulfanyl)pyrazolo[1,5-a]pyridin-3-yl]amine (100 mg) in methanol (10 mL), ((1-ethoxycyclopropyl)oxy)trimethylsilane (60 μL), acetic acid (298 μL) and sodium cyanoborohydride (171 mg) were added and the mixture was heated to reflux for 6 hours. After cooling the reaction mixture to room temperature, saturated aqueous sodium hydrogencarbonate was added, extraction was performed with ethyl acetate, and the organic layer washed with brine. After drying the obtained organic layer over anhydrous magnesium sulfate and filtering it, the solvent was concentrated under reduced pressure, the residue was purified by silica gel column chromatography, and the title compound (74 mg) was obtained from the n-hexane:ethyl acetate (10:1) fraction as a yellow oil.

$^1$H NMR (400 MHz, CDCl$_3$) δ −0.01-0.04 (m, 2H), 0.26-0.36 (m, 2H), 0.46-0.52 (m, 4H), 0.80-0.90 (m, 1H), 2.00 (s, 3H), 2.41 (s, 3H), 2.43 (s, 3H), 2.88-2.94 (m, 1H), 2.98-3.06 (m, 2H), 3.69 (s, 3H), 6.50 (dd, J=1.6, 6.8 Hz, 1H), 6.68 (s, 1H), 6.76 (s, 1H), 7.02 (dd, J=6.8, 8.8 Hz, 1H), 7.42 (dd, J=1.6, 8.8 Hz, 1H).

The compound of Example 225 was synthesized according to the production method of Example 224.

Example 225

N-Cyclopropyl-N-[7-(2-methoxy-4,6-dimethylphenyl)-2-(methylsulfanyl)pyrazolo[1,5-a]pyridin-3-yl]-N-tetrahydro-2-furanylmethylamine (Light Yellow Oil)
$^1$H NMR (400 MHz, CDCl$_3$) δ 0.42-0.57 (m, 4H), 1.55-1.64 (m, 1H), 1.75-1.95 (m, 3H), 2.00 (s, 3H), 2.40 (s, 3H), 2.42 (s, 3H), 2.86-2.92 (m, 1H), 3.06-3.13 (m, 1H), 3.42-3.48 (m, 1H), 3.64-3.71 (m, 4H), 3.79-3.88 (m, 2H), 6.50 (dd, J=1.6, 6.8 Hz, 1H), 6.67 (s, 1H), 6.75 (s, 1H), 7.04 (dd, J=6.8, 8.8 Hz, 1H), 7.40 (dd, J=1.6, 8.8 Hz, 1H).

Example 226

N3-Cyclopropylmethyl-N3-[7-(2-methoxy-4,6-dimethylphenyl)-2-(methylsulfanyl)pyrazolo[1,5-a]pyridin-3-yl]nicotinamide Triethylamine (0.038 mL) and chloronicotinic acid hydrochloride (20 mg) were added to a solution of N-cyclopropylmethyl-N-[7-(2-methoxy-4,6-dimethylphenyl)-2-(methylsulfanyl)pyrazolo[1,5-a]pyridin-3-yl]amine (33 mg) in dichloromethane (0.8 mL) while cooling on ice, and the mixture was stirred at the same temperature for 1 hour. Saturated aqueous sodium hydrogencarbonate was added while cooling on ice, extraction was performed with ethyl acetate, and the extract washed with brine, dried over anhydrous magnesium sulfate and concentrated under reduced pressure. The residue was purified by silica gel column chromatography (ethyl acetate:n-hexane=3:2) to obtain the title compound (36 mg) as white crystals.

$^1$H NMR (400 MHz, CDCl$_3$) δ 0.08-0.33 (m, 2H), 0.37-0.54 (m, 2H), 1.03-1.17 (m, 1H), 2.02 (s, 3H), 2.31 (s, 3H), 2.38 (s, 3H), 3.52-3.62 (m, 1H), 3.67 (s, 3H), 3.87-3.97 (m, 1H), 6.57 (dd, J=1.3, 6.8 Hz, 1H), 6.65 (s, 1H), 6.69 (s, 1H), 6.95 (dd, J=4.8, 8.0 Hz, 1H), 7.17 (dd, J=6.8, 8.8 Hz, 1H), 7.27 (dd, J=1.3, 8.8 Hz, 1H), 7.62 (d, J=8.0 Hz, 1H), 8.31 (d, J=4.8 Hz, 1H), 8.56 (s, 1H).

The compound of Example 227 was synthesized according to the production method of Example 226.

Example 227

N1-[7-(2-Methoxy-4,6-dimethylphenyl)-2-(methylsulfanyl)pyrazolo[1,5-a]pyridin-3-yl]-N1-(3-pyridylmethyl)-1-cyclopropanecarboxyamide (White Amorphous Substance)
$^1$H NMR (400 MHz, CDCl$_3$) δ 0.61-0.71 (m, 2H), 1.01-1.11 (m, 2H), 1.45-1.52 (m, 1H), 1.91 (s, 3H), 2.39 (s, 3H), 2.40 (s, 3H), 3.67 (s, 3H), 4.57 (d, J=14.0 Hz, 1H), 5.25 (d, J=14.0 Hz, 1H), 6.58 (d, J=6.8 Hz, 1H), 6.66 (s, 1H), 6.75 (s, 1H), 6.77 (d, J=8.8 Hz, 1H), 7.04 (dd, J=6.8, 8.8 Hz, 1H), 7.11 (dd, J=4.8, 8.0 Hz, 1H), 7.57 (d, J=8.0 Hz, 1H), 8.30 (s, 1H), 8.41 (d, J=4.8 Hz, 1H).

Example 228

N,N-Dicyclopropylmethyl-N-[7-(2-methoxy-4,6-dimethylphenyl)-2-(methylsulfinyl)pyrazolo[1,5-a]pyridin-3-yl]amine m-Chloroperbenzoic acid (234 mg) was added to a solution of N,N-dicyclopropylmethyl-N-[7-(2-methoxy-4,6-dimethylphenyl)-2-(methylsulfanyl)pyrazolo[1,5-a]pyridin-3-yl]amine (200 mg) in dichloromethane (10 mL) at 0° C., and the mixture was stirred for 2 hours. Water was added to the reaction mixture, extraction was performed with ethyl acetate, the extract washed with saturated aqueous sodium hydrogencarbonate and brine and dried over magnesium sulfate, and the solvent was distilled off under reduced pressure. The residue was subjected to silica gel column chromatography (20 g), and the title compound (162 mg) was obtained from the n-hexane:ethyl acetate (1:1) fraction as a light yellow oil.

$^1$H NMR (400 MHz, CDCl$_3$) δ −0.02-0.08 (m, 4H), 0.28-0.38 (m, 4H), 0.80-0.94 (m, 2H), 1.94 (s, 1.5H), 2.00 (s, 1.5H), 2.39 (s, 3H), 2.96 (s, 1.5H), 2.97 (s, 1.5H), 3.04-3.16 (m, 4H), 3.64 (s, 1.5H), 3.66 (s, 1.5H), 6.66 (s, 0.5H), 6.67 (s, 0.5H), 6.72 (dd, J=2.6, 6.9 Hz, 0.5H), 6.73 (dd, J=2.6, 6.9 Hz, 0.5H), 6.74 (s, 0.5H), 6.76 (s, 0.5H), 7.15 (dd, J=6.8, 8.9 Hz, 0.5H), 7.16 (dd, J=6.8, 8.9 Hz, 0.5H), 7.60-7.68 (m, 1H).

Example 229

N,N-Dicyclopropylmethyl-N-[7-(2-methoxy-4,6-dimethylphenyl)-2-(methylsulfonyl)pyrazolo[1,5-a]pyridin-3-yl]amine m-Chloroperbenzoic acid (91 mg) was added to a solution of N,N-dicyclopropylmethyl-N-[7-(2-methoxy-4,6-dimethylphenyl)-2-(methylsulfinyl)pyrazolo[1,5-a]pyridin-3-yl]amine (162 mg) in dichloromethane (10 mL) at 0° C., and the mixture was stirred for 4 hours. Water was added to the reaction mixture, extraction was performed with ethyl acetate, the extract washed with saturated aqueous sodium hydrogencarbonate and brine and dried over magnesium sulfate, and the solvent was distilled off under reduced pressure. The residue was subjected to silica gel column chromatography (10 g), and the title compound (9 mg) was obtained from the n-hexane:ethyl acetate (1:2) fraction as a yellow oil.

$^1$H NMR (400 MHz, CDCl$_3$) δ −0.02-0.08 (m, 4H), 0.24-0.34 (m, 4H), 0.79-0.92 (m, 2H), 1.96 (s, 3H), 2.38 (s, 3H), 3.08 (dd, J=3.7, 6.8 Hz, 4H), 3.21 (s, 3H), 3.64 (s, 3H), 6.66 (s, 1H), 6.75 (s, 1H), 6.78 (dd, J=1.4, 6.9 Hz, 1H), 7.19 (dd, J=6.9, 8.9 Hz, 1H), 7.72 (dd, J=1.4, 8.9 Hz, 1H).

Example 230

N,N-Dicyclopropylmethyl-N-[2-methoxy-7-(2-methoxy-4,6-dimethylphenyl)pyrazolo[1,5-a]pyridin-3-yl]amine 2-Methoxy-7-(2-methoxy-4,6-dimethylphenyl)-3-nitrosopyrazolo[1,5-a]pyridine (200 mg) was suspended in ethanol (10 mL), and then water (5 mL), acetic acid (0.5 mL) and zinc powder (200 mg) were added and the mixture was heated and stirred at 60° C. for 1 hour. The reaction mixture was filtered, water was added to the filtrate, extraction was performed with ethyl acetate and the organic layer was washed with saturated aqueous sodium hydrogencarbonate and brine. The obtained organic layer was dried over anhydrous magnesium sulfate and filtered, and then the solvent was concentrated under reduced pressure to obtain 2-methoxy-7-(2-methoxy-4,6-dimethylphenyl)pyrazolo[1,5-a]pyridine-3-amine as a crude product. This was dissolved in tetrahydrofuran (5 mL) without purification, and after adding cyclopropanecarboxyaldehyde (0.166 mL) and 3 M aqueous sulfuric acid (0.739 mL), sodium borohydride (56 mg) was added in five portions while vigorously stirring on ice, and stirring was continued for 1 hour. Saturated aqueous sodium hydrogencarbonate was added to the reaction mixture, extraction was performed with ethyl acetate, and the extract washed with brine. After drying over anhydrous magnesium sulfate and filtration, the solvent was concentrated under reduced pressure, the residue was purified by silica gel column chromatography, and the title compound (240 mg) was obtained from the n-hexane:ethyl acetate (30:1) fraction as a yellow oil.

$^1$H NMR (400 MHz, CDCl$_3$) δ −0.02-0.04 (m, 4H), 0.26-0.34 (m, 4H), 0.80-0.90 (m, 2H), 2.00 (m, 3H), 2.41 (s, 3H), 2.87-2.98 (m, 4H), 3.70 (s, 3H), 3.86 (s, 3H), 6.44 (dd, J=1.6, 6.8 Hz, 1H), 6.69 (s, 1H), 6.77 (s, 1H), 7.02 (dd, J=6.8, 8.8 Hz, 1H), 7.39 (dd, J=1.6, 8.8 Hz, 1H).

The compounds of Examples 231 to 236 were synthesized according to the production method of Example 230.

Example 231

N-[2-Methoxy-7-(2-methoxy-4,6-dimethylphenyl)pyrazolo[1,5-a]pyridin-3-yl]-N,N-ditetrahydro-2H-4-pyranylamine (Light Brown Powder)
$^1$H NMR (400 MHz, CDCl$_3$) δ 1.42-1.56 (m, 4H), 1.72-1.80 (m, 4H), 1.99 (s, 3H), 3.33-3.43 (m, 6H), 3.70 (s, 3H), 3.83 (s, 3H), 3.90-3.96 (m, 4H), 6.43 (dd, J=1.6, 6.8 Hz, 1H), 6.68 (s, 1H), 6.76 (s, 1H), 7.04 (dd, J=6.8, 8.8 Hz, 1H), 7.26 (dd, J=1.6, 8.8 Hz, 1H).

Example 232

N,N-Dicyclopropylmethyl-N-[7-(2,6-dimethoxy-4-methylphenyl)-2-methoxypyrazolo[1,5-a]pyridin-3-yl]amine (White Crystals)
$^1$H NMR (400 MHz, CDCl$_3$) δ −0.03-0.05 (m, 4H), 0.27-0.34 (m, 4H), 0.78-0.91 (m, 2H), 2.44 (s, 3H), 2.87-2.96 (m, 4H), 3.71 (s, 6H), 3.87 (s, 3H), 6.47 (dd, J=1.3, 6.8 Hz, 1H), 6.50 (s, 2H), 7.01 (dd, J=6.8, 8.8 Hz, 1H), 7.37 (dd, J=1.3, 8.8 Hz, 1H).

Example 233

N,N-Dicyclopropylmethyl-N-[7-(2,4-dimethoxy-6-methylphenyl)-2-methoxypyrazolo[1,5-a]pyridin-3-yl]amine (Yellow Oil)
$^1$H NMR (400 MHz, CDCl$_3$) δ −0.05-0.05 (m, 4H), 0.23-0.33 (m, 4H), 0.79-0.91 (m, 2H), 2.02 (s, 3H), 2.85-2.99 (m, 4H), 3.68 (s, 3H), 3.86 (s, 3H), 3.87 (s, 3H), 6.40 (dd, J=1.5, 6.8 Hz, 1H), 6.43 (d, J=2.2 Hz, 1H), 6.47 (d, J=2.2 Hz, 1H), 7.01 (dd, J=6.8, 8.8 Hz, 1H), 7.38 (dd, J=1.5, 8.8 Hz, 1H).

Example 234

N-[7-(2-Chloro-6-methoxy-4-methylphenyl)-2-methoxypyrazolo[1,5-a]pyridin-3-yl]-N,N-dicyclopropylmethylamine (White Crystals)
$^1$H NMR (400 MHz, CDCl$_3$) δ −0.04-0.06 (m, 4H), 0.24-0.35 (m, 4H), 0.79-0.90 (m, 2H), 2.42 (s, 3H), 2.86-2.99 (m, 4H), 3.71 (s, 3H), 3.87 (s, 3H), 6.46 (dd, J=1.3, 6.8 Hz, 1H), 6.74 (s, 1H), 6.97 (s, 1H), 7.03 (dd, J=6.8, 8.8 Hz, 1H), 7.42 (dd, J=1.3, 8.8 Hz, 1H).

Example 235

N,N-Dicyclopropylmethyl-N-[2-methoxy-7-(4-methoxy-2,6-dimethylphenyl)pyrazolo[1,5-a]pyridin-3-yl]amine (Light Yellow Crystals)
$^1$H NMR (400 MHz, CDCl$_3$) δ −0.05-0.02 (m, 4H), 0.25-0.31 (m, 4H), 0.79-0.90 (m, 2H), 2.03 (s, 6H), 2.86-2.98 (m, 4H), 3.85 (s, 3H), 3.85 (s, 3H), 6.33 (dd, J=1.5, 6.8 Hz, 1H), 6.70 (s, 2H), 7.01 (dd, J=6.8, 8.8 Hz, 1H), 7.39 (dd, J=1.5, 8.8 Hz, 1H).

Example 236

N-[7-(2-Chloro-4-methoxyphenyl)-2-methoxypyrazolo[1,5-a]pyridin-3-yl]-N,N-dicyclopropylmethylamine (Yellow Oil)
$^1$H NMR (400 MHz, CDCl$_3$) δ −0.02-0.05 (m, 4H), 0.27-0.33 (m, 4H), 0.78-0.89 (m, 2H), 2.86-2.97 (m, 4H), 3.88 (s, 3H), 3.90 (s, 3H), 6.47 (dd, J=1.5, 6.8 Hz, 1H), 6.92 (dd, J=2.6, 8.6 Hz, 1H), 7.01 (dd, J=6.8, 8.8 Hz, 1H), 7.06 (d, J=2.6 Hz, 1H), 7.43 (dd, J=1.5, 8.8 Hz, 1H), 7.45 (d, J=8.6 Hz, 1H).

Example 237 tert-Butyl N-[7-(2,4-dimethoxy-6-methylphenyl)-2-methoxypyrazolo[1,5-a]pyridin-3-yl]carbamate After dissolving tert-butyl N-(7-bromo-2-methoxypyrazolo[1,5-a]pyridin-3-yl)carbamate (300 mg) in 1,2-dimethoxyethane (10 mL) and water (5 mL), 6-methyl-2,4-dimethoxyphenylboric acid (258 mg), tetrakis(triphenylphosphine)palladium(0) complex (203 mg) and barium hydroxide octahydrate (415 mg) were added and the mixture was heated and stirred at 80° C. for 3 hours. Water was added to the reaction mixture, extraction was performed with ethyl acetate and the extract washed with brine. After drying the obtained organic layer over anhydrous magnesium sulfate and filtering it, the solvent was concentrated under reduced pressure, the residue was purified by silica gel column chromatography, and the title compound (230 mg) was obtained from the n-hexane:ethyl acetate (5:1) fraction as a brown oil.

$^1$H NMR (400 MHz, CDCl$_3$) δ 1.53 (s, 9H), 2.02 (s, 3H), 3.66 (s, 3H), 3.87 (s, 3H), 3.90 (s, 3H), 6.42 (d, J=2.0 Hz, 1H), 6.47 (d, J=2.0 Hz, 1H), 6.49 (dd, J=1.2, 6.8 Hz, 1H), 6.94 (dd, J=6.8, 8.8 Hz, 1H), 7.26-7.33 (m, 1H).

Example 238

N-Cyclopropylmethyl-N-[7-(2,4-dimethoxy-6-methylphenyl)-2-methoxypyrazolo[1,5-a]pyridin-3-yl]-N-tetrahydro-2-furanylmethylamine After dissolving tert-butyl N-[7-(2,4-dimethoxy-6-methylphenyl)-2-methoxypyrazolo[1,5-a]pyridin-3-yl]carbamate (50 mg) in N,N-dimethylformamide (2 mL), sodium hydride (60%, 15 mg) was added while cooling on ice, and then 2-tetrahydrofuranylmethyl chloride (16 µL) was added and the mixture was stirred for 3 hours at 60° C. under a nitrogen stream. Water was added to the reaction mixture, extraction was performed with ethyl acetate and the extract washed with brine. After drying over anhydrous magnesium sulfate and filtration, the solvent was concentrated under reduced pressure to obtain tert-butyl N-[7-(2,4-dimethoxy-6-methylphenyl)-2-methoxypyrazolo[1,5-a]pyridin-3-yl]-N-tetrahydro-2-furanylmethylcarbamate. The crude product was dissolved in ethyl acetate (2 mL) without purification, a 4 N hydrochloric acid/ethyl acetate solution (4 mL) was added, and the mixture was stirred at 40° C. for 1 hour. The reaction mixture was neutralized with 5 N aqueous sodium hydroxide while cooling on ice, and then extraction was performed with ethyl acetate and the organic layer washed with water and brine. The obtained organic layer was dried over anhydrous magnesium sulfate and filtered, and the solvent was concentrated under reduced pressure to obtain N-[7-(2,4-dimethoxy-6-methylphenyl)-2-methoxypyrazolo[1,5-a]pyridin-3-yl]-N-tetrahydro-2-furanylmethylamine as a crude product. This was dissolved in tetrahydrofuran (2 mL) without purification, and after adding cyclopropanecarboxyaldehyde (27 µL) and 3 M aqueous sulfuric acid (0.121 mL), sodium borohydride (9 mg) was added in five portions while vigorously stirring on ice, and stirring was continued for 30 minutes. Saturated aqueous sodium hydrogencarbonate was added to the reaction mixture, extraction was performed with ethyl acetate, the solvent was concentrated, the residue was purified by silica gel column chromatography, and the title compound (31 mg) was obtained from the n-hexane:ethyl acetate (5:1) fraction as a yellow oil.

$^1$H NMR (400 MHz, CDCl$_3$) δ −0.06-0.01 (m, 2H), 0.25-0.32 (m, 2H), 0.80-0.90 (m, 1H), 1.52-1.70 (m, 1H), 1.74-1.95 (m, 3H), 2.01 (s, 1.5H), 2.03 (s, 1.5H), 2.80-3.06 (m, 3H), 3.26-3.35 (m, 1H), 3.65-3.72 (m, 4H), 3.80-3.90 (m, 8H), 6.38-6.42 (m, 1H), 6.44 (s, 1H), 6.47 (s, 1H), 6.99-7.05 (m, 1H), 7.34-7.40 (m, 1H).

The compounds of Examples 239 to 255 below were synthesized according to the production methods of Examples 237 and 238.

Example 239

N-Cyclopropylmethyl-N-[2-methoxy-7-(2-methoxy-4,6-dimethylphenyl)pyrazolo[1,5-a]pyridin-3-yl]-N-tetrahydro-3-furanylmethylamine (Light Yellow Oil)

$^1$H NMR (400 MHz, CDCl$_3$) δ −0.08-0.04 (m, 2H), 0.22-0.36 (m, 2H), 0.78-0.88 (m, 1H), 1.60-1.70 (m, 1H), 1.85-1.97 (m, 1H), 2.00 (s, 3H), 2.21-2.31 (m, 1H), 2.41 (s, 3H), 2.75-2.89 (m, 2H), 2.92-3.03 (m, 1H), 3.09-3.19 (m, 1H), 3.54-3.82 (m, 4H), 3.70 (s, 3H), 3.85 (s, 3H), 6.41 (dd, J=1.5, 6.8 Hz, 1H), 6.59 (s, 1H), 6.76 (s, 1H), 7.03 (dd, J=6.8, 8.8 Hz, 1H), 7.31 (dd, J=1.5, 8.8 Hz, 1H).

Example 240

N-[7-(2-Chloro-6-methoxy-4-methylphenyl)-2-methoxypyrazolo[1,5-a]pyridin-3-yl]-N-cyclopropylmethyl-N-tetrahydro-3-furanylmethylamine (Yellow Oil)

$^1$H NMR (400 MHz, CDCl$_3$) δ −0.06-0.03 (m, 2H), 0.26-0.35 (m, 2H), 0.78-0.87 (m, 1H), 1.57-1.68 (m, 1H), 1.85-1.97 (m, 1H), 2.20-2.31 (m, 1H), 2.42 (s, 3H), 2.78-2.88 (m, 2H), 2.93-3.03 (m, 1H), 3.10-3.19 (m, 1H), 3.56-3.84 (m, 4H), 3.71 (s, 3H), 3.86 (s, 3H), 6.47 (d, J=6.8 Hz, 1H), 6.74 (s, 1H), 6.97 (s, 1H), 7.04 (dd, J=6.8, 8.8 Hz, 1H), 7.34 (d, J=8.8 Hz, 1H).

Example 241

N-[7-(2-Chloro-4-methoxyphenyl)-2-methoxypyrazolo[1,5-a]pyridin-3-yl]-N-cyclopropylmethyl-N-tetrahydro-3-furanylmethylamine (Yellow Oil)

$^1$H NMR (400 MHz, CDCl$_3$) δ −0.02-0.08 (m, 2H), 0.28-0.38 (m, 2H), 0.75-0.87 (m, 1H), 1.58-1.69 (m, 1H), 1.84-1.95 (m, 1H), 2.16-2.29 (m, 1H), 2.78-2.86 (m, 2H), 2.93-3.01 (m, 1H), 3.09-3.18 (m, 1H), 3.57-3.85 (m, 4H), 3.88 (s, 3H), 3.89 (s, 3H), 6.48 (dd, J=1.3, 6.8 Hz, 1H), 6.92 (dd, J=2.4, 8.8 Hz, 1H), 7.03 (dd, J=6.8, 8.8 Hz, 1H), 7.06 (d, J=2.4 Hz, 1H), 7.34 (dd, J=1.3, 8.8 Hz, 1H), 7.45 (d, J=8.8 Hz, 1H).

Example 242

N-[7-(2-Chloro-4-methoxyphenyl)-2-methoxypyrazolo[1,5-a]pyridin-3-yl]-N-cyclopropylmethyl-N-tetrahydro-2-furanylmethylamine (Yellow Oil)

$^1$H NMR (400 MHz, CDCl$_3$) δ −0.03-0.04 (m, 2H), 0.27-0.34 (m, 2H), 0.78-0.88 (m, 1H), 1.49-1.68 (m, 2H), 1.71-1.95 (m, 2H), 2.82-2.95 (m, 2H), 2.98-3.05 (m, 1H), 3.27-3.35 (m, 1H), 3.53-3.72 (m, 1H), 3.78-3.88 (m, 2H), 3.88 (s, 3H), 3.90 (s, 3H), 6.48 (dd, J=1.3, 6.8 Hz, 1H), 6.91 (dd, J=2.4, 8.4 Hz, 1H), 7.03 (dd, J=6.8, 8.8 Hz, 1H), 7.06 (d, J=2.4 Hz, 1H), 7.42 (dd, J=1.3, 8.8 Hz, 1H), 7.44 (d, J=8.4 Hz, 1H).

Example 243

N-Cyclopropylmethyl-N-[7-(2,4-dimethoxy-6-methylphenyl)-2-methoxypyrazolo[1,5-a]pyridin-3-yl]-N-tetrahydro-3-furanylmethylamine (Light Yellow Oil)

$^1$H NMR (400 MHz, CDCl$_3$) δ −0.06-0.02 (m, 2H), 0.25-0.35 (m, 2H), 0.77-0.86 (m, 1H), 1.55-1.70 (m, 1H), 1.86-1.96 (m, 1H), 2.02 (s, 1.5H), 2.03 (s, 1.5H), 2.22-2.30 (m, 1H), 2.76-2.88 (m, 2H), 2.93-3.02 (m, 1H), 3.10-3.18 (m, 1H), 3.55-3.62 (m, 1H), 3.63-3.68 (m, 1H), 3.68 (s, 1.5H), 3.69 (s, 1.5H), 3.73-3.85 (m, 2H), 3.86 (s, 3H), 3.87 (s, 3H), 6.41 (dd, J=1.2, 6.8 Hz, 1H), 6.43 (d, J=2.0 Hz, 1H), 6.47 (d, J=2.0 Hz, 1H), 7.02 (dd, J=6.8, 8.8 Hz, 1H), 7.28-7.32 (m, 1H).

Example 244

N-Cyclopropylmethyl-N-[7-(2,6-dimethoxy-4-methylphenyl)-2-methoxypyrazolo[1,5-a]pyridin-3-yl]-N-tetrahydro-3-furanylmethylamine (Yellow Amorphous)

$^1$H NMR (400 MHz, CDCl$_3$) δ −0.02-0.04 (m, 2H), 0.28-0.36 (m, 2H), 0.78-0.90 (m, 1H), 1.58-1.70 (m, 1H), 1.85-1.96 (m, 1H), 2.20-2.33 (m, 1H), 2.44 (s, 3H), 2.83 (d, J=6.8 Hz, 2H), 2.98 (dd, J=8.5, 12.0 Hz, 1H), 3.14 (dd, J=6.7, 12.0 Hz, 1H), 3.59 (dd, J=5.9, 8.5 Hz, 1H), 3.62-3.86 (m, 3H), 3.72 (s, 6H), 3.87 (s, 3H), 6.49 (dd, J=1.5, 6.7 Hz, 1H), 6.51 (s, 2H), 7.03 (dd, J=6.8, 8.8 Hz, 1H), 7.30 (dd, J=1.5, 8.8 Hz, 1H).

Example 245

N-Cyclopropylmethyl-N-[7-(2,6-dimethoxy-4-methylphenyl)-2-methoxypyrazolo[1,5-a]pyridin-3-yl]-N-tetrahydro-2-furanylmethylamine (Yellow Crystals)

$^1$H NMR (400 MHz, CDCl$_3$) δ −0.02-0.04 (m, 2H), 0.28-0.36 (m, 2H), 0.80-0.93 (m, 1H), 1.60-1.72 (m, 1H), 1.73-1.96 (m, 3H), 2.45 (s, 3H), 2.83-2.96 (m, 2H), 3.02 (dd, J=7.0, 12.0 Hz, 1H), 3.33 (dd, J=5.7, 12.0 Hz, 1H), 3.64-3.76 (m, 1H), 3.72 (s, 6H), 3.80-3.92 (m, 1H), 3.87 (s, 3H), 6.49 (dd, J=1.3, 6.8 Hz, 1H), 6.51 (s, 2H), 7.03 (dd, J=6.8, 8.9 Hz, 1H), 7.37 (dd, J=1.5, 8.8 Hz, 1H).

Example 246

N-Cyclopropylmethyl-N-[2-methoxy-7-(2-methoxy-4,6-dimethylphenyl)pyrazolo[1,5-a]pyridin-3-yl]-N-tetrahydro-2-furanylmethylamine (Yellow Oil)

$^1$H NMR (400 MHz, CDCl$_3$) δ −0.08-0.03 (m, 2H), 0.22-0.33 (m, 2H), 0.80-0.92 (m, 1H), 1.56-1.70 (m, 1H), 1.73-1.96 (m, 3H), 1.99 (s, 3H), 2.40 (s, 3H), 2.80-3.06 (m, 3H), 3.25-3.37 (m, 1H), 3.63-3.72 (m, 1H), 3.69 (s, 3H), 3.79-3.91 (m, 2H), 3.85 (s, 3H), 6.40 (dd, J=1.3, 6.8 Hz, 1H), 6.68 (s, 1H), 6.76 (s, 1H), 7.02 (dd, J=6.8, 8.8 Hz, 1H), 7.37 (dd, J=1.3, 8.8 Hz, 1H).

Example 247

N-Cyclopropylmethyl-N-[7-(2,6-dimethoxy-4-methylphenyl)-2-methoxypyrazolo[1,5-a]pyridin-3-yl]-N-(3-furylmethyl)amine (Yellow Crystals)

$^1$H NMR (400 MHz, CDCl$_3$) δ −0.02-0.04 (m, 2H), 0.28-0.36 (m, 2H), 0.80-0.92 (m, 1H), 2.45 (s, 3H), 2.87 (d, J=6.6 Hz, 2H), 3.71 (s, 6H), 3.88 (s, 3H), 4.11 (s, 2H), 6.34-6.38 (m, 1H), 6.48 (dd, J=1.5, 6.9 Hz, 1H), 6.50 (s, 2H), 7.00 (dd, J=6.8, 8.8 Hz, 1H), 7.22-7.32 (m, 3H).

Example 248

N-Cyclopropylmethyl-N-[7-(2,6-dimethoxy-4-methylphenyl)-2-methoxypyrazolo[1,5-a]pyridin-3-yl]-N-(2-furylmethyl)amine (Yellow Oil)

$^1$H NMR (400 MHz, CDCl$_3$) δ −0.02-0.06 (m, 2H), 0.28-0.37 (m, 2H), 0.80-0.94 (m, 1H), 2.43 (s, 3H), 2.93 (d, J=6.6 Hz, 2H), 3.70 (s, 6H), 3.86 (s, 3H), 4.24 (s, 2H), 6.07 (d, J=3.1 Hz, 1H), 6.22 (dd, J=1.8, 3.1 Hz, 1H), 6.46 (dd, J=1.3, 6.8 Hz, 1H), 6.49 (s, 2H), 6.98 (dd, J=6.8, 8.8 Hz, 1H), 7.21 (dd, J=1.5, 8.8 Hz, 1H), 7.24-7.34 (m, 1H).

Example 249

N-[7-(2-Chloro-6-methoxy-4-methylphenyl)-2-methoxypyrazolo[1,5-a]pyridin-3-yl]-N-cyclopropylmethyl-N-tetrahydro-2-furanylmethylamine (Yellow Oil)

$^1$H NMR (400 MHz, CDCl$_3$) δ −0.02-0.04 (m, 2H), 0.28-0.36 (m, 2H), 0.82-0.92 (m, 1H), 1.60-1.72 (m, 2H), 1.78-1.98 (m, 2H), 2.45 (s, 3H), 2.84-2.98 (m, 2H), 3.02-3.08 (m, 1H), 3.30-3.38 (m, 1H), 3.68-3.74 (m, 1H), 3.74 (s, 3H), 3.82-3.92 (m, 2H), 3.88 (s, 3H), 6.49 (d, J=7.2 Hz, 1H), 6.77 (s, 1H), 6.99 (s, 1H), 7.06 (dd, J=6.8, 8.8 Hz, 1H), 7.43 (dd, J=1.6, 9.2 Hz, 1H).

MS (ESI) m/z 456 MH$^+$

Example 250

N-[2-Methoxy-7-(2-methoxy-4,6-dimethylphenyl)pyrazolo[1,5-a]pyridin-3-yl]-N-propyl-N-tetrahydro-3-furanylmethylamine (Yellow Oil)

$^1$H NMR (400 MHz, CDCl$_3$) δ 0.89 (t, J=7.6 Hz, 3H), 1.32-1.42 (m, 2H), 1.56-1.66 (m, 1H), 1.86-1.96 (m, 1H), 1.99 (s, 1.5H), 2.00 (s, 1.5H), 2.18-2.28 (m, 1H), 2.41 (s, 3H), 2.88-2.96 (m, 3H), 3.05-3.12 (m, 1H), 3.53-3.58 (m, 1H), 3.63-3.69 (m, 1H), 3.70 (s, 3H), 3.72-3.83 (m, 2H), 3.85 (s, 3H), 6.41 (dd, J=1.6, 6.8 Hz, 1H), 6.68 (s, 1H), 6.76 (s, 1H), 7.03 (dd, J=6.8, 8.8 Hz, 1H), 7.25-7.28 (m, 1H).

Example 251

N-[2-Methoxy-7-(2-methoxy-4,6-dimethylphenyl)pyrazolo[1,5-a]pyridin-3-yl]-N-propyl-N-tetrahydro-2-furanylmethylamine (Yellow Oil)

$^1$H NMR (400 MHz, CDCl$_3$) δ 0.87 (t, J=7.6 Hz, 3H), 1.35-1.44 (m, 2H), 1.58-1.66 (m, 1H), 1.74-1.96 (m, 3H), 1.99 (s, 1.5H), 2.00 (s, 1.5H), 2.41 (s, 3H), 2.94 (dd, J=6.8, 12.4 Hz, 1H), 2.99 (t, J=7.6 Hz, 1H), 3.25 (ddd, J=4.0, 5.6, 12.4 Hz, 1H), 3.64-3.70 (m, 1H), 3.70 (s, 3H), 3.80-3.85 (m, 2H), 3.85 (s, 3H), 6.40 (dd, J=1.2, 6.8 Hz, 1H), 6.68 (s, 1H), 6.76 (s, 1H), 7.03 (dd, J=6.8, 8.8 Hz, 1H), 7.34 (td, J=1.8, 6.8 Hz, 1H).

Example 252

N-Cyclopropylmethyl-N-[2-methoxy-7-(4-methoxy-2,6-dimethylphenyl)pyrazolo[1,5-a]pyridin-3-yl]-N-tetrahydro-3-furanylmethylamine (Yellow Oil)

$^1$H NMR (400 MHz, CDCl$_3$) δ −0.10-0.00 (m, 2H), 0.22-0.32 (m, 2H), 0.76-0.86 (m, 1H), 1.58-1.69 (m, 1H), 1.86-1.97 (m, 1H), 2.02 (s, 3H), 2.03 (s, 3H), 2.20-2.31 (m, 1H), 2.79-2.86 (m, 2H), 2.93-3.02 (m, 1H), 3.10-3.19 (m, 1H), 3.55-3.61 (m, 1H), 3.63-3.71 (m, 1H), 3.72-3.85 (m, 2H), 3.84 (s, 3H), 3.85 (s, 3H), 6.34 (dd, J=1.3, 6.8 Hz, 1H), 6.70 (s, 2H), 7.02 (dd, J=6.8, 8.8 Hz, 1H), 7.32 (dd, J=1.3, 8.8 Hz, 1H).

Example 253

N-Cyclopropylmethyl-N-7-[2-(fluoromethoxy)-4,6-dimethylphenyl]-2-methoxypyrazolo[1,5-a]pyridin-3-yl-N-tetrahydro-3-furanylmethylamine (Yellow Oil)

$^1$H NMR (400 MHz, CDCl$_3$) δ −0.04-0.06 (m, 2H), 0.24-0.36 (m, 2H), 0.78-0.90 (m, 1H), 1.60-1.72 (m, 1H), 1.90-1.98 (m, 1H), 2.08 (br s, 3H), 2.22-2.32 (m, 1H), 2.45 (s, 3H), 2.80-2.90 (m, 2H), 2.96-3.04 (m, 1H), 3.14-3.20 (m, 1H), 3.58-3.86 (m, 4H), 3.86 (s, 3H), 5.38-5.66 (m, 2H), 6.45 (dd, J=1.2, 6.8 Hz, 1H), 6.96 (s, 1H), 6.99 (s, 1H), 7.06 (dd, J=6.8, 8.8 Hz, 1H), 7.35 (dd, J=1.2, 8.8 Hz, 1H).

Example 254

N-Cyclopropyl-N-[7-(2,6-dimethoxy-4-methylphenyl)-2-methoxypyrazolo[1,5-a]pyridin-3-yl]-N-(1,3-dioxolan-2-ylmethyl)amine (Yellow Oil)

$^1$H NMR (400 MHz, CDCl$_3$) δ −0.02-0.04 (m, 2H), 0.28-0.32 (m, 2H), 0.82-0.92 (m, 1H), 2.44 (s, 3H), 2.94 (d, J=6.8 Hz, 2H), 3.30 (d, J=4.4 Hz, 2H), 3.70 (s, 6H), 3.82-3.86 (m, 2H), 3.87 (s, 3H), 3.92-3.98 (m, 2H), 4.91 (t, J=4.4 Hz, 1H), 6.48 (dd, J=1.6, 6.8 Hz, 1H), 6.49 (s, 2H), 7.02 (dd, J=6.8, 8.8 Hz, 1H), 7.38 (dd, J=1.6, 8.8 Hz, 1H).

MS (ESI) m/z 454 MH$^+$

Example 255

N-Cyclopropyl-N-[7-(2,6-dimethoxy-4-methylphenyl)-2-methoxypyrazolo[1,5-a]pyridin-3-yl]-N-[2-(1,3-dioxolan-2-yl)ethyl]amine (Yellow Oil)

$^1$H NMR (400 MHz, CDCl$_3$) δ −0.02-0.04 (m, 2H), 0.28-0.34 (m, 2H), 0.82-0.92 (m, 1H), 1.74-1.82 (m, 2H), 2.44 (s, 3H), 2.87 (d, J=6.8 Hz, 2H), 3.22 (t, J=7.2 Hz, 2H), 3.71 (s, 6H), 3.82-3.90 (m, 2H), 3.86 (s, 3H), 3.92-4.00 (m, 2H), 4.97 (t, J=4.4 Hz, 1H), 6.47 (dd, J=1.6, 6.8 Hz, 1H), 6.49 (s, 2H), 7.00 (dd, J=6.8, 8.8 Hz, 1H), 7.31 (dd, J=1.6, 8.8 Hz, 1H).

MS (ESI) m/z 468 MH$^+$

Example 256

N-Cyclopropylmethyl-N-[2-methoxy-7-(2-methoxy-4,6-dimethylphenyl)pyrazolo[1,5-a]pyridin-3-yl]-N-tetrahydro-2H-4-pyranylmethylamine After dissolving N-cyclopropylmethyl-N-[2-methoxy-7-(2-methoxy-4,6-dimethylphenyl)pyrazolo[1,5-a]pyridin-3-yl]amine (134 mg) in tetrahydrofuran (10 mL), tetrahydro-2H-4-pyrancarbaldehyde (131 mg) and sodium triacetoxyborohydride (243 mg) were added, and the mixture was stirred at room temperature for 1 hour. Saturated aqueous sodium hydrogencarbonate was added to the obtained reaction mixture, extraction was performed with ethyl acetate, and the extract washed with brine. After drying over anhydrous magnesium sulfate and filtration, the solvent was concentrated under reduced pressure, the residue was purified by silica gel column chromatography, and the title compound (120 mg) was obtained from the n-hexane:ethyl acetate (4:1) fraction as a yellow amorphous.

$^1$H NMR (400 MHz, CDCl$_3$) δ −0.03-0.12 (m, 2H), 0.30-0.44 (m, 2H), 0.84-0.97 (m, 1H), 1.30-1.44 (m, 2H), 1.58-1.74 (m, 1H), 1.78-1.90 (m, 2H), 2.08 (s, 3H), 2.49 (s, 3H), 2.82-2.96 (m, 2H), 2.97-3.10 (m, 2H), 3.38 (dt, J=2.0, 12.0 Hz, 2H), 3.79 (s, 3H), 3.93 (s, 3H), 3.96-4.06 (m, 2H), 6.49 (dd, J=1.3, 6.8 Hz, 1H), 6.77 (s, 1H), 6.85 (s, 1H), 7.10 (dd, J=6.8, 8.8 Hz, 1H), 7.39 (dd, J=1.3, 8.8 Hz, 1H).

The compounds of Examples 257 to 266 below were synthesized according to the production method of Example 256.

Example 257

N-Cyclopropylmethyl-N-[2-methoxy-7-(2-methoxy-4,6-dimethylphenyl)pyrazolo[1,5-a]pyridin-3-yl]-N-tetrahydro-2H-4-pyranylamine (Yellow Oil)

$^1$H NMR (400 MHz, CDCl$_3$) δ −0.10--0.01 (m, 2H), 0.20-0.28 (m, 2H), 0.70-0.80 (m, 1H), 1.44-1.56 (m, 2H), 1.78-1.85 (m, 2H), 2.00 (s, 3H), 2.41 (s. 3H), 2.87-2.99 (m, 2H), 3.14-3.34 (m, 2H), 3.34-3.42 (m, 2H), 3.70 (s, 3H), 3.84 (s, 3H), 3.92-3.98 (m, 2H), 6.41 (dd, J=1.6, 6.8 Hz, 1H), 6.69 (s, 1H), 6.76 (s, 1H), 7.03 (dd, J=6.8, 8.8 Hz, 1H), 7.32 (dd, J=1.6, 8.8 Hz, 1H).

Example 258

N-[7-(2-Chloro-4-methoxyphenyl)-2-methoxypyrazolo[1,5-a]pyridin-3-yl]-N-cyclopropylmethyl-N-tetrahydro-2H-4-pyranylamine (Yellow Oil)

$^1$H NMR (400 MHz, CDCl$_3$) δ −0.05-0.04 (m, 2H), 0.21-0.30 (m, 2H), 0.68-0.78 (m, 1H), 1.41-1.55 (m, 2H), 1.75-1.85 (m, 2H), 2.89-2.96 (m, 2H), 3.12-3.22 (m, 1H), 3.32-3.42 (m, 2H), 3.88 (s, 3H), 3.89 (s, 3H), 3.88-3.98 (m, 2H), 6.49 (dd, J=1.3, 6.8 Hz, 1H), 6.92 (dd, J=2.4, 8.8 Hz, 1H), 7.03 (dd, J=6.8, 8.8 Hz, 1H), 7.06 (d, J=2.4 Hz, 1H), 7.36 (dd, J=1.3, 8.8 Hz, 1H), 7.45 (d, J=8.8 Hz, 1H).

Example 259

N-Cyclopropylmethyl-N-[7-(2,4-dimethoxy-6-methylphenyl)-2-methoxypyrazolo[1,5-a]pyridin-3-yl]-N-tetrahydro-2H-4-pyranylamine (Yellow Oil)

$^1$H NMR (400 MHz, CDCl$_3$) δ −0.06--0.02 (m, 2H), 0.20-0.28 (m, 2H), 0.70-0.80 (m, 1H), 1.44-1.55 (m, 2H), 1.78-1.86 (m, 2H), 2.02 (s, 3H), 2.88-3.00 (m, 2H), 3.14-3.24 (m, 1H), 3.34-3.42 (m, 2H), 3.69 (s, 3H), 3.85 (s, 3H), 3.87 (s, 3H), 3.92-3.98 (m, 2H), 6.41 (dd, J=1.6, 6.8 Hz, 1H), 6.44 (d, J=2.0 Hz, 1H), 6.47 (d, J=2.0 Hz, 1H), 7.03 (dd, J=6.8, 8.8 Hz, 1H), 7.31 (dd, J=1.6, 8.8 Hz, 1H).

Example 260

N-Cyclopropylmethyl-N-[7-(2,6-dimethoxy-4-methylphenyl)-2-methoxypyrazolo[1,5-a]pyridin-3-yl]-N-tetrahydro-2H-4-pyranylamine (Yellow Crystals)
$^1$H NMR (400 MHz, CDCl$_3$) δ −0.03-0.06 (m, 2H), 0.24-0.33 (m, 2H), 0.72-0.85 (m, 1H), 1.46-1.60 (m, 2H), 1.80-1.90 (m, 2H), 2.47 (s, 3H), 2.97 (d, J=6.6 Hz, 2H), 3.16-3.28 (m, 1H), 3.41 (dt, J=1.8, 12.0 Hz, 2H), 3.74 (s, 6H), 3.89 (s, 3H), 3.93-4.03 (m, 2H), 6.52 (dd, J=1.5, 7.0 Hz, 1H), 6.54 (s, 2H), 7.06 (dd, J=6.8, 8.8 Hz, 1H), 7.34 (dd, J=1.3, 8.9 Hz, 1H).

Example 261

N-Cyclopropylmethyl-N-[2-methoxy-7-(2-methoxy-4,6-dimethylphenyl)pyrazolo[1,5-a]pyridin-3-yl]-N-tetrahydro-2H-3-pyranylamine (Yellow Oil)
$^1$H NMR (400 MHz, CDCl$_3$) δ −0.02-0.06 (m, 2H), 0.26-0.38 (m, 2H), 0.78-0.88 (m, 1H), 1.32-1.44 (m, 1H), 1.62-1.76 (m, 2H), 2.09 (s, 3H), 2.09-2.16 (m, 1H), 2.50 (s, 3H), 2.94-3.08 (m, 2H), 3.20-3.30 (m, 3H), 3.79 (s, 3H), 3.84-3.92 (m, 1H), 3.94 (s, 3H), 4.12-4.22 (m, 1H), 6.51 (dd, J=1.2, 6.8 Hz, 1H), 6.78 (s, 1H), 6.85 (s, 1H), 7.13 (dd, J=6.8, 8.8 Hz, 1H), 7.39 (dd, J=1.6, 9.2 Hz, 1H).

Example 262

N-Cyclopropylmethyl-N-[7-(2,6-dimethoxy-4-methylphenyl)-2-methoxypyrazolo[1,5-a]pyridin-3-yl]-N-tetrahydro-2H-4-pyranylmethylamine (Yellow Crystals)
$^1$H NMR (400 MHz, CDCl$_3$) δ −0.04-0.08 (m, 2H), 0.28-0.40 (m, 2H), 0.80-0.94 (m, 1H), 1.20-1.38 (m, 2H), 1.52-1.70 (m, 1H), 1.74-1.84 (m, 2H), 2.47 (s, 3H), 2.84 (d, J=6.6 Hz, 2H), 2.97 (d, J=6.9 Hz, 2H), 3.33 (dt, J=2.0, 12.0 Hz, 2H), 3.75 (s, 6H), 3.89 (s, 3H), 3.90-4.00 (m, 2H), 6.52 (dd, J=1.4, 6.9 Hz, 1H), 6.54 (s, 2H), 7.04 (dd, J=6.8, 8.8 Hz, 1H), 7.33 (dd, J=1.4, 8.8 Hz, 1H).

Example 263

N-[7-(2-Chloro-6-methoxy-4-methylphenyl)-2-methoxypyrazolo[1,5-a]pyridin-3-yl]-N-cyclopropylmethyl-N-tetrahydro-2H-4-pyranylamine (Yellow Solid)
$^1$H NMR (400 MHz, CDCl$_3$) δ −0.02-0.02 (m, 2H), 0.28-0.32 (m, 2H), 0.74-0.84 (m, 1H), 1.50-1.64 (m, 2H), 1.84-1.92 (m, 2H), 2.47 (s, 3H), 2.99 (br d, J=6.4 Hz, 2H), 3.20-3.30 (m, 1H), 3.40-3.48 (m, 2H), 3.77 (s, 3H), 3.90 (s, 3H), 3.96-4.04 (m, 2H), 6.53 (dd, J=1.6, 8.8 Hz, 1H), 6.79 (s, 1H), 7.02 (s, 1H), 7.09 (dd, J=6.8, 8.8 Hz, 1H), 7.41 (dd, J=1.2, 8.8 Hz, 1H).
MS (ESI) m/z 456 MH$^+$

Example 264

N-Cyclopropylmethyl-N-[2-methoxy-7-(4-methoxy-2,6-dimethylphenyl)pyrazolo[1,5-a]pyridin-3-yl]-N-tetrahydro-2H-4-pyranylamine (Yellow Oil)
$^1$H NMR (400 MHz, CDCl$_3$) δ −0.10-−0.05 (m, 2H), 0.17-0.24 (m, 2H), 0.67-0.78 (m, 1H), 1.42-1.55 (m, 2H), 1.77-1.87 (m, 2H), 2.02 (s, 6H), 2.90-2.96 (m, 2H), 3.13-3.23 (m, 1H), 3.33-3.43 (m, 2H), 3.83 (s, 3H), 3.85 (s, 3H), 3.90-3.99 (m, 2H), 6.35 (dd, J=1.3, 6.8 Hz, 1H), 6.70 (s, 2H), 7.02 (dd, J=6.8, 8.8 Hz, 1H), 7.32 (dd, J=1.3, 8.8 Hz, 1H).

Example 265

N-[2-Methoxy-7-(2-methoxy-4,6-dimethylphenyl)pyrazolo[1,5-a]pyridin-3-yl]-N-tetrahydro-2H-4-pyranyl-N-tetrahydro-2H-4-pyranylmethylamine (White Amorphous)
$^1$H NMR (400 MHz, CDCl$_3$) δ 1.16-1.29 (m, 2H), 1.39-1.59 (m, 3H), 1.64-1.84 (m, 4H), 1.99 (s, 3H), 2.41 (s, 3H), 2.90-3.04 (m, 3H), 3.20-3.40 (m, 4H), 3.70 (s, 3H), 3.83 (s, 3H), 3.86-3.97 (m, 4H), 6.41 (dd, J=1.3, 6.8 Hz, 1H), 6.68 (s, 1H), 6.75 (s, 1H), 7.02 (dd, J=6.8, 8.8 Hz, 1H), 7.21 (dd, J=1.3, 8.8 Hz, 1H).

Example 266

N-Cyclopropylmethyl-N-[7-(2,6-dimethoxy-4-methylphenyl)-2-methoxypyrazolo[1,5-a]pyridin-3-yl]-N-(1,3-oxazol-2-ylmethyl)amine (Yellow Oil)
$^1$H NMR (400 MHz, CDCl$_3$) δ −0.02-0.10 (m, 2H), 0.28-0.38 (m, 2H), 0.82-0.96 (m, 1H), 2.43 (s, 3H), 2.97 (d, J=6.6 Hz, 2H), 3.69 (s, 6H), 3.84 (s, 3H), 4.38 (s, 2H), 6.44-6.53 (m, 1H), 6.49 (s, 2H), 7.00 (s, 1H), 7.01 (dd, J=6.7, 8.8 Hz, 1H), 7.27 (dd, J=1.5, 8.8 Hz, 1H), 7.55 (s, 1H).
MS (ESI) m/z 449 MH$^+$

Example 267

N-[7-(2-Methoxy-4,6-dimethylphenyl)-2-(methylsulfanyl)pyrazolo[1,5-a]pyridin-3-yl]-N-(2-pyridyl)amine After dissolving [7-(2-methoxy-4,6-dimethylphenyl)-2-(methylsulfanyl)pyrazolo[1,5-a]pyridin-3-yl]amine (40 mg) in toluene (1 mL), 2-bromopyridine (0.013 mL), sodium t-butoxide (25 mg) and dichlorobis(tri-o-tolylphosphine)palladium complex (3 mg) were added and the mixture was heated and stirred at 120° C. for 5 hours. The mixture was cooled to room temperature, water was added, and extraction was performed with ethyl acetate. The organic layer washed with brine, dried over anhydrous magnesium sulfate and concentrated under reduced pressure. The obtained residue was purified by silica gel column chromatography, and the title compound (12 mg) was obtained from the ethyl acetate:n-hexane (1:2) fraction as white crystals.
$^1$H NMR (400 MHz, CDCl$_3$) δ 2.05 (s, 3H), 2.35 (s, 3H), 2.40 (s, 3H), 3.70 (s, 3H), 6.61 (dd, J=1.3, 6.8 Hz, 1H), 6.68 (s, 1H), 6.76 (s, 1H), 6.89 (ddd, J=0.8, 4.8, 7.2 Hz, 1H), 6.97 (dd, J=0.8, 8.4 Hz, 1H), 7.06 (dd, J=6.8, 8.8 Hz, 1H), 7.14 (dd, J=1.3, 8.8 Hz, 1H), 7.54 (ddd, J=0.8, 7.2, 8.4 Hz, 1H), 8.31 (dd, J=0.8, 4.8 Hz, 1H).

Example 268

N-Cyclopropylmethyl-N-[7-(2-methoxy-4,6-dimethylphenyl)-2-(methylsulfanyl)pyrazolo[1,5-a]pyridin-3-yl]-N-(2-pyridyl)amine The title compound (4 mg) was obtained as light yellow crystals in the same manner as Example 267 using N-cyclo propylmethyl-N-[2-ethyl-7-(2-methoxy-4,6-dimethylphenyl)pyrazolo[1,5-a]pyridin-3-yl]amine (50 mg), with Pd$_2$(dba)$_3$CHCl$_3$ as the catalyst, and also using 2,2'-bis(diphenylphosphino)-1,1'-binaphthyl and sodium t-butoxide.

$^1$H NMR (400 MHz, CDCl$_3$) δ 0.05-0.17 (m, 2H), 0.29-0.41 (m, 2H), 1.09-1.20 (m, 1H), 2.04 (s, 3H), 2.40 (s, 3H), 2.42 (s, 3H), 3.72 (s, 3H), 6.18 (d, J=8.4 Hz, 1H), 6.58 (dd, J=4.8, 7.2 Hz, 1H), 6.62 (dd, J=0.8, 6.8 Hz, 1H), 6.71 (s, 1H), 6.79 (s, 1H), 7.12 (dd, J=6.8, 8.8 Hz, 1H), 7.23 (dd, J=0.8, 8.8 Hz, 1H), 7.29 (dd, J=7.2, 8.4 Hz, 1H), 8.22 (d, J=4.8 Hz, 1H).

The compounds of Examples 269 and 270 were synthesized according to the production methods of Examples 267 and 268.

Example 269

N-[7-(2,6-Dimethoxy-4-methylphenyl)-2-(methylsulfanyl)pyrazolo[1,5-a]pyridin-3-yl]-N-propyl-N-(2-pyridyl)amine (Light Yellow Crystals)
$^1$H NMR (400 MHz, CDCl$_3$) δ 0.90-0.96 (m, 3H), 1.60-1.75 (m, 2H), 2.41 (s, 3H), 2.45 (s, 3H), 3.74 (s, 6H), 6.14 (d, J=8.8 Hz, 1H), 6.52 (s, 2H), 6.55 (dd, J=4.8, 7.2 Hz, 1H), 6.69 (dd, J=1.3, 6.8 Hz, 1H), 7.11 (dd, J=6.8, 8.8 Hz, 1H), 7.15 (dd, J=1.3, 8.8 Hz, 1H), 7.25 (dd, J=7.2, 8.8 Hz, 1H), 8.21 (d, J=4.8 Hz, 1H).

Example 270

N-Cyclopropylmethyl-N-[7-(2,6-dimethoxy-4-methylphenyl)-2-methoxypyrazolo[1,5-a]pyridin-3-yl]-N-(2-pyridyl)amine (Light Yellow Crystals)
$^1$H NMR (400 MHz, CDCl$_3$) δ 0.09-0.17 (m, 2H), 0.32-0.40 (m, 2H), 1.09-1.21 (m, 1H), 2.45 (s, 3H), 3.74 (s, 6H), 3.87 (s, 6H), 6.28 (d, J=8.4 Hz, 1H), 6.52 (s, 2H), 6.53 (dd, J=5.0, 7.2 Hz, 1H), 6.61 (dd, J=1.3, 6.8 Hz, 1H), 7.08 (dd, J=6.8, 8.8 Hz, 1H), 7.12 (dd, J=1.3, 8.8 Hz, 1H), 7.27 (dd, J=7.2, 8.4 Hz, 1H), 8.18 (d, J=5.0 Hz, 1H).

Example 271

3-(2,5-Diethyl-1H-1-pyrrolyl)-7-(2,6-dimethoxy-4-methylphenyl)-2-ethylpyrazolo[1,5-a]pyridine After dissolving 7-(2,6-dimethoxy-4-methylphenyl)-2-ethyl-3-nitropyrazolo[1,5-a]pyridine (600 mg) in a mixture of ethanol (30 mL) and water (30 mL), acetic acid (3 mL) and zinc powder (600 mg) were added and the mixture was stirred at 60° C. for 2 hours. The ethanol of the obtained reaction mixture was distilled off under reduced pressure, and then saturated aqueous sodium hydrogencarbonate and ethyl acetate were added to the residue and extraction was performed with ethyl acetate. The obtained organic layers were combined, washed with water and dried over anhydrous magnesium sulfate, and the solvent was distilled off under reduced pressure to obtain 7-(2,6-dimethoxy-4-methylphenyl)-2-ethylpyrazolo[1,5-a]pyridine-3-amine (500 mg) as a crude product.

The obtained crude 7-(2,6-dimethoxy-4-methylphenyl)-2-ethylpyrazolo[1,5-a]pyridin-3-amine (160 mg) was dissolved in toluene (50 mL), and then 3,6-octanedione (1 g) and acetic acid (15 mL) were added and the mixture was heated to reflux for 4 hours. The toluene of the obtained reaction mixture was distilled off under reduced pressure, and then saturated aqueous sodium hydrogencarbonate was added to the residue and extraction was performed with ethyl acetate. The extracted organic layer washed with water and dried over anhydrous magnesium sulfate, and the solvent was distilled off under reduced pressure. The obtained residue was subjected to silica gel column chromatography, and the title compound (19 mg) was obtained from the n-hexane:ethyl acetate (10:1) fraction as white crystals.

$^1$H NMR (400 MHz, CDCl$_3$) δ 1.07 (t, J=7.6 Hz, 3H), 1.08 (t, J=7.6 Hz, 6H), 2.25 (q, J=7.6 Hz, 2H), 2.26 (q, J=7.6 Hz, 2H), 2.45 (s, 3H), 2.55 (q, J=8.0 Hz, 2H), 3.73 (s, 6H), 5.99 (s, 2H), 6.54 (s, 2H), 6.73 (dd. J=2.0, 6.4 Hz, 1H), 7.10-7.15 (m, 2H).

The compounds of Examples 272 to 276 were synthesized according to the production method of Example 25.

Example 272

N3-Cyclopropylmethyl-N3-tetrahydro-3-furanylmethyl-7-[6-(dimethylamino)-4-methyl-3-pyridyl]-2-ethylpyrazolo[1,5-a]pyridin-3-amine (Yellow Oil)
$^1$H NMR (400 MHz, CDCl$_3$) δ −0.05-0.05 (m, 2H), 0.35-0.42 (m, 2H), 0.80-0.90 (m, 1H), 1.25 (t, J=7.6 Hz, 3H), 1.55-1.70 (m, 1H), 1.85-1.95 (m, 1H), 2.07 (s, 3H), 2.20-2.30 (m, 1H), 2.77 (q, J=7.6 Hz, 2H), 2.90 (d, J=6.8 Hz, 2H), 3.06-3.11 (m, 1H), 3.14 (s, 6H), 3.17-3.25 (m, 2H), 3.60-3.84 (m, 4H), 6.46 (s, 1H), 6.53 (dd, J=1.6, 6.8 Hz, 1H), 7.02 (dd, J=6.8, 8.8 Hz, 1H), 7.45 (dd, J=1.6, 9.2 Hz, 1H), 8.16 (s, 1H).

Example 273

N3-Cyclopropylmethyl-N3-tetrahydro-3-furanylmethyl-7-[6-(dimethylamino)-2,4-dimethyl-3-pyridyl]-2-ethylpyrazolo[1,5-a]pyridin-3-amine (Yellow Oil)
$^1$H NMR (400 MHz, CDCl$_3$) δ −0.05-0.00 (m, 2H), 0.30-0.40 (m, 2H), 0.75-0.90 (m, 1H), 1.21 (t, J=7.2 Hz, 3H), 1.60-1.70 (m, 1H), 1.85-1.97 (m, 4H), 2.14 (s, 3H), 2.22-2.32 (m, 1H), 2.75 (q, J=7.6 Hz, 2H), 2.91 (d, J=6.4 Hz, 2H), 3.05-3.15 (m, 7H), 3.20-3.28 (m, 1H), 3.59-3.88 (m, 4H), 6.31 (s, 2H), 6.46 (dd, J=1.6, 6.8 Hz, 1H), 7.00 (dd. J=6.8, 9.2 Hz, 1H), 7.43 (dd, J=1.2, 8.8 Hz, 1H).

Example 274

N-Cyclopropylmethyl-N-(1,3-dioxolan-2-ylmethyl)-N-[2-ethyl-7-(4-methoxy-2,6-dimethylphenyl)pyrazolo[1,5-a]pyridin-3-yl]amine (Yellow Oil)
$^1$H NMR (400 MHz, CDCl$_3$) δ −0.04-0.04 (m, 2H), 0.34-0.38 (m, 2H), 0.84-0.96 (m, 1H), 1.25 (t, J=7.6 Hz, 3H), 2.05 (s, 6H), 2.81 (q, J=7.6 Hz, 2H), 3.07 (d, J=6.8 Hz, 2H), 3.41 (d, J=4.4 Hz, 2H), 3.86-3.90 (m, 2H), 3.87 (s, 3H), 3.98-4.04 (m, 2H), 6.47 (dd, J=1.2, 6.8 Hz, 1H), 6.73 (s, 2H), 7.05 (dd, J=6.8, 8.8 Hz, 1H), 7.51 (dd, J=1.2, 8.8 Hz, 1H).

Example 275

N3-Cyclopropylmethyl-N3-(1,3-dioxolan-2-ylm-ethyl)-7-[6-(dimethylamino)-4-methyl-3-pyridyl]-2-ethylpyrazolo[1,5-a]pyridin-3-amine (Yellow Oil)

$^1$H NMR (400 MHz, CDCl$_3$) δ −0.02-0.04 (m, 2H), 0.32-0.38 (m, 2H), 0.80-0.92 (m, 1H), 1.28 (t, J=7.6 Hz, 3H), 2.08 (s, 3H), 2.81 (q, J=7.6 Hz, 2H), 3.03 (d, J=6.8 Hz, 2H), 3.15 (s, 6H), 3.36 (d, J=4.4 Hz, 2H), 3.80-3.88 (m, 2H), 3.92-4.00 (m, 2H), 4.91 (t, J=4.4 Hz, 1H), 6.46 (s, 1H), 6.53 (dd, J=1.6, 6.8 Hz, 1H), 7.02 (dd, J=6.8, 8.8 Hz, 1H), 7.49 (dd, J=1.6, 8.8 Hz, 1H), 8.16 (s, 1H).

Example 276

N3-Cyclopropylmethyl-N3-(1,3-dioxolan-2-ylm-ethyl)-7-[6-(dimethylamino)-2,4-dimethyl-3-py-ridyl]-2-ethylpyrazolo[1,5-a]pyridin-3-amine (Yellow Oil)

$^1$H NMR (400 MHz, CDCl$_3$) δ −0.02-0.04 (m, 2H), 0.32-0.38 (m, 2H), 0.82-0.92 (m, 1H), 1.26 (t, J=7.6 Hz, 3H), 1.99 (s, 3H), 2.18 (s, 3H), 2.81 (q, J=7.6 Hz, 2H), 3.07 (d, J=6.8 Hz, 2H), 3.16 (s, 6H), 3.04 (d, J=4.4 Hz, 2H), 3.82-3.90 (m, 2H), 3.96-4.02 (m, 2H), 4.96 (t, J=4.4 Hz, 1H), 6.34 (s, 1H), 6.48 (dd, J=1.2, 6.8 Hz, 1H), 7.03 (dd, J=6.8, 8.8 Hz, 1H), 7.50 (dd, J=1.2, 8.8 Hz, 1H).

The compounds of Examples 277 to 286 were synthesized according to the production method of Example 47.

Example 277

N-[7-(2,6-Dimethoxy-4-methylphenyl)-2-ethylpyra-zolo[1,5-a]pyridin-3-yl]-N-propyl-N-tetrahydro-2H-4-pyranylmethylamine (Yellow Oil)

$^1$H NMR (400 MHz, CDCl$_3$) δ 0.87 (t, J=7.3 Hz, 3H), 1.20 (t, J=7.6 Hz, 3H), 1.22-1.32 (m, 2H), 1.39 (ddq, J=7.3, 7.3, 7.3 Hz, 2H), 1.51-1.63 (m, 1H), 1.70-1.78 (m, 2H), 2.43 (s, 3H), 2.74 (q, J=7.6 Hz, 2H), 2.93-2.98 (m, 2H), 2.97 (dd, J=7.3, 7.3 Hz, 2H), 3.26-3.35 (m, 2H), 3.70 (s, 6H), 3.90-3.97 (m, 2H), 6.51 (s, 2H), 6.59 (dd, J=1.3, 6.8 Hz, 1H), 7.00 (dd, J=6.8, 8.8 Hz, 1H), 7.41 (dd, J=1.3, 8.8 Hz, 1H).

Example 278

N-Butyl-N-[7-(2,6-dimethoxy-4-methylphenyl)-2-ethylpyrazolo[1,5-a]pyridin-3-yl]-N-tetrahydro-2H-4-pyranylmethylamine (Yellow Oil)

$^1$H NMR (400 MHz, CDCl$_3$) δ 0.86 (t, J=7.1 Hz, 3H), 1.20 (t, J=7.6 Hz, 3H), 1.16-1.42 (m, 6H), 1.49-1.63 (m, 1H), 1.66-1.80 (m, 2H), 2.43 (s, 3H), 2.73 (q, J=7.6 Hz, 2H), 2.95 (d, J=7.0 Hz, 2H), 3.00 (t, J=7.1 Hz, 2H), 3.30 (dt, J=2.0, 12.0 Hz, 2H), 3.70 (s, 6H), 3.88-4.00 (m, 2H), 6.51 (s, 2H), 6.59 (dd, J=1.4, 6.9 Hz, 1H), 7.00 (dd, J=6.8, 8.8 Hz, 1H), 7.41 (dd, J=1.4, 8.8 Hz, 1H).

MS (ESI) m/z 466 MH$^+$

Example 279

N-Cyclobutylmethyl-N-[7-(2,6-dimethoxy-4-meth-ylphenyl)-2-ethylpyrazolo[1,5-a]pyridin-3-yl]-N-tetrahydro-2H-4-pyranylmethylamine (Yellow Oil)

$^1$H NMR (400 MHz, CDCl$_3$) δ 1.21 (t, J=7.6 Hz, 3H), 1.17-1.32 (m, 2H), 1.50-1.66 (m, 3H), 1.67-1.94 (m, 6H), 2.25-2.40 (m, 1H), 2.43 (s, 3H), 2.72 (q, J=7.5 Hz, 2H), 2.93 (d, J=7.0 Hz, 2H), 3.04 (d, J=7.1 Hz, 2H), 3.31 (dt, J=1.9, 12.0 Hz, 2H), 3.69 (s, 6H), 3.88-4.00 (m, 2H), 6.51 (s, 2H), 6.59 (dd, J=1.3, 6.8 Hz, 1H), 7.00 (dd, J=7.0, 8.8 Hz, 1H), 7.39 (dd, J=1.5, 8.8 Hz, 1H).

MS (ESI) m/z 478 MH$^+$

Example 280

N-Butyl-N-[2-ethyl-7-(2,4,6-trimethoxyphenyl)pyra-zolo[1,5-a]pyridin-3-yl]-N-tetrahydro-2H-4-pyranyl-methylamine (Light Yellow Crystals)

$^1$H NMR (400 MHz, CDCl$_3$) δ 0.85 (t, J=6.8 Hz, 3H), 1.21 (t, J=7.6 Hz, 3H), 1.22-1.40 (m, 6H), 1.50-1.60 (m, 1H), 1.70-1.77 (m, 2H), 2.73 (q, J=7.6 Hz, 2H), 2.95 (d, J=6.8 Hz, 2H), 3.00 (t, J=6.8 Hz, 2H), 3.26-3.34 (m, 2H), 3.70 (s, 6H), 3.88 (s, 3H), 3.90-3.96 (m, 2H), 6.24 (s, 2H), 6.58 (dd, J=1.6, 6.8 Hz, 1H), 6.99 (dd, J=6.8, 8.8 Hz, 1H), 7.39 (dd, J=1.6, 8.8 Hz, 1H).

Example 281

N-Cyclobutylmethyl-N-[2-ethyl-7-(2,4,6-trimethox-yphenyl)pyrazolo[1,5-a]pyridin-3-yl]-N-tetrahydro-2H-4-pyranylmethylamine (Light Yellow Crystals)

$^1$H NMR (400 MHz, CDCl$_3$) δ 1.21 (t, J=7.6 Hz, 3H), 1.23-1.30 (m, 2H), 1.52-1.62 (m, 3H), 1.71-1.82 (m, 4H), 1.82-1.92 (m, 2H), 2.27-2.36 (m, 1H), 2.72 (q, J=7.6 Hz, 2H), 2.93 (d, J=6.8 Hz, 2H), 3.03 (d, J=7.2 Hz, 2H), 3.26-3.34 (m, 2H), 3.69 (s, 6H), 3.88 (s, 3H), 3.90-3.96 (m, 2H), 6.24 (s, 2H), 6.57 (dd, J=1.2, 6.8 Hz, 1H), 6.99 (dd, J=6.8, 8.8 Hz, 1H), 7.37 (dd, J=1.2, 8.8 Hz, 1H).

Example 282

N-Cyclopropylmethyl-N-[2-ethyl-7-(2,4,6-tri-methoxyphenyl)pyrazolo[1,5-a]pyridin-3-yl]-N-tet-rahydro-2H-4-pyranylmethylamine (Light Yellow Crystals)

$^1$H NMR (400 MHz, CDCl$_3$) δ −0.02-0.03 (m, 2H), 0.34-0.40 (m, 2H), 0.80-0.90 (m, 1H), 1.23 (t, J=7.6 Hz, 3H), 1.23-1.34 (m, 2H), 1.54-1.64 (m, 1H), 1.73-1.80 (m, 2H), 2.78 (q, J=7.6 Hz, 2H), 2.89 (d, J=6.8 Hz, 2H), 3.05 (d, J=6.8 Hz, 2H), 3.27-3.36 (m, 2H), 3.71 (s, 6H), 3.89 (s, 3H), 3.92-3.97 (m, 2H), 6.26 (s, 2H), 6.59 (dd, J=1.6, 6.8 Hz, 1H), 7.00 (dd, J=6.8, 8.8 Hz, 1H), 7.43 (dd, J=1.6, 8.8 Hz, 1H).

Example 283

N-[7-(2,6-Dimethoxy-4-methylphenyl)-2-ethylpyrazolo[1,5-a]pyridin-3-yl]-N,N-ditetrahydro-2H-4-pyranylmethylamine (Yellow Amorphous)

$^1$H NMR (400 MHz, CDCl$_3$) δ 1.21 (t, J=7.6 Hz, 3H), 1.20-1.31 (m, 4H), 1.52-1.60 (m, 2H), 1.70-1.78 (m, 4H), 2.44 (s, 3H), 2.74 (q, J=7.6 Hz, 2H), 2.93 (d, J=6.8 Hz, 4H), 3.26-3.34 (m, 4H), 3.71 (s, 6H), 3.90-3.96 (m, 4H), 6.52 (s, 2H), 6.62 (dd, J=1.6, 6.8 Hz, 1H), 7.02 (dd, J=6.8, 8.8 Hz, 1H), 7.41 (dd, J=1.6, 8.8 Hz, 1H).

Example 284

N3-Cyclopropylmethyl-N3-tetrahydro-2H-4-pyranylmethyl-7-[6-(dimethylamino)-4-methyl-3-pyridyl]-2-ethylpyrazolo[1,5-a]pyridin-3-amine (Yellow Oil)

$^1$H NMR (400 MHz, CDCl$_3$) δ −0.02-0.04 (m, 2H), 0.33-0.41 (m, 2H), 0.78-0.91 (m, 1H), 1.28 (t, J=7.5 Hz, 3H), 1.23-1.36 (m, 2H), 1.54-1.67 (m, 1H), 1.72-1.82 (m, 2H), 2.10 (s, 3H), 2.80 (q, J=7.5 Hz, 2H), 2.90 (d, J=6.8 Hz, 2H), 3.07 (d, J=7.1 Hz, 2H), 3.17 (s, 6H), 3.33 (dt, J=2.0, 12.0 Hz, 2H), 3.92-4.00 (m, 2H), 6.48 (s, 1H), 6.55 (dd, J=1.5, 6.8 Hz, 1H), 7.03 (dd, J=6.8, 8.8 Hz, 1H), 7.48 (dd, J=1.4, 8.8 Hz, 1H), 8.19 (s, 1H).

Example 285

N3-Cyclopropylmethyl-N3-tetrahydro-2H-4-pyranylmethyl-7-[6-(dimethylamino)-2,4-dimethyl-3-pyridyl]-2-ethylpyrazolo[1,5-a]pyridin-3-amine (Yellow Oil)

$^1$H NMR (400 MHz, CDCl$_3$) δ −0.08-−0.02 (m, 2H), 0.29-0.35 (m, 2H), 0.76-0.87 (m, 1H), 1.21 (t, J=7.6 Hz, 3H), 1.22-1.34 (m, 2H), 1.54-1.66 (m, 1H), 1.72-1.81 (m, 2H), 1.96 (s, 3H), 2.15 (s, 3H), 2.75 (q, J=7.6 Hz, 2H), 2.84-2.90 (m, 2H), 3.02-3.07 (m, 2H), 3.12 (s, 6H), 3.27-3.36 (m, 2H), 3.90-3.98 (m, 2H), 6.30 (s, 1H), 6.44 (dd, J=1.3, 6.8 Hz, 1H), 6.98 (dd, J=6.8, 8.8 Hz, 1H), 7.43 (dd, J=1.3, 8.8 Hz, 1H).

Example 286

N-Cyclopropylmethyl-N-[7-(2,4-dimethoxy-6-methylphenyl)-2-ethylpyrazolo[1,5-a]pyridin-3-yl]-N-tetrahydro-2H-4-pyranylmethylamine (Yellow Oil)

$^1$H NMR (400 MHz, CDCl$_3$) δ −0.05-0.00 (m, 2H), 0.31-0.36 (m, 2H), 0.77-0.87 (m, 1H), 1.21 (t, J=7.6 Hz, 3H), 1.22-1.32 (m, 2H), 1.56-1.64 (m, 1H), 1.72-1.80 (m, 2H), 2.00 (s, 3H), 2.72-2.79 (m, 2H), 2.87 (d, J=6.4 Hz, 2H), 3.04 (d, J=6.8 Hz, 2H), 3.27-3.35 (m, 2H), 3.67 (s, 3H), 3.85 (s, 3H), 3.90-3.96 (m, 2H), 6.43 (d, J=2.0 Hz, 1H), 6.47 (d, J=2.0 Hz, 1H), 6.49 (d, J=1.2, 6.8 Hz, 1H), 6.99 (dd, J=6.8, 8.8 Hz, 1H), 7.43 (dd, J=1.2, 8.8 Hz, 1H).

The compounds of Examples 287 to 292 were synthesized according to the production methods of Examples 102 and 103.

Example 287

N-Cyclopropylmethyl-N-[7-(2-methoxy-4,6-dimethylphenyl)-2-(methylsulfanyl)pyrazolo[1,5-a]pyridin-3-yl]-N-[(3-methyl-5-isoxazolyl)methyl]amine (Light Yellow Oil)

$^1$H NMR (400 MHz, CDCl$_3$) δ −0.01-0.06 (m, 2H), 0.31-0.38 (m, 2H), 0.82-0.92 (m, 1H), 1.96 (s, 3H), 2.22 (s, 3H), 2.39 (s, 3H), 2.44 (s, 3H), 2.97-3.03 (m, 2H), 3.66 (s, 3H), 4.43 (s, 2H), 5.95 (s, 1H), 6.49 (dd, J=1.3, 6.8 Hz, 1H), 6.65 (s, 1H), 6.73 (s, 1H), 7.03 (dd, J=6.8, 8.8 Hz, 1H), 7.32 (dd, J=1.3, 8.8 Hz, 1H).

Example 288

N3-Cyclopropylmethyl-N3-[6-(dimethylamino)-2-pyridyl]methyl-7-(2-methoxy-4,6-dimethylphenyl)-2-(methylsulfanyl)pyrazolo[1,5-a]pyridin-3-amine (Yellow Oil)

$^1$H NMR (400 MHz, CDCl$_3$) δ −0.05-0.02 (m, 2H), 0.25-0.32 (m, 2H), 0.84-0.93 (m, 1H), 1.97 (s, 3H), 2.39 (s, 3H), 2.45 (s, 3H), 2.94-3.00 (m, 2H), 3.04 (s, 6H), 3.66 (s, 3H), 4.37 (s, 2H), 6.34 (d, J=8.2 Hz, 1H), 6.47 (dd, J=1.3, 6.8 Hz, 1H), 6.66 (s, 1H), 6.74 (s, 1H), 6.99 (d, J=7.3 Hz, 1H), 7.01 (dd, J=6.8, 8.8 Hz, 1H), 7.42 (dd, J=7.3, 8.2 Hz, 1H), 7.47 (dd, J=1.3, 8.8 Hz, 1H).

Example 289

N-Cyclopropylmethyl-N-(5-isoxazolylmethyl)-N-[7-(2-methoxy-4,6-dimethylphenyl)-2-(methylsulfanyl)pyrazolo[1,5-a]pyridin-3-yl]amine (Light Yellow Oil)

$^1$H NMR (400 MHz, CDCl$_3$) δ −0.02-0.08 (m, 2H), 0.31-0.41 (m, 2H), 0.83-0.93 (m, 1H), 1.96 (s, 3H), 2.40 (s, 3H), 2.44 (s, 3H), 2.98-3.08 (m, 2H), 3.66 (s, 3H), 4.52 (s, 2H), 6.14 (d, J=1.2 Hz, 1H), 6.51 (dd, J=1.3, 6.8 Hz, 1H), 6.66 (s, 1H), 6.75 (s, 1H), 7.04 (dd, J=6.8, 8.8 Hz, 1H), 7.31 (dd, J=1.3, 8.8 Hz, 1H), 8.10 (d, J=1.2 Hz, 1H).

Example 290

N-[7-(2,6-Dimethoxy-4-methylphenyl)-2-(methylsulfanyl)pyrazolo[1,5-a]pyridin-3-yl]-N-(1,3-dioxolan-2-ylmethyl)-N-propylamine (Light Yellow Crystals)

$^1$H NMR (400 MHz, CDCl$_3$) δ 0.87 (t, J=7.2 Hz, 3H), 1.40 (tq, J=7.2, 7.2 Hz, 2H), 2.44 (s, 3H), 2.44 (s, 3H), 3.14 (t, J=7.2 Hz, 2H), 3.29 (d, J=4.4 Hz, 2H), 3.81 (s, 6H), 3.82-3.88 (m, 2H), 3.92-4.00 (m, 2H), 4.92 (t, J=4.4 Hz, 1H), 6.48 (s, 2H), 6.57 (dd, J=1.6, 6.8 Hz, 1H), 7.04 (dd, J=6.8, 8.8 Hz, 1H), 7.42 (d, J=8.8 Hz, 1H).

Example 291

N-Cyclopropylmethyl-N-[7-(2,6-dimethoxy-4-methylphenyl)-2-(methylsulfanyl)pyrazolo[1,5-a]pyridin-3-yl]-N-(1,3-dioxolan-2-ylmethyl)amine (Light Yellow Oil)

$^1$H NMR (400 MHz, CDCl$_3$) δ −0.04-0.06 (m, 2H), 0.28-0.34 (m, 2H), 0.82-0.92 (m, 1H), 2.42 (s, 3H), 2.44 (s, 3H), 3.02 (d, J=6.4 Hz, 2H), 3.36 (d, J=4.4 Hz, 2H), 3.67 (s, 6H), 3.78-3.84 (m, 2H), 3.90-3.98 (m, 2H), 4.92 (t, J=4.4 Hz, 1H), 6.47 (s, 2H), 6.56 (dd, J=1.2, 6.8 Hz, 1H), 7.02 (dd, J=7.2, 8.8 Hz, 1H), 7.43 (dd, J=1.2, 8.8 Hz, 1H).

Example 292

N-[7-(2,6-Dimethoxy-4-methylphenyl)-2-(methylsulfanyl)pyrazolo[1,5-a]pyridin-3-yl]-N-(1,3-dioxolan-2-ylmethyl)-N-tetrahydro-3-furanylmethylamine (Yellow Oil)

$^1$H NMR (400 MHz, CDCl$_3$) δ 1.56-1.66 (m, 1H), 1.86-1.96 (m, 1H), 2.20-2.32 (m, 1H), 2.44 (s, 3H), 2.44 (s, 3H), 3.08-3.16 (m, 1H), 3.22-3.32 (m, 3H), 3.56-3.68 (m, 2H), 3.69 (s, 6H), 3.72-3.84 (m, 2H), 3.84-3.88 (m, 2H), 3.94-3.98 (m, 2H), 4.93 (t, J=4.4 Hz, 1H), 6.48 (s, 2H), 6.59 (dd, J=1.2, 6.8 Hz, 1H), 7.06 (dd, J=7.2, 8.8 Hz, 1H), 7.39 (dd, J=1.6, 8.8 Hz, 1H).

The compounds of Examples 293 and 294 were synthesized according to the production method of Example 159.

Example 293

N-[7-(2,6-Dimethoxy-4-methylphenyl)-2-(methylsulfanyl)pyrazolo[1,5-a]pyridin-3-yl]-N-(1,3-dioxolan-2-ylmethyl)-N-tetrahydro-2H-4-pyranylmethylamine (Yellow Oil)

$^1$H NMR (400 MHz, CDCl$_3$) δ 1.22-1.32 (m, 2H), 1.50-1.60 (m, 1H), 1.76-1.84 (m, 2H), 2.44 (s, 3H), 2.44 (s, 3H), 3.09 (d, J=6.8 Hz, 2H), 3.25 (d, J=4.4 Hz, 2H), 3.24-3.36 (m, 2H), 3.70 (s, 6H), 3.82-3.88 (m, 2H), 3.90-3.98 (m, 4H), 4.92 (t, J=4.4 Hz, 1H), 6.49 (s, 2H), 6.59 (dd, J=1.2, 6.8 Hz, 1H), 7.05 (dd, J=6.8, 8.8 Hz, 1H), 7.40 (d, J=8.8 Hz, 1H).

Example 294

N-[7-(2,6-Dimethoxy-4-methylphenyl)-2-(methylsulfanyl)pyrazolo[1,5-a]pyridin-3-yl]-N,N-ditetrahydro-2H-4-pyranylmethylamine (Light Yellow Amorphous)

$^1$H NMR (400 MHz, CDCl$_3$) δ 1.21-1.32 (m, 4H), 1.48-1.61 (m, 2H), 1.74-1.83 (m, 4H), 2.43 (s, 3H), 2.44 (s, 3H), 2.89-2.95 (m, 4H), 3.26-3.35 (m, 4H), 3.70 (s, 6H), 3.89-3.96 (m, 4H), 6.48 (s, 2H), 6.59 (dd, J=1.3, 6.8 Hz, 1H), 7.04 (dd, J=6.8, 8.8 Hz, 1H), 7.31 (dd, J=1.3, 8.8 Hz, 1H).

The compounds of Examples 295 to 298 were synthesized according to the production methods of Examples 237 and 238.

Example 295

N-[7-(2,6-Dimethoxy-4-methylphenyl)-2-methoxypyrazolo[1,5-a]pyridin-3-yl]-N-(1,3-dioxolan-2-ylmethyl)-N-tetrahydro-3-furanylmethylamine (Yellow Oil)

$^1$H NMR (400 MHz, CDCl$_3$) δ 1.54-1.66 (m, 1H), 1.86-1.96 (m, 1H), 2.18-2.32 (m, 1H), 2.44 (s, 3H), 2.98-3.06 (m, 1H), 3.14-3.24 (m, 3H), 3.52-3.68 (m, 2H), 3.71 (s, 6H), 3.72-3.84 (m, 2H), 3.86 (s, 3H), 3.90-3.98 (m, 2H), 4.91 (t, J=4.4 Hz, 1H), 6.48 (dd, J=1.2, 6.8 Hz, 1H), 6.49 (s, 2H), 7.04 (dd, J=6.8, 8.8 Hz, 1H), 7.30 (dd, J=1.2, 8.8 Hz, 1H).

Example 296

N3-Cyclopropylmethyl-N3-tetrahydro-3-furanylmethyl-7-[6-(dimethylamino)-2,4-dimethyl-3-pyridyl]-2-methoxypyrazolo[1,5-a]pyridin-3-amine (Yellow Oil)

$^1$H NMR (400 MHz, CDCl$_3$) δ −0.09-0.01 (m, 2H), 0.23-0.33 (m, 2H), 0.75-0.86 (m, 1H), 1.58-1.69 (m, 1H), 1.86-1.96 (m, 1H), 1.97 (s, 3H), 2.15 (s, 3H), 2.20-2.30 (m, 1H), 2.79-2.85 (m, 2H), 2.94-3.01 (m, 1H), 3.10-3.18 (m, 1H), 3.13 (s, 6H), 3.55-3.61 (m, 1H), 3.63-3.70 (m, 1H), 3.71-3.83 (m, 2H), 3.84 (s, 3H), 6.29 (s, 1H), 6.34 (dd, J=1.3, 6.8 Hz, 1H), 6.99 (dd, J=6.8, 8.8 Hz, 1H), 7.29 (dd, J=1.3, 8.8 Hz, 1H).

Example 297

N3-Cyclopropylmethyl-N3-tetrahydro-3-furanylmethyl-7-[6-(dimethylamino)-4-methyl-3-pyridyl]-2-methoxypyrazolo[1,5-a]pyridin-3-amine (Yellow Oil)

$^1$H NMR (400 MHz, CDCl$_3$) δ −0.06-0.05 (m, 2H), 0.25-0.36 (m, 2H), 0.75-0.87 (m, 1H), 1.57-1.68 (m, 1H), 1.84-1.96 (m, 1H), 2.11 (s, 3H), 2.15-2.29 (m, 1H), 2.78-2.85 (m, 2H), 2.92-3.01 (m, 1H), 3.08-3.17 (m, 1H), 3.15 (s, 6H), 3.56-3.69 (m, 2H), 3.70-3.83 (m, 2H), 3.89 (s, 3H), 6.41 (dd, J=1.3, 6.8 Hz, 1H), 6.44 (s, 1H), 7.01 (dd, J=6.8, 8.8 Hz, 1H), 7.31 (dd, J=1.3, 8.8 Hz, 1H), 8.13 (s, 1H).

Example 298

N-Cyclopropylmethyl-N-(1,3-dioxolan-2-ylmethyl)-N-[2-methoxy-7-(4-methoxy-2,6-dimethylphenyl)pyrazolo[1,5-a]pyridin-3-yl]amine (Yellow Oil)

$^1$H NMR (400 MHz, CDCl$_3$) δ −0.04-0.06 (m, 2H), 0.24-0.34 (m, 2H), 0.84-0.96 (m, 1H), 2.07 (s, 6H), 2.99 (d, J=6.8 Hz, 2H), 3.35 (d, J=4.4 Hz, 2H), 3.84-3.92 (m, 2H), 3.89 (s, 6H), 3.94-4.04 (m, 2H), 4.98 (t, J=4.4 Hz, 1H), 6.39 (d, J=6.8 Hz, 1H), 6.74 (s, 2H), 7.07 (dd, J=6.8, 8.8 Hz, 1H), 7.44 (d, J=8.8 Hz, 1H).

The compounds of Examples 299 to 312 were synthesized according to the production method of Example 256.

Example 299

N-Butyl-N-[7-(2,6-dimethoxy-4-methylphenyl)-2-methoxypyrazolo[1,5-a]pyridin-3-yl]-N-tetrahydro-2H-4-pyranylmethylamine (Yellow Oil)
$^1$H NMR (400 MHz, CDCl$_3$) δ 0.83-0.89 (m, 3H), 1.18-1.38 (m, 6H), 1.55-1.60 (m, 1H), 1.68-1.77 (m, 2H), 2.44 (s, 3H), 2.86 (d, J=6.8 Hz, 2H), 2.90-2.95 (m, 2H), 3.25-3.32 (m, 2H), 3.71 (s, 6H), 3.85 (s, 3H), 3.88-3.96 (m, 2H), 6.46-6.49 (m, 1H), 6.49 (s, 2H), 7.00 (dd, J=6.4, 8.8 Hz, 1H), 7.22-7.24 (m, 1H).

Example 300

N-Cyclobutylmethyl-N-[7-(2,6-dimethoxy-4-methylphenyl)-2-methoxypyrazolo[1,5-a]pyridin-3-yl]-N-tetrahydro-2H-4-pyranylmethylamine (Light Yellow Crystals)
$^1$H NMR (400 MHz, CDCl$_3$) δ 1.18-1.30 (m, 2H), 1.50-1.62 (m, 3H), 1.70-1.90 (m, 6H), 2.28-2.36 (m, 1H), 2.43 (s, 3H), 2.84 (d, J=7.2 Hz, 2H), 2.95 (d, J=7.2 Hz, 2H), 3.25-3.33 (m, 2H), 3.70 (s, 6H), 3.85 (s, 3H), 3.88-3.94 (m, 2H), 6.47 (dd, J=1.2, 6.8 Hz, 1H), 6.49 (s, 2H), 7.00 (dd, J=6.8 Hz, 1H), 7.22 (dd, J=1.2, 8.8 Hz, 1H).

Example 301

N-[7-(2,6-Dimethoxy-4-methylphenyl)-2-methoxypyrazolo[1,5-a]pyridin-3-yl]-N-(1,3-dioxolan-2-ylmethyl)-N-tetrahydro-2H-4-pyranylmethylamine (Yellow Oil)
$^1$H NMR (400 MHz, CDCl$_3$) δ 1.20-1.32 (m, 2H), 1.50-1.62 (m, 1H), 1.74-1.82 (m, 2H), 2.44 (s, 3H), 2.99 (d, J=7.2 Hz, 2H), 3.18 (d, J=4.4 Hz, 2H), 3.24-3.32 (m, 2H), 3.72 (s, 6H), 3.80-3.86 (m, 2H), 3.87 (s, 3H), 3.90-3.98 (m, 4H), 4.89 (t, J=4.4 Hz, 1H), 6.49 (dd, J=1.6, 6.8 Hz, 1H), 6.50 (s, 2H), 7.03 (dd, J=6.8, 8.8 Hz, 1H), 7.30 (dd, J=1.6, 8.8 Hz, 1H).

Example 302

N-Butyl-N-[7-(2,6-dimethoxy-4-methylphenyl)-2-methoxypyrazolo[1,5-a]pyridin-3-yl]-N-tetrahydro-2H-4-pyranylamine (White Crystals)
$^1$H NMR (400 MHz, CDCl$_3$) δ 0.79-0.87 (m, 3H), 1.23-1.36 (m, 4H), 1.45-1.54 (m, 2H), 1.77-1.86 (m, 2H), 2.44 (s, 3H), 3.01-3.13 (m, 3H), 3.32-3.41 (m, 2H), 3.72 (s, 6H), 3.86 (s, 3H), 3.90-3.98 (m, 2H), 6.49 (dd, J=1.3, 6.8 Hz, 1H), 6.50 (s, 2H), 7.02 (dd, J=6.8, 8.8 Hz, 1H), 7.25 (dd, J=1.3, 8.8 Hz, 1H).

Example 303

N-Cyclobutylmethyl-N-[7-(2,6-dimethoxy-4-methylphenyl)-2-methoxypyrazolo[1,5-a]pyridin-3-yl]-N-tetrahydro-2H-4-pyranylamine (White Amorphous)
$^1$H NMR (400 MHz, CDCl$_3$) δ 1.43-1.85 (m, 6H), 2.19-2.29 (m, 1H), 2.44 (s, 3H), 3.00-3.10 (m, 3H), 3.31-3.40 (m, 2H), 3.71 (s, 6H), 3.85 (s, 3H), 3.90-3.98 (m, 2H), 6.48 (dd, J=1.3, 6.8 Hz, 1H), 6.50 (s, 2H), 7.02 (dd, J=6.8, 8.8 Hz, 1H), 7.24 (dd, J=1.3, 8.8 Hz, 1H).

Example 304

N-[7-(2-Chloro-4-methoxyphenyl)-2-methoxypyrazolo[1,5-a]pyridin-3-yl]-N-tetrahydro-3-furanylmethyl-N-tetrahydro-2H-4-pyranylamine (Light Yellow Amorphous)
$^1$H NMR (400 MHz, CDCl$_3$) δ 1.41-1.65 (m, 3H), 1.74-1.91 (m, 3H), 2.08-2.17 (m, 1H), 2.93-3.08 (m, 2H), 3.11-3.18 (m, 1H), 3.30-3.40 (m, 2H), 3.54-3.72 (m, 3H), 3.75-3.83 (m, 1H), 3.87 (s, 3H), 3.88 (s, 3H), 3.90-3.97 (m, 2H), 6.50 (dd, J=1.3, 6.8 Hz, 1H), 6.91 (dd, J=2.4, 8.4 Hz, 1H), 7.04 (dd, J=6.8, 8.8 Hz, 1H), 7.06 (d, J=2.4 Hz, 1H), 7.25 (dd, J=1.3, 8.8 Hz, 1H), 7.43 (d, J=8.4 Hz, 1H).

Example 305

N-[7-(2-Chloro-4-methoxyphenyl)-2-methoxypyrazolo[1,5-a]pyridin-3-yl]-N-tetrahydro-2H-4-pyranyl-N-tetrahydro-2H-4-pyranylmethylamine (Light Yellow Amorphous)
$^1$H NMR (400 MHz, CDCl$_3$) δ 1.17-1.30 (m, 2H), 1.36-1.54 (m, 3H), 1.65-1.74 (m, 2H), 1.75-1.83 (m, 2H), 2.91-3.05 (m, 3H), 3.20-3.29 (m, 2H), 3.30-3.39 (m, 2H), 3.88 (s, 3H), 3.88 (s, 3H), 3.85-3.97 (m, 4H), 6.50 (dd, J=1.3, 6.8 Hz, 1H), 6.91 (dd, J=2.4, 8.4 Hz, 1H), 7.02 (dd, J=6.8, 8.8 Hz, 1H), 7.06 (d, J=2.4 Hz, 1H), 7.25 (dd, J=1.3, 8.8 Hz, 1H), 7.45 (d, J=8.4 Hz, 1H).

Example 306

N-Butyl-N-[2-methoxy-7-(2,4,6-trimethoxyphenyl)pyrazolo[1,5-a]pyridin-3-yl]-N-tetrahydro-2H-4-pyranylmethylamine (Yellow Oil)
$^1$H NMR (400 MHz, CDCl$_3$) δ 0.85 (t, J=6.8 Hz, 3H), 1.19-1.36 (m, 6H), 1.49-1.55 (m, 1H), 1.70-1.77 (m, 2H), 2.87 (d, J=7.2 Hz, 2H), 2.93 (t, J=7.2 Hz, 2H), 3.25-3.32 (m, 2H), 3.71 (s, 6H), 3.86 (s, 3H), 3.89 (s, 3H), 3.89-3.94 (m, 2H), 6.24 (s, 2H), 6.48 (dd, J=1.6, 6.8 Hz, 1H), 7.00 (dd, J=6.8, 8.8 Hz, 1H), 7.23 (dd, J=1.6, 8.8 Hz, 1H).

Example 307

N-Cyclobutylmethyl-N-[2-methoxy-7-(2,4,6-trimethoxyphenyl)pyrazolo[1,5-a]pyridin-3-yl]-N-tetrahydro-2H-4-pyranylmethylamine (Yellow Oil)
$^1$H NMR (400 MHz, CDCl$_3$) δ 1.20-1.30 (m, 2H), 1.49-1.60 (m, 3H), 1.70-1.86 (m, 6H), 2.28-2.35 (m, 1H), 2.83 (d, J=7.2 Hz, 2H), 2.95 (d, J=7.2 Hz, 2H), 3.25-3.32 (m, 2H), 3.70 (s, 6H), 3.86 (s, 3H), 3.88 (s, 3H), 3.88-3.94 (m, 2H), 6.23 (s, 2H), 6.47 (dd, J=1.6, 6.8 Hz, 1H), 7.00 (dd, J=6.8, 8.8 Hz, 1H), 7.21 (dd, J=1.6, 8.8 Hz, 1H).

Example 308

N-Cyclopropylmethyl-N-[2-methoxy-7-(2,4,6-tri-methoxyphenyl)pyrazolo[1,5-a]pyridin-3-yl]-N-tetrahydro-2H-4-pyranylmethylamine (Yellow Oil)

$^1$H NMR (400 MHz, CDCl$_3$) δ −0.02-0.02 (m, 2H), 0.28-0.34 (m, 2H), 0.80-0.90 (m, 1H), 1.18-1.32 (m, 2H), 1.50-1.60 (m, 1H), 1.72-1.77 (m, 2H), 2.80 (d, J=6.4 Hz, 2H), 2.94 (d, J=7.2 Hz, 2H), 3.25-3.32 (m, 2H), 3.71 (s, 6H), 3.86 (s, 3H), 3.88 (s, 3H), 3.88-3.94 (m, 2H), 6.24 (s, 2H), 6.47 (dd, J=1.6, 6.8 Hz, 1H), 6.99 (dd, J=6.8, 8.8 Hz, 1H), 7.28 (dd, J=1.6, 8.8 Hz, 1H).

Example 309

N3-Cyclopropylmethyl-N3-tetrahydro-2H-4-pyranylmethyl-7-[6-(dimethylamino)-2,4-dimethyl-3-pyridyl]-2-methoxypyrazolo[1,5-a]pyridin-3-amine (Yellow Oil)

$^1$H NMR (400 MHz, CDCl$_3$) δ −0.02-0.04 (m, 2H), 0.30-0.38 (m, 2H), 0.82-0.96 (m, 1H), 1.28-1.43 (m, 2H), 1.57-1.72 (m, 1H), 1.79-1.89 (m, 2H), 2.05 (s, 3H), 2.24 (s, 3H), 2.87 (d, J=6.6 Hz, 2H), 3.03 (d, J=7.1 Hz, 2H), 3.21 (s, 6H), 3.38 (dt, J=2.0, 12.0 Hz, 2H), 3.93 (s, 3H), 3.96-4.05 (m, 2H), 6.38 (s, 1H), 6.42 (dd, J=1.5, 6.8 Hz, 1H), 7.07 (dd, J=6.8, 8.8 Hz, 1H), 7.38 (dd, J=1.4, 8.8 Hz, 1H).

Example 310

N3-Cyclopropylmethyl-N3-tetrahydro-2H-4-pyranylmethyl-7-[6-(dimethylamino)-4-methyl-3-pyridyl]-2-methoxypyrazolo[1,5-a]pyridin-3-amine (Yellow Oil)

$^1$H NMR (400 MHz, CDCl$_3$) δ −0.03-0.08 (m, 2H), 0.29-0.38 (m, 2H), 0.78-0.94 (m, 1H), 1.24-1.38 (m, 2H), 1.50-1.66 (m, 1H), 1.73-1.84 (m, 2H), 2.15 (s, 3H), 2.84 (d, J=6.8 Hz, 2H), 2.98 (d, J=7.1 Hz, 2H), 3.19 (s, 6H), 3.33 (dt, J=1.6, 12.0 Hz, 2H), 3.93 (s, 3H), 3.90-4.00 (m, 2H), 6.45 (dd, J=0.6, 6.8 Hz, 1H), 6.49 (s, 1H), 7.05 (dd, J=6.8, 7.3 Hz, 1H), 7.36 (dd, J=0.7, 8.8 Hz, 1H), 8.19 (s, 1H).

Example 311

N-[7-(2-Chloro-4-methoxyphenyl)-2-methoxypyrazolo[1,5-a]pyridin-3-yl]-N,N-ditetrahydro-2H-4-pyranylmethylamine (Yellow Oil)

$^1$H NMR (400 MHz, CDCl$_3$) δ 1.18-1.31 (m, 4H), 1.46-1.58 (m, 2H), 1.70-1.80 (m, 4H), 2.81-2.88 (m, 4H), 3.24-3.34 (m, 4H), 3.88 (s, 3H), 3.89 (s, 3H), 3.89-3.96 (m, 4H), 6.50 (dd, J=1.3, 6.8 Hz, 1H), 6.91 (dd, J=2.4, 8.4 Hz, 1H), 7.02 (dd, J=6.8, 8.8 Hz, 1H), 7.06 (d, J=2.4 Hz, 1H), 7.25 (dd, J=1.3, 8.8 Hz, 1H), 7.46 (d, J=8.4 Hz, 1H).

Example 312

N-Cyclopropylmethyl-N-[7-(2,4-dimethoxy-6-methylphenyl)-2-methoxypyrazolo[1,5-a]pyridin-3-yl]-N-tetrahydro-2H-4-pyranylmethylamine (Yellow Oil)

$^1$H NMR (400 MHz, CDCl$_3$) δ −0.05-0.00 (m, 2H), 0.23-0.34 (m, 2H), 0.76-0.86 (m, 1H), 1.22-1.33 (m, 2H), 1.50-1.60 (m, 1H), 1.68-1.80 (m, 2H), 2.02 (s, 3H), 2.74-2.86 (m, 2H), 2.89-3.00 (m, 2H), 3.29 (dt, J=2.0, 11.6 Hz, 2H), 3.69 (s, 3H), 3.85 (s, 3H), 3.86 (s, 3H), 3.88-3.94 (m, 2H), 6.39 (dd, J=1.2, 6.8 Hz, 1H), 6.42 (d, J=2.0 Hz, 1H), 6.46 (d, J=2.0 Hz, 1H), 7.00 (dd, J=6.8, 9.2 Hz, 1H), 7.29 (dd, J=1.2, 9.2 Hz, 1H).

The compounds of Examples 313 to 314 were synthesized according to the production method of Example 40.

Example 313

N-Cyclopropylmethyl-N-[2-ethyl-7-(4-ethyl-2,6-dimethoxyphenyl)pyrazolo[1,5-a]pyridin-3-yl]-N-tetrahydro-3-furanylmethylamine (Yellow Oil)

$^1$H NMR (400 MHz, CDCl$_3$) δ −0.04-0.02 (m, 2H), 0.32-0.40 (m, 2H), 0.78-0.88 (m, 1H), 1.12-1.36 (m, 6H), 1.56-1.64 (m, 1H), 1.82-1.92 (m, 1H), 2.18-2.30 (m, 1H), 2.66-2.78 (m, 4H), 2.84-2.92 (m, 2H), 3.02-3.10 (m, 1H), 3.18-3.24 (m, 1H), 3.76-3.82 (m, 4H), 3.69 (s, 6H), 6.51 (s, 2H), 6.57 (dd, J=1.2, 6.8 Hz, 1H), 6.99 (dd, J=6.8, 8.8 Hz, 1H), 7.40 (dd, J=1.2, 8.8 Hz, 1H).

Example 314

N-Cyclopropylmethyl-N-[2-ethyl-7-(4-ethyl-2,6-dimethoxyphenyl)pyrazolo[1,5-a]pyridin-3-yl]-N-tetrahydro-2H-4-pyranylmethylamine (Yellow Oil)

$^1$H NMR (400 MHz, CDCl$_3$) δ −0.02-0.04 (m, 2H), 0.34-0.40 (m, 2H), 0.80-0.88 (m, 1H), 1.22-1.36 (m, 2H), 1.24 (t, J=7.6 Hz, 3H), 1.35 (t, J=7.6 Hz, 3H), 1.54-1.66 (m, 1H), 1.74-1.82 (m, 2H), 2.74 (q, J=7.6 Hz, 2H), 2.79 (q, J=7.6 Hz, 2H), 2.90 (d, J=6.8 Hz, 2H), 3.60 (d, J=7.2 Hz, 2H), 3.30-3.38 (m, 2H), 3.73 (s, 6H), 3.92-3.98 (m, 2H), 6.55 (s, 2H), 6.61 (dd, J=1.6, 6.8 Hz, 1H), 7.01 (dd, J=6.8, 8.8 Hz, 1H), 7.44 (dd, J=1.2, 8.8 Hz, 1H).

In the Examples and Production Examples throughout the present specification, aldehyde compounds, halogenated compounds and sulfonates such as dihydro-2H-pyran-3(4H) one [CAS NO. 23462-75-1], (R)-3-tetrahydropyrancarboxyaldehyde [CAS NO. 143810-10-0], (S)-3-tetrahydropyrancarboxyaldehyde [CAS NO. 141822-85-7], (±)-3-tetrahydropyrancarboxyaldehyde [CAS NO. 77342-93-9], 3-formyl-5,6-dihydro-2H-pyran [CAS NO. 13417-49-7], 2-oxazolecarboxyaldehyde [CAS NO. 65373-52-6], 6-dimethylamino-2-pyridinecarboxyaldehyde [CAS NO. 208110-83-2], 6-dimethylamino-3-pyridinecarboxyaldehyde [CAS NO. 149805-92-5], 3-methyl-5-isoxazolemethanol methanesulfonate [CAS NO. 96603-41-7], 3-(phenylmethoxy)-1-butanol 4-methylbenzenesulfonate [CAS NO. 96556-29-5], [(2-bromo-1-methylethoxy)methyl]-benzene [CAS NO. 135364-12-4], 5-(bromomethyl)isoxazole [CAS NO. 69735-35-9] and the like may be used as starting materials.

TEST EXAMPLES

Compounds of the present invention were evaluated in regard to Corticotropin-Releasing Factor Receptor (CRFR) binding affinity and inhibition of cAMP production. The test methods and results were as follows.

Test Example 1

CRFR Binding Experiment (1) Preparation of CRFR-Expressing Cells

Membrane fraction of the cell highly expressing human CRFR1 was used as the experimental material for a CRFR binding experiment. The CRFR expressing cells were prepared in the following manner. The full-length CRFR1 gene was obtained from a human brain cDNA library (Quick-Clone™, Clontech) by PCR. The obtained DNA fragments were inserted into cloning vectors and the base sequences were determined. cDNA having the correct base sequence was then relinked to an expression vector (pcDNA3.1™, Invitrogen). The CRFR1 expression vector was introduced into HEK293 cells, and the resistant cells which grew in cell medium containing G418 (1 mg/ml) were cloned by limiting dilution. From these cloned cells, the clones with high binding affinity between the membrane fraction and sauvagine per unit of protein in the binding experiment described below were selected out and used for the final experiment.

(2) Preparation of Membrane Fraction

The cloned cells obtained in (1) were collected and disrupted with an ultrasonic generator in sonicate buffer (D-PBS (−) 10 mM $MgCl_2$, 2 mM EGTA). The suspension obtained from ultrasonic disruption was centrifuged (46,000×g, 10 minutes), and the precipitate was resuspended in sonicate buffer and the same procedure was repeated. The final precipitate was then suspended in binding buffer (D-PBS(−) 10 mM $MgCl_2$, 2 mM EGTA, 1.5% BSA, 0.15 mM bacitracin, 1×protease inhibitor cocktail (COMPLETE™, Boehringer)), and used as the membrane fraction after adjusting the protein concentration to 1.6 mg/ml.

(3) Binding Experiment

The sauvagine binding experiment was conducted following the protocol of SPA™ (Amersham Pharmacia), using a 96-well plate. The experiment was conducted according to the SPA beads instruction manual. After allowing 40 mg of the membrane fraction protein, 0.5 mg of SPA beads and 50 pM of $^{125}$I-sauvagine (Amersham Pharmacia) to stand at room temperature for 2 hours in the presence of the test compound, the mixture was centrifuged (1000×g, 5 minutes) and the radioactivity of each well was measured with a TopCount™ (Packard).

(4) Calculation of Binding Affinity

The radioactivity for non-radioactive sauvagine added in a 1000-fold excess was subtracted from each value as the non-specific binding, and the radioactivity of a sample without addition of the test substance (control) was defined as 100%, with each value represented as a percentage (% of control). A graph was drawn with the concentration of the test substance plotted on the horizontal axis and the percentage (% of control) plotted on the vertical axis, and the concentration which resulted in a 50% value for the percentage (% of control) was determined from the graph to calculate the $IC_{50}$ value.

Test Example 2 cAMP Production Inhibition Experiment Using AtT-20 Cells (1) Test Procedure

The AtT-20 cells were of a mouse pituitary gland tumor-derived cell line which is known to respond to Corticotropin-Releasing Factor (CRF), leading to activation of the intracellular adenylate cyclase system, production of cyclic AMP (cAMP), and release of adrenocorticotropic hormone (ACTH) (Biochem. Biophys. Res. Com. 106, 1364-1371, 1982). For the experiment, the cells (1×10$^5$) were suspended in D-MEM medium (0.1% FBS) and seeded in a 96-well plate, phosphodiesterase inhibitor (IBMX, Calbiochem) was added to a final concentration of 1 mM, and were cultured at 37° C. for 30 minutes. A dilution of the test compound was added, culturing was continued for 30 minutes at 37° C., and CRF (30 nM) was added and culturing was continued for 30 minutes at 37° C. The cells were collected by centrifugation (500×g, 5 minutes) and lysed with lysis buffer (0.2% dodecyltrimethylammonium bromide), and the intracellular cAMP production was quantified by the HTRF method. A cAMP kit HTRF (CIS Diagnostics Co., Ltd.) was used for the cAMP quantification.

(2) Calculation of cAMP Production Inhibition

The obtained data were processed in the following manner. The cAMP production of cells to which 30 nM CRF had been added was defined as 100% (control), and the value for each specimen was represented as a percentage (% of control). A graph was drawn with the concentration of the test substance plotted on the horizontal axis and the percentage (% of control) plotted on the vertical axis, and the concentration which resulted in a 50% value for the percentage (% of control) was determined from the graph to calculate the $IC_{50}$ value.

<Test Results>

In Test Example 1, the compound of the invention exhibited excellent binding affinity for CRFR, with an $IC_{50}$ value of 5-5000 nM. In Test Example 2, the compound of the invention exhibited excellent inhibition against CRF-dependent cAMP production. Some of the results are shown below in Table 1.

TABLE 1

| Compound No. (Example No.) | CRF1 receptor binding affinity $IC_{50}$ (nM) | Adenylate cyclase activity $IC_{50}$ (nM) |
|---|---|---|
| Example 3 | 50 | 130 |
| Example 6 | 160 | 200 |
| Example 25 | 210 | 550 |
| Example 27 | 55 | 300 |
| Example 103 | 90 | 400 |
| Example 108 | 50 | 20 |

INDUSTRIAL APPLICABILITY

As explained above, the present invention provides novel pyrazolo[1,5-a]pyridine compounds having CRF receptor antagonistic activity, their salts and novel pharmaceutical compositions comprising them. The compounds of the invention or their salts exhibit excellent antagonism against CRF receptors and particularly against CRF1 receptor, while having low toxicity and high safety, and are therefore highly useful as drugs. The compounds of the invention and pharmaceutical compositions comprising them are useful for treatment or prevention of diseases associated with CRF and/or CRF receptors, and particularly they are useful as therapeutic or prophylactic agents for depression and depressive symptoms (major depression, single-episode depression, recurrent depression, depression-induced child abuse, postpartum depression, etc.), mania, anxiety, generalized anxiety disorder, panic disorder, phobias, obsessive-compulsive disorder, posttraumatic stress disorder, Tourette's syndrome, autism, affective disorder, dysthymia, bipolar disorder, cyclothymic personality, schizophrenia, peptic ulcer, irritable bowel syndrome, ulcerative colitis, Crohn's disease, diarrhea, constipation, postoperative ileus, stress-associated gastrointestinal disorders, nervous vomiting, and the like.

The invention claimed is:

1. A pharmaceutical composition comprising a compound represented by the general formula or a salt thereof:

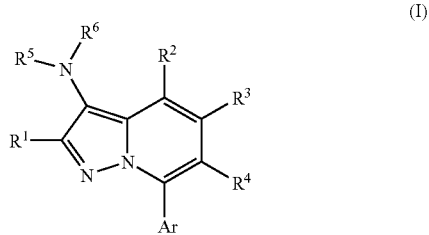

wherein $R^1$ represents a hydrogen, halogen, nitro, cyano or the formula —$G^1R^{1a}$ (wherein $G^1$ represents a single bond, methylene, oxygen, sulfur, sulfinyl, sulfonyl, —C(O)—, —C(O)O—, —OC(O)—, —$NR^{1b}$—, —C(O)—$NR^{1b}$—, —S(O)$_2$—$NR^{1b}$—, $NR^{1b}$C(O)— or —$NR^{1b}$—S(O)$_2$—; and $R^{1a}$ and $R^{1b}$ each independently represents a hydrogen, $C_{1-10}$ alkyl, $C_{2-10}$ alkenyl, $C_{2-10}$ alkynyl, $C_{3-8}$ cycloalkyl or $C_{5-8}$ cycloalkenyl);

$R^2$, $R^3$ and $R^4$ each independently represents a hydrogen, halogen, cyano, nitro, hydroxyl, $C_{6-14}$ aryl, a 5- to 14-membered heteroaryl group or the formula —$G^2$—$R^{2a}$ (wherein $G^2$ represents a single bond, $C_{1-6}$ alkylene, oxygen, sulfur, sulfinyl, sulfonyl, —C(O)—, —C(O)O—, —OC(O)—, —$NR^{2b}$—, —C(O)—$NR^{2b}$—, —S(O)$_2$—$NR^{2b}$—, —$NR^{2b}$—C(O)— or —$NR^{2b}$—S(O)$_2$—;

$R^{2a}$ and $R^{2b}$ each independently represents a hydrogen, $C_{1-6}$ alkyl optionally substituted with 1-3 halogens, $C_{2-10}$ alkenyl, $C_{2-10}$ alkynyl, $C_{3-8}$ cycloalkyl or $C_{5-8}$ cycloalkenyl);

$R^2$ and $R^3$ or $R^3$ and $R^4$ optionally bond together to form a 5- to 7-membered ring optionally containing 1 to 4 hetero atoms in the ring and optionally containing carbonyl in the ring;

$R^5$ and $R^6$ each independently represents the formula —$X^5$—$X^6$—$X^7$ (wherein $X^5$ represents a single bond or —CO—; $X^6$ represents a single bond, —$NR^{3a}$—, oxygen, sulfur, sulfinyl, sulfonyl, $C_{1-10}$ alkylene, $C_{2-10}$ alkenylene or $C_{2-10}$ alkynylene; and $X^7$ and $R^{3a}$ each independently represents a hydrogen, $C_{1-10}$ alkyl, $C_{2-10}$ alkenyl, $C_{2-10}$ alkynyl, $C_{3-8}$ cycloalkyl, $C_{5-8}$ cycloalkenyl, $C_{6-14}$ aryl, a 5- to 14-membered heteroaryl group, a 4- to 14-membered heterocyclic group, a 9- to 11-membered benzene fused ring group, an 8- to 11-membered heteroaryl fused ring group or a bicyclic 7- to 12-membered hydrocarbon ring group);

$R^5$ and $R^6$ optionally bond together to form a 5- to 10-membered ring optionally containing 1 to 4 hetero atoms in the ring and optionally containing carbonyl in the ring;

$R^6$ and $R^2$ optionally bond together to form a 6- to 7-membered ring optionally containing 1 or 2 hetero atoms in the ring and optionally containing carbonyl in the ring; and Ar represents $C_{6-14}$ aryl, a 5- to 14-membered heteroaryl group, a 9- to 11-membered benzene fused ring group or an 8- to 11-membered heteroaryl fused ring group; with the proviso that $R^{1a}$, $R^{1b}$, $R^{3a}$, $X^6$, $X^7$, and Ar may each independently have 1 to 4 groups selected from the group consisting of halogen, cyano, hydroxyl, nitro, $C_{1-6}$ alkoxy, $C_{3-8}$ cycloalkyl, $C_{1-6}$ alkyl, dimethylamino, methylenedioxy, ethylenedioxy, a formula —$V^1$—$V^2$—$V^3$ (wherein $V^1$ represents a single bond, $C_{1-6}$ alkylene, $C_{2-6}$ alkenylene, $C_{2-6}$ alkynylene, oxygen, sulfur, carbonyl, —CO—O—, —O—CO— or $NR^{3b}$—; $V^2$ represents a single bond or $C_{1-6}$ alkylene; and $V^3$ and $R^{3b}$ each independently represents $C_{1-6}$ alkyl, $C_{2-6}$ alkenyl, $C_{2-6}$ alkynyl, $C_{3-8}$ cycloalkyl, $C_{5-8}$ cycloalkenyl, $C_{6-14}$ aryl, a 5- to 14-membered heterocyclic group, a 4- to 14-membered heterocyclic group, hydrogen, halogen, hydroxyl, cyano, $C_{1-6}$ alkoxy or a formula —$N(R^{3c})R^{3d}$ (wherein $R^{3c}$ and $R^{3d}$ each independently represents a hydrogen or $C_{1-6}$ alkyl)), a formula —$V^4$—$V^5$ (wherein $V^4$ represents a single bond, oxygen, sulfur, sulfinyl or sulfonyl and $V^5$ represents $C_{1-6}$ alkyl optionally substituted with 1 to 3 halogens or $C_{3-8}$ cycloalkyl) and a formula —$N(R^{5a})R^{5b}$ (wherein $R^{5a}$ and $R^{5b}$ each independently represents a hydrogen or $C_{1-6}$ alkyl).

2. The pharmaceutical composition of claim 1, wherein the compound or the salt thereof is a Corticotropin-Releasing Factor (CRF)-1 receptor or Corticotropin-Releasing Factor (CRF)-2 receptor antagonist.

3. The pharmaceutical composition of claim 1, which is a therapeutic agent for depression, depressive symptom, or irritable bowel syndrome.

4. The pharmaceutical composition of claim 1, which is a therapeutic agent for depression, anxiety, or irritable bowel syndrome.

5. The pharmaceutical composition of claim 1, which is a therapeutic agent for depression, depressive symptom, anxiety or irritable bowel syndrome.

6. A method of treating depression, anxiety, or irritable bowel syndrome, comprising:
single or multiple administration of the pharmaceutical composition of claim 1 to a patient in need thereof.

7. A method of treating depression, depressive symptom, or irritable bowel syndrome, comprising:
single or multiple administration of the pharmaceutical composition of claim 1 to a patient in need thereof.

8. A method of treating depression, depressive symptom, anxiety or irritable bowel syndrome, comprising:
single or multiple administration of a therapeutically effective dose of the pharmaceutical composition of claim 1 thereof to a patient in need thereof.

* * * * *